United States Patent [19]
Chambon et al.

[11] Patent Number: 6,031,149
[45] Date of Patent: Feb. 29, 2000

[54] GENETICALLY ENGINEERED MICE CONTAINING ALTERATIONS IN THE GENES ENCODING RETINOIC ACID RECEPTOR PROTEINS

[75] Inventors: Pierre Chambon, Blaesheim, France; Thomas Lufkin, New York, N.Y.; David Lohnes, Montreal, Canada; Manuel Mark, Marschwiller, France; Andree Dierich, Strasbourg, France; Philippe Gorry, Pessac, France; Philippe Kastner; Marianne Lemeur, both of Strasbourg, France; Cathy Mendelsohn, Englewood, N.J.

[73] Assignees: Institut National De La Santé Et De La Recherche Médicale; Centre National De La Recherche Scientifique, both of Paris Cedex; Université Louis Pasteur, Strausberg Cedex, all of France; E.R. Squibb & Sons, Inc., Princeton, N.J.

[21] Appl. No.: 08/580,713

[22] Filed: Dec. 29, 1995

Related U.S. Application Data

[62] Continuation-in-part of application No. 08/373,224, which is a continuation-in-part of application No. 08/062,850, filed as application No. PCT/US94/05746, May 18, 1994, abandoned.

[51] Int. Cl.$^7$ .............................. C12N 5/00; C12N 15/00; C12N 15/09; C12N 15/63
[52] U.S. Cl. .............................. 800/2; 435/477; 435/463; 435/6; 435/91.1; 435/354; 435/375; 435/377; 424/9.21
[58] Field of Search ................................. 800/2, DIG. 1, 800/DIG. 4, 18, 22, 25; 435/172.3, 6, 172.1, 91.1, 354, 375, 377, 477, 463; 424/9, 9.21

[56] References Cited

U.S. PATENT DOCUMENTS

| | | | |
|---|---|---|---|
| 4,981,784 | 1/1991 | Evans et al. | 435/6 |
| 5,364,783 | 11/1994 | Ruley et al. | 435/235.1 |

FOREIGN PATENT DOCUMENTS

WO 95/30741   11/1995   WIPO .

OTHER PUBLICATIONS

Allenby, G. et al., "Retinoic acid receptors and retinoid X receptors: Interactions with endogenous retinoic acids", *Proc. Natl. Acad. Sci. USA* 90:30–34 (Jan. 1993).

Adra, C. N. et al., "Cloning and expression of the mouse pgk–1 gene and the nucleotide sequence of its promoter", *Gene* 60:65–74 (1987).

Beato, M., "Gene Regulation by Steroid Hormones", *Cell* 56:335–344 (1989).

Brand, N. J. et al., "Characterization of a functional promoter for the human retinoic acid receptor–alpha (hRAR–α)", *Nucl. Acids Res.* 18(23):6799–6806 (1990).

Brookfield, J., "Can genes be truly redundant?", *Curr. Biol.* 2(10):553–554 (Oct. 1992).

Bugge, T. H. et al., "RXRα, a promiscuous partner of retinoic acid and thyroid hormone receptors", *EMBO J.* 11(4):1409–1418 (Apr. 1992).

Capecchi, M. R., "The New Mouse Genetics: Altering the Genome by Gene Targeting", *TIG* 5(3):70–76 (1989).

Capecchi, M. R., "Altering the Genome by Homologous Recombination", *Science* 244:1288–1292 (1989).

Chisaka, O. et al., "Developmental defects of the ear, cranial nerves and hindbrain resulting from targeted disruption of the mouse homeobox gene Hox–1.6", *Nature* 355:516–520 (Feb. 1992).

Conlon, R. A. et al., "Exogenous retinoic acid rapidly induces anterior ectopic expression of murine Hox–2 genes in vivo", *Development* 116(2):357–368 (Oct. 1992).

Creech Kraft, J., "Pharmacokinetics, placental transfer, and teratogenicity of 13–cis–retinoic acid, its isomer and metabolites", in: *Retinoids in Normal Development and Teratogenesis*, Morris–Kay, G. M., ed., Oxford University Press: Oxford, England, pp. 267–280 (Jun. 1992).

DeChiara, T. M. et al., "A growth–deficiency phenotype in heterozygous mice carrying an insulin–like growth factor II gene disrupted by targeting", *Nature* 345:78–80 (1990).

De Luca, L. M., "Retinoids and their receptors in differentiation, embryogenesis, and neoplasia", *FASEB J.* 5:2924–2933 (1991).

Dollé, P. et al., "Differential expression of genes encoding α, β and γ retinoic acid receptors and CRABP in the developing limbs of the mouse", *Nature* 342:702–705 (1989).

Dollé, P. et al., "Retinoic acid receptors and cellular retinoid binding proteins:I. A systematic study of their differential pattern of transcription during mouse organogenesis", *Development* 110:1133–1151 (1990).

Dollé, P. et al., "Developmental expression of murine retinoid X receptor (RXR) genes", *Mech. Development* 45:91–104 (1994).

Duboule, D. et al., "The Vertebrate Limb: A Model System to Study the Hox/HOM Gene Network during Development and Evolution", *BioEssays* 14(6):375–384 (Jun. 1992).

Durand, B. et al., "All–Trans and 9–Cis Retinoic Acid Induction of CRABPII Transcription Is Mediated by RAR–RXR Heterodimers Bound to DR1 and DR2 Repeated Motifs", *Cell* 71:73–85 (Oct. 1992).

(List continued on next page.)

*Primary Examiner*—Jasemine C. Chambers
*Assistant Examiner*—Jill D. Schmuck
*Attorney, Agent, or Firm*—Sterne, Kessler, Goldstein & Fox P.L.L.C.

[57] ABSTRACT

The present invention provides mice which are deficient in the normal expression of one or more members of the RAR or RXR class of receptors, to mice heterozygous for such deficiency, and to cell lines, preferably pluripotent or totipotent cell lines, which are heterozygous or homozygous for such deficiency. The present invention further provides the use of any of the above mice and cell lines in situations where the absence of at least one RAR or RXR receptors, or the normal expression thereof, is desirable.

11 Claims, 67 Drawing Sheets

OTHER PUBLICATIONS

Ellinger–Ziegelbauer, H. et al., "A retinoic acid receptor expressed in the early development of *Xenopus laevis*", *Genes Develop.* 5:94–104 (1991).

Evans, R. M., "The Steroid and Thyroid Hormone Receptor Superfamily", *Science* 240:889–895 (1988).

Giguere, V. et al., "Identification of a receptor for the morphogen retinoic acid", *Nature* 330:624–629 (1987).

Giguère, V. et al., "Identification of a Novel Isoform of the Retinoic Acid Receptor γ Expressed in the Mouse Embryo", *Mol. Cell. Biol.* 10(5):2335–2340 (1990).

Green, S. et al., "Nuclear receptors enhance our understanding of transcription regulation", *TIG* 4(11):309–314 (1988).

Green, S., "Promiscuous liaisons", *Nature* 361:590–591 (Feb. 1993).

Gronemeyer, H., "Transcription Activation by Estrogen and Progesterone Receptors", *Annu. Rev. Genet.* 25:89–123 (1991).

Hunt, P. et al., "A distinct Hox code for the branchial region of the vertebrate head", *Nature* 353:861–864 (1991).

Jegalian, B. G. et al., "Homeotic Transformations in the Mouse Induced by Overexpression of a Human Hox3.3 Transgene", *Cell* 71:901–910 (Dec. 1992).

Kastner, P. et al., "Murine isoforms of retinoic acid receptor γ with specific patterns of expression", *Proc. Natl. Acad. Sci. USA* 87:2700–2704 (1990).

Kastner, P. et al., "Genetic Analysis of RxRα Developmental Function: Convergence of RXR and RAR Signaling Pathways in Heart and Eye Morphogenesis", *Cell* 78:987–1003 (1994).

Kessel, M. et al., "Variations of Cervical Vertebrae after Expression of a Hox–1.1 Transgene in Mice", *Cell* 61:301–308 (1990).

Kessel, M. et al., "Homeotic Transformations of Murine Vertebrae and Concomitant Alternation of Hox Codes Induced by Retinoic Acid", *Cell* 67:89–104 (1991).

Kessel, M., "Respecification of vertebral identities by retinoic acid", *Develop.* 115(2):487–501 (Jun. 1992).

Kliewer, S. A. et al., "Retinoid X receptor interacts with nuclear receptors in retinoic acid, thyroid hormone and vitamin $D_3$ signalling", *Nature* 355:446–449 (Jan. 1992).

Krust, A. et al., "A third human retinoic acid receptor, hRAR–γ", *Proc. Natl. Acad. Sci. USA* 86:5310–5314 (1989).

Lammer, E. J. et al., "Retinoic Acid Embryopathy", *New Eng. J. Med.* 313(14):837–841 (1985).

Langston, A. W. et al., "Identification of a retinoic acid responsive enhancer 3' of the murine homeobox gene Hox–1.6", *Mech. Develop.* 38:217–228 (Sep. 1992).

LaRosa, G. J. et al., "An early effect of retinoic acid: Cloning of an mRNA (Era–1) exhibiting rapid and protein synthesis–independent induction during teratocarcinoma stem cell differentiation", *Proc. Natl. Acad. Sci. USA* 85:329–333 (1988).

Laudet, V. et al., "Flexible friends", *Curr. Biol.* 2(6):293–295 (Jun. 1992).

Lee, S. S.–T. et al., "Targeted Disruption of the α Isoform of the Peroxisome Proliferator–Activated Receptor Gene in Mice Results in Abolishment of the Pleiotropic Effects of Peroxisome Proliferators", *Mol. Cell. Biol.* 15(6):3012–3022 (1995).

Leid, M. et al., "Purification, Cloning, and RXR Identity of the HeLA Cell Factor with Which RAR or TR Heterodimerizes to Bind Target Sequences Efficiently", *Cell* 68:377–395 (Jan. 1992).

Leid, M. et al., "Multiplicity generates diversity in the retinoic acid signalling pathways", *TIBS* 17:427–433 (Oct. 1992).

Le Mouellic, H. et al., "Homeosis in the Mouse Induced by a Null Mutation in the Hox–3.1 Gene", *Cell* 69:251–264 (Apr. 1992).

Leroy, P. et al., "Multiple isoforms of the mouse retinoic acid receptor α are generated by alternative splicing and differential induction by retinoic acid", *EMBO J.* 10(1):59–69 (1991).

Leroy, P. et al., "Mouse retinoic acid receptor α2 isoform is transcribed from a promoter that contains a retinoic acid response element" *Proc. Natl. Acad. Sci. USA* 88:10138–10142 (1991).

Li, E. et al., "Normal development and growth of mice carrying a targeted disruption of the α1 retinoic acid receptor gene", *Proc. Natl. Acad. Sci. USA* 90:1590–1594 (Feb. 1993).

Linney, E., "Retinoic Acid Receptors: Transcription Factors Modulating Gene Regulation, Development, and Differentiation", *Curr. Top. Develop. Biol.* 27:309–350 (Oct. 1992).

Liu, Q. et al., "The Mouse Retinoid–X Receptor–γ Gene: Genomic Organization and Evidence for Functional Isoforms", *Mol. Endocrin.* 7(5):651–658 (May 1993).

Lohnes, D. et al., "Function of Retinoic Acid Receptor γ in the Mouse", *Cell* 73:643–658 (May 1993).

Lohnes, D. et al., "Function of the retinoic acid receptors (RARs) during development: (I) Craniofacial and skeletal abnormalities in RAR double mutants", *Develop.* 120:2723–2748 (1994).

Lufkin, T. et al., "Disruption of the Hox–1.6 Homeobox Gene Results in Defects in a Region Corresponding to Its Rostral Domain of Expression", *Cell* 66:1105–1119 (1991).

Lufkin, T. et al., "Homeotic transformation of the occipital bones of the skull by ectopic expression of a homeobox gene", *Nature* 359:835–841 (Oct. 1992).

Lufkin, T. et al., "High postnatal lethality and testis degeneration in retinoic acid receptor α mutant mice", *Proc. Natl. Acad. Sci. USA* 90:7225–7229 (Aug. 1993).

Mangelsdorf, D. J. et al., "Characterization of three RXR genes that mediate the action of 9–cis retinoic acid", *Genes Develop.* 6(3):329–344 (Mar. 1992).

Marks, M. S. et al., "H–2RIIBP (RXRβ) heterodimerization provides a mechanism for combinatorial diversity in the regulation of retinoic acid and thyroid hormone responsive genes", *EMBO J.* 11(4):1419–1435 (Apr. 1992).

Marshall, H. et al., "Retinoic acid alters hindbrain Hox code and induces transformation of rhombomeres ⅔ into a ⅘ identity", *Nature* 360:737–741 (Dec. 1992).

Mendelsohn, C. et al., "Developmental analysis of the retinoic acid–inducible RAR–β2 promoter in transgenic animals" *Develop.* 113:723–734 (1991).

Mendelsohn, C. et al., "Function of the retinoic acid receptors (RARs) during development: (II) Multiple abnormalities at various stages of organogenesis in RAR double mutants", *Develop.* 120:2749–2771 (1994).

Mohanty–Hejmadi, P. et al., "Limbs generated at site of tail amputation in marbled balloon frog after vitamin A treatment", *Nature* 355:352–353 (Jan. 1992).

Morriss–Kay, G. M. et al., "Effects of retinoic acid excess on expression of Hox–2.9 and Krox–20 and on morphological segmentation in the hindbrain of mouse embryos", *EMBO J.* 10(10):2985–2995 (1991).

Nagata, T. et al., "The mouse Rxrb gene encoding RXRβ: genomic organization and two mRNA isoforms generated by alternative splicing of transcripts initiated from CpG island promoters", *Gene* 142:183–189 (1994).

Nagpal, S. et al., "Promoter Context–and Response Element–Dependent Specificity of the Transcriptional Activation and Modulating Functions of Retinoic Acid Receptors", *Cell* 70:1007–1019 (Sep. 1992).

Nagpal, S. et al., "RARs and RXRs: evidence for two autonomous transactivation functions (AF–1 and AF–2) and heterodimerization in vivo", *EMBO J.* 12(6):2349–2360 (Jun. 1993).

Papalopulu, N. et al., "The expression of murine Hox–2 genes is dependent on the differentiation pathway and displays a collinear sensitivity to retinoic acid in F9 cells and Xenopus embryos", *Nucl. Acids Res.* 19(20):5497–5506 (1991).

Petkovich, M. et al., "A human retinoic acid receptor which belongs to the family of nuclear receptors", *Nature* 330:444–450 (1987).

Pollock, R. A. et al., "Altering the Boundaries of Hox3.1 Expression: Evidence for Antipodal Gene Regulation", *Cell* 71:911–923 (Dec. 1992).

Pöpperl, H. et al., "Identification of a Retinoic Acid Response Element Upstream of the Murine Hox–4.2 Gene", *Mol. Cell. Biol.* 13(1):257–265 (Jan. 1993).

Ruberte, E. et al., "Specific spatial and temporal distribution of retinoic acid receptor gamma transcripts during mouse embryogenesis", *Develop.* 108:213–222 (1990).

Ruberte, E. et al., "Retinoic acid receptors and cellular retinoid binding proteins: II. Their differential pattern of transcription during early morphogenesis in mouse embryos", *Develop.* 111:45–60 (1991).

Schwartzberg, P. L. et al., "Germ–Line Transmission of a c–abl Mutation Produced by Targeted Gene Disruption in ES Cells", *Science* 246:799–803 (1989).

Shen, S. et al., "Embryonic stem cells stably transfected with mRARβ$_2$–lacZ exhibit specific expression in chimeric embryos", *Int. J. Dev. Biol.* 36:465–476 (Dec. 1992).

Shenefelt, R. E., "Morphogenesis of Malformations in Hamsters Caused by Retinoic Acid: Relation to Dose and Stage at Treatment", *Teratol.* 5:103–118 (1972).

Simeone, A. et al. "Sequential activation of HOX2 homeobox genes by retinoic acid in human embryonal carcinoma cells", *Nature* 346:763–766 (1990).

Simeone, A. et al., "Differential regulation by retinoic acid of the homeobox genes of the four HOX loci in human embryonal carcinoma cells" *Mech. Develop.* 33:215–227 (1991).

Smithies, O. et al., "Insertion of DNA sequences into the human chromosomal β–globin locus by homologous recombination", *Nature* 317:230–234 (1985).

Sucov, H. M. et al., "RXRα mutant mice establish a genetic basis for vitamin A signaling in heart morphogenesis", *Genes Develop.* 8:1007–1018 (1994).

Tabin, C. J., "Retinoids, Homeoboxes, and Growth Factors: Toward Molecular Models for Limb Development", *Cell* 66:199–217 (1991).

Tautz, D., "Redundancies, Development and the Flow of Information", *BioEssays* 14(4):263–266 (Apr. 1992).

Thomas, K. R. et al., "Site–Directed Mutagenesis by Gene Targeting in Mouse Embryo–Derived Stem Cells", *Cell* 51:503–512 (1987).

Thompson, J. N. et al., "Vitamin A and reproduction in rats", *Proc. Royal Soc.* 159:510–535 (1964).

van Pelt, A. M. M. et al., "Retinoic Acid Is Able to Reinitiate Spermatogenesis in Vitamin A–Deficient Rats and High Replicate Doses Support the Full Development of Spermatogenic Cells" *Endocrinol.* 128(2):697–704 (1991).

Wald, G., "Molecular Basis of Visual Excitation", *Science* 162:230–239 (1968).

Webster, W. S. et al., "Isotretinoin Embryopathy and the Cranial Neural Crest: An In Vivo and In Vitro Study", *J. Craniofacial Genet. Develop. Biol.* 6:211–222 (1986).

Wilson, J. G. et al., "An Analysis of the Syndrome of Malformations Induced by Maternal Vitamin A Deficiency. Effects of Restoration of Vitamin A at Various Times During Gestation", *Amer. J. Anat.* 92(2):189–217 (1953).

Yu, V. C. et al., "RXRβ: A Coregulator That Enhances Binding of Retinoic Acid, Thyroid Hormone, and Vitamin D Receptors to Their Cognate Response Elements", *Cell* 67:1251–1266 (1991).

Yu, V. C. et al., "Transcriptional regulation by the nuclear receptor superfamily", *Curr. Opin. Biotech.* 3:597–602 (Dec. 1992).

Zelent, A. et al., "Cloning of murine α and β retinoic acid receptors and a novel receptor γ predominantly expressed in skin", *Nature* 339:714–717 (1989).

Zelent, A. et al., "Differentially expressed isoforms of the mouse retinoic acid receptor β are generated by usage of two promoters and alternative splicing", *EMBO J.* 10(1):71–81 (1991).

Zhang, X.–K. et al., "Retinoid X receptor is an auxiliary protein for thyroid hormone and retinoic acid receptors", *Nature* 355:441–446 (Jan. 1992).

Zijlstra, M. et al., "Germ–line transmission of a disrupted β$_2$–microglobulin gene produced by homologous recombination in embryonic stem cells", *Nature* 342:435–438 (1989).

Zimmer, A. et al., "Induction of a RARβ2–lacZ transgene by retinoic acid reflects the neuromeric organization of the central nervous system", *Develop.* 116(4):977–983 (Dec. 1992).

Accili, D., and Taylor, S.I., "Targeted inactivation of the insulin receptor gene in mouse 3T3–L1 fibroblasts via homologous recombination," *Proc. Natl. Acad. Sci. USA* 88:4708–4712 (1991).

Mangelsdorf, D.J., et al., "Nuclear receptor that identifies a novel retinoic acid response pathway," *Nature* 345:224–229 (1990).

Mullins, L.J., and Mullins, J.J., "Perspectives Series: Molecular Medicine in Genetically Engineered Animals," *J. Clin. Invest.* 97(7):1557–1560 (Apr. 1996).

A. Espeseth Genes & Development 3:1647–56 ('89).

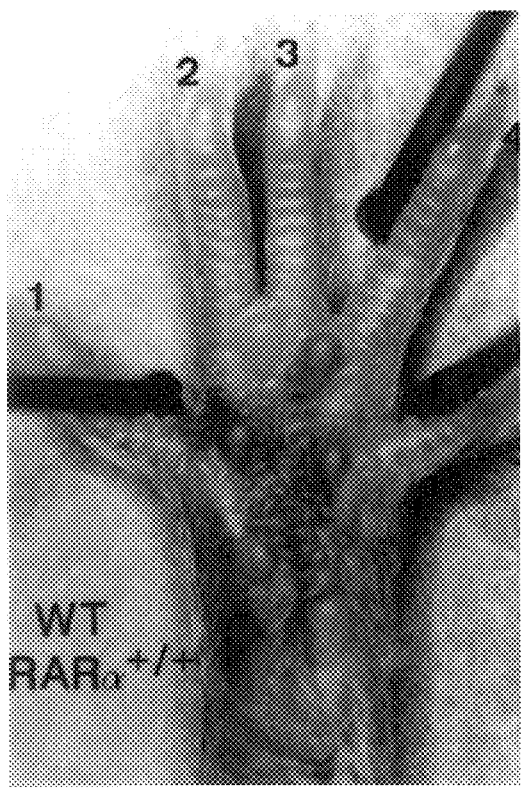
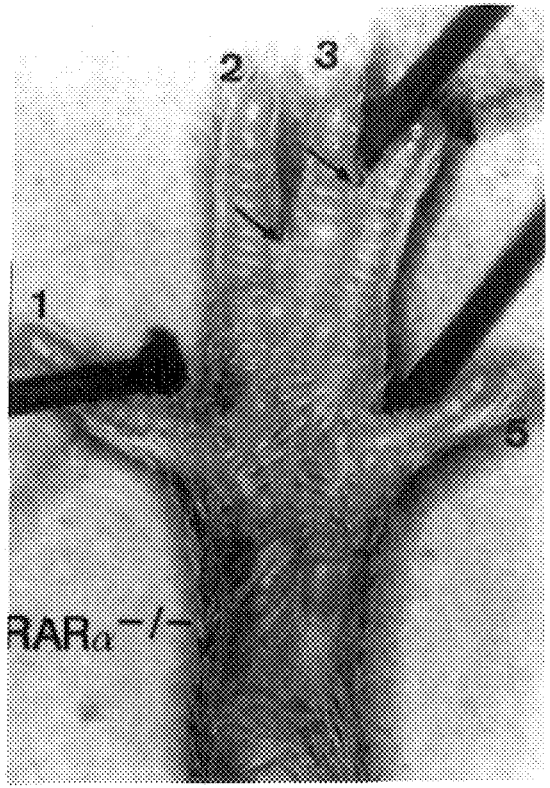
FIG.7A  FIG.7B
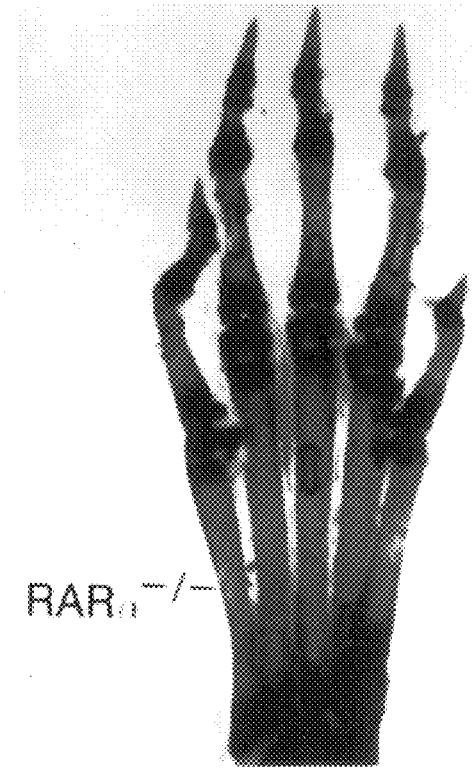
FIG.7C  FIG.7D 14.5 dpc 12.5 dpc 14.5 dpc

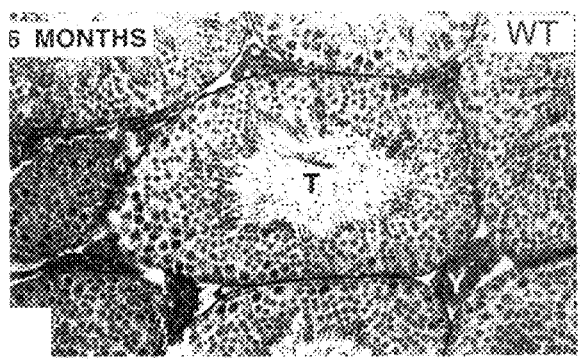 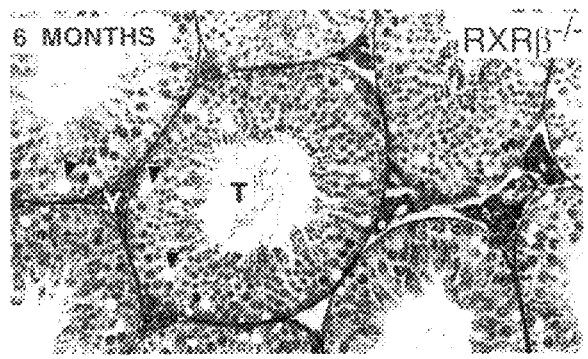
FIG.26A                    FIG.26B

FIG.31A
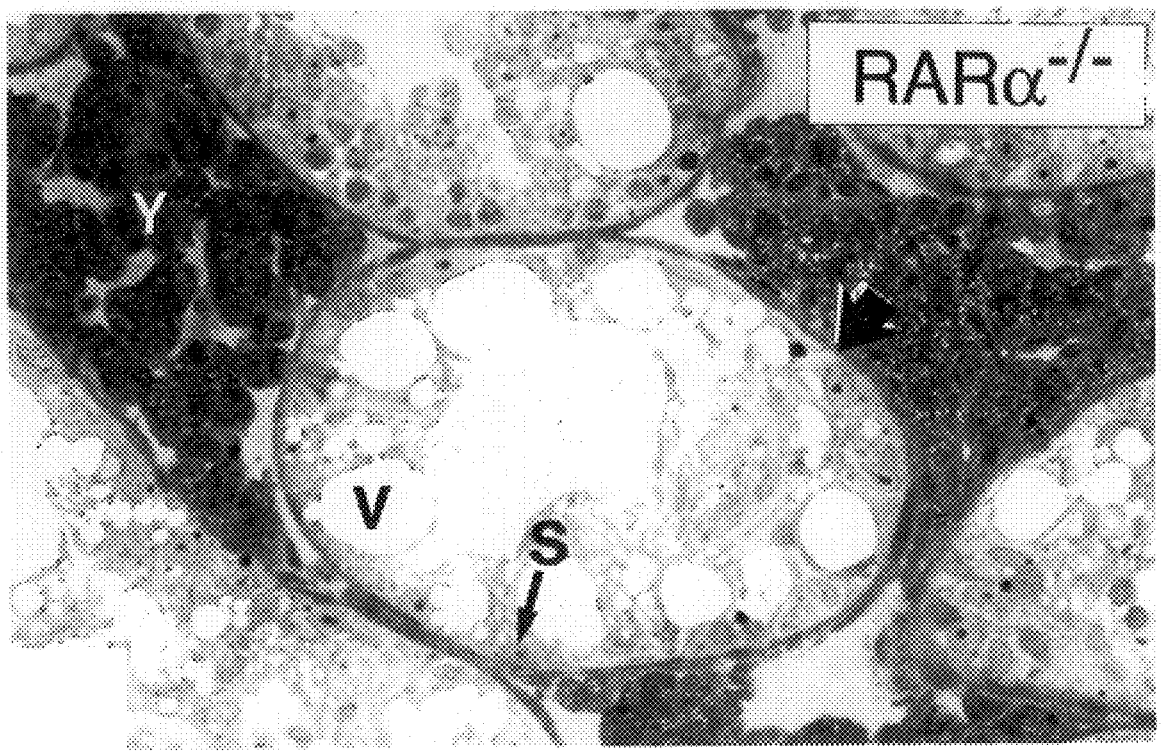
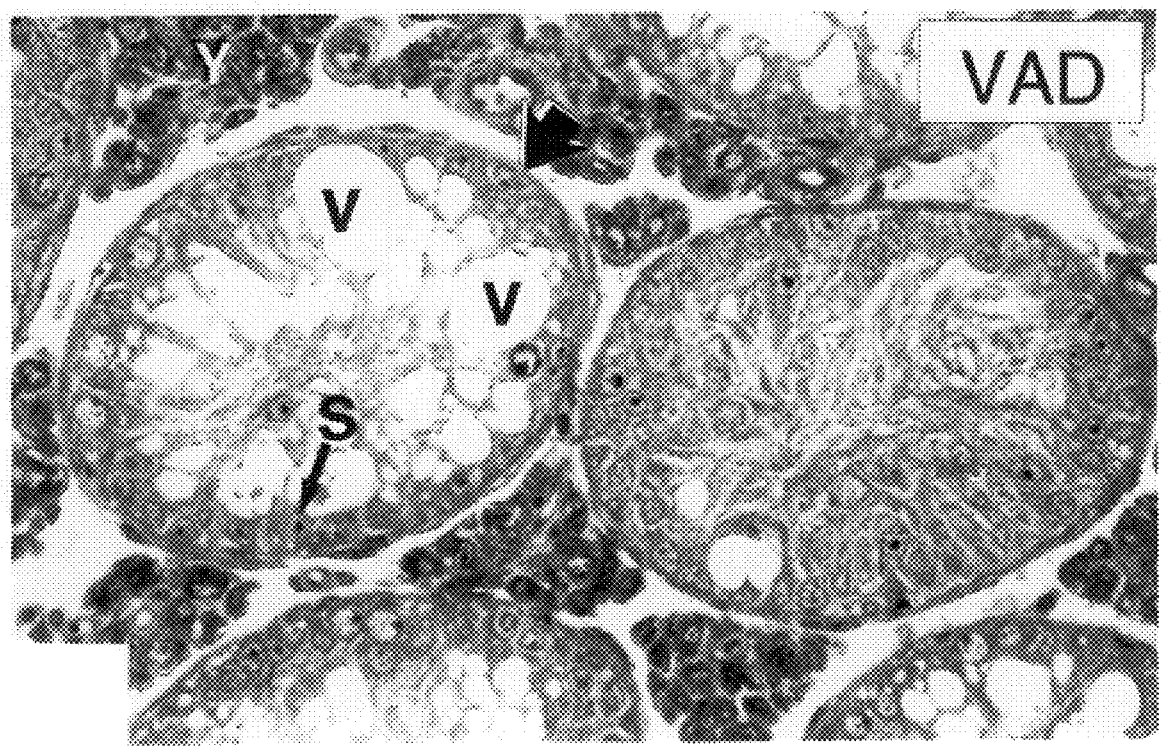
FIG.31B

GENETICALLY ENGINEERED MICE CONTAINING ALTERATIONS IN THE GENES ENCODING RETINOIC ACID RECEPTOR PROTEINS

CROSS REFERENCE TO RELATED APPLICATION

This application is a continuation-in-part of U.S. patent application Ser. No. 08/373,224, filed Jun. 27, 1995, which is a continuation-in-part of U.S. patent application Ser. No. 08/062,850, filed May 18, 1993 now abandoned, and a 371 PCT/US94/05746, filed May 18, 1994. The contents of U.S. patent application Ser. Nos. 08/373,224 and 08/062,850 are incorporated herein by reference.

BACKGROUND OF THE INVENTION

1. Field of the Invention

The present invention relates to the fields of retinoic acid receptor (RAR) biology and transgenic mice. Specifically, the present invention relates to mice which are deficient in the normal expression of one or more of the genes encoding members of the RAR or RXR class of receptors, to mice heterozygous for such deficiency, to cell lines, preferably pluripotent or totipotent cell lines, which are heterozygous or homozygous for such deficiency, and to methods of using said mice or said cell lines to identify agonists and antagonists of specific members of the RAR or RXR class of receptors.

2. Description of the Related Art

It has long been established that retinoids (vitamin A derivatives) are crucial for normal growth, vision, maintenance of numerous tissues, reproduction and overall survival (Wolbach, S. B., and Howe, P. R., J. Exp. Med. 42:753–777 (1925); for reviews and refs see Sporn et al., *The retinoids*, Vols. 1 and 2, Sporn et al., eds., Academic Press, Orlando, Fla. (1984); Livrea and Packer, in *Retinoids*, Livrea and Packer, eds., Marcel Dekker, New York (1993)). In addition offspring of vitamin A deficient (VAD) dams exhibit a number of developmental defects, indicating that retinoids are also important during embryogenesis (Wilson, J. G., et al., *Am. J. Anat.* 92:189–217 (1953)). With the exceptions of vision (Wald, 1968) and possibly of spermatogenesis in mammals (Thompson et al., *Proc. Royal Soc.* 159:510–535 (1964); van Pelt, H. M. M., and De Rooij, D. G., *Endocrinology* 128:697–704 (1991); and refs therein), most of the effects generated by VAD in fetuses, young, and adult animals can be prevented and/or reversed by retinoic acid (RA) administration (Wilson, J. G., et al., *Am. J. Anat.* 92:189–217 (1953); Thompson et al., *Proc. Royal Soc.* 159:510–535 (1964)). The dramatic teratogenic effects of maternal RA administration on mammalian embryos (Shenefelt, R. E., *Teratology* 5, 103–108 (1972); Lammer et al., *N. Eng. J. Med.* 313:837–841 (1985); Webster, W. S. et al., *J. Cranofac. Genet. Dev. Biol.* 6:211–222 (1986); Kessel and Gruss, *Cell* 67:89–104 (1991); Kessel, M., *Development* 115:487–501 (1992); Creech Kraft, J., "Pharmacokinetics, placental transfer, and teratogenicity of 13-cis-retinoic acid, its isomer and metabolites," In *Retinoids in Normal Development and Teratogenesis*, G. M. Morriss-Kay, ed., Oxford University Press, pp. 267–280 (1992)), and the spectacular effects of topical administration of retinoids on embryonic development of vertebrates and limb regeneration in amphibians (Mohanty-Hejmadi et al., *Nature* 355:352–353 (1992); for review and refs see Tabin, C. J., *Cell* 66:199–217 (1991)), has markedly contributed to the belief that RA could in fact be a morphogen (conferring positional information during development), and may also play a critical role during organogenesis.

With the exception of visual perception (Wald, G. et al., *Science* 162:230–239 (1968)), the molecular mechanisms underlying the highly diverse effects of retinoids has remained obscure until recently. The discovery of nuclear receptors for RA (Petkovich et al., *Nature* 330:444–450 (1987); Giguère et al., *Nature* 330:624–629 (1987)) has greatly advanced the understanding of how these simple molecules could exert their pleiotropic effects (for reviews see Leid et al., *TIBS* 17:427–433 (1992); Linney, E., *Current Topics in Dev. Biol.* 27:309–350 (1992)). It is thought that the effects of the RA signal are mediated through two families of receptors which belong to the superfamily of ligand-inducible transcriptional regulatory factors that include steroid/thyroid hormone and vitamin D3 receptors (for reviews see Evans, R. M., *Science* 240:889–895 (1988); Green and Chambon, *Trends Genet.* 4:309–314 (1988); Beato, M., *Cell* 56:335–344 (1989); Gronemeyer, H., *Ann. Rev. Genet.* 25:89–123 (1991); de Luca, L. M., *FASEB J.* 5:2924–2933 (1991); Linney, E., *Current Topics in Dev. Biol.* 27:309–350 (1992); Yu, V. C. et al., *Cur. Op. Biotech.* 3:597–602 (1992); Leid et al., *TIBS* 17:427–433 (1992)).

The RAR family (RARα, β and γ and their isoforms) are activated by both all-trans and 9-cis RA, whereas the retinoid X receptor family (RXRα, β and γ) are activated exclusively by 9-cis RA (for review and refs see de Luca, L. M., *FASEB J.* 5:2924–2933 (1991); Linney, E., *Current Topics in Dev. Biol.* 27:309–350 (1992); Yu, V. C. et al., *Cur. Op. Biotech.* 3:597–602 (1992); Leid et al., *TIBS* 17:427–433 (1992); Kastner et al., "The role of nuclear retinoic acid receptors in the regulation of gene expression," in *Vitamin A in health and disease*, R. Blomhoff, ed., Marcel Dekker, New York (1993); Allenby et al., *Proc. Natl. Acad. Sci. USA* 90:30–34 (1993)). Within a given species, the DNA binding (region C) and the ligand binding (region E) domains of the three RAR types are highly similar, whereas the C-terminal region F and the middle region D exhibit no or little similarity. The amino acid sequences of the three RAR types are also notably different in their B regions, and their main isoforms (α1 and α2, β1 to β4, and γ1 and γ2) further differ in their N-terminal A regions (reviewed in Leid et al., *TIBS* 17:427–433 (1992)). Similarly, the RXRs characterized to date also markedly differ in their N-terminal A/B regions (Leid et al., *TIBS* 17:427–433 (1992); Leid et al., *Cell* 68:377–395 (1992); Mangelsdorf et al., *Genes and Dev.* 6:329–344 (1992)). Amino acid sequence comparisons revealed that the interspecies conservation of a given RAR or RXR type is greater than the similarity found between the three RAR or RXR types within a given species (reviewed in Leid et al., *TIBS* 17:427–433 (1992)). This interspecies conservation is particularly striking in the N-terminal A regions of the various RARα, β and γ isoforms, whose A region amino acid sequences are very divergent from each other. Taken together with the distinct spatio-temporal expression patterns observed for the transcripts of each RAR and RXR type in the developing embryo and various adult mouse tissues (Zelent, A., et al., *Nature* 339:714–717 (1989); Dollé et al., *Nature* 342:702–705 (1989); Dollé et al., *Development* 110:1133–1151 (1990); Ruberte et al., *Development* 108:213–222 (1990); Ruberte et al., *Development* 111:45–60 (1991); Mangelsdorf et al., *Genes and Dev.* 6:329–344 (1992)) this interspecies conservation has suggested that each RAR and RXR type (and isoform) may perform unique functions. This hypothesis is further supported by the finding that the various RAR isoforms and RXR types contain two transcriptional activation functions (AFs) located in the N-terminal A/B region (AF-1) and in the C-terminal E region (AF-2), which can synergistically, and to some extent differentially, activate various RA-responsive promoters (Leid et al., *TIBS* 17:427–433 (1992); Nagpal et al., *Cell* 70:1007–1019 (1992); Nagpal et al., *EMBO J.*, in press (1993)). Moreover, it has been shown that activation of RA-responsive promoters likely occurs through RAR:RXR heterodimers rather than through homodimers (Yu, V. C. et al., *Cell* 67:1251–1266 (1991); Leid et al., *Cell* 68:377–395 (1992b); Durand et al., *Cell* 71:73–85 (1992);Nagpal et al., *Cell* 70:1007–1019 (1992); Zhang, X. K., et al., *Nature* 355, 441–446 (1992); Kliewer et al., *Nature* 355:446–449 (1992); Bugge et al., *EMBO J.* 11:1409–1418 (1992); Marks et al., *EMBO J.* 11:1419–1435 (1992); for reviews see Yu, V. C. et al., *Cur. Op. Biotech.* 3:597–602 (1992); Leid et al., *TIBS* 17:427–433 (1992); Laudet and Stehelin, *Curr. Biol.* 2:293–295 (1992); Green, S., *Nature* 361:590–591 (1993)). Thus, the basis for the highly pleiotropic effect of retinoids may reside, at least in part, through the control of different subsets of retinoid-responsive promoters by cell-specifically expressed heterodimeric combinations of RAR:RXR types (and isoforms), whose activity may be regulated by cell-specific levels of all-trans and 9-cis RA (Leid et al., *TIBS* 17:427–433 (1992).

The apparently ubiquitous distribution of RARα transcripts (mainly the RARα1 isoform; Zelent, A., et al., *Nature* 339:714–717 (1989); Leroy et al., *EMBO J.* 10:59–69 (1991); Leroy et al., *Proc. Natl. Acad. Sci. USA* 88:10138–10142 (1991); Dollé et al., *Nature* 342:702–705 (1989); Dollé et al., *Development* 110:1133–1151 (1990); Ruberte et al., *Development* 111:45–60 (1991); E. Ruberte, P. Dollé, D. Decimo and P. C., unpublished results) during development and in adult tissues suggests that RARα1 may play some general housekeeping function (Brand et al., *Nucl. Acid Res.* 18:6799–6806 (1990); Leroy et al., *EMBO J.* 10:59–69 (1991)). RARβ transcripts exhibit a more restricted pattern of distribution in developing embryos and adult tissues, suggesting that RARα isoforms could be involved in the differentiation of certain epithelia, as well as in the ontogenesis of the nervous system (Dollé et al., *Development* 110:1133–1151 (1990); Ruberte et al., *Development* 111:45–60 (1991); Mendelsohn et al., *Development* 113:723–734 (1991)). In situ hybridization studies indicate that RARγ transcripts are apparently restricted to the pre-somitic caudal region of day 8.0 p.c. embryos, and to the frontonasal mesenchyme, pharyngeal arches, sclerotomies and limb bud mesenchyme at day 8.5 to 11.5 p.c. At later stages, RARγ transcripts are found in precartilaginous condensations (day 12.5 p.c.), with subsequent restriction to cartilage and differentiating squamous keratinizing epithelia (day 13.5 p.c.), regardless of their embryonic origin (Dollé et al., *Nature* 342:702–705 (1989); Dollé et al., *Development* 110:1133–1151 (1990); Ruberte et al., *Development* 108:213–222 (1990)). These observations suggest a role for RARγ in morphogenesis, chondrogenesis and differentiation of squamous epithelia (Dollé et al., *Development* 110:1133–1151 (1990); Ruberte et al., *Development* 108:213–222 (1990)). In addition, Northern blot analysis indicates that the RARγ2 isoform is the predominant isoform in the early embryo (day 8.5 to 9.5 p.c.), whereas RARγ1 is the predominant RARγ isoform transcript found later in embryogenesis as well as in newborn and adult skin (Kastner et al., *Proc. Natl. Acad. Sci. USA* 87:2700–2704 (1990)).

The mouse is the model of preference in the study of the mammalian genetic system, and a great deal of research has been performed to map the murine genome.

It would be of great importance to be able to establish a living model wherein the role of the various members of the RAR class of receptors could be studied in a definitive manner.

Accordingly, it is an object of the present invention to generate strains of mice which do not express, or express at undetectable levels, one or more members of the RAR or RXR class of receptors. Such mice would be of great value for a better understanding of the role each of the members of the RAR or RXR class of receptors because such animals and cell lines would allow direct testing of the function of specific genes, either deleted or reintroduced by transgenesis, and would serve as an assay system to identify compounds which act as antagonists or agonists of specific members of the RAR or RXR class of receptors.

SUMMARY OF THE INVENTION

To establish the actual functional role of RAR and RXR isoforms in vivo during mouse development and post-natal life, the present invention describes the generation of transgenic mice, produced via homologous recombination in embryonic stem (ES) cells, in which RARγ2, all RARγ isoforms, RARα1, all RARα isoforms, RARβ$_2$, all RXRα isoforms, or all RXRβ isoforms have been functionally inactivated.

Thus, the present invention provides mice and mouse cell lines which are deficient in the normal expression (either incapable of total or detectable functional expression) of one or more subtypes or specific isoforms of RAR or RXR receptors. Specifically, the present invention describes mice and cell lines which have been genetically altered such that the normal expression of one or more of the genes encoding a subtype or specific isoform of a RAR or RXR receptor has been disrupted such that it no longer encodes functional or detectable levels of the given receptor subtype or isoform.

The invention further provides mice and cell lines which are heterozygous for the above deficiency.

Utilizing one or more of the aforementioned mice or cell lines, the present invention further provides methods of identifying antagonists and agonists of specific members of the RAR or RXR class of receptors. Specifically, the isoform or subtype of RAR or RXR specific for a given agent, and the effects the agent has on inducing RA dependent expression, can be assayed by first incubating an agent with a cell line, a transgenic mouse, or cells or tissues derived therefrom, which is deficient in the normal expression of one or more isoforms or subtypes of RAR or RXR receptors, and then determining the amount of agent bound or determining the level of RA dependent gene expression which is induced in the cell lines, or specific tissues of the transgenic mice.

Figure 1A:
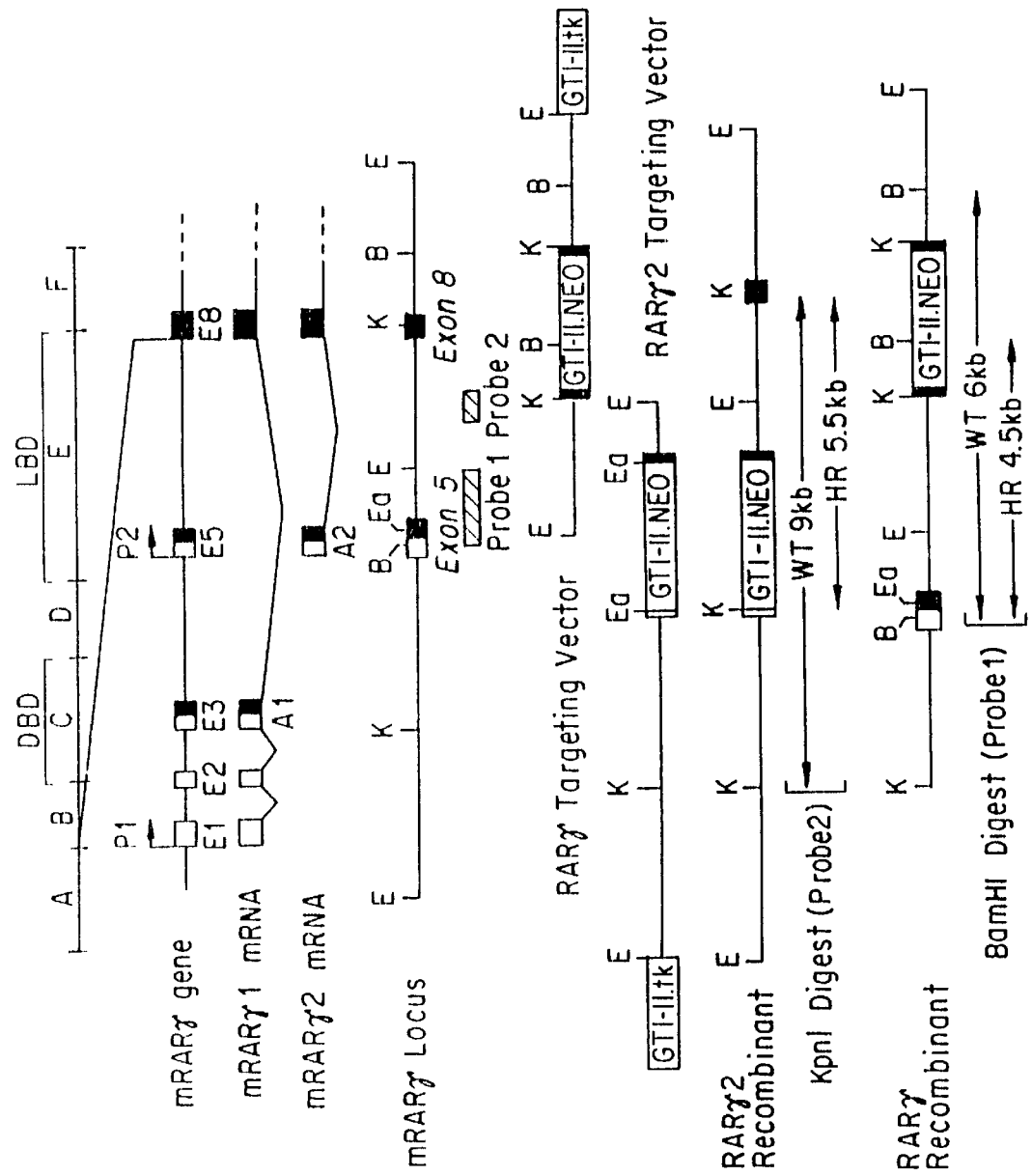
FIG. 1 (Panels *a–d*). Generation of RARγ mutant mice.

RARγ locus, RARγ2 and RARγ targeting constructs, targeted loci, heterozygote inbreeding analysis, and RNase protection analysis.

(Panel *a*) Diagram of the RAR≡ locus, targeting constructs and targeted alleles. The RARγ A to F regions, the DNA-binding domain (DBD) and ligand-binding domain (LBD) are shown at the top, as are the alternate promoters (P1 and P2) and alternate splicing of exons (E1–E8) which generate the major RARγ isoforms, RARγ1 and RARγ2. The two targeting constructs are shown below the RARγ locus. Plasmid vector sequences are not shown, nor are the constructs drawn to scale. The predicted RARγ2 and RARγ targeted alleles, the restriction enzyme digests and the DNA probes (Probes 1 and 2) used for Southern blotting are shown below. The locations of the neomycin resistance and HSV tk genes are denoted by GTI-II.NEO and GTI-II.tk respectively. B, BamHI; E, EcoRI; Ea, EagI; K, KpnI.

(Panel b) Southern blot analysis of offspring from intermatings of RARγ2$^{+/-}$ (top) or RARγ$^{+/-}$ (bottom) mice. The positions of the wild type (WT,+) and mutant (−) alleles are shown to the right and the size of each allele is shown to the left of each blot. The genotype is indicated above each lane. +/+, WT; +/−, heterozygote; −/−, homozygote. The probes (Probe 1, RARγ analysis; Probe 2, RARγ2 analysis) and digests (KpnI, RARγ2; BamHI, RARγ) correspond to the probes and restriction digests shown in panel a.

(Panel c) Representation of the strategy for RNase protection analysis of WT and mutated RARγ transcripts. RARγ1 and RARγ2 WT transcripts are represented at the top of the figure, with the predicted RARγ2 and RARγ mutated transcripts shown immediately below. NEO indicates the position of the neomycin resistance gene in each transcript resulting from targeting of the respective cognate alleles. The riboprobe used to detect WT and mutated RARγ transcripts is shown in the middle of the diagram, followed by the protected fragments for both WT and mutated RARγ1 and RARγ2 RNAs as indicated on the left. The identity and size in nucleotides (nt) for each protected fragment is shown on the right of the figure. mut, protected fragment derived from RNase protection of mutated RARγ transcripts.

(Panel d) RNase protection analysis of RNA from either day 10.5 p.c. (RARγ2) or day 13.5 p.c. (RARγ) WT, heterozygote and homozygote embryos for either the RARγ2 (lanes 1–3) or RARγ (lanes 4–6) disruption. The identities of the protected fragments are indicated to the right. The size of the RARγ2 WT, RARγ2 mutant or RARγ1 WT fragments are indicated to the left of each gel. The source of the RNA used in the protection assays was as follows; lane 1, RARγ2 WT; lane 2, RARγ2$^{+/-}$; lane 3, RARγ2$^{-/-}$; lane 4, RARγ WT; lane 5, RARγ$^{+/-}$; lane 6, RARγ$^{-/-}$. The Histone H4 protection was included as an internal control for the quantitation and integrity of the RNA samples. The protected fragment for the RARγ1 mutated transcript obtained from RARγ$^{-/-}$ or RARγ$^{+/-}$ samples was not seen on this autoradiogram due to the small size of the fragment (41 nt; see panel c).

FIG. 2 (Panels a–l). Axial skeletal and tracheal cartilage defects in RARγ null fetuses.

Figure 3A:
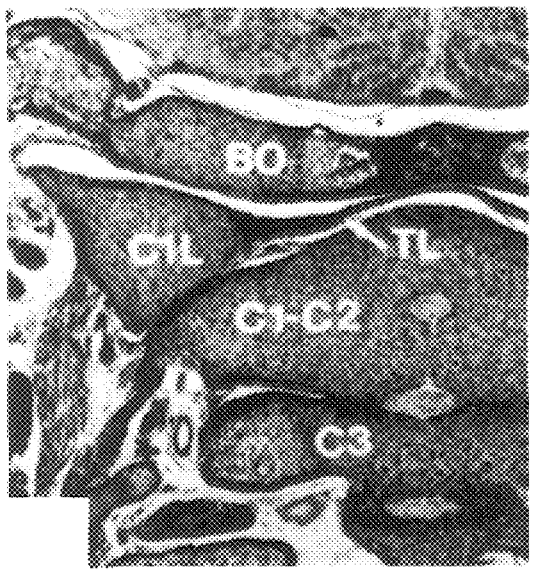
Figure 3B:
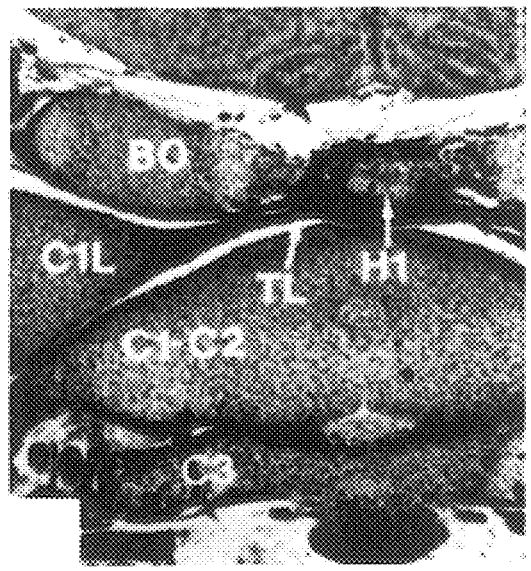
Figure 3C:
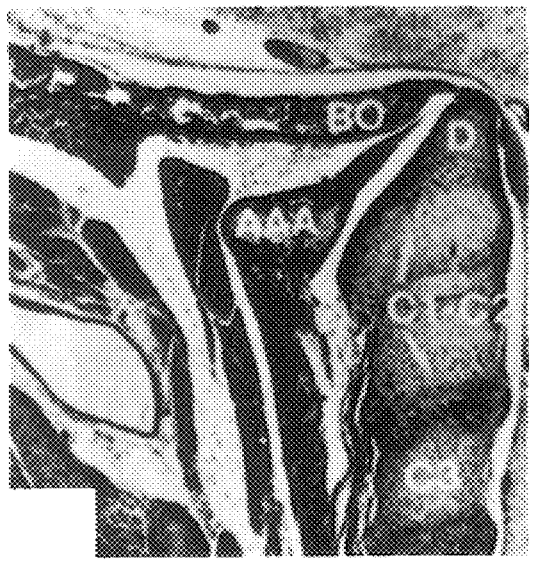
Figure 3D:
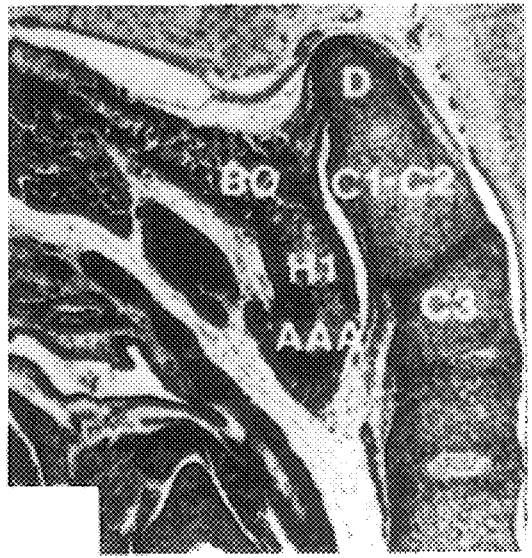
Figure 3E:
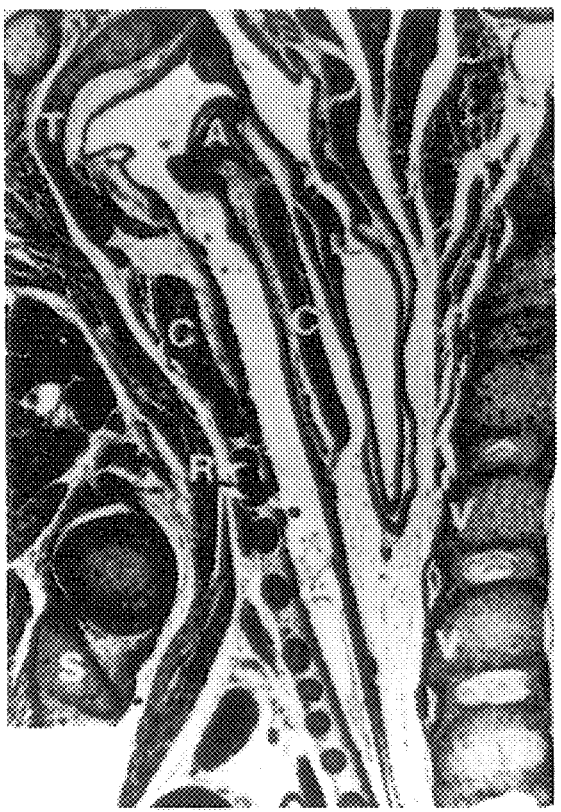
Figure 3F:
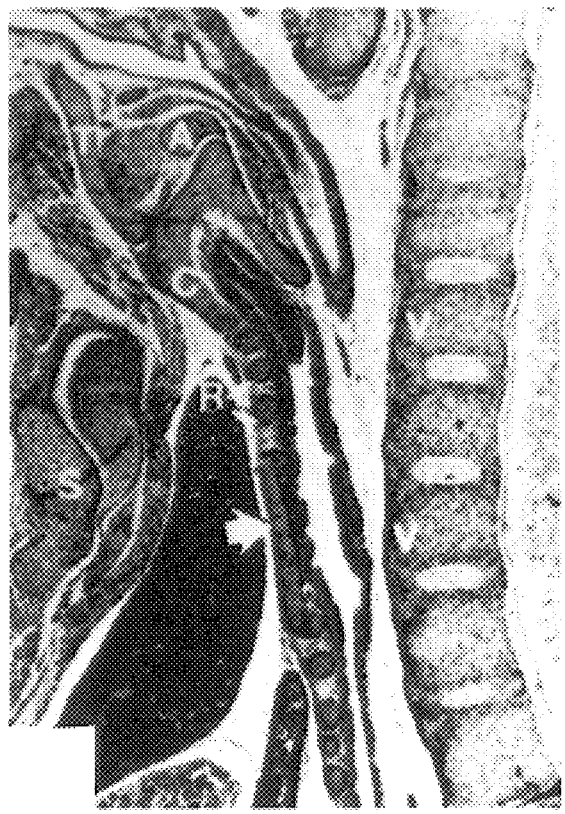
Figure 4A:
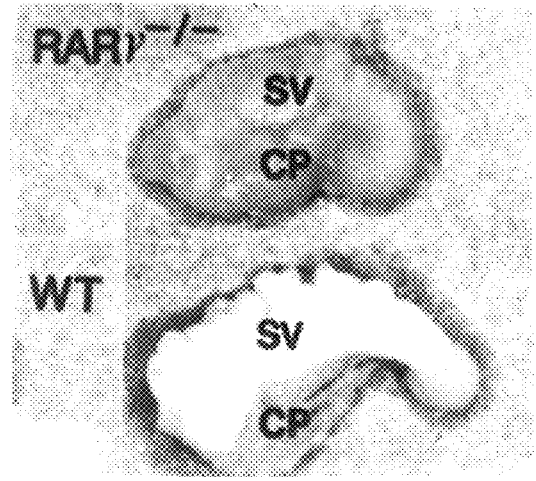
Figure 4B:
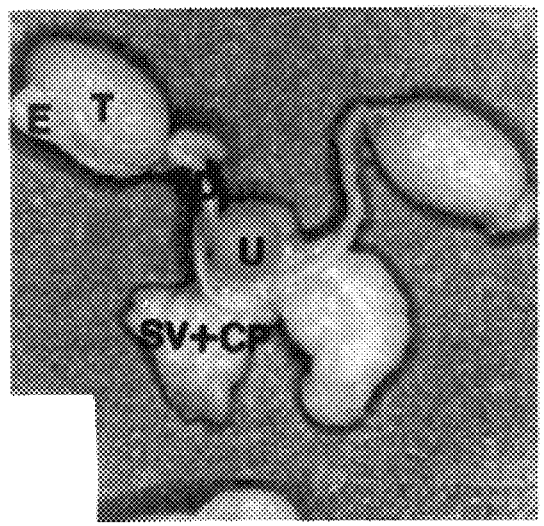
Figure 4C:
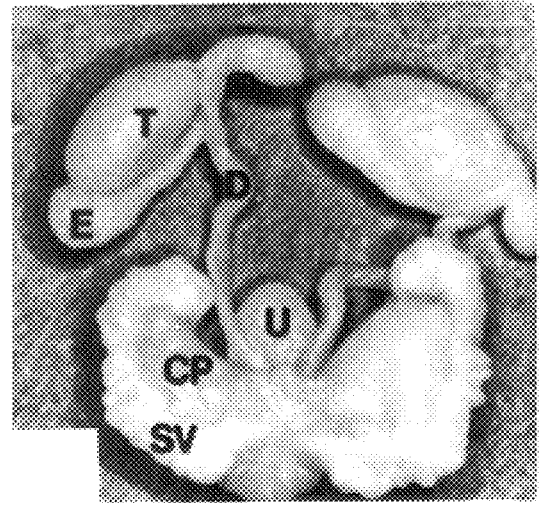
Figure 4D:
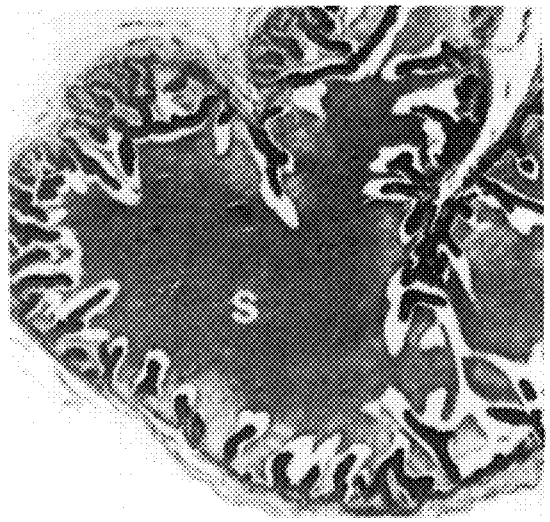
Figure 4E:
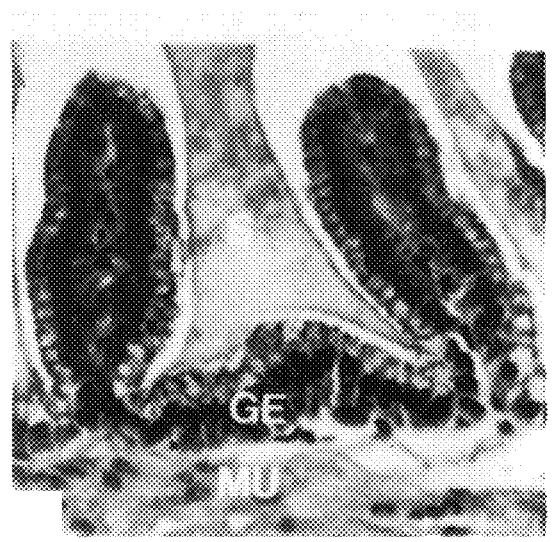
Figure 4F:
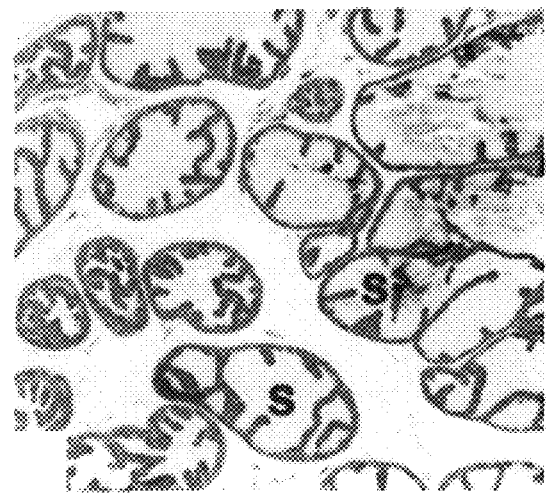
Figure 4G:
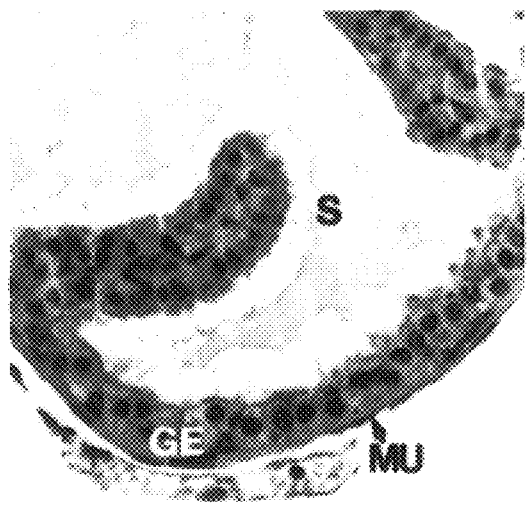
Figure 4H:
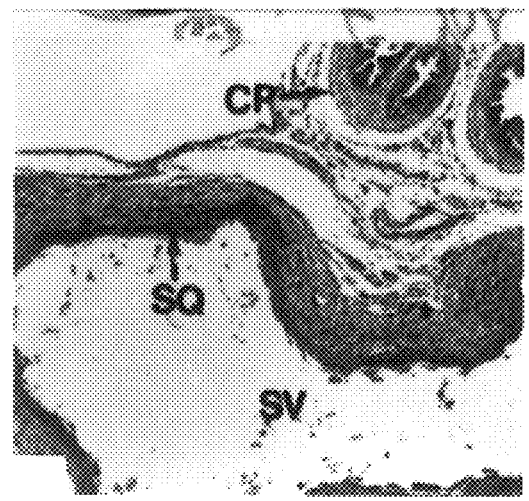
Figure 4I:
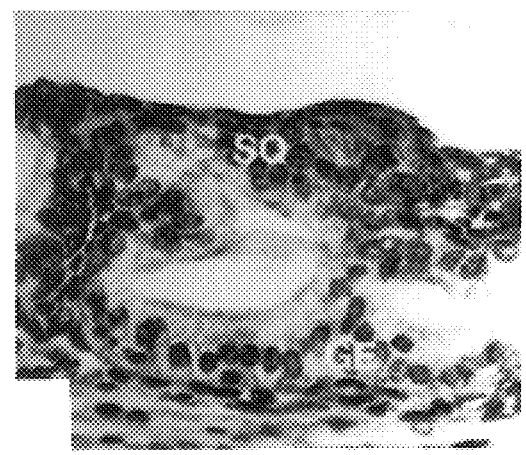
Figure 4J:
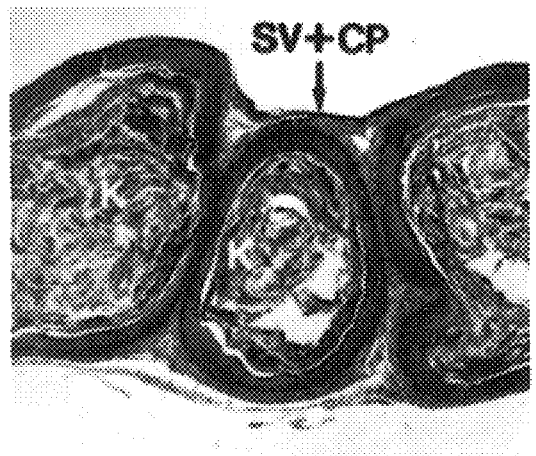
Figure 4K:
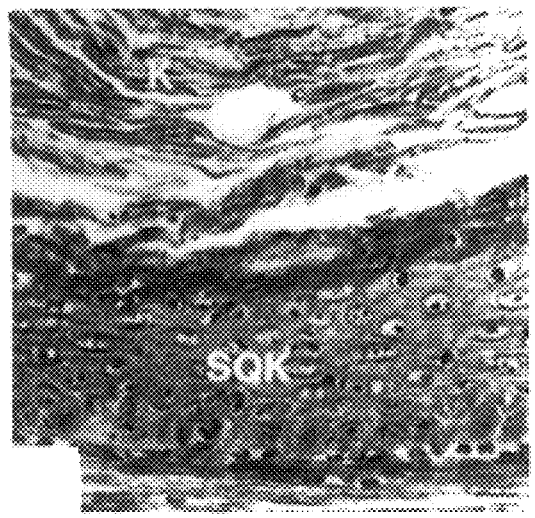
Figure 4L:
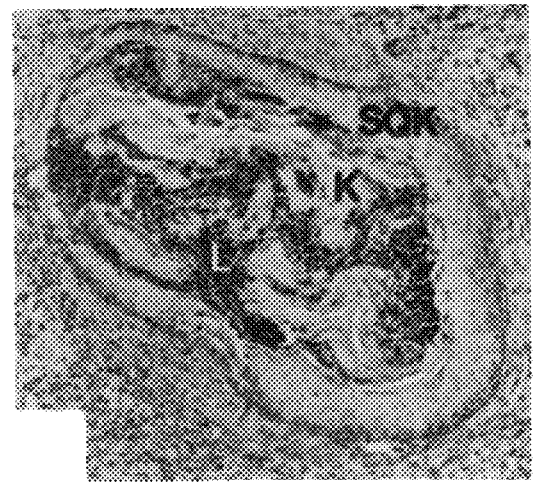
Figure 4M:
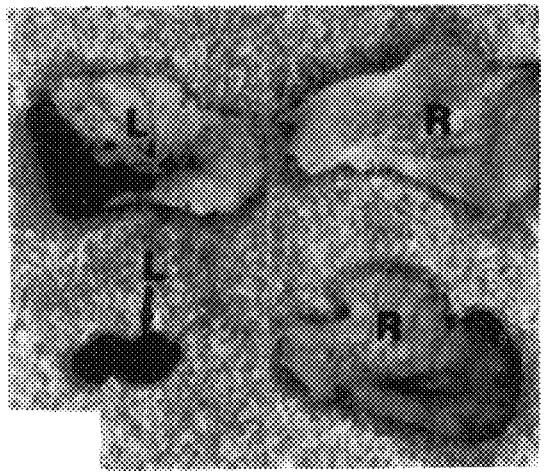
Figure 4N:
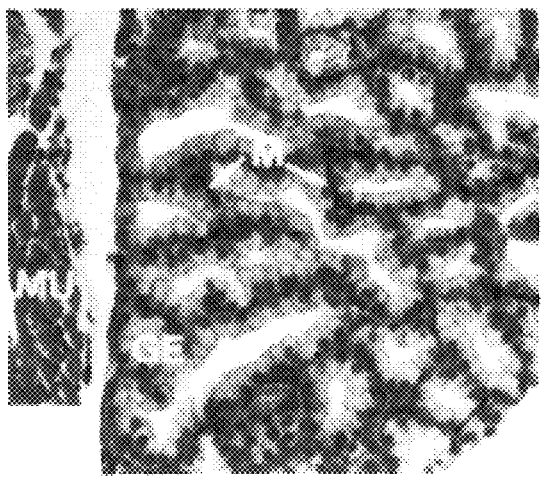
Figure 4O:
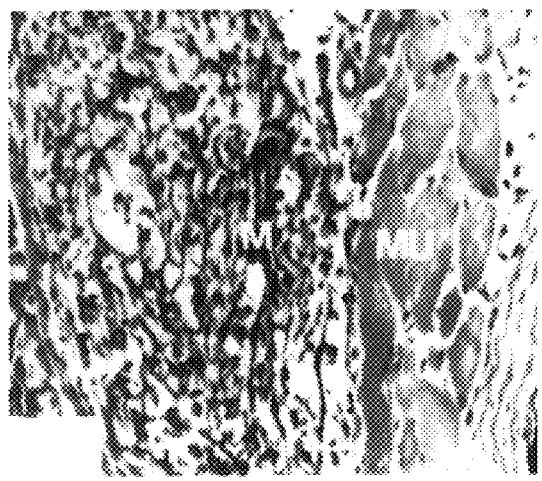

(a to d), lateral view of the occipital, cervical and upper thoracic region of WT (a, c) and RARγ$^{-/-}$ (b, d) skeletons. (a and b), the large arrow in panel b between the basioccipital bone (BO) and the anterior arch of the atlas (AAA) indicates an ossified fusion between these structures (see also FIG. 3a to d); the large arrow in panel b between "C1" and the third cervical vertebra indicates a fusion between the neural arches of these vertebrae; AAA*, ectopic anterior arch of atlas; "C1", anterior transformation of the second cervical vertebra to a first cervical identity; "C6", anterior transformation of the seventh cervical vertebra to a sixth cervical identity (see also panels i to l); C1 to C7, first to seventh cervical vertebrae; E, exoccipital bone; T1, first thoracic vertebra; TR, tympanic ring. (c and d), fusion of first and second ribs (large arrow in panel d), fusion and disruption of tracheal cartilaginous rings (T in panel d, compare to T in panel c; see also FIG. 3e and f), and ectopic anterior arch of the atlas (AAA* in panel d, compare to panels a and c). Numbering (1 and 2) indicates the first and second vertebrosternal ribs. (e, f and g), lateral (e and f) and ventral (g) views of WT (e) or RARγ$^{-/-}$ (f and g) skeletons. *8 (panel f) or R8* (panel g) indicates anterior transformation of the eighth thoracic vertebra to a seventh thoracic identity; arrows indicate bilateral fusions between the first and second ribs (panel g, see also panel d). Numbering (1–7 in panels e and f), normal vertebrosternal ribs; R1–R13 (panel g), ribs. (h), the large arrow indicates fusion between the first and second cervical vertebrae (compare to panel a). (i to l), fifth to seventh cervical vertebrae from either a WT (i) or RARγ$^{-/-}$ (j to l) skeletons. (i), normal aspect of fifth, sixth and seventh cervical vertebrae showing normal foramina transversaria (FT) on the fifth and sixth vertebrae, and the normal (bilateral) positioning of the tuberculi anterior (TA) on the sixth vertebra; (j to l), unilateral anterior transformation of the seventh cervical vertebrae to a sixth vertebral identity ("C6"; panels j to l) inferred from the presence of ectopic tuberculi anterior on the seventh cervical vertebrae ("TA"; panels j to l), and either a complete or partial ectopic foramina transversarium ("FT" or large arrow respectively; panel j); unilateral anterior transformation of the sixth cervical vertebra to a fifth cervical identity ("C5"; panels j to l) inferred from the lack of a tuberculum anterior (arrowhead, panels j to l). Limbs were removed from the skeletons to facilitate analysis. All skeletons were derived from day 18.5 p.c. fetuses with the exception of the skeleton shown in panel h, which was from an 8 day p.p. animal.

FIG. 3 (Panels a–f). Skeletal defects in RARγ null homozygotes at the cranio-vertebral junction and malformation of the cartilaginous tracheal rings.

(a) and (b) frontal histological sections of WT (a) and RARγ$^{-/-}$ day 18.5 p.c. fetus (b) at the level of the rostral border of the foramen occipital magnum. In the RARγ$^{-/-}$ animal, the basioccipital (BO) is attached to the lateral mass of the first cervical vertebra (C1L) by the transverse ligament of the atlas (TL) due to the persistence of the first hypochordal bar (H1 in panel b; compare with a); C1–C2, fused bodies of the atlas (C1) and axis (C2); C3, third cervical vertebra. (c and d), sagittal median sections in the occipital and upper cervical region of a WT (c) or RARγ$^{-/-}$ (d) day 18.5 p.c. fetus. A persistent first hypochordal bar (H1) joins the basioccipital (BO) to the anterior arch of the atlas (AAA) in the RARγ$^{-/-}$ fetus. D, axis dens. (e and f), sagittal median histological sections through the cervicothoracic region of a WT (e) or RARγ$^{-/-}$ day 18.5 p.c. fetus (f). Some of the tracheal cartilaginous rings (R) in the RARγ$^{-/-}$ fetus are fused ventrally (large arrow in panel f). A, arytenoid cartilage; C, cricoid cartilage; T, thyroid cartilage; S, sternum; V, vertebrae.

FIG. 4 (Panels a–o). Glandular defects in RARγ null homozygotes (a–k), stratified squamous metaplasia of the epithelia of the seminal vesicles and cranial prostates in 3-month-old RARγ$^{-/-}$ mice.

(a), comparison of ventral views of the left seminal vesicle (SV) and of the cranial prostate (CP) of RARγ$^{-/-}$ and WT littermates. The white color of the WT seminal vesicle is due to the secretion products (S in panel d) of the glandular epithelium which accumulate within the lumen of the organ. The RARγ$^{-/-}$ seminal vesicle is atrophic and does not display the characteristic white color of the functional organ of normal, sexually mature, males. The histology of this specimen is shown in panels h and i. (b and c), view from above (b) and dorsal view (c) of the seminal vesicles (SV) and cranial prostates (CP) of two RARγ$^{-/-}$ mice, dissected with the testes (T), epididymis (E), vas deferens (D) and urinary bladder (U), and photographed at the same magnification. The aspect of the seminal vesicle (SV) and cranial prostate (CP) of RARγ$^{-/-}$ mice varies from atrophic (panel b) to hypertrophic (e.g. the cranial prostate on the right of the picture in panel c). Hypertrophy was always associated with histological signs of inflammation (see panel l). In the specimen shown in panel b, the seminal vesicle and the cranial prostate (SV+CP) are indistinguishable by both anatomical and histological criteria (see panels j and k). (d–g), histological sections of the seminal vesicle (panels d and e) and cranial prostate (panels f and g) of a 3-month-old WT mouse. The wild-type seminal vesicle is an elongated hollow organ (panel d) whereas the wild-type cranial prostate (CP, or coagulating gland) is composed of several tubules (panel f). Both glands display very irregular lumens filled with secretion products (S, panels d–g). Their walls consist of a mucosa, forming multiple folds and septa, and in a peripheral layer of smooth muscle cells (MU, panels e, g). The glandular epithelia (GE, panels e, g) are simple columnar. (h–l), histological sections of the seminal vesicle and cranial prostate of three different RARγ$^{-/-}$ mice; panels h and i, correspond to the RARγ$^{-/-}$ specimen displayed in panel a; in the seminal vesicle (SV), the epithelium is stratified, squamous and nonkeratinized (SQ); in the cranial prostate, foci of normal glandular epithelial cells (GE, enlarged in i) and patches of squamous nonkeratinized metaplasia (SQ) coexist; the lumens of both glands are devoid of secretion products; panels j and k correspond to the specimen displayed in panel b; both glands are replaced by large cysts filled with desquamated keratinized cells (K); the cysts are lined by a stratified squamous keratinizing epithelium (SQK) resembling normal epidermis; panel l shows an histological section of the specimen displayed in panel c; the connective tissue of the seminal vesicle is markedly hyperplastic and infiltrated with leukocytes (L) which also occupy the spaces between the desquamated keratinized cells (K) within the lumen of the gland. (m–o), atrophy of the Harderian glands in 3-month-old RARγ$^{-/-}$ mice; panel m, dorsal view of the left (L) and right (R) Harderian glands of two different RARγ$^{-/-}$ mice; the right glands display a normal aspect: conical-shaped with medially-directed tips; the base of the gland on the upper left of the photograph is atrophic and colored in black: this aspect reflects a lack of part of the glandular epithelium without concomitant disappearance of the melanocyte-rich connective tissue of the gland (see panel o); the unformed black structure displayed on the lower left of the photograph replaced the left Harderian gland in the orbit of this mouse; panels n and o, frontal sections through the orbits of a RARγ$^{-/-}$ mouse at the level of the left (panel n) and right (panel o) Harderian glands; panel n, the histological structure of the Harderian gland is normal: it consists of tubules lined by a simple cuboidal glandular epithelium (GE), and of an intertubular connective tissue containing numerous melanocytes (M); in panel o, the epithelium of the Harderian gland is absent. An intraorbital accumulation of closely-packed melanocytes indicates the place where the gland should have been located. MU, orbital muscle. x54 (d, f, h,j); x134 (l); x268 (n,o); x540 (e, g, i, k).

FIG. 5 (Panels a–h). Retinoic acid-induced skeletal malformations.

(a to d), lateral views of untreated WT (a), day 8.5 p.c. RA-treated RARγ$^{-/-}$ (b), RARγ$^{+/-}$ (c) and RARγ$^{+/+}$ (d) skeletons. C, T, L and S; first cervical, thoracic, lumbar, and sacral vertebrae, respectively. (e to h), higher magnification ventral views of the specimens shown in panels a to d; T14* and T15* in panels f and g indicate additional thoracic vertebrae formed by anterior transformation of the first and second lumbar vertebrae, respectively; L1* in panels f and g indicate anterior transformation of the second lumbar vertebrae to a first lumbar identity; L6* and S1* in panel f denote anterior transformation of the first and second sacral vertebrae to a sixth lumbar and first sacral identity, respectively; the arrow in panel h indicates degenerate ribs; T13, L1, L6 and S1 in panel e, normal position of the last thoracic, first and last lumbar and first sacral vertebrae, respectively. Limbs, which were present in all cases, were removed to facilitate analysis.

FIG. 6 (Panels a–d)

(Panel a) Diagram of the RARα targeting constructs, wild type RARα locus, and disrupted alleles. The various regions of the RARα protein (A–F), the DNA-binding domain (DBD) and ligand-binding domain (LBD) are indicated at the top (Leroy et al., EMBO J. 10:59 (1991)). The alternate promoter (P1 or P2) usage and alternate splicing of exons (E1–E8), which generate the α1 and α2 isoforms, are also shown. The two targeting constructs are drawn above the wild type (WT) RARα locus. The RARα1 targeting construct (left) has the neomycin resistance gene (NEO) inserted into the A1 region encoded by Exon 3 (E3), and has a HSV-thymidine kinase gene (tk) at its 5' end. The RARα targeting construct (right; note that it does not include the tk gene) has the neomycin resistance gene (NEO) inserted into the B region which is encoded by Exon 8 (E8).

The plasmid vector sequences are not shown. The structure of the targeted alleles, and the restriction enzyme digests and DNA probes used for Southern blotting, are indicated below. B, BglII; H, HindIII; K, KpnI; N, NotI; R, EcoRI; RV, EcoRV; S, SpeI; Sa, SalI; X, XbaI.

(Panel b) Southern blots of offspring from intermatings of mice heterozygous for either RARα or RARα1 disruptions. The positions of the wild type (+) and mutant (−) alleles are indicated, as well as their size. Genotypes of the offspring are indicated below. +/+, wild type; +/−, heterozygote; −/−, homozygote. The probes indicated (PROBE 1 and PROBE 2) correspond to the probes diagrammed in panel a.

(Panel c) RNAse protection analysis of RNA from day 13.5 p.c. +/+, +/− and −/− embryos for either the RARα (lanes 1–4) or RARα1 (lanes 5–7) disruptions. The identities of the protected fragments (RARα, RARβ, RARγ, CRABPI, CRABPII, and Histone H4) are indicated by the arrows. In the case of RARβ and RARγ only the protected fragments corresponding to the major isoforms RARβ2 and RARγ1 are shown; similar results were obtained for the other isoforms (RARβ1, β3 and β4; RARγ2; data not shown). The source of RNAs used in the protection assays was as follows: lane 1, tRNA (negative control); lane 2, RARα +/−; lane 3, +/+; lane 4, RARα −/−; lane 5, +/+; lane 6, RARα1 +/−; lane 7, RARα1 −/−. The Histone H4 RNA protection was included as a control for the integrity and quantitation of the RNA samples.

(Panel d) Western blot analysis of day 13.5 p.c. embryo nuclear proteins isolated from RARα +/+, +/−, and −/− embryos. Embryos from RARα heterozygote matings were removed at day 13.5 p.c., the yolk sac taken for DNA genotyping, and each embryo was frozen individually on dry ice and stored at −80° C. (Lufkin et al., Cell 66:1105 (1991)).

Nuclear protein extracts were derived from: lanes 1 and 2, transfected Cos-1 cells expressing RARα1 and RARα2, respectively (positive controls); lane 3, RARα +/+embryos; lane 4, RARα −/− embryos; lane 5 and 6, RARα −/− embryos; lanes 7–10, transfected Cos-1 cells expressing either RARβ1, β2, β3 or β4 (positive control); lane 11, RARα +/+ embryos; lane 12, RARα +/− embryos; lane 13 and 14, RARα −/− embryos. RARα-specific and RARβ-specific antisera were used in lanes 1–6 and 7–14, respectively. 1–5 μg of Cos-1 transfected protein extract and 70 μg of embryo nuclear protein extract was loaded per lane (except in lanes 5 and 13 where ~35 µg protein was loaded). Note that the upper band seen in lanes 3–6 corresponds to a non-specific immunoreaction.

FIG. 7 (Panels a–d). Webbed digits of a 2 week-old RARα null homozygote offspring. Ventral view of left hind-limbs from 2-week old wildtype (a, c) and RARα homozygote (b,d) animals. Note in b the presence of skin between digits 2, 3, and 4 resulting in a "webbed" limb. Panels c and d correspond to Alizarin red/alcian blue stained skeletons of the limbs shown in panels a and b. Note in d, the absence of any ossified connection between the phalanges indicating that the "webbed" phenotype did not involve any skeletal fusion. Alizarin red/alcian blue staining of skeletons was performed as described elsewhere (Lufkin et al., Nature 359:835–841 (1992)).

FIG. 8 (Panels a–h). Degenerative lesions in testes of four to five month-old RARα null homozygotes.

Comparison of histological sections through the testes (panels a–f) and epididymal ducts (panels g–h) of wild type (panels a, d and g) and RARα null homozygote males (panels b, c, e, f and h), both five month-old. Panel a, the parenchyma of wild type testes (RARα heterozygote testes were identical) is composed of seminiferous tubules (T) with active spermatogenesis and intertubular spaces containing capillaries (CP) and Leydig cells (L). Note that the aspect of the seminiferous epithelium (or germinal epithelium) varies between tubules at different stages of the spermatogenic cycle; however, all tubules contain primary spermatocytes (C, in panel a). Each of these cells will eventually yield four spermatozoids. Panels b and c, the parenchyma of RARα homozygote testes shows a patchy pattern of seminiferous tubule lesions. These cover a wide spectrum, ranging from rare tubules with complete spermatogenesis (e.g. T1) to tubules containing only Sertoli cells (e.g. T2) which may be enlarged, thus filling the tubules (e.g., T2 in panel c). A majority of tubules lack primary spermatocytes (C). In addition, the seminiferous epithelium shows numerous large, clear, rounded spaces (vacuole-like, V) and occasional clusters of degenerating spermatogenic cells (large arrow in panel c). In the intertubular spaces, focal hyperplasia of the Leydig cells (L) is observed between atrophic seminiferous tubules (panel c). This hyperplasia is likely to result from the decrease in tubular diameter (compare T3 in panel c with T panel a; see ref. 40). Panels d, e and f, correspond to high magnification micrographs of the walls of seminiferous tubules. Panel d, in wild type testes, the seminiferous epithelium consists of supporting cells, the Sertoli cells (S) and spermatogenic cells. The spermatogenic cells proliferate from stem spermatogonia (G), located in contact with the basement membrane (B), and differentiate from the periphery towards the lumen of the seminiferous tubules. This process yields different ontogenetically-related cell types arranged in concentric layers, i.e. spermatogonia (G), primary spermatocytes (C), round spermatids (D), and maturing spermatozoids (Z). Panels e and f, are two different aspects of the seminiferous epithelium in RARα null homozygote males. Most frequently, the early stages of spermatogenic cell differentiation (e.g. spermatogonia and primary spermatocytes) are missing (panel e: in such a degenerate epithelium spermatogenesis no longer occurs). In rare cases, all stages of spermatogenic cell differentiation, including the round spermatids (D) and maturing spermatozoids (Z) are seen (panel f). Panel g, section through the tail of a wild type epididymal duct; spermatozoids (Z) fill the lumen. Panel h, section through the tail of a RARα homozygote epididymal duct; the lumen of the duct contains acidophilic (blue) material which is also present within large vacuoles (V) in the epithelium lining the duct (E), possibly as a consequence of extensive cellular absorption; spermatozoids (Z) are occasionally identified in the lumen.

B, basement membrane of the seminiferous tubules; C, primary spermatocytes; CP, capillaries; D, round spermatids; E, epithelium of the epididymal duct; G, spermatogonia; L, Leydig cells; S, Sertoli cells; T, seminiferous tubules; V, vacuoles; Z, spermatozoids. Organs were immersed-fixed in Bouin's fluid. Paraffin sections, 5 µm thick, were stained with Groat's hematoxylin and Mallory's trichrome.

FIG. 9 (Panels a–b). Targeted disruption of the RARβ2 locus.

(Panel a) A schematic drawing of the RARβ locus is shown at the top, illustrating the alternatively spliced RARβ isoforms and their respective promoters (Zelent et al., EMBO J. 10:71–81 (1991)). Below is shown the portion of RARβ2 genomic locus (Exon 4, E4). At the bottom, the RARβ2 targeting vector and the expected structure of the recombinant mutant allele are shown. Note that in the targeting vector the initial 5' XhoI site has been destroyed, and replaced by a SalI site derived from the HSV-TK cassette.

(Panel b) Southern hybridization experiments employing a probe derived from sequences 5' to the targeting vector (probe 1, FIG. 9a) or a full-length neomycin gene probe are shown as indicated. Genomic DNA prepared from targeted ES cells (BH1, BH32 and BH45) and a cell line harboring randomly integrated copies of the targeting vector (BH68) were digested with Kpnl, BamHl and Xbal, and subjected to Southern hybridization. Note on the left that DNAs derived from the targeted cell lines contain in addition to the normal allele (the 6.5kb Kpnl fragment, the 20 kb BamHI fragment and the 15 kb Xbal fragment), the fragments representing the mutant allele (4.3 kb for Kpnl, 9.5kb for BamHl and 9.0 kb for Xbal) which hybridize with probe 1, while the randomly targeted ES cell DNA (BH68) contains only the wild type alleles. B, X, K, Xh, N and S BamHl, Xbal, Kpnl, Xhol, Notl and Sall restriction enzyme sites, respectively.

Figure 10:
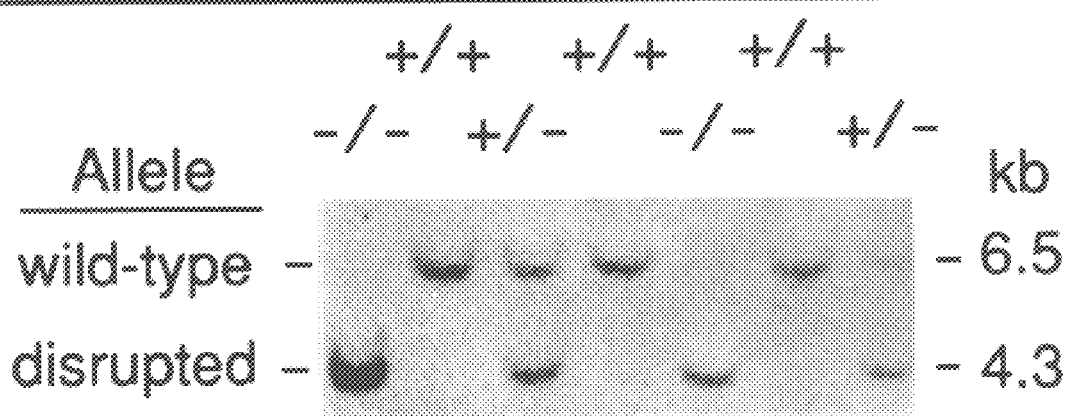

FIG. 10. Southern blot analysis.

Southern blot of DNA derived from one week-old offspring of heterozygous RARβ2+/– intercrosses showing the presence of homozygous (–/–, containing just the 4.3 kb Kpnl fragment), heterozygous (+/–, containing both the 4.3 and 6.5kb Kpnl fragments) and wild type (+/–, containing just the 6.5 kb Kpnl fragment) alleles. Below is shown the distribution of wild type, heterozygous and homozygous mutant one month-old offspring from intercrosses of animals heterozygous for the RARβ2 mutant allele. Note that the homozygous offspring are present at the expected Mendelian ratio (27%) indicating that there is no postnatal lethality associated with RARβ2 disruption.

Figure 11:
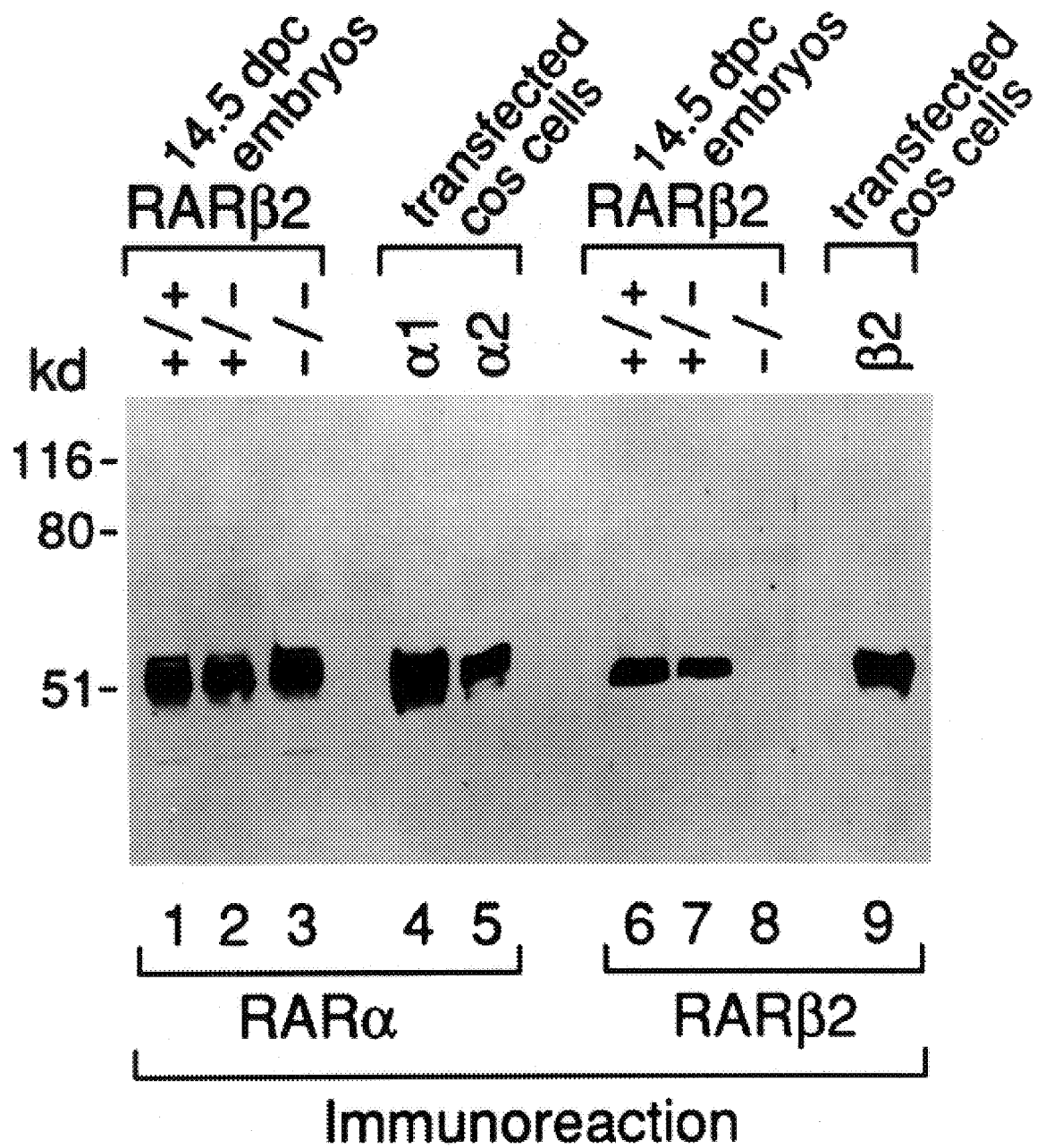

FIG. 11. Lack of RARβ2 protein in RARβ2–/– embryos.

Immunodetection experiments employing nuclear extracts prepared from 14.5 dpc wild type (lanes 1 and 6), heterozygous (lanes 2 and 7) and homozygous (lanes 3 and 8) mutant embryos are shown. At left (lanes 1–5), extracts were subjected to direct immunoblotting with a rabbit polyclonal antibody directed against the F-region of RARα. Lanes 4 and 5 contain extracts prepared from Cos-1 cells transfected with RARα1 and RARα2 expression vectors, respectively. Note that the 51 kd reactive protein corresponding to the RARα1 isoform is present at similar levels in all three embryo extracts (lanes 1–3). At right, the nuclear extracts were immunoprecipitated with a mouse monoclonal antibody specific for the A2-region of the RARβ2 isoform;

the protein precipitate was then subjected to immunoblotting with a polyclonal antibody directed against the RARβ F-region (lanes 6–8). A nuclear extract derived from Cos-1 cells transfected with the RARβ2 expression vector was migrated along side the immunoprecipitates to serve as a size comparison (lane 9). Note the absence of the 51 kd RARβ2 protein in the mutant embryo.

FIG. 12 (Panels a–b). RARβ, RARα and RARγ RNA analysis.

(Panel a) RARβ isoform RNAs in wild type, heterozygote and homozygote mutant embryos. A scheme and the results of RT-PCR experiments are shown. Total RNA prepared from wild type (+/+), heterozygous (+/−) and homozygous (−/−) mutants. 13.5 dpc embryos were analyzed for the presence of RARβ1/β3 and RARβ2 transcripts. Following RT-PCR amplification, cDNA products were migrated on 2% agarose gels, and subjected to Southern hybridization employing oligonucleotide probes specific for these RAR isoforms. As a control, a cDNA fragment corresponding to the RARα1 isoform was amplified (20 cycles) from the 3 RNA preparations, employing a 5'-primer (primer 5, 5'-ATAGCAGTTCCTGCCCAACAC-3', spanning nucleotides 589–609 in the RARα1 A1-region, Leroy et al., 1991 a) and a 3' primer derived from the RARα C-region (primer 6,5'-GATGCTTCGTCGGAAGAAGC-3'; spanning nucleotides 908–927) to generate an expected product of 338nt. Note that all 3 embryo RNA preparations contained similar levels of the 338nt RARα1 cDNA (shown at the right). To detect the presence of RARβ2 transcripts (Zelent et al., EMBO J. 10:71–81 (1991), a 5'-primer corresponding to nucleotides 504–523 in the RARβ2 A2-region (primer 2, 5'-GATCCTGGATTTCTACACCG-3') and a 3' primer spanning nucleotides 716–736 in the RARβ C-region (primer 1, 5'-TGGTAGCCCGAGACTTGTCCT-3') were employed to generate a 232nt cDNA product (shown at right, note the product is present in equal amounts in wild type, heterozygous and homozygous RARβ2 mutant RNAs). To test for the possible presence of wild-type RARβ2 transcripts in RARβ2 mutants, a 5' primer (primer 3, spanning nucleotides 369–388 in the RARβ2 5'-UT, 5-GCGAGAGTTTGATGGAGTTC-3') and primer 1 located in the RARβ C-region were employed to amplify a 367nt wild-type product. Note that this product is detectable in wild type embryo RNA, while it is undetectable in homozygote RNAs. To detect the presence of RARβ1/β3 transcripts (Zelent et al., EMBO J. 10:71–81 (1991)) in the 3 RNA preparations, a primer located at positions 469–488 in the common RARβ1/β3 A1-region (primer 4, 5'-GAAGCCTGAAGCATGAGCAC-3') and primer 1 located in the RARβ C-region were employed in 30 cycles of amplification to generate products of 306nt for the RARβ1 isoform and 387 nt for the RARβ3 isoform (shown at the right). Note that RARβ1 and β3 transcripts were present in all 3 RNA preparations.

(Panel b) Determination of RARα and RARγ isoform RNA in wild type, heterozygote and homozygote mutant embryos using RNAse protection assays. A schematic illustration of the probes and expected protected fragments are shown. Total RNA prepared from 13.5 dpc wild-type (+/+), heterozygous (+/−) and homozygous (−/−) RARβ2 mutant embryos was employed in the reactions. Riboprobes were as follows (Lufkin et al., Proc. Natl. Acad. Sci. USA 90:7225–7229 (1993)): the RARα2 antisense probe included the region corresponding to the RARα2 initiation codon through the RARα C-region to generate protected RNA fragments of 379nt for RARα2 and 210nt for RARα1; the RARγ2 antisense probe spanned the RARγ2 A2-region through the C-region to generate protected RNA fragments of 345nt (RARγ2) and 154nt (RARγ1). The histone 4 antisense riboprobe used as an internal control generated a 130nt RNA fragment. Control lanes correspond to the protected RNA fragments obtained with in vitro transcribed sense RNA.

FIG. 13 (Panels a–c). RARβ2 promoter activity in wild type and RARβ2 null mutant embryos.

(Panel a) A whole mount of a 10.5 dpc wild-type embryo expressing the RARβ2/lacZ transgene stained for β-galactosidase activity. Note that promoter activity is visible in the caudal hindbrain up to the rostral boundary of rhombomere 7 (arrowhead).

(Panels b and c) Whole mounts of RARβ2 null embryos (littermates) expressing the RARβ2 promoter/lacZ transgene exposed to RA in utero at 10.5 dpc and stained for β-gal activity 4 hours later. Note that the RA-induced rostral shift in promoter activity is similar in the hindbrains of both mutant and wild type embryos (denoted by arrowheads at the approximate level of rhombomere 1 in b and c, see text). Note also the increased labeling of neural crest cells migrating towards the heart (arrow). Abbreviations: ot, otocyst; nt, neural tube.

FIG. 14 (Panels a–h). Alteration of the pre-otic hindbrain in RA-treated RARβ2 null embryo.

(a–e) show different views of a RARβ2+/+ (wild type) embryo and of a RARβ2−/− mutant embryo which were exposed to RA at 7.25 dpc, collected at 9.0 dpc and hybridized as whole-mounts to a Hoxb-1 probe. (a) and (b), profile views; (c) and (d), hindbrain viewed from the back; (e), ventral view of the mutant embryo. Note that the forebrain vesicles are partially truncated in the wild type embryo (panel a) and almost lacking in the mutant embryo (panel b). The Hoxb-1 signal extends rostrally almost to the extremity of the neuroepithelium. (f–h), three parallel sagittal sections of a RARβ2−/− mutant emryo, which had been subjected to the same RA treatment. The plane of the sections progress from lateral (f) to medial (h) regions. Two neighboring sections hybridized to the Hoxb-1 (middle column) or the Krox-20 (right column) probe are shown under dark-field illumination (signal grains appear white). Only rhombomeres whose boundaries can be tentatively identified are indicated. Hoxb-1 transcripts extend up to the rostral extremity of the neuroepithelium, and a severe truncation of the forebrain is also evident on these sections (panels g and h). ot, otocyst; h, heart.

Figure 15A:
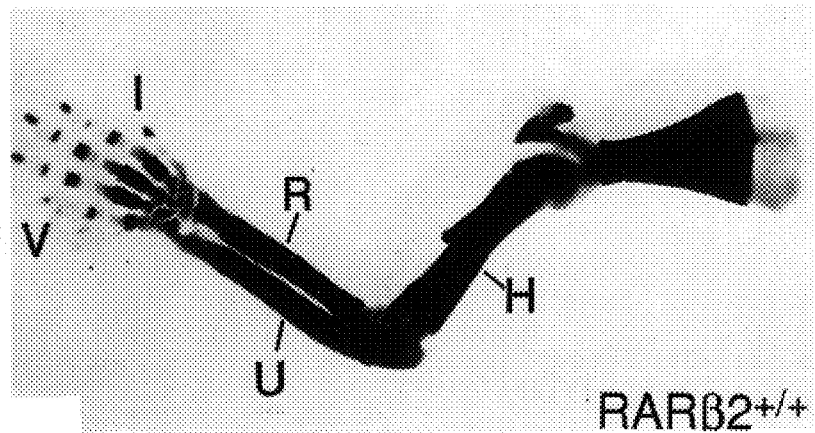
Figure 15B:
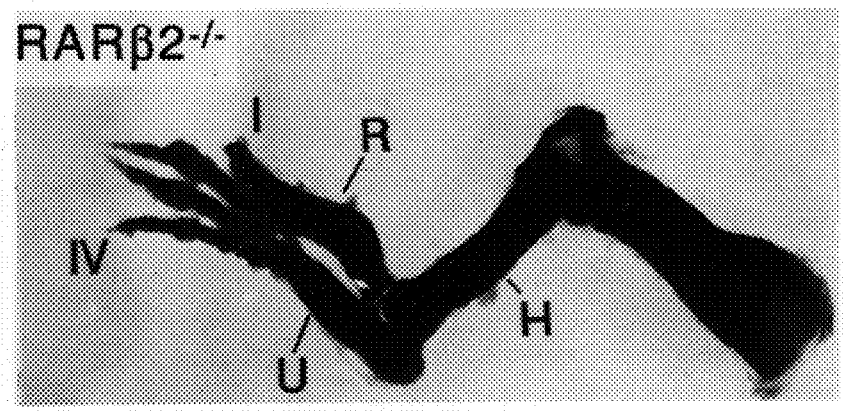
Figure 15C:
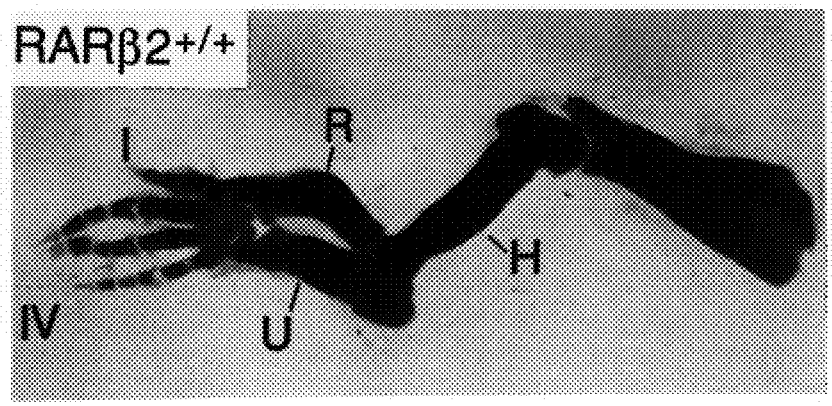

FIG. 15 (Panels a–c). RA-induced limb malformations in wild type and RARβ2 null mutant fetuses.

Embryos were exposed to RA by maternal gavage with all-trans RA (80 mg/kg) at 11.5 dpc, fetuses were collected at 18.5 dpc, and stained with alcian blue and alizarin red to visualize cartilage and bone.

(Panel a) A whole-mount of an alcian blue/alizarin red stained forelimb from a wild type 18.5 dpc fetus. Limbs from RA-treated 18.5 dpc fetuses are shown in b and c.

(Panel b) A forelimb from an RA-treated RARβ2 null fetus.

(Panel c) A forelimb from an RA-treated wild type fetus. Note that the 5th digit is absent in both wild type and mutant RA-treated fetuses, and that the radii and ulnae are truncated and malformed in similar fashions. H, humerus, R. radius, U, ulna, I, IV and V, 1st, 4th and 5th digit, respectively.

FIG. 16 (Panels a–d). Targeting the RXRα Gene.

(Panels a) A map of the RXRα genomic region of interest is shown on top. Probe A is a 2 kb BamHl fragment (the 5'

BamHl site corresponds to the 5' end of the genomic clone (arrow)); probe B is the 2 kb Hindlll-Smal fragment. Bg: Bglll; Sp:Spel; B:BamHl; H: Hindlll; S: Smal; RV: EcoRV; Xb: Xbal.

(Panel b) Detection of wild-type (WT) and mutant alleles by Southern Blot analysis. Placental DNAs from 12.5 dpc embryos recovered from a cross between heterozygote mice were digested with BamHl and Bglll and analyzed by Southern Blot with probe B.

(Panel c) Northern Blot analysis. 30 μg of total RNA from WT (+/+), heterozygote (+/−) and homozygote (−/−) embryos was analyzed by Northern Blotting with a complete RXRα cDNA probe or the 36B4 constant probe.

(Panel d) Western blot analysis. 15 μg of nuclear extract prepared from +/+ (lane 2), +/− (lane 3) or −/− (lane 4) 12.5 dpc embryos were analyzed by Western blot with an anti-RXRα polyclonal antibody directed against the N-terminal A/B region. The absence of signal in the −/− lane is not due to an absence of protein in the corresponding extract, since staining of the same membrane with amido black revealed a similar pattern of proteins in all 3 extracts (not shown).

Figure 17:
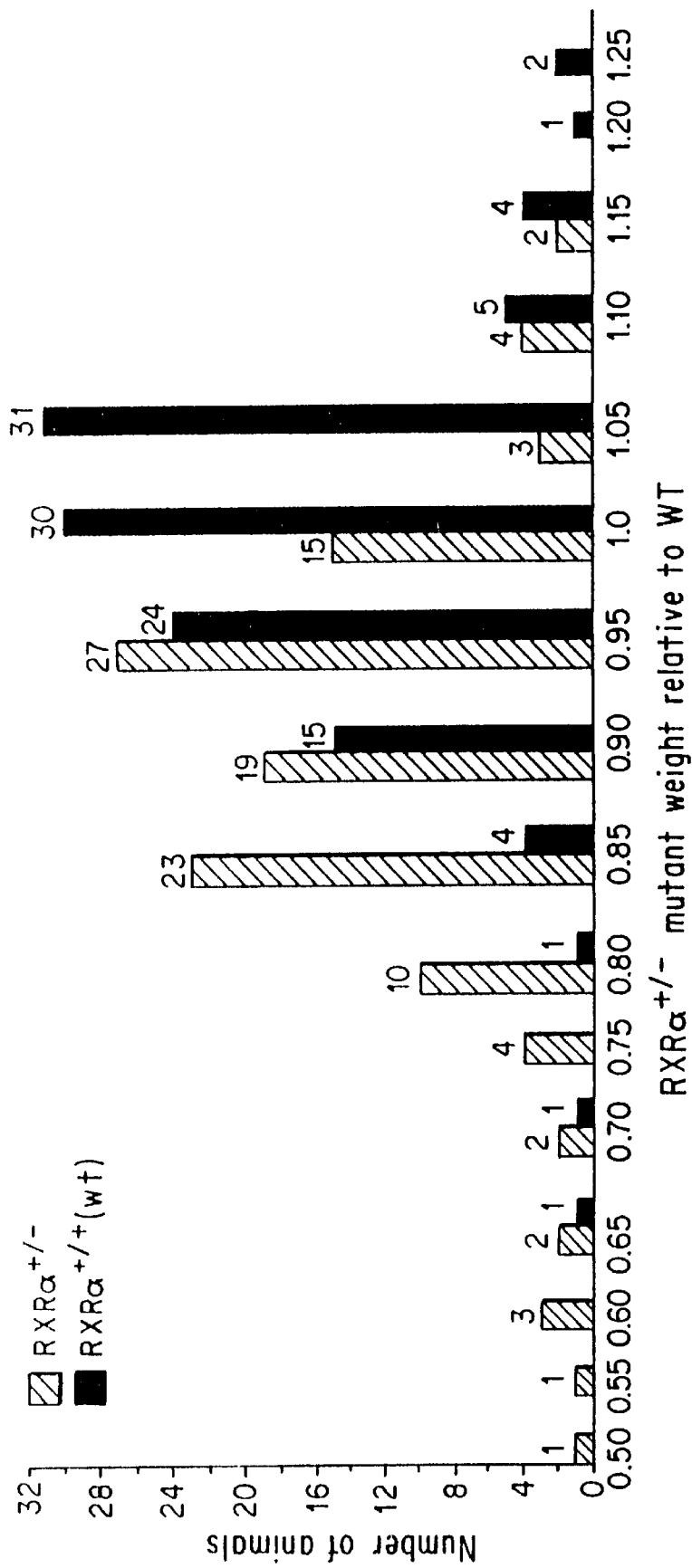

FIG. 17. Distribution of the weight of wild type and heterozygous animals.

Mice derived from crosses between WT and heterozygous parents were weighed at 2–3 weeks of age. The weight of each animal was expressed as the ratio of its weight relative to the average weight of WT animals of the same litter. Weight ratio were then grouped within classes differing from each other by 0.05 ratio increment (abscisa). The numbers of heterozygote (white bars) and WT animals (black bars) in each class is indicated on the ordinate.

FIG. 18 (Panels a–h). External appearance of RXRα null mutant fetuses.

Comparison of external features between 14.5 dpc WT (a and c), RXRα−/− (b and d), RXRα/RARγ (d, e and f) and RXRα/RARα(c) mutant fetuses.

(Panels a and b) Lateral view of WT (a) and RXRα−/−(b). The arrows in the WT (a) indicate blood vessels which are not visible in the RXRα mutant. The arrow in the RXRα−/− (b) points out the abnormal eye.

(Panels c–e) In RXRα−/− (d) and RXRα+/−RARγ−/− mutants (e) the palpebral fissure, limited by the dorsal and ventral eyelids (DE and VE), is smaller than in the WT (c); and the ventral retina is occulted by the ventral eyelid (VE).

(Panel f) In the RXRα−/−RARγ+/− the palpebral fissure is smaller than in the RXRα−/− (d) and the ventral retina is not visible.

(Panel g) In the RXRα−/−RARγ−/− fetus there is no palpebral fissure and all the eye is masked by the surface ectoderm and a layer of mesenchyme.

(Panel h) In the RXRα−/−RARα+/− fetus a unilateral coloboma of the iris (CI) is apparent.

Abbreviations: Cl, coloboma of the iris; DE, dorsal eyelid; DR, dorsal retina; P, pupilia; VE, ventral eyelid.

FIG. 19 (Panels a–h). Heart defects in RXRA null mutant.

Comparison of the heart in WT (a, c, e and g) and RXRα−/− (b, d, f and h) embryos.

(Panels a and b) Frontal sections of 14.5 dpc fetuses at level of the right atrioventricular canal (AV).

(Panels c and d) Sections of 10.5 dpc embryos at the level of the atrioventricular endocardial cushions (EC).

(Panels e and f) Detail of the ventricular wall in 16.5 dpc fetuses.

Abbreviations: A, atrium; AO, aorta; AV, atrioventricular canal; CL, compact layer; CT, cono truncus; EC, endocardial cushions; VS, ventricular septum; IVC, interventricular communication; LV, left ventricle; PT, pulmonary trunk; RA, right atrium; RV, right ventricle; T, trabeculation of the myocardium wall; TL, trabecular layer; V, ventricle. Magnifications: 55× (a and b), 138× (c, d, e, f, g and h).

FIG. 20 (Panels a–d). Electron microscopy of the heart of RXRα null mutants.

Ultrastructural features of the outer portion of the ventricular myocardium in WT (a and b) and RXRα−/− (c and d) 14.5 dpc fetuses.

(Panel a) Low power magnification of the outer compact layer of the WT ventricular myocardium.

(Panel b) Higher magnification of the demarcated area in (a), showing that the myofibrils (M) are present in the cytoplasm, but do not display the sarcomeric organization (S in d). These myocardial cells also contain rough endoplasmic reticulum (RER) and abundant polyribosomes (P). No sarcoplasmic reticulum (SR in d) was visible in this outer layer of the myocardium.

(Panel c) RXRα−/− myocardium comparable area and magnification as shown in (a) for WT.

(Panel d) Higher magnification of the demarcated area in (c). The cells in the outer area of the myocardium exhibit myofibrils; some of them are organized in sarcomeres (S). These cells also display a well developed sarcoplasmic reticulum (SR). Both, sarcomeres and sarcoplasmic reticulum indicate that these cells are at a more advanced stage of differentiation than the compact layer cells in the WT fetus (a and b).

Abbreviations: E, epicardial cell; En, endothelial cell; M, myofibrils; P, polyribosomes; RER, rough endoplasmatic reticulum; S, sarcomere; SR, sarcoplasmic reticulum. Magnifications: 4000× (a and c), 25000× (b and d).

FIG. 21 (Panels a–f). Eye development in RXRα null mutants.

Comparison of the eye development in WT (a, c and e) and RXRα−/− mutants (b,d and f).

(Panels a and b) Frontal sections through the eye of WT (a) and RXRα−/− (b) 11.5 dpc embryos.

(Panels c and d) Frontal sections of 12.5 dpc WT (c) and RXRα−/− (d) embryos.

(Panels e and f) Frontal sections of 15.5 dpc fetuses.

Abbreviations: AC, anterior chamber; C, cornea; C*, thicker cornea; CON, coloboma of the optic nerve; DE, dorsal eyelid; DJ, dorsal conjunctival sac; DR, dorsal retina; F, persistent retrolenticular membrane; FE, fused eyelids; J, conjunctival sac; L, lens; ON, optic nerve; RE, root of the eyelid; SE, surface ectoderm; V, vitreous body; VE, ventral eyelid; VJ, ventral conjunctival sac; VR, ventral retina. Magnifications: 55× (e and f), 138× (a, b, c and d).

FIG. 22 (Panels a–l). Eye defects in RXRα−/−, RXRα/RARγ and RXRα/RARα double mutants.

Frontal sections through the eye of 12.5 dpc (e), 14.5 dpc (a, b, c, d, f, g, h, i and j) and 16.5 dpc (k and l) fetuses. Genotypes as indicated.

Abbreviations: AC, anterior chamber; C, cornea; C*, thicker cornea; CE, corneal epithelium; CL, corneal-lenticular stalk; CON, coloboma of the optic nerve; CS, corneal stroma; EOM, extraocular mesenchyme; DE, dorsal eyelid; DJ, dorsal conjunctival sac, DR, dorsal retina; ER, eversion of the retina; F, persistent retrolenticular membrane; L, lens; ON, optic nerve; PR, pigment retina; RE, root of the eyelid; SC, sclera; SE, surface ectoderm; V, vitreous body; VE, ventral eyelid; VJ, ventral conjunctival sac; VR, ventral retina. Magnifications: 138× (a, b, c, d, e, f and g), 280× (h, k and l), 550 × (i and j).

FIG. 23 (Panels a–i). Three dimensional computer reconstruction of WT, RXRα–/– and RXRα–/–RARγ–/– eyes.

Three dimensional computer reconstruction from serial frontal histological sections of the eye of WT (a, d and g), RXRα–/– (b, e and h) and RXRα–/– RARγ–/– (c, f and i) 14.5 dpc fetuses.

(Panels a, b and c) Dorsal views of the eye; the surface ectoderm has been removed.

(Panels d, e and f) External views of the eye in which the surface ectoderm has been rendered transparent.

(Panels g, h and i) Ventral views of the eye without the surface ectoderm. In the RXRα–/– (b, e and h) it is possible to appreciate the rotation of the eye around the dorso-ventral axis toward the snout. Note in the external view that the dorsal and ventral eyelids (DE and VE) are closer than in the WT eye (d). In the external view of the RXRα–/–RARγ–/– eye (f) it is possible to see the surface ectoderm invagination of the cornea lenticular stalk (CL) and the eversion of the retina (ER).

Abbreviations: CL, corneal-lenticular stalk; DE, dorsal eyelid; ER, eversion of the retina; L, lens; PR, pigment retina; VE, ventral eyelid.

Magnification: 49× (a–i).

Figure 24A:
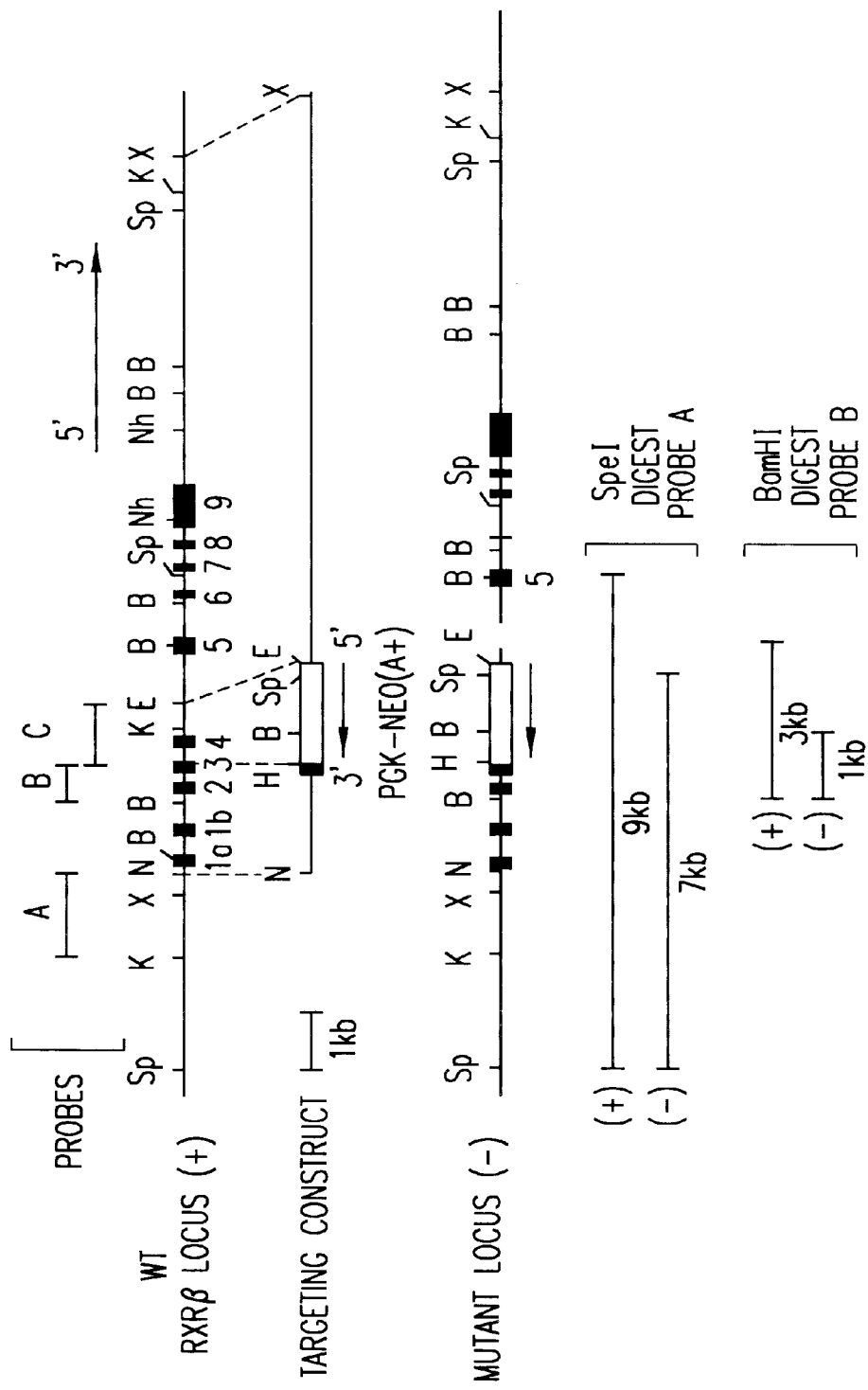
Figure 24B:
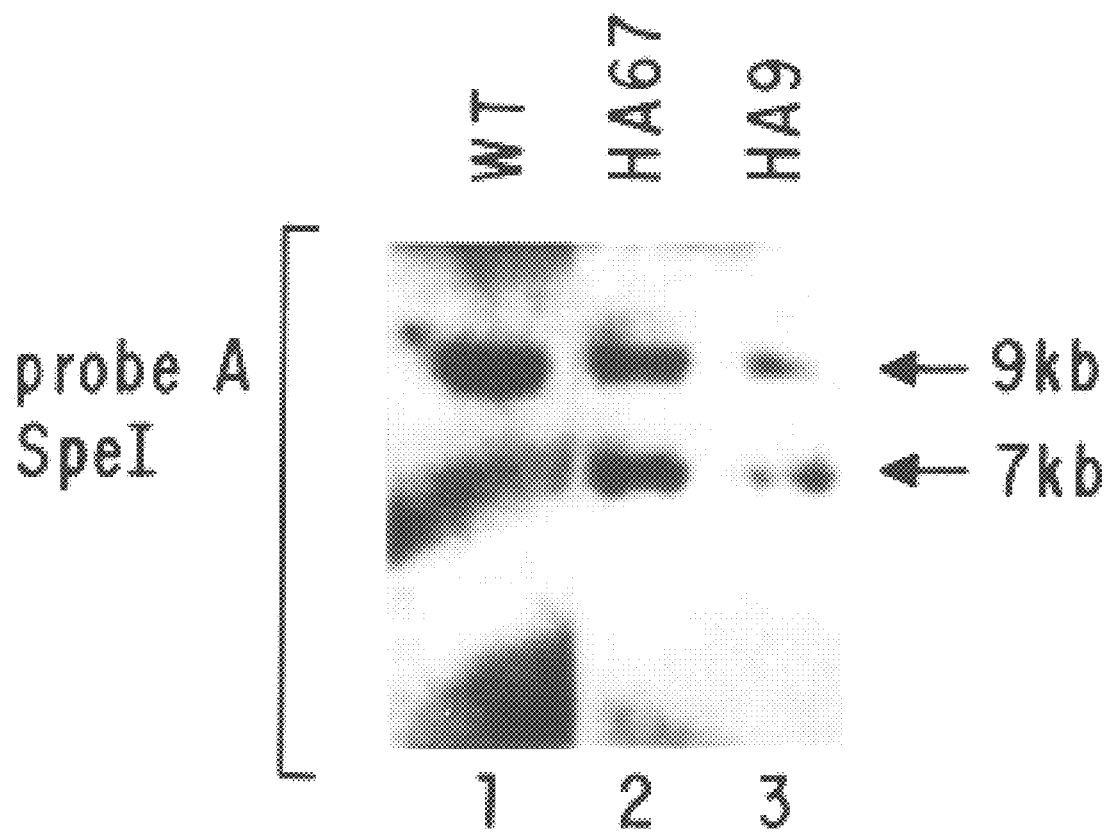

FIG. 24 (Panels a–c). The RXRβ mutation. (a) Targeting the RXRβ gene. A map of the WT RXRβ gene is shown on top. Black boxes indicate exons (numbering as in Nagata et al., Gene 142: 183–189 (1994)). Probe A is a NotI-KpnI fragment, probe B is a 500 bp BamHI-HindIII fragment immediately upstream of the deleted region; probe C is the HindIII-EcoRI fragment (corresponding to the deleted region). Sp, SpeI; K, KpnI; N, NotI; B, BamHI; E, EcoRI; Nh, NheI; X, XhoI; H, HindIII. (b) Targeted ES cells. Southern blot analysis of SpeI-restricted DNA from wild type (WT), and the HA67 and HA9 ES cell clones, analysed with the 5' probe A. (c) Southern blot analysis of mutant mice. The top panel shows the analysis of a litter using BamHI restricted DNA and probe B. The lower panel corresponds to an identical blot hybridized with probe C.

FIG. 25 (Panels a–g). Comparison of spermatozoa from the caudal epididymis in wild type (WT) and RXRβ$^{-/-}$ mutants, as indicated. (a,b) are semi-thin histological sections, illustrating the paucity of mutant spermatozoa. (c) corresponds to a smear, showing three spermatozoa displaying coiling of their tails. (d–g) are thin sections illustrating malformations of the acrosome and mitochondrial sheats in mutant spermatozoa; the insert corresponds to a high magnification of the box in (d). A, acrosomes; E, epididymal epithelium; H, head of spermatozoa, M, mitochondrial sheat; N, nuclei of spermatozoa; X, axoneme. The arrowheads, the large arrows and the open arrows point to the coiled tails and the defects of the acrosomes and mitochondrial sheats, respectively. Magnification ×860 (a–c), ×10.000 (d–g) and ×25.000 (insert).

FIG. 26 (Panels a–j). Failure of spermatid release and progressive testicular degeneration in RXRβ$^{-/-}$ males. Sections through the testes of wildtype (WT; a, c and e) and RXRβ$^{-/-}$ males (b, d, f, and g–j) at 6 months (a–f), 8 months (g and i) and 12 months (h and j). A, acrosomes; B, basement membrane; L, lipid droplets; P, pachytene spermatocytes; R, preleptotene spermatocytes; S, Sertoli cell nucleus; T, seminiferous tubules; V, vacuoles of degeneration; Y, Leydig cells. The numbers in the white dots refer to the degree of maturation (steps) of the spermatids. Arrowheads in b and f, lipid-containing "vacuoles"; unlabelled arrows, retained step 16 spermatids. Note that the focal hyperplasia of the Leydig cells (Y) in (g) and the oedema of the intertubular space in (h) represent classical secondary alterations to seminiferous tubule atrophy. Hematoxylin-trichrome (a, b, g and h), alcian blue (c and d) and periodic acid-Shiff-hematoxylin (e, f, i and j). Same magnifications in a, b, g and h (×260) and in c–f, i and j (×860).

Figure 27:
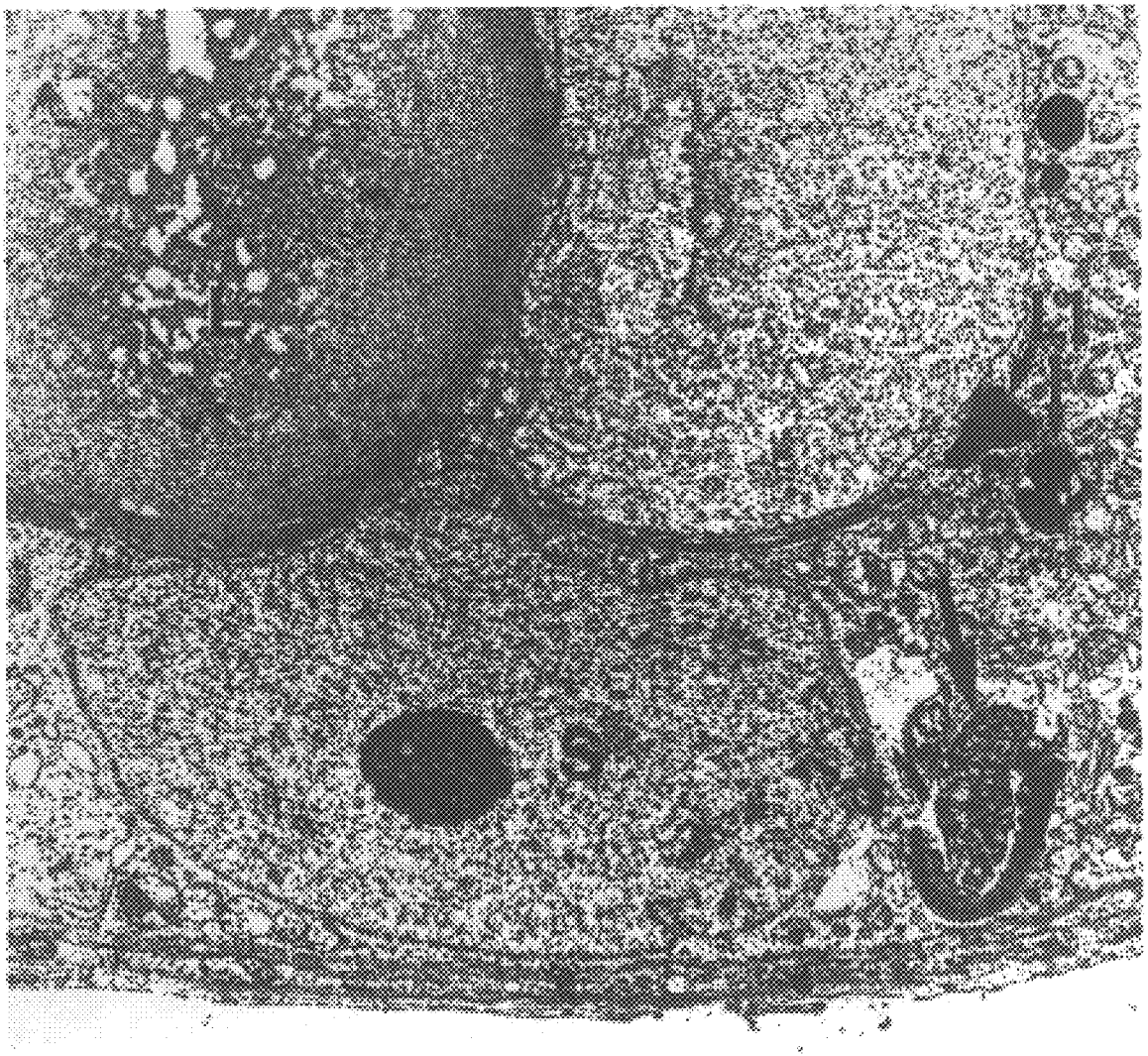

FIG. 27. Basal portion of a 6 month-old RXRβ$^{-/-}$ mutant Sertoli cell in a stage IX seminiferous tubule. L, lipid droplet; LI, lysosomes; S, Sertoli cell nucleus; arrow, phagocytized elongated spermatid. Magnification: ×9000.

Figure 28A:
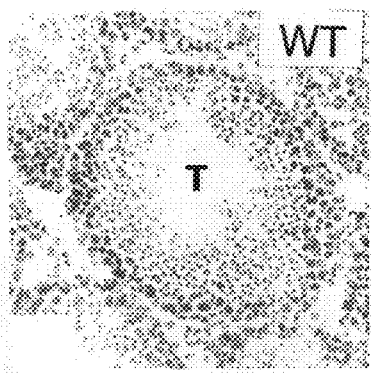
Figure 28B:
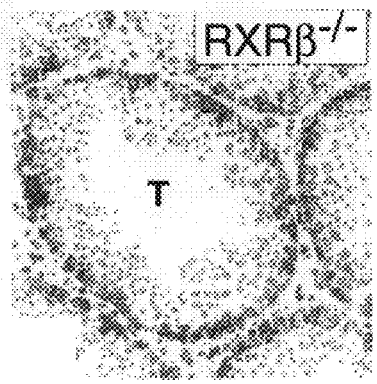
Figure 28C:
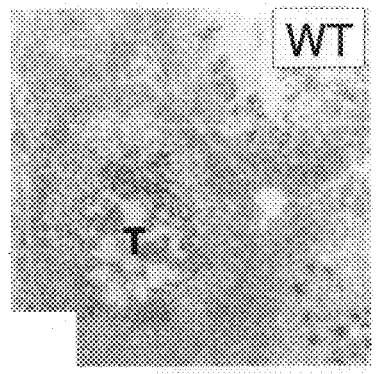
Figure 28D:
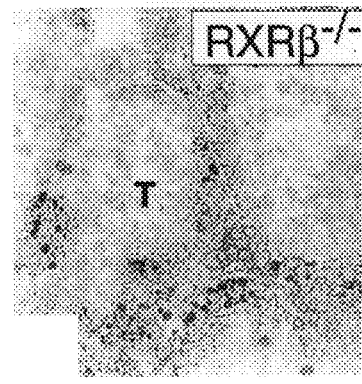
Figure 28E:
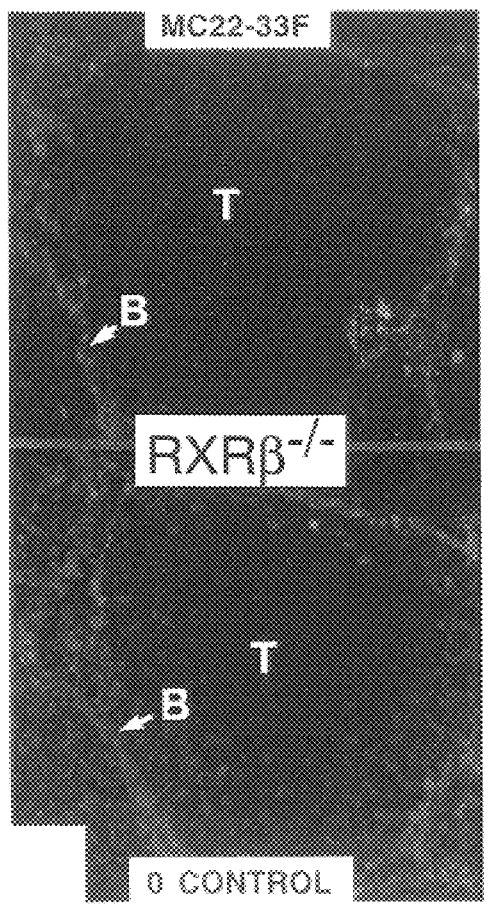
Figure 28F:
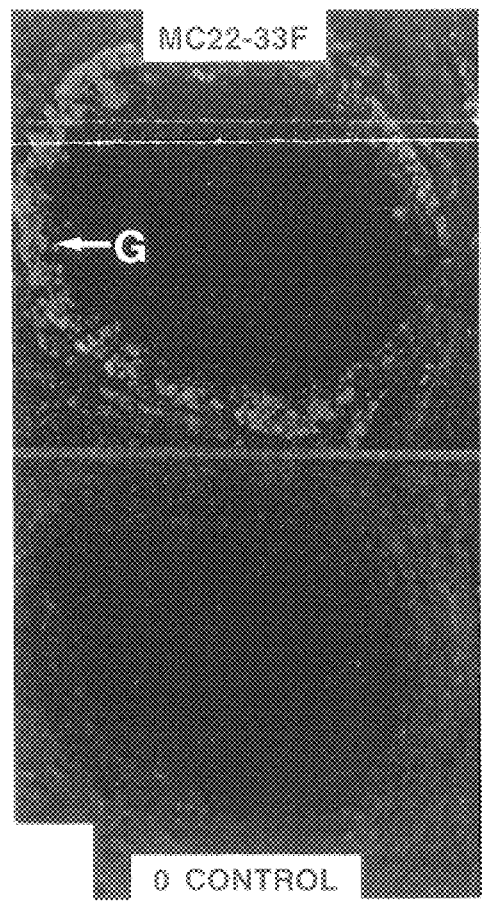
Figure 28G:
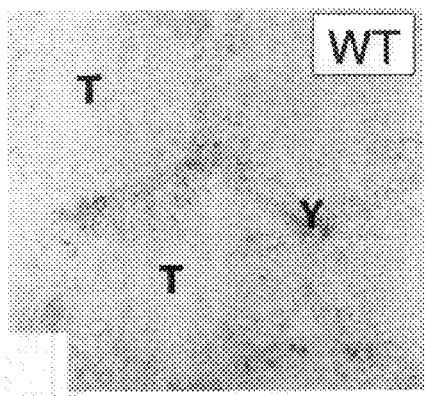
Figure 28H:
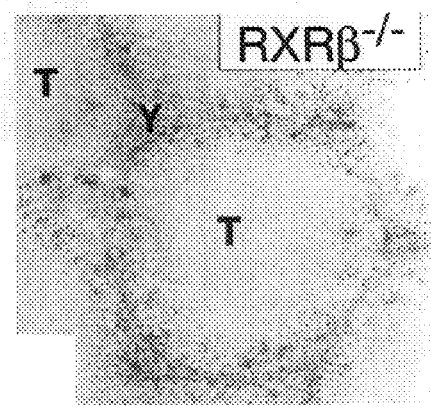
Figure 28:
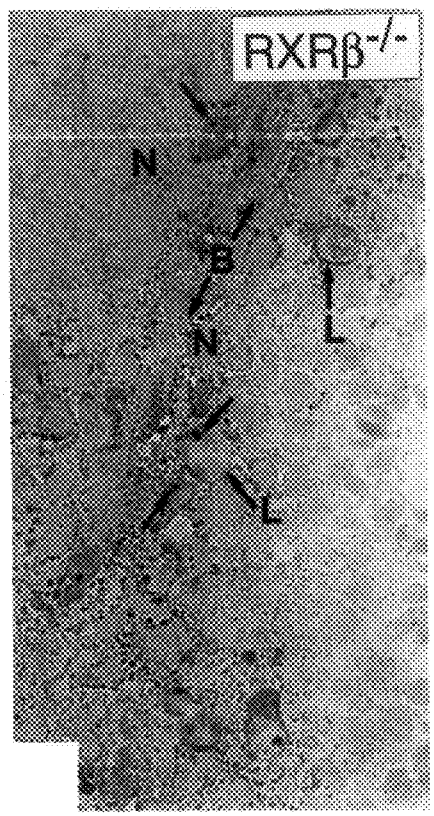
Figure 29A:
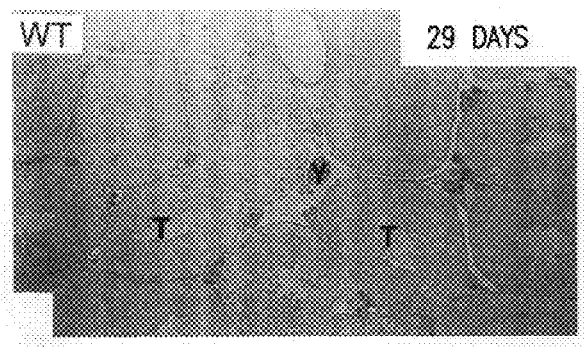
Figure 29B:
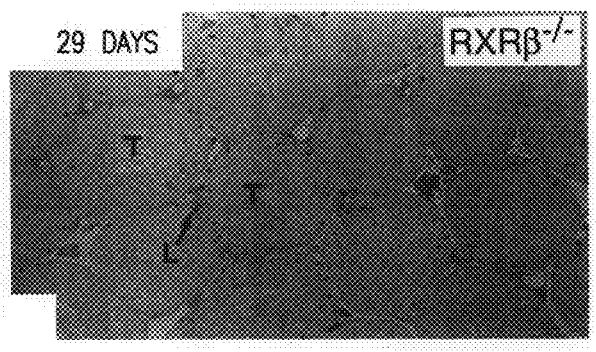
Figure 29C:
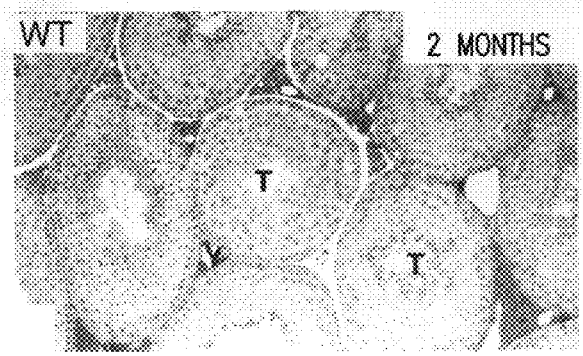
Figure 29D:
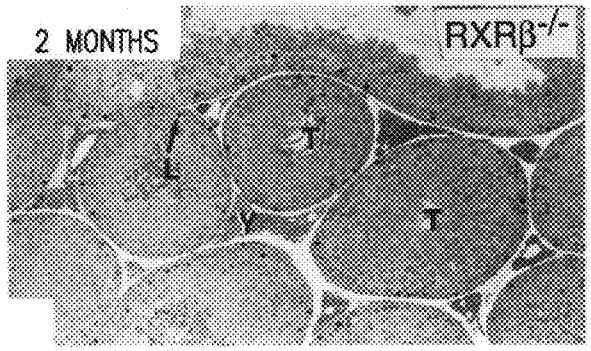
Figure 29E:
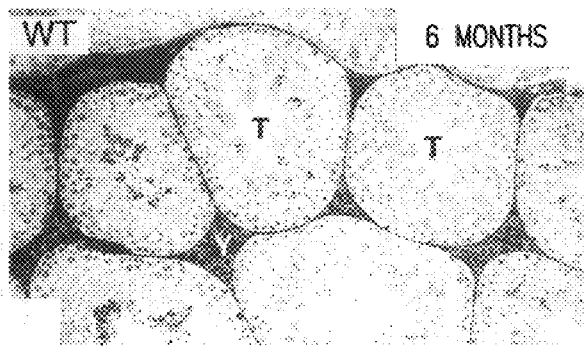
Figure 29F:
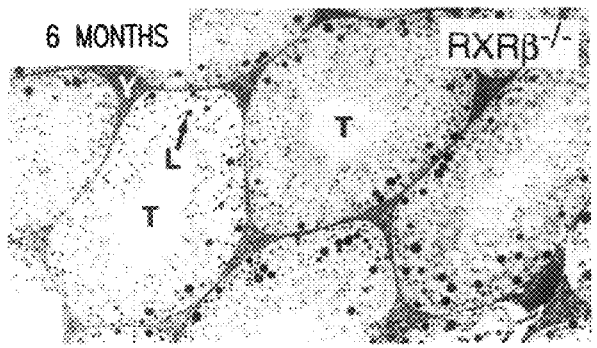
Figure 29G:
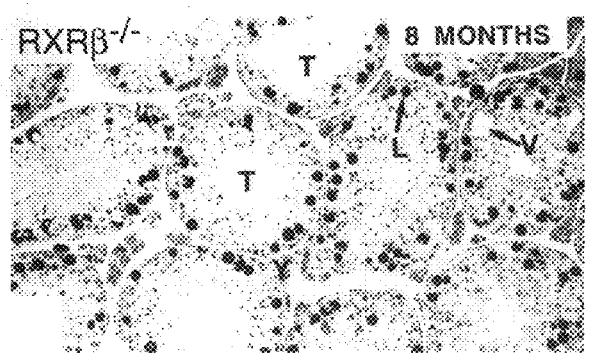
Figure 29H:
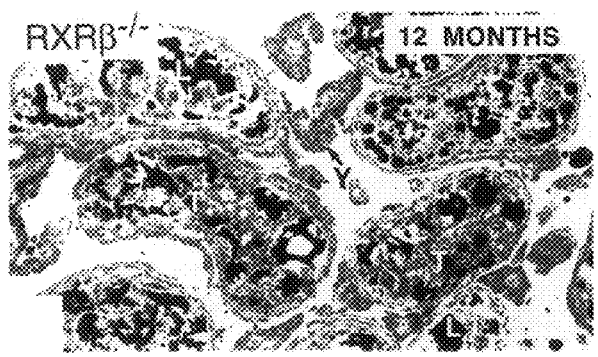

FIG. 28 (Panels a–i). Lipids and lysosomal structures in RXRβ$^{-/-}$ mutant testis. (a–e) and (g–i) represent frozen sections through the testes of 6 month-old wildtype (WT; a, c and g) and RXRβ$^{-/-}$ (b, d, h and i) males. (a) and (b), staining with oil red O. (c) and (d), staining with osmium tetroxide. (e), immunofluorescence staining of a RXRβ$^{-/-}$ seminiferous tubule with the anti-phospholipid antibody (MC22-33F, top) or non-immune rat IgM (0 control, bottom), on consecutive sections. (f), immunostaining of an antral follicle with MC22-33F (top) or non immune rat IgM (0 control, bottom) on consecutive sections. (g–i), detection of acid phosphatase activity [after staining with oil red O in (i)]. B, level of the basement membrane of the seminiferous tubule; G, granulosa cells; L, lipid droplets in Sertoli cells. N, nuclei; T, seminiferous tubules; Y, Leydig cells. Arrows point to lysosomes in (i). Magnifications: ×130 (a–d, g and h), ×200 (e and f) and ×860 (i).

FIG. 29 (Panels a–h). Lipid accumulation in RXRβ$^{-/-}$ mutant testis: early appearance, prior to the completion of spermatogenesis (29 days) and increase with the age of the animal, as indicated. Photomicrographs of semi-thin sections from osmium-fixed testes without (a and b) or with counterstaining (c–h) with alcian blue. Lipids (L) appear as brown or black dots or spots in the seminiferous tubules (T). Y, Leydig cells. V, vacuoles of degeneration. Magnification ×170.

FIG. 30 (Panels a–g). Comparison of the localization of RXRβ (b, d) and RXRα (c, e) transcripts in a wild type adult testis and immunoperoxidase staining with an antibody directed against RXRβ of wildtype (WT; f) and RXRβ$^{-/-}$ (g) testis. (a), bright field and (b,c) dark fields. In (d) and (e), the in situ hybridization signal is shown in false colors after computer processing of a bright field view and dark field view of the same section (see Vonesch et al., Dev. Dyn. 199: 199–213 (1994) for further details). In (f) and (g) a strong positive signal is exclusively detected in wildtype Sertoli cells. Immunostaining is absent from wild type germ cells and from mutant Sertoli cells and germ cells. The weak staining of the mutant and wild type Leydig cells (L) corresponds to background staining since it can be observed even when omitting the anti-RXRβ antibody in the immunostaining sequence. EP, epididymis; T, seminiferous tubules; S, Sertoli cells or spermatogonia; P, pachytene spermatocytes; RS, round spermatids; ES, elongated spermatids. Magnifications: ×17 (a–c) and ×250 (d–g).

FIG. 31 (Panels a–b). Comparison of semi-thin sections from osmium-fixed, resin-embedded testes of the seminiferous tubules of 6 month-old RARα$^{-/-}$ mutant (a) and vitamin A-deficient (VAD) (b) mice. The VAD males were the F1 offsprings of dams fed a VAD diet, and raised on a VAD diet from the time of weaning. The large arrows point to similar tubules having lost their germ cells and thus containing only Sertoll cells (S); the cytoplasm of the Sertoli cells contains large vacuoles (V) which are devoid of lipids. Y: Leydig cells. Magnification: ×520.

DESCRIPTION OF THE PREFERRED EMBODIMENTS

The present invention provides; 1) mice which are deficient in expressing either functional, normal levels, or detectable levels of one or more members of the RAR or RXR family of receptors, 2) mice heterozygous for such a deficiency, 3) cell lines, preferably pluripotent or totipotent cell lines, which are heterozygous or homozygous for such deficiency, and 4) methods of using the cell lines and mice of the present invention, or tissues derived therefrom, to identify antagonists and agonists of RXR or RAR receptors.

The present invention is based on the novel observation that homologous recombination can be used to replace one or more of the sequences encoding a member of the RAR or RXR family of receptors with a sequence which either prevents expression of all of the isoforms of a given subtype or a specific isoform of RAR or RXR receptor, or with a sequence which encodes an altered form of the receptor. The examples provided below demonstrate that gene replacement techniques can be used to knock out or alter the expression of one or more of the RAR or RXR family of receptors.

In one embodiment, the present invention provides mice and cell lines which have been altered to contain a sequence which confers a deficiency in the normal expression of at least one member of the RAR or RXR class of proteins. The cell lines and mice of the present invention can be heterozygous or homozygous for the desired trait, provided that the mice or cell lines contain the altered RAR or RXR coding sequence.

As used herein, a mouse or cell line is said to be altered to contain a sequence which conveys a deficiency in the normal expression of a member of the RAR or RXR class of receptors if recombinant techniques are utilized to insert, delete or replace sequences encoding for, or directing the expression of, one or more members of the RAR or RXR family of receptors. The insertion, deletion or replacement within such sequences has the effect of altering the normal level of expression of the given sequence or altering the activity of the protein which is expressed.

Mice can be altered such that the mouse expresses a lower level of the protein when compared to a non-altered mouse (in some cases a mouse "deficient" in expressing normal levels of a protein will be incapable of expressing detectable levels of the given protein). In some instances, where a mouse is altered such that a target gene is deleted or a large insertion is generated within the target sequence, the mouse will not produce detectable levels of the given receptor. However, in some instances it may be possible for extremely low quantities of the given receptor to be produced, although such product may, in itself, be inoperative, or not functional in its usual physiological actions.

As used herein, "normal expression" is defined as the level of expression which is present in a wild-type or non-altered animal. A variety of techniques known in the art can be used to quantitate the level at which a given protein is expressed. These include, but are not limited to immunological techniques such as an ELISA, RIA, or western blot, or quantitative analytical techniques such as spectroscopy or flame chromatography.

Alternatively the mice of the present invention can be altered so as to express an altered form of the given protein. Mice can be altered such that a specific mutation is introduced into a given region of a subtype or specific isoform of a RAR or RXR. Alternatively, mice can be altered such that the subtype or specific isoform of a RAR or RXR is altered (for example, the sequence encoding RAR-γ can be replaced with sequence encoding RAR-α) and the subsequent effects observed.

As used herein, the RAR and RXR class or family of receptors is defined as proteins which share the overall structure and sequence organization of members of the nuclear receptor proteins thus far identified as RAR or RXR receptors. These include, but are not limited to, all the various subtypes and isoforms of RAR and RXR, for example the alpha, beta, and gamma subtypes, and the RAR-α1, RAR-α2, RAR-β1, RAR-β2 and RAR-γ1 and RAR-γ2 isoforms disclosed in Krust et al., *Proc. Natl. Acad. Sci. USA* 86:5310–5314 (1989); Giguère et al., *Mol. Cell. Biol.* 10:2335–2340 (1990), Kastner et al., Proc. Natl. Acad. Sci. USA 87:2700–2704 (1990), Leroy et al., *Embo J.* 10:59–69 (1991), Zelent et al., *Embo J.* 10:71–81 (1991) herein incorporated by reference.

As used herein, a "subtype" of RAR or RXR receptor is identified by the presence of a subtype specific sequence which occurs within the A, B and/or D regions of the receptor. All isoforms from a given organism of a specific RAR or RXR subtype, for example all isoforms of human RXR-β, possess a conserved sequence within one of these regions which defines the subtype.

As used herein, an "isoform" of a particular subtype of RAR or RXR receptor is identified by sequence heterogeneity which is present in the A region of the RAR or RXR receptor. The various isoforms of a RAR or RXR receptor from a given organism will possess differing A region sequences.

Using the procedures outlined in the Examples presented below as well as those known in the art, one of ordinary skill can generate vectors for altering the expression of one or more subtypes or specific isoforms of RAR or RXR receptors without undue experimentation. Specifically, an individual wishing to use homologous recombination (HR) to disrupt a specific subtype or isoform of RAR or RXR first uses the sequences encoding one of the various RARs or RXRs disclosed in Krust et al., *Proc. Natl. Acad. Sci. USA* 86:5310–5314 (1989), Giguère et al., *Mol. Cell. Biol.* 10:2335–2340 (1990), Kastner et al., *Proc. Natl Acad. Sci. USA* 87:2700–2704 (1990), Leroy et al., *Embo J* 10:59–69 (1991), Zelent et al., *Embo J*. 10:71–81 (1991) to isolate a genomic fragment harboring a region of the receptor of interest, modifies a certain region of the genomic fragment to create a null allele for the receptor, and then uses this modified genomic sequence to perform HR. For example, Example 1 describes vectors which either selectively inactivate the entire RAR-γ subtype (these vectors contain modified sequences from the B region of RAR-γ) or inactivate only the RAR-γ2 isoform (these vectors contain modified sequences from the A region of RAR-γ2). Example 2 describes vectors which either selectively inactivate the entire RAR-α subtype (these vectors contain modified sequences from the B region of RAR-α) or inactivate only the RAR-α1 isoform (these vectors contain modified sequences from the A region of RAR-γ1).

The mice and cell lines of the present invention are preferably obtained by methods known in the art as homologous recombination (HR). This method has long been known in lower eukaryotes (e.g. yeast), and has recently been described for the mouse (for review, see Capecchi, M., *TIG* 5(3):70–76 (1989) and also see Smithies, 0., et al., *Nature* 317:230 (1985); Zijlstra, M., et al., *Nature* 342:435 (1989); Schwartzberg, P. L., et al., *Science* 246:799 (1989); DeChiara, T. M., et al., *Nature* 345:78 (1990)).

Homologous recombination essentially comprises isolating genomic sequences containing the target gene, employing known genetic engineering techniques to mutate or otherwise disable or modify the gene, and then reintroducing the gene into the relevant species. This is achieved by preparing a culture of pluripotent, or totipotent, cells, typically taken from embryos (ES cells). The advantage of these cells is that they can be successfully cultured for a large number of generations under conditions in which they will not differentiate and can be reintroduced into recipient embryos.

A sample of mouse pluripotent embryonic cells (ES-$D_3$), which can be used to reproducibly obtain the mice and cell lines of the dislcosed invention, was deposited under the Budapest Treaty at the International Depository Authority Type Culture Collection at the address of 12301 Parklawn Drive, Rockville, Md. 20852, USA on May 6, 1994. The ATCC designation for this cell line is CRL11632.

Typically the technique of electroporation, is used to render the ES cells capable of taking up exogenous DNA. The modified gene is then introduced, in a suitable manner, to these cells. Once taken up, recombination may occur, although this may be by random integration as well as by homologous recombination.

To select cells in which a recombination event has taken place, a selectable marker sequence may be used. For example, it is well known to employ the bacterial Neo gene to confer resistance to neomycin, or an analogue thereof, such as G418. The marker gene may be inserted in the gene to be modified, thereby disabling the target gene, while providing a positive selectable marker. Clones which are Neo$^+$ have integrated the vector.

To further select homologous recombinants, the ends of the modified gene may have other markers inserted, such as the Herpes Simplex Virus thymidine kinase (HSVTK) gene. In a HR event, the HSVTK genes will not be recombined, and the marker will not be transferred. Therefore, the desired recombinant will be resistant to, for example, Gancyclovir, which is converted into a toxic metabolite when the HSVTK gene product is present (after a non-homologous recombination event).

Correct clones may be identified by the technique of PCR or by genomic Southern blotting.

Subsequently, when a suitable clone has been identified, the ES cells may be injected into early-stage embryos, (blastocysts), and reintroduced into a pseudopregnant female.

Chimeric animals will generally result from at least some of these embryos, their tissues deriving in part from the selected clone. Thus, the germ-line may also be chimeric, spermatozoa or ova containing the modified gene. Progeny deriving from such germ cells will be heterozygous for the gene.

The heterozygous progeny can be cross-bred to yield homozygous animals. Confirmation of the allelic structure of the mice can be ascertained by Southern blotting, for example.

The present invention also envisages cell lines suitable for generating mice of the invention, and techniques for generating such lines and mice.

Thus, to obtain mice according to the present invention, one skilled in the art can use the strategy of homologous recombination (HR) in embryonic stem cells (ES cells) to replace the wild-type sequences encoding a member of the RAR or RXR family of receptors with an altered sequence.

The absence of one or more members of the RAR or RXR class of proteins in a cell line or animal allows one skilled in the art to screen for genes and agents which can restore the altered mice to a wild-type phenotype, as well as to screen for agents which act as agonists or antagonists of one or more members of the RAR or RXR class of receptors.

The mice and cell lines of the present invention allow the investigation, at the cellular level as well as at the in vivo level, of a system which lacks one or more subtypes or specific isoforms of RAR or RXR receptors. This will allow researchers to establish the importance of each of the various subtypes or isoforms of RAR or RXR receptors.

The mice and cell lines of the present invention may also be deficient in the expression of other genes, and thus provide the opportunity to study the interactions of RAR and RXR proteins with other proteins or the effects these proteins have on RA dependent gene expression.

Thus, it will be appreciated that there are many uses to which the mice and cell lines of the present invention may be put. They are particularly useful in studying any aspect of RA mediated gene expression and tissue specific expression of various RAR/RXR receptors. Also, as described below, the mice and cell lines of the present invention may be used to identify agonists and antagonists of specific members of the RAR/RXR class of receptors.

The mice and cell lines of the present invention can be used to assay for agents which act as antagonists or agonists of specific members of the RAR or RXR class of receptors. In general, the agent which is to be tested will be incubated with one or more of the cell lines or mice of the present invention, or tissues derived therefrom, and the level of binding of the agent is determined or the effect the agent has on development or gene expression is monitored.

As used herein, incubate is defined as contacting the compound or agent under investigation with the appropriate cell or tissue of the invention; or administering the agent or compound to the appropriate mouse of the invention via any one of the well-known routes of administration including: enteral, intravenous, subcutaneous, and intramuscular.

For example, the cell lines and mice of the present invention, or tissues derived therefrom, can be used in an assay system comprising the steps of: (a) incubating an agent with one or more of the cell lines or mice of the present invention, or cells or tissues derived therefrom; and (b) determining whether the agent binds to the cells, tissues, or mice, or determining the effects the agent has on development or gene expression.

In performing such an assay, one skilled in the art will be able to determine which subtype or isoform of RAR or RXR receptor an agent binds to, and hence determine what specific receptor(s) are utilized by a given compound. Additionally one can determine in which tissues a given RAR/RXR receptor is active.

The agents screened in the above assay can be, but are not limited to, peptides, carbohydrates, and vitamin derivatives. The agent can be selected, and screened at random, rationally selected or rationally designed using protein modeling techniques.

For random screening, agents such as peptides, carbohydrates, or derivatives of RA, are selected at random and are assayed for their ability to bind to one of the heterodimers present in mice or cell lines described in the present invention using either direct or indirect methods.

Alternatively, agents may be rationally selected. As used herein, an agent is said to be "rationally selected" when the agent is chosen based on the physical structure of a known ligand of the heterodimer. For example, assaying compounds possessing a retinol like structure would be considered a rational selection since retinol like compounds will bind to a variety of the heterodimers.

Since highly purified RAR and RXR proteins are now available, X-ray crystallography and NMR-imaging techniques can be used to identify the structure of the ligand binding site present on these proteins. Utilizing such information, computer modeling systems are now available that allows one to "rationally design" an agent capable of binding to a defined structure (Hodgson, *Biotechnology* 8:1245–1247 (1990)), Hodgson, *Biotechnology* 9:609–613 (1991)).

As used herein, an agent is said to be "rationally designed" if it is selected based on a computer model of the ligand binding site of the RAR or RXR protein.

In one aspect of the above-described assay, the cell line or mouse, in addition to being altered in the expression of one or more of the members of the RAR or RXR class of receptors, is altered such that it contains a marker sequence, such as luciferase, beta galactosidase, or chloramphenicol acyltransferase, operably linked to a RAR or RXR response element (RARE or RXRE). The agent which is to be tested is incubated with the altered cell or mouse, or tissues derived therefrom, and the expression of the reporter sequence is assayed. In this fashion, agents can be identified which are capable of either stimulating or inhibiting the expression of a DNA sequence which is controlled by a specific RARE or RXRE.

The following Examples serve only to illustrate the invention, and are not to be construed as in any way limiting on the invention.

EXAMPLE 1

Function of Retinoic Acid Receptor γ (RARγ) in the Mouse

Experimental Procedures
RARγ2 and RARγ Homologous Recombination Targeting Vectors Both RARγ2 and RARγ were targeted using the "replacement" strategy (Capecchi, *Science* 244:1288–1292 (1989)). For the RARγ2 disruption, the construct was prepared as follows; a 9 kb EcoRI fragment containing exon 5 (RARγ2 specific A domain) was subcloned from phage λG1 mRARγ (Kastner et al., *Proc. Natl. Acad. Sci. USA* 87:2700–2704 (1990)) into the vector pTZ19U (Pharmacia). Most of the RARγ2 5' untranslated region and part of the sequences encoding the A2 region (nucleotides 81 to 342; numbering as in Kastner et al., *Proc. Natl. Acad. Sci. USA* 87:2700–2704 (1990)) were then deleted by site-directed mutagenesis. The GTI-II NEO cassette was obtained as a NotI fragment by PCR amplification of the plasmid p566 (Lufkin et al., *Cell* 66:1105–1119 (1991)) using the oligonucleotides 5' ATGCGGCCGCGGTACCCAGATCTGGG (SEQ. ID NO. 1) and 5' ATGCGGCCGCTCATTTCGAAC-CCCAGAG (SEQ ID NO. 2) and was subcloned into the EagI site present in exon 5. Thus, in this construct, part of the RARγ2 5' untranslated region and A2 region sequences up to amino acid 19 (which includes all methionines in this region) were replaced with the GTI-II NEO sequences. The genomic fragment, containing the NEO insert, was subsequently subcloned into a HSV TK expression cassette [derived from p511 (Lufkin et al., *Cell* 66:1105–1119 (1991))]. This construct, designated γ9.1, had 7.5 kb and 1.5 kb of homologous sequence 5' and 3' of the NEO insertion respectively. The construct was linearized at the unique SalI or SfiI sites present in the polycloning site prior to electroporation of D3 ES cells. For targeting all isoforms of RARγ, a 6 kb EcoRI subclone, contiguous with the fragment used to disrupt RARγ2, was subcloned from λG1 mRARγ into pTZ19U in which the KpnI site in the polylinker had been destroyed by blunting with T4 DNA polymerase. A NEO cassette derived from p566 (Lufkin et al., *Cell* 66:1105–1119 (1991)) was cloned into the unique KpnI site present in E8 which contains the B region common to all RARγ isoforms (amino acid 75 of RARγ1). A HSV TK expression cassette, derived from p511 (Lufkin et al., *Cell* 66:1105–1119 (1991)), was then cloned into the unique SalI site present in the polycloning site of pTZ 19U, to yield the final targeting vector designated γ6.1. This construct had 2.8 kb and 3.2 kb of homologous sequence 5' and 3' of the NEO insert respectively, and was linearized at the unique HindIII site in the polylinker prior to electroporation of D3 ES cells.

Electroporation conditions, cell culture, G418 and gancyclovir selection, DNA preparation, PCR analysis, Southern blot analysis and generation of chimeric mice were as described previously (Lufkin et al., *Cell* 66:1105–1119 (1991)). Initial screening for the RARγ2 disruption was performed by the PCR using DNA pooled from 5 separate ES cell clones, with the nested primers 5' ATACCCA-GATATTTCTGACTCAG 3' (SEQ. ID NO. 3); 5' CAGAT-GCCAGCCAATGTGCCCA 3' (SEQ. ID. NO. 4) (genomic sequence 3' of boundary of homologous recombination) and 5' ACCGCTTCCTCGTGCTTTACGGTA 3' (SEQ. ID NO. 5); 5' GCCGCTCCCGATTCGCAGCGCAT 3' (SEQ. ID NO. 6) (NEO sequence). DNA from individual colonies from pools positive by the PCR were then analyzed by genomic Southern blotting. Probe 1 corresponds to a 1.6 kb BamHI-EcoRI genomic fragment derived from phage λG1 mRARγ respectively; probe 2 corresponds to exon seven of RARγ6 (Kastner et al., *Proc. Natl. Acad. Sci. USA* 87:2700–2704 (1990)). Additional probes (not shown) including NEO and HSV tk were used to establish the fidelity of the recombination events.

RNase protection analysis

Total RNA was prepared from either day 10.5 or 13.5 p.c. embryos or various tissues by the single-step guanidinium-isothiocyanate-phenol technique (Chomczynski and Sacchi, *Analytical Biochem.* 162:156–159 (1987)) with the addition of a second phenol-chloroform extraction step. Approximately 40 μg of RNA was used per hybridization. The conditions for the preparation of probes and the hybridization reaction were essentially as described previously (Sambrook et al., in *Molecular Cloning: A Laboratory Manual*, Cold Spring Harbor Laboratory Press, Cold Spring Harbor, N.Y. (1987). The plasmid constructs used as templates for the preparation of the antisense riboprobes are described elsewhere (Lufkin et al., "High postnatal lethality and testis degeneration in retinoic acid receptor α (RARα) null mice," (*Proc. Natl. Acad. Sci. USA*, in press 1993)).

Histological and skeletal analysis

For whole mount skeletal analysis, fetuses were collected at day 18.5 p.c. and stored at −20° C. Skeletons were prepared as previously described (Lufkin et al., *Nature* 359:835–841 (1992)). For histological analysis, fetuses were skinned and then fixed in Bouin's fluid. Paraffin sections, 7 μm thick, were stained with Groat's hematoxylin and Mallory's trichrome. Organs were fixed in 10% formalin, and histological sections, 5 μm thick, were stained with hematoxylin and eosin.

Retinoic acid treatment.

RARγ$^{+/-}$ heterozygote animals were mated overnight and the presence of a vaginal plug at noon the next day considered as day 0.5 p.c. At various times, pregnant females received a single dose of RA dissolved in sunflower seed oil at a final delivery of 100 mg RA per kg animal.

Results

Homologous recombination and germ line transmission

Figure 1B:
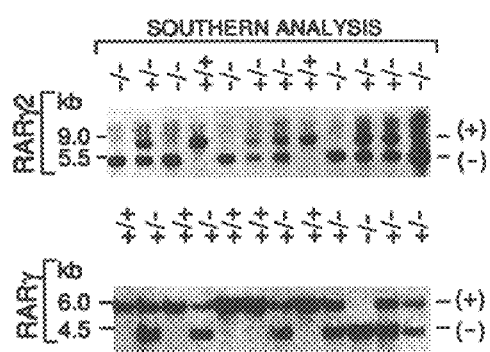

An approach based on positive-negative selection (Capecchi, Science 244:1288–1292 (1989)) was employed to create a null allele in embryonic stem (ES) cells for either RARγ2 or all RARγ isoforms (Kastner et al., Proc. Natl. Acad. Sci. USA 87:2700–2704 (1990); FIG. 1a). For disruption of RARγ2, a neomycin phosphotransferase expression cassette (NEO) was subcloned into the RARγ2-specific exon 5 at the position corresponding to amino acid 19 (Kastner et al., Proc. Natl. Acad. Sci. USA 87:2700–2704 (1990)). This targeting vector yielded a total of six "disrupted" ES cell clones (from a total of 186), of which three were injected into blastocysts to derive chimeras. Two chimeras (derived from EA36 and EB1 ES clones) tested positive for germ line transmission (data not shown); although similar results were obtained for offspring from either line, only those corresponding to EB1 are presented here. Southern blot and RNase protection analysis indicated that homologous recombination resulted in the planned disruption; secondary integration events, duplications or rearrangements were not detected (FIG. 1b and d, and data not shown). Due to the nature of this disruption, some truncated RARγ protein could possibly be synthesized via reinitiation of translation at the AUG codon located at position 41 in the B region of the mutated receptor transcript. It is important to note that this putative protein would also lack the distinctive A2 region of the RARγ2 isoform, and therefore, that its synthesis should still allow an analysis of any specific function of this isoform.

The whole RARγ gene was disrupted using a construct in which the NEO cassette was inserted in exon 8 (B region), which is common to all RARγ isoforms (at amino acid 75 of RARγ1; FIG. 1a and Kastner et al., Proc. Natl. Acad. Sci. USA 87:2700–2704 (1990)). Eleven "disrupted" ES cell clones were obtained using this construct (from a total of 72 colonies), of which nine were injected into blastocysts to derive chimeras. One chimera (AA71) passed the mutation to its offspring, and all results presented were derived from this line. The AA71 cell line was deposited on Aug. 4, 1998 with European Collection of Cell Cultures, at the address of Salisbury, Wiltshire SP4 0JG, UK, and given an accession number 98080416. Southern blot and RNase protection analysis showed that, as for RARγ2, the planned disruption was successful (FIG. 1b and d, and data not shown). Reinitiation of translation of the mutated RARγ transcript could theoretically occur via the AUG corresponding to amino acid position 122 of RARγ1. However, since the corresponding methionine is located between the two zinc fingers of the C region, the putative resulting protein would be non-functional, as it would contain only the second zinc finger, and therefore would not be able to bind to RA response elements (Leid et al., Cell 68:377–395 (1992b)). RARγ2 null homozygotes are apparently normal Analysis of RARγ2$^{+/-}$×RARγ2$^{+/-}$ or RARγ2$^{-/-}$× RARγ2$^{+/-}$ offspring gave a Mendelian distribution for the mutation (Table I). Both RARγ2$^{-/-}$ males and females were fertile (Table I, RARγ2$^{-/-}$×RARγ2$^{+/-}$ crosses, and data not shown), and appeared indistinguishable from their wild-type (WT) or RARγ2$^{+/-}$ littermates. Histological examination of serial sections and whole mount skeletal analysis of day 18.5 p.c. RARγ2 null fetuses delivered by caesarian did not reveal any abnormalities.

Figure 1D:
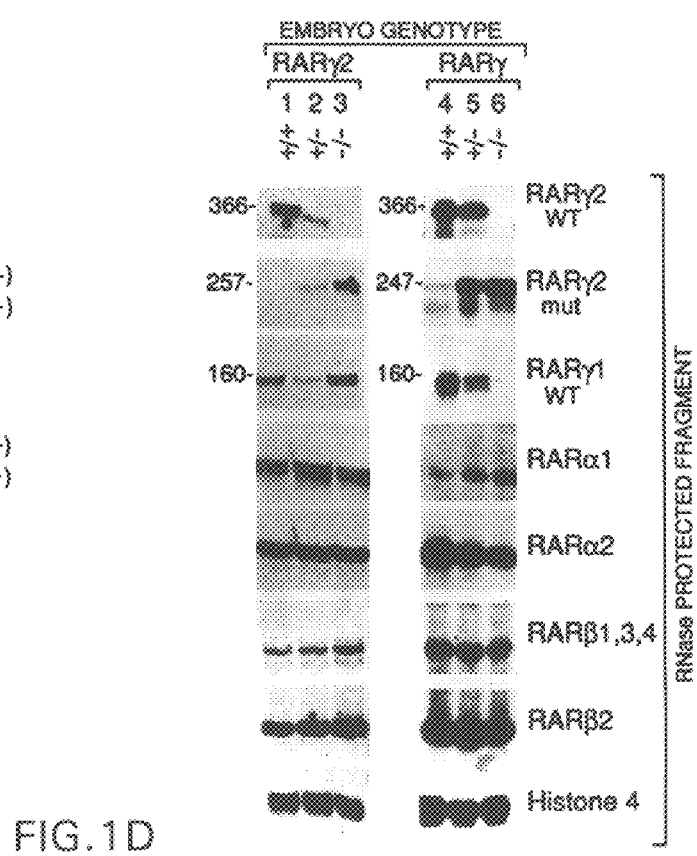
Figure 1C:
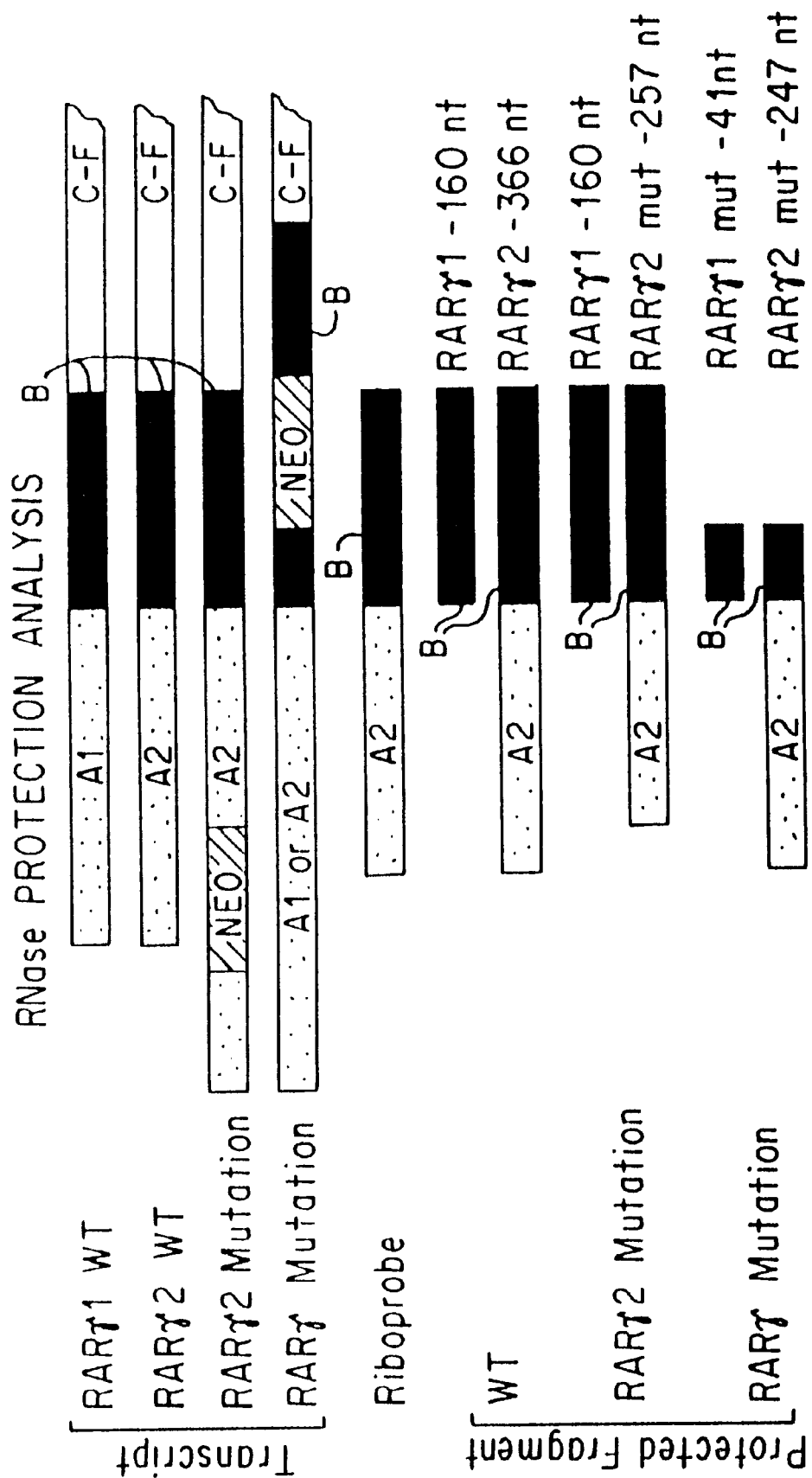

The lack of an overt phenotype for the RARγ2 disruption could not be attributed to alternative splicing of the mutated transcript, as RNase protection analysis of RNA extracted from either RARγ2$^{-/-}$ day 10.5 p.c. whole embryos or adult lung showed only the predicted transcript, nor were transcripts encoding any other RARs apparently induced to compensate for the loss of this receptor (FIG. 1c and d, and data not shown).

TABLE 1

Offspring Viabliity of RARγ Mutant Mice

| | Genotype of RARγ$^{+/-}$ X RARγ$^{+/-}$ Crosses | | |
|---|---|---|---|
| | +/+ | +/– | –/– |
| Day 18.5 p.c. | 69 (1.0) | 146 (2.1) | 65 (0.9) |
| 1–3 weeks old | 142 (1.0) | 297 (2.1) | 73 (0.5) |
| 1 month old | 140 (1.0) | 295 (2.1) | 53 (0.4) |
| 3 months old | 138 (1.0) | 292 (2.1) | 28 (0.2) |
| | Genotype of RARγ2$^{+/-}$ X RARγ2$^{+/-}$ Crosses | | |
| | +/+ | +/– | –/– |
| 1–2 months old | 41 (1.0) | 93 (2.3) | 38 (0.9) |
| | Genotype of RARγ2$^{-/-}$ X RARγ2$^{+/-}$ Crosses | | |
| | | +/– | –/– |
| 1–2 months old | | 47 (1.0) | 48 (1.0) |

Table I. Offspring viability of RARγ mutant mice. Genotype analysis was performed using DNA prepared from either the placenta (day 18.5 p.c.) or tail tips (1 week- 3 months p.p.). The number of RARγ or RARγ2 WT offspring or fetuses was arbitrarily assigned a value of 1.0, and the relative ratios of heterozygote and homozygote animals calculated accordingly (number in parenthesis).

Growth-deficiency and early lethality of RARγ null homozygotes

Disruption of all isoforms reduced by about 50% the expected number of RARγ$^{-/-}$ offspring when genotyping was performed at 1–3 weeks of age (Table I). Moreover, these RARγ$^{-/-}$ animals had a higher mortality rate than their RARγ$^{+/-}$ or WT littermates, with less than 40% surviving to 3 months of age (Table I). Interestingly, the mutation was not embryonic lethal, as a Mendelian distribution was observed for day 18.5 p.c. fetuses delivered by caesarian section. Moreover, the RARγ null fetuses did not exhibit any visible abnormalities, and survived as well as their littermates for more than 24 hours when segregated from dams. However, approximately 50% of these RARγ null fetuses were selectively cannibalized within 24 hours when placed with adoptive mothers.

4–5 day post-partum (p.p.) RARγ$^{-/-}$ animals were often growth-deficient, typically 40–80% the weight of heterozygote or WT siblings (data not shown), yet displayed no obvious malformations (with the exceptions noted below) at any stage examined to date. However, these smaller RARγ null animals exhibited a higher mortality rate in the following 1–2 months (Table I), which resulted in the remaining RARγ$^{-/-}$ animals having a body weight which approached that of WT littermates at 3 months (data not shown).

The expression of RARα isoforms was not grossly affected by RARγ disruption, as seen by RNase protection analysis using RNA extracted from day 13.5 p.c. embryos or adult lung, testes, vas deferens, seminal vesicles and prostate (FIG. 1d, and data not shown). Neither did in situ hybridization analysis reveal any obvious changes in the expression pattern of RARα or β transcripts in day 10.5 p.c. RARγ$^{-/-}$ embryos (P. Dollé, D. L. and P. C., unpublished results). Furthermore, when compared with WT or RARγ$^{+/-}$ embryos, the expression pattern of a RA-inducible RARβ2 P2 promoter LacZ reporter (Mendelsohn et al., *Development* 113:723–734 (1991)) was not altered at day 9.0 or 13.5 p.c. in RARγ$^{-/-}$ embryos from either normal or RA-treated dams (data not shown).

Homeotic transformations in RARγ null animals 25 out of 29 day 18.5 p.c. RARγ$^{-/-}$ fetuses exhibited various malformations of the axial skeleton at different frequencies, none of which were found in wild-type littermates (Table II). Homeotic transformations included: (i) anterior transformation of the axis (second cervical vertebra, C2) to an atlas (first cervical vertebra, C1) identity as evidenced by a thickening of the neural arches and the presence of an ectopic anterior arch of the atlas (AAA*) fused to C2 ("C1" in FIG. 2, compare panel *a* with *b* and *d*; however, note that the axis dens was still present and therefore that the C2 to C1 transformation was not complete); (ii) unilateral anterior transformation of C7 to a sixth vertebral identity ("C6") with a concomitant unilateral anterior transformation of C6 to a fifth cervical identity ("C5"), as evidenced by the presence of a tuberculum anterior ("TA") and a foramina transversarium ("FT") on C7 (WT C7, unlike C3 to C6 vertebrae, has noforamina transversaria, see panel *i*), and lack of a tuberculum anterior on C6, respectively (compare FIG. 2*a* with 2*b*; and 2*i* with 2*j*, *k* and *l*; note in panel 2*j* that the C7 to C6 transformation is almost bilateral, thick arrow); and (iii) anterior transformation of the eighth thoracic vertebra to a seventh thoracic identity, resulting in eight instead of seven vertebrostemal ribs (compare FIG. 2*e* with 2*f* and *g*). This last transformation was also found at a low frequency in heterozygote animals (Table II), indicating that the specification of this segment could be particularly sensitive to RARγ gene dosage effects.

TABLE II

Skeletal Abnormalities in RARγ$^{-/-}$ Offspring

| | RARγ Genotype | | |
|---|---|---|---|
| | +/+ | +/− | −/− |
| Fetuses Examined at Day 18.5 p.c. | 33 | 36 | 29 |
| Abnormal Fetuses | 0 | 3 (*%) | 25 (86%) |
| Vertebral Abnormalities | | | |
| Transformations | | | |
| Basioccipital/C1 AAAfusion[a] | 0 | 0 | 8 (25%) |
| C2 to C1[c] | 0 | 0 | 5 (17%) |
| C7 to C6[b] | 0 | 0 | 4 (13%) |
| 8 vertebrosternal ribs[d] | 0 | 3 (11%) | 10 (33%) |
| Ribs 1 & 2 fused[d] | 0 | 0 | 4 (13%) |
| Malformations | | | |
| C1 bifidus[b] | 0 | 0 | 2 (7%) |
| C2 bifidus[b] | 0 | 0 | 3 (10%) |
| C1 & C2 fused[c] | 0 | 0 | 1 (3%) |
| C2 & C3 fused[b] | 0 | 0 | 4 (13%) |
| Malformed Tracheal Cartilage | 0 | 0 | 29 (100%) |

Table II. Skeletal abnormalities in RARγ null mutant offspring. Genotyping was performed using DNA from the placenta of day 18.5 p.c. offspring. Skeletons were prepared, and abnormalities scored under a dissecting microscope. Malformations of symmetrical structures were scored whether they were bilateral or unilateral.
[a]includes 3 fetuses analyzed by histological sections
[b]only or mostly unilateral
[c]bilateral
[d]unilateral or bilateral.

Figure 2A:
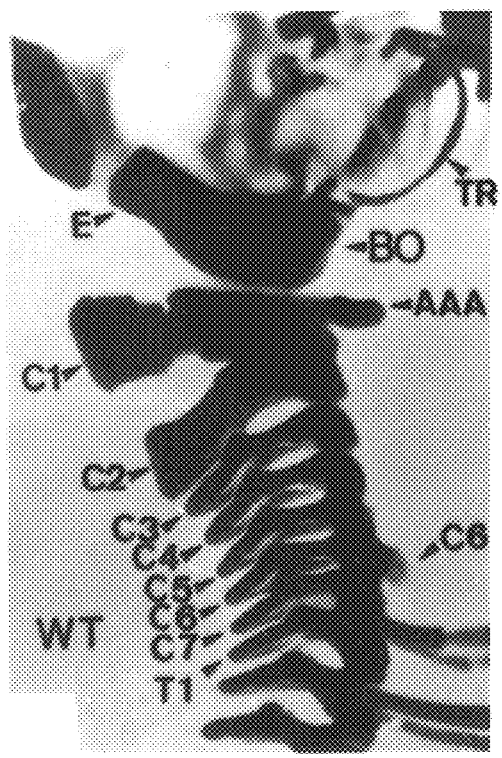
Figure 2B:
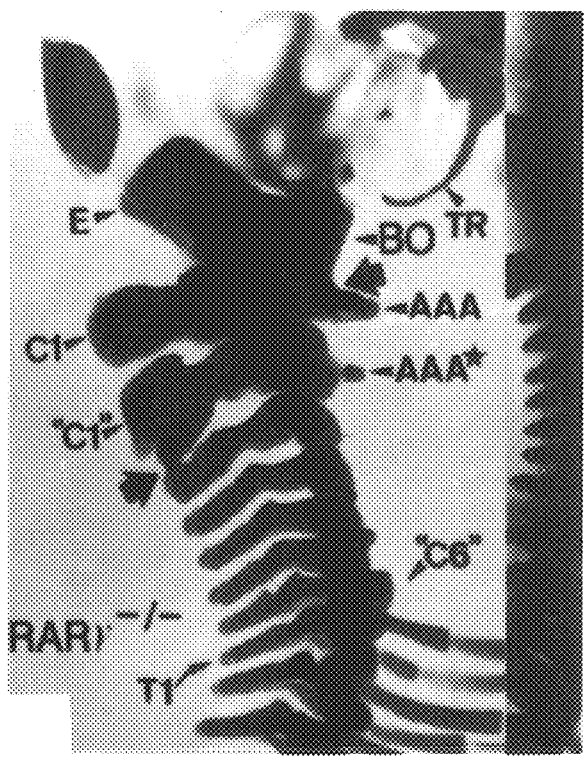
Figure 2C:
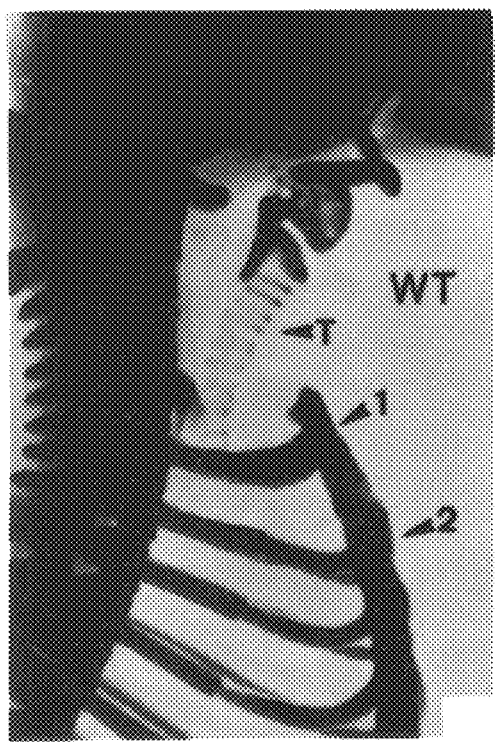
Figure 2D:
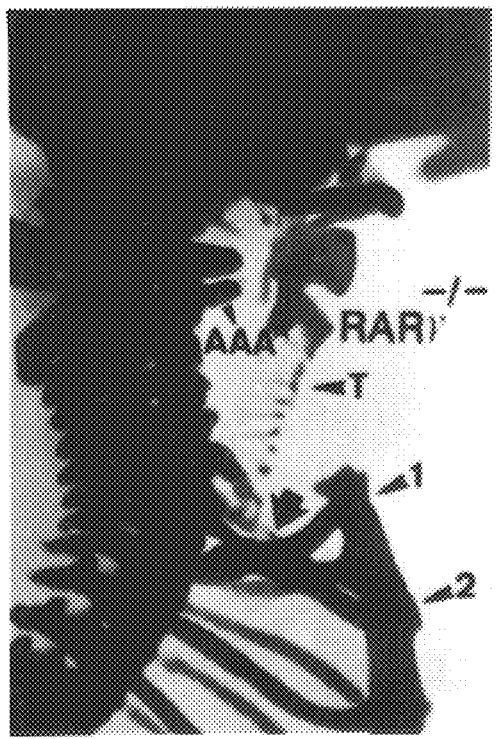
Figure 2E:
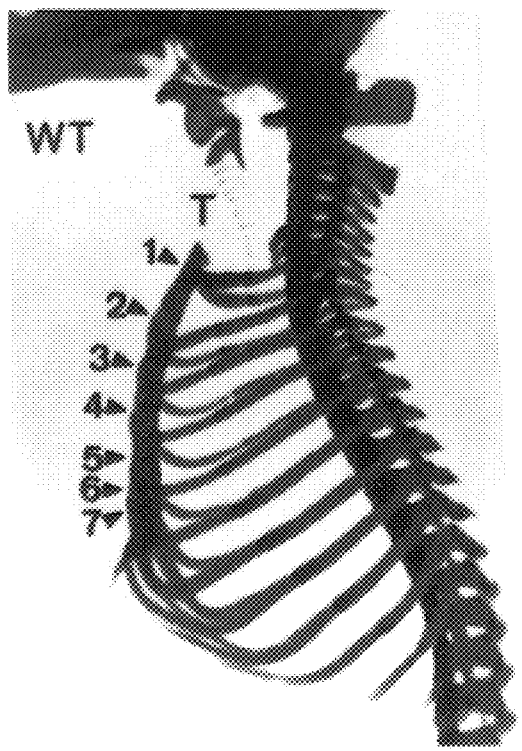
Figure 2F:
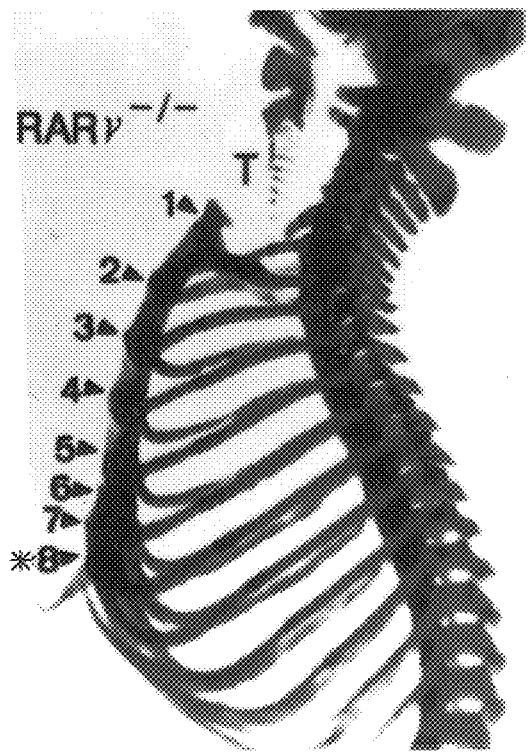
Figure 2G:
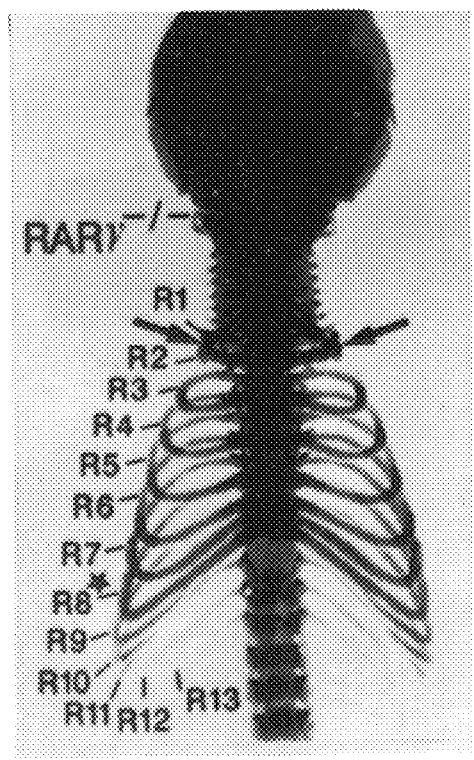
Figure 2H:
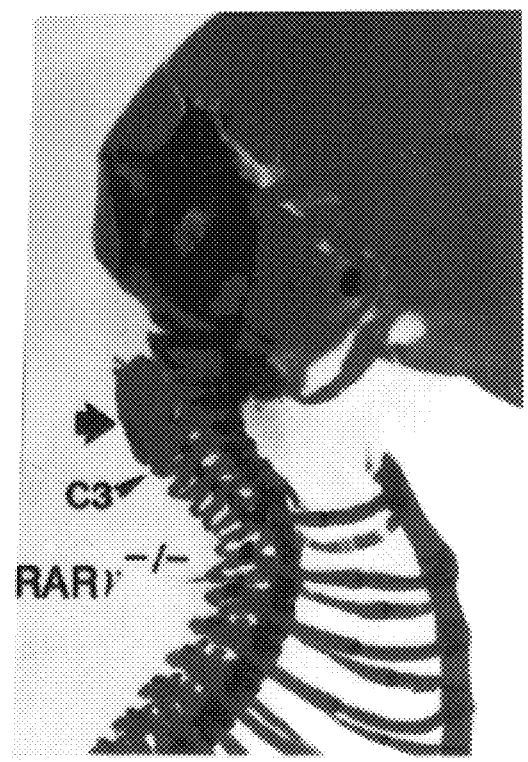
Figure 2I:
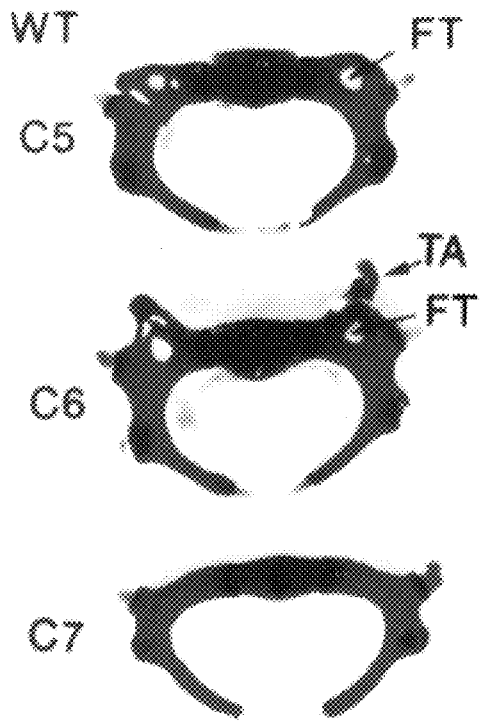
Figure 2J:
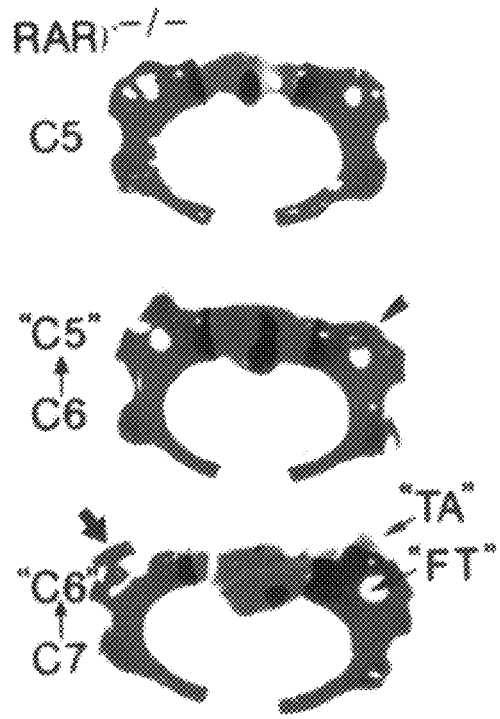
Figure 2K:
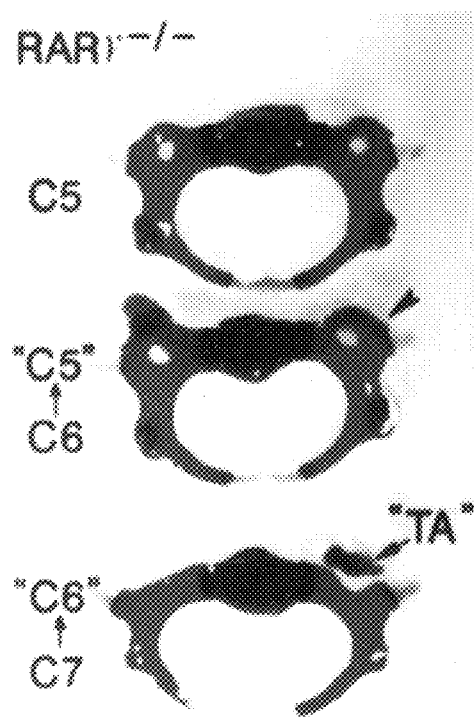
Figure 2L:
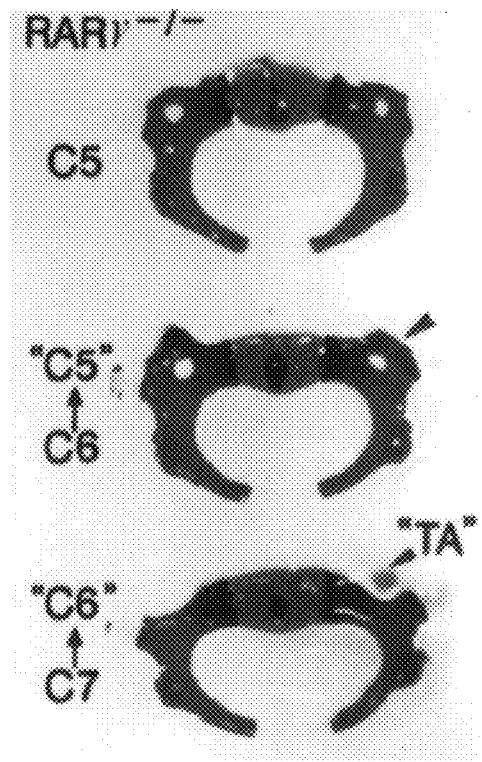

Two malformations present in RARγ$^{-/-}$ animals which could also represent homeotic transformations included fusion of the first and second ribs (FIG. 2*c* and *d*), and fusion of the basioccipital bone to the anterior arch of the atlas (compare FIG. 2*a* and *b*, FIGS. 3*a–d*). The fusion of the first and second ribs may represent an anterior transformation of the second thoracic vertebra to a first thoracic identity. However, the characteristic processus spinous was still present on the second thoracic vertebra. The fusion between the basioccipital bone and the anterior arch of the atlas may result from the abnormal persistence of the first hypochordal bar. Hypochordal, or subnotochordal, bars are normally formed by the ventral union of the left and right cephalic prevertebral components (derived from the sclerotomic mesenchyme) beneath the notochord (Hamilton, In: *An Introduction to Embryology*, B. H. Willier, ed. (New York: Henry Holt) 1952). In mouse embryos, three hypochordal bars are formed which are localized opposite the ventral side of the first and second cervical prevertebrae and are visible in day 12 p.c. embryos as mesenchymal condensations distinct from those of the bodies of these prevertebrae (Theiler, In: *Advances in Anatomy, Embryology and Cell Biology*, Volume 112, F. Beck, W. Driz and J. E. Pauly, eds (Heidelberg: Springer Verlag), pp 1–99 (1988)). The first (rostral most) and third hypochordal bars become incorporated, while still mesenchymal, into the caudal edge of the basioccipital bone and into the body of the axis, respectively. The second hypochordal bar normally persists, chondrifies and subsequently ossifies to form the anterior arch of the atlas. In RARγ$^{-/-}$ day 18.5 p.c. fetuses the first hypochordal bar often persists as a small median cartilage (H1 in FIG. 3, panels *b* and *d*) fused to the caudal edge of the basioccipital bone (BO). In this situation the caudal edge of the basioccipital bone becomes attached to the lateral mass of atlas (C1L) by the transverse ligament of the atlas (TL, see panel *b*), and/or is fused through an osseous bridge to the anterior arch of the atlas (panel *d*; see also FIG. 2 panel *b*). This persistence can be interpreted as a posterior homeotic transformation of the basioccipital bone (i.e., this bone has acquired an additional structure which is characteristic of the wild-type atlas), whereas the persistence of the third hypochordal bar, which is frequently observed in RARγ$^{-/-}$ fetuses (see FIG. 2 panels *b* and *d*, AAA*), may correspond to an anterior homeotic transformation (i.e., the third hypochordal bar acquires the characteristics of the second hypochordal bar). Additional homeotic transformations of the axial skeleton may be present in RARγ$^{-/-}$ animals that cannot be identified due to lack of morphological landmarks, as has been previously discussed (Kessel and Gruss, *Cell* 67:89–104 (1991)), e.g. it is possible that the entire cervical region of the homozygote null mutant displayed in FIG. 2*b* has undergone an anterior homeotic transformation.

Malformations of cartilage-derived structures in RARγ null mice

Additional malformations involving cartilage-derived structures in RARγ$^{-/-}$ animals included (i) ossified fusions between the neural arches of either C1 and C2 or C2 and C3 (compare FIG. 2*a* with 2*b* and h, thick arrows, and data not shown); (ii) bifidus of the neural arch of the first or second cervical vertebrae (Table II, and data not shown); and (iii) malformation of the tracheal cartilaginous rings (fusion of the cartilaginous rings on the ventral side of the trachea and disruption of the rings; compare T in FIG. 2*c* with 2*d* and *f*, and 3*e* with 3*f*). Note that this latter malformation was found in all of the RARγ$^{-/-}$ animals (Table II). No other bone or cartilage malformations were noted.

Glandular and epithelial defects in RARγ null mice

RARγ$^{-/-}$ animals were often found with closed and encrusted eyelids on one or both sides (data not shown). This phenotype became apparent approximately 2 weeks after birth (ie. after normal eye opening; data not shown). Subsequent analysis of these animals revealed in some cases a bilateral absence of the Harderian gland epithelium (in 2 of 8 RARγ$^{-/-}$ offspring examined; the ocular Harderian glands, together with the palpebral glands, provide lubrication of the edges of the eyelids). In other cases, one of the Harderian glands was normal, whereas the epithelium of the contralateral gland was partially or totally absent (in 2 of 8 RARγ$^{-/-}$ offspring examined, FIG. 4, panels m to o, and data not shown). This malformation is probably congenital, as histological analysis of a day 18.5 p.c. RARγ$^{-/-}$ fetus revealed bilateral absence of the Harderian glandular epithelium (data not shown). In other animals exhibiting the "closed and encrusted eyelid" phenotype the Harderian glands appeared histologically normal, thus suggesting that they could be simply functionally impaired. Wild type and heterozygote animals never exhibited this phenotype.

Histological analysis of the genito-urinary tract of 5 RARγ$^{-/-}$ males at day 18.5 p.c. or 3 weeks p.p. failed to reveal any abnormality. However, RARγ$^{-/-}$ males which survived to sexual maturity (8 weeks or older) never impregnated females. Subsequent analysis showed that in all cases (8 out of 8), the seminal vesicles and prostate glands exhibited squamous metaplasia and/or keratinization of the glandular epithelia (FIG. 4, compare panels d–g (WT controls) with panels h–l (mutants)). The mucosal folds and septa characteristic of normal seminal vesicles and prostate are often completely missing in RARγ$^{-/-}$ mutants (panels h, j and l; compare to wild type glands in panels d and f) and in some cases, the two glands cannot be distinguished from one another on the basis of histological criteria (panel j). The glandular epithelia (GE, panels e and g) are replaced by a squamous stratified epithelia of either the non-keratinizing (SQ, panels h and i) or of the keratinizing (SQK, panels j to l) type. The lumens of the glands contain little or no secretion product (S in panels d and f; compare to panels h, j and l). On a macroscopic scale, one can note: (i) an atrophy of the seminal vesicles (SV; compare RARγ$^{-/-}$ and WT SV in panel a; note the loss of the characteristic white coloration of the functional SV of normal, sexually mature, animals; see also panel b); (ii) an atrophy of the cranial prostate (CP; compare RARγ$^{-/-}$ CP in panel b to WT CP in panel a; note that the SV and CP in panel b are indistinguishable); (iii) in some cases, hypertrophy of the cranial prostate (compare the CP on the right of panel c to the contralateral gland); this hypertrophy is probably generated by an infection of the gland causing focal destruction of the metaplastic epithelium accompanied by foreign body reactions to the retained keratinizing cells (see panel l). Interestingly, RNase protection analysis using tissues from WT animals revealed that RARγ1 was the major RAR transcript expressed in the seminal vesicle and prostate glands of mature males, whereas RARα and β RNAs were barely detectable under conditions where their expression was readily revealed in tissues such as vas deferens, testes and lung (data not shown). No genito-urinary defects were seen in RARγ$^{-/-}$ females, which were fertile.

Resistance to retinoic acid treatment

Figure 5A:
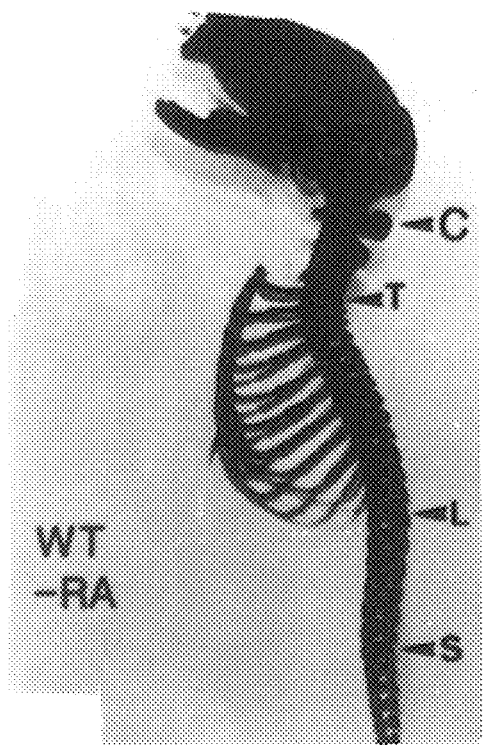
Figure 5B:
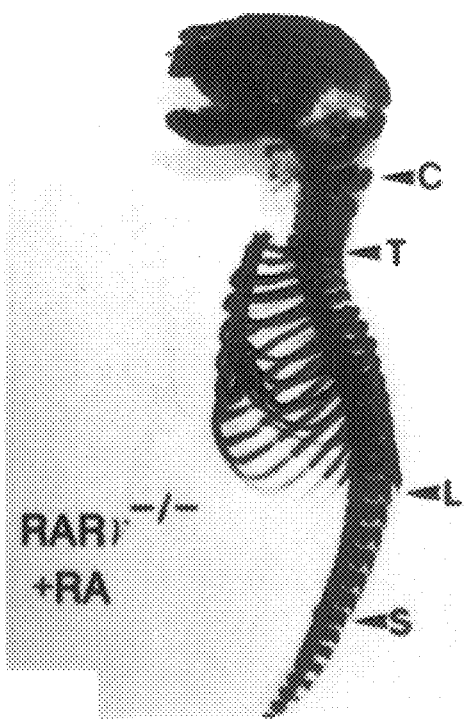
Figure 5C:
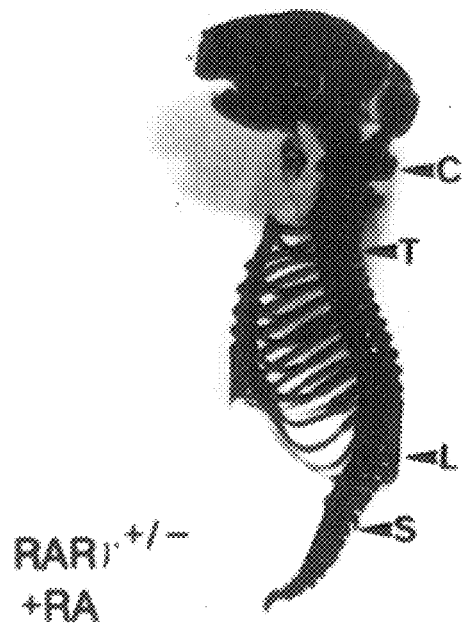
Figure 5D:
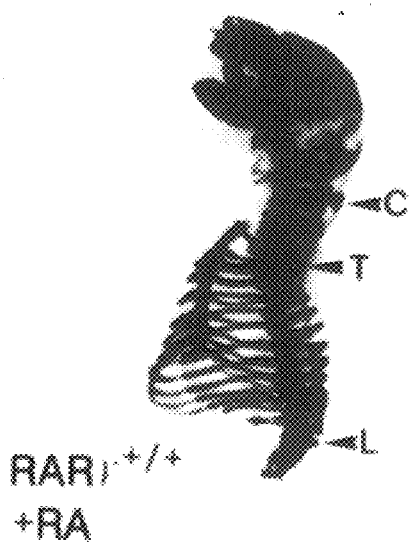
Figure 5E:
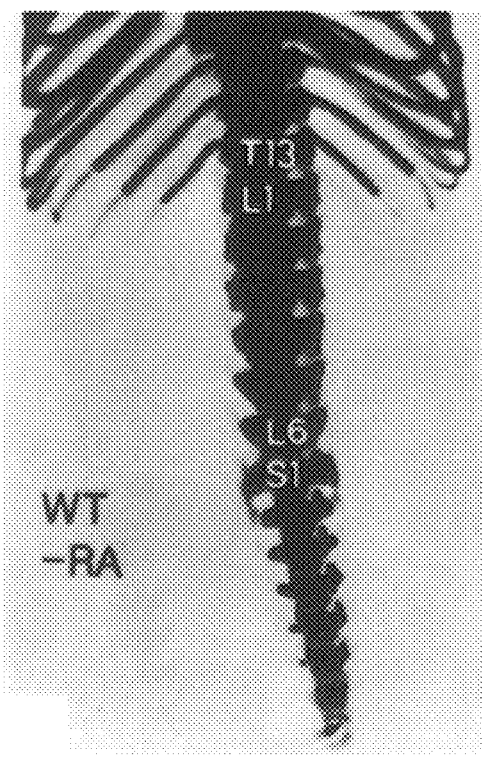

In the mouse, exposure to RA at day 8.5–9.0 p.c. has been shown to cause, among other abnormalities, craniofacial malformations, homeotic transformations of the axial skeleton, and spina bifida with complete truncation of the caudal axial skeleton (for refs see the "Description of the Related Art" section above and Gruss, Cell 67:89–104 (1991); Kessel, M., Development 115:487–501 (1992); see also FIG. 5d and h). To determine if any of these malformations could be mediated by RARγ, pregnant dams from heterozygote crosses were treated with RA at day 8.5 or 9.0 p.c., and we examined day 18.5 p.c. fetuses for skeletal malformations. Strikingly, none of the RARγ$^{-/-}$ embryos exposed to RA at day 8.5 p.c. developed spina bifida, truncation of the axial skeleton in the post-thoracic region, degenerate or fused ribs, disorganized vertebral centres or malformed neural arches in the lower thoracic-lumbar-sacral region (FIG. 5b and f, Table III). All WT fetuses exhibited these malformations as previously described (Kessel, M., Development 115:487–501 (1992); FIG. 5d and h, Table III). Interestingly, RARγ heterozygotes were partially resistant to these RA-induced truncations (compare FIG. 5c to d and g to h; see Table III), suggesting that a critical level of RARγ must be present for RA to fully induce these defects. RARγ$^{+/-}$ animals, however, always exhibited lumbo-sacral vertebral malformations, including fusion of the neural arches and disorganized vertebral centres (FIG. 5c and g, Table III). Under identical conditions, RARγ2$^{-/-}$ animals exhibited the same type and frequency of RA-induced malformations as control littermates (data not shown).

Figure 5F:
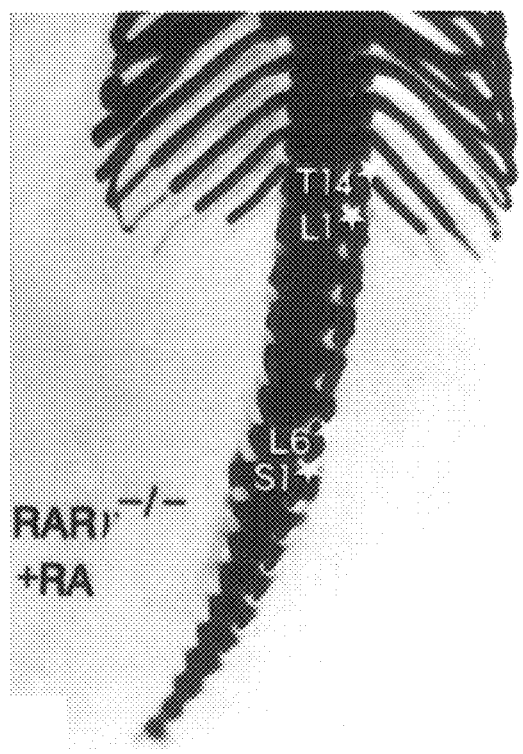
Figure 5G:
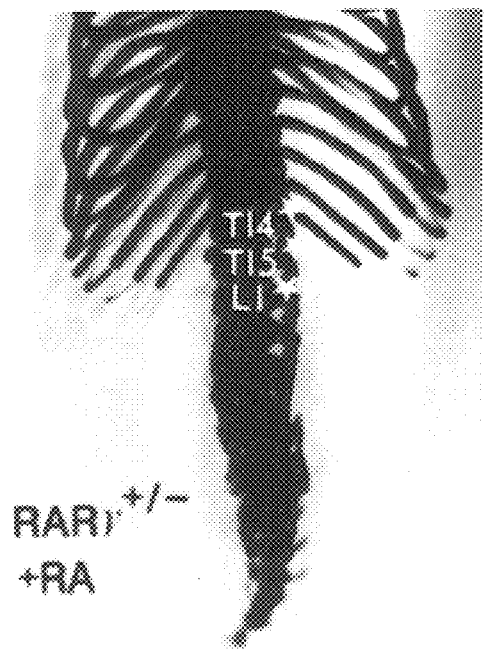
Figure 5H:
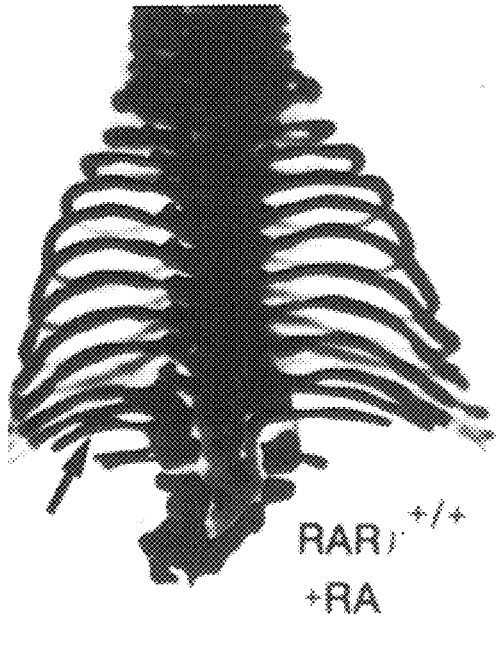

As expected from previous studies (Kessel, M., Development 115:487–501 (1992)), treatment of WT embryos with RA at day 9.0 p.c. led to progressively more posterior truncations and associated defects when compared to treatment at day 8.5 p.c. (Table III, and data not shown). Again, these malformations were never observed in RARγ$^{-/-}$ littermates (Table III). In contrast, RARγ was apparently not involved in RA-induced craniofacial malformations or thoracic homeotic transformations, e.g. anterior transformations of the eighth thoracic vertebra (Table III, FIG. 5f). Strikingly, lumbar to thoracic, sacral to lumbar and lumbar to sacral vertebral transformations also occurred in RA-treated RARγ null homozygotes (FIG. 5f, Table III, and data not shown). Similar transformations were previously seen by Kessel and Gruss, Cell 67:89–104 (1991) in WT animals treated with a lower dose of RA.

TABLE III

Comparison of RA-Induced Skeletcil Malformations In Wild Type, RARγ$^{+/-}$ And RARγ$^{-/-}$ Offspring

|  | RA treatment at day 8.5 p.c. RARγ genotype | | | RA treatment at day 9.0 p.c. RARγ genotype | | |
| --- | --- | --- | --- | --- | --- | --- |
|  | +/+ | +/- | -/- | +/+ | +/- | -/- |
| Number of fetuses examined at day 18.5 p.c. | 11 | 16 | 10 | 13 | 24 | 18 |
| Malformations |  |  |  |  |  |  |
| Craniofacial malformations Homeotic transformations: | 11 (100%) | 16 (100%) | 10 (100%) | 13 (100%) | 24 (100%) | 18 (100%) |

TABLE III-continued

Comparison of RA-Induced Skeletcil Malformations In Wild Type, RARγ[+/−] And RARγ[−/−] Offspring

| | RA treatment at day 8.5 p.c. RARγ genotype | | | RA treatment at day 9.0 p.c. RARγ genotype | | |
|---|---|---|---|---|---|---|
| | +/+ | +/− | −/− | +/+ | +/− | −/− |
| 8 vertebrostemal ribs (T8→T7) | 7 (64%) | 8 (50%) | 6 (50%) | 7 (54%) | 9 (38%) | 11 (61%) |
| 14 or 15 ribs (L→T) | 6 (54%) | 14 (87%) | 7 (70%) | 7 (54%) | 8 (33%) | 11 (61%) |
| Number of lumbar vertebrae: 5 | NA | NA | 1 (10%) | NA | NA | 1 (7%) |
| 6 | NA | NA | 9 (90%) | NA | NA | 15 (83%) |
| 7 | NA | NA | 0 (0%) | NA | NA | 3 (16%) |
| Caudal truncations | 11 (100%) | 13 (81%) | 0 (0%) | 13 (100%) | 14 (58%) | 0 (0%) |
| Malformed lumbar/sacral vertebrae | NA | 3 (19%) | 0 (0%) | NA | 10 (42%) | 0 (0%) |
| Degenerate ribs | 10 (91%) | 6 (38%) | 0 (0%) | 0 (0%) | 0 (0%) | 0 (0%) |

Table III.
Comparison of RA-induced skeletal malformations in wild type, RARγ[+/−] and RARγ[−/−] offspring.
Genotypes were derived from analysis of DNA from the placenta of day 18.5 p.c. fetuses from dams that had received a single dose of RA (100 mg/kg) at either day 8.5 or 9.0 p.c. Skeletons were prepared, and malformations scored under a dissecting microscope. Where possible, fetuses from the same litter were compared.
NA; not applicable.

Discussion

The results clearly demonstrate that the expression of at least one functional RARγ isoform is essential for normal development and physiology of the mouse. The results also show that RARγ is directly involved in the transduction of the retinoic acid signal in the animal, since some of the abnormalities seen in the RARγ null mutant mice have been previously described in animals fed a vitamin A deficient (VAD) diet, and some of the teratogenic effects of maternal RA administration do not occur in RARγ null fetuses.
Abnormalities in RARγ null mice and in animals fed a VAD diet.

Retardation of growth, emaciation, atrophy of certain organs and gross changes occurring in the eye are the main macroscopic alterations which are characteristic of animals fed a VAD diet (Wolbach, S. B., and Howe, P. R., *J. Exp. Med.* 42:753–777 (1925); for reviews and refs, see Sporn et al., *The retinoids*, Vols. 1 and 2, Sporn et al., eds., Academic Press, Orlando, Fla. (1984); Livrea and Packer, in *Retinoids*, Livrea and Packer, eds., Marcel Dekker, New York (1993)). These animals eventually die, with no obvious lethal lesions. The viability of RARγ null homozygotes is similarly impaired and no distinctive lethal lesions could be identified. Interestingly, there is a marked variability in early lethality of RARγ deficient animals, which appears to be correlated with growth-deficiency. A similar observation has been made in the case of RARα null animals (Lufkin et al., "High postnatal lethality and testis degeneration in retinoic acid receptor α (RARα) null mice," (*Proc. Natl. Acad. Sci. USA*, in press (1993))). Whether this reflects concerted effects of RARα and RARγ on the same processes whose failure leads to early death, or whether RARα and RARγ act independently on different pathways whose impairment can independently lead to death, is unknown.

Wide-spread squamous metaplasia and/or keratinizing squamous metaplasia of various epithelia is a landmark of vitamin A deprivation (Wolbach, S. B., and Howe, P. R., *J. Exp. Med.* 42:753–777 (1925); Underwood, J. N., "Vitamin A in animal and human nutrition," in *The retinoids*, Vol. 1, Sporn, M. B., et al., eds. (Academic Press, Inc., Orlando, Fla.), pp. 282–392 (1984)). This occurs in the respiratory tract (in the nares, as well as in the larynx, trachea and bronchi), in the alimentary tract (submaxillary glands, parotid gland, accessory salivary glands of the tongue and pharynx, and pancreatic ducts), in the genitourinary tract (bladder, renal pelvis, uterus and oviducts, epididymis, prostate, seminal vesicles), and eyes and related glands (conjunctiva, Meibomian gland ducts, cornea, intra and extra-orbital lacrimal glands, and Harderian glands). It was found that the seminal vesicles and prostate glands of RARγ null homozygote mature males exhibit a similar keratinizing squamous metaplasia to that described in VAD, and in which it can be reversed by RA. (Wolbach, S. B., and Howe, P. R., *J. Exp. Med.* 42:753–777 (1925); Dowling and Wald, Proc. Natl. Acad. Sci. USA 46:587–608 (1960); Howell et al., *J. Reprod. Fertil.* 5:159–167 (1963)). These epithelial transformations most probably account for the sterility of RARγ deficient males. In marked contrast, all other epithelia which exhibit squamous metaplasia in VAD animals (see above) appear normal in RARγ null animals, suggesting that the other RARs, or RXRs, can substitute for RARγ in the retinoid maintenance of these unaffected tissues. This possibility is supported by the observation that RARγ1 transcripts are the only RAR transcripts which we could detect in prostate and seminal vesicles.

Approximately 75% of the offspring of VAD females exhibit a broad array of congenital malformations which affect, among others, the eye, genitourinary tract (e.g. agenesis of the seminal vesicles and prostate), aortic arches, heart, lungs, diaphragm, kidneys, and the genital ducts (Wilson, J. G., et al., *Am. J. Anat.* 92:189–217 (1953)), none of which were seen in day 18.5 p.c. RARγ null homozygotes. Interestingly, squamous metaplasia, but not agenesis of the seminal vesicle and prostate glands occurred in RARγ[−/−] males, implicating a different RAR type in development of these organs. RARγ deficient fetuses did, however, exhibit two congenital malformations (apart from axial skeleton abnormalities). The agenesis of the Harderian gland, in which retinoic acid preferentially accumulates (Sharma et al., "Comparative distribution of retinol and all-trans retinoic acid in pregnant hamsters," in *Retinoids*, Livrea and Packer, eds., Marcel Dekker, New York, pp. 569–584 (1993)), is particularly remarkable in view of its great variability, since not all animals were similarly affected. The lack of keratinizing squamous metaplasia in the Harderian glands of RARγ null homozygotes (although it is frequently observed in VAD animals; see above), indicates that RARγ is specifically involved in Harderian gland organogenesis, but not in the maintenance of its glandular epithelium. The second congenital malformation, that of tracheal cartilaginous rings, is also remarkable, since it is the only malformation present in all RARγ null fetuses at day 18.5 p.c., and also because this cartilage is the only one affected even though RARγ is expressed in all cartilages during organogenesis (Ruberte et al., *Development* 108:213–222 (1990)). Hence, if RARγ has a general function in cartilage formation as suggested (Ruberte et al., *Development* 108:213–222 (1990)), the other RARs (or RXRs) must be able to fulfill this role in all other cartilages (e.g. larynx and bronchi). This suggests a specific role for RARγ in the development of the tracheal cartilaginous rings, since RARα transcripts are also found in the mesenchyme of the developing trachea (Dollé et al., Development 110:1133–1151 (1990)).

Approximately 50% of the RARγ null newborns are selectively cannibalized within 24 hours by their mothers. Hence, a fraction of these newborns must exhibit some abnormality that not yet detected, but is clearly recognized by mice. This phenotype was not scored in offspring from VAD dams.

Axial specification in RARγ null homozygotes

Gain-of-function (Kessel et al., *Cell* 61:301–308 (1990)); Lufkin et al., *Nature* 359:835–841 (1992)) and loss-of-function (Le Mouellic et al., *Cell* 69:251–264 (1992)) studies have shown that some Hox genes specify the identity of occipital bones and vertebrae. Although there are noteworthy exceptions (Pollock et al., *Cell* 71:911–923 (1992); Jegalian and De Robertis, *Cell* 71:901–910 (1992)), gain-of-function mutations lead to posteriorizations, while loss-of-function mutations lead to anteriorizations. That Hox gene expression could be controlled during development by retinoic acid has been suggested by the observation that some Hox gene transcripts accumulate in cultured embryonal carcinoma (EC) cells exposed to RA (most notably those of the most 3' Hox paralogues, e.g. Hoxa-1; for refs see Simeone et al, *Nature* 346:763–766 (1990); Simeone et al., *Mech. Dev.* 33:215–228 (1991); LaRosa and Gudas, *Proc. Natl. Acad. Sci. USA* 85:329–333 (1988); Papalopulu et al., *Nuc. Acids. Res.* 19:5497–5506 (1991)). Furthermore, it has been shown that RA administration at various times during gestation results in both changes in the expression of some Hox genes along the anterioposterior axis (Morriss-Kay et al., *EMBO J.* 10:2985–2995 (1991); Conlon and Rossant, *Development* 116:357–368 (1992); Marshall et al., *Nature* 360:737–741 (1992)) and anterior or posterior homeotic transformations of vertebrae, depending on the precise time of RA administration and the vertebral region which is affected (Kessel and Gruss, *Cell* 67:89–104 (1991); Kessel, M., *Development* 115:487–501 (1992)).

Loss of RARγ leads to homeotic transformations (mainly anteriorizations) which occur with variable frequencies along the anteroposterior axis, demonstrating that its presence, and presumably also RA, is required for proper specification of some cervical and thoracic vertebrae. Whether this specification is directly exerted through Hox genes remains to be established by in situ hybridization analysis. Interestingly, Hoxb-4 (Hox-2.6) gene knock-outs also result in an identical axis to atlas anterior transformation. Moreover, Hoxb-4 expression is altered in embryos from RA-treated dams (Conlon and Rossant, *Development* 116:357–368 (1992)) and Hoxd-4 (Hox-4.2), a paralogue of Hoxb-4, has been shown to contain a RA-response element (Pöpperl and Featherstone, *Mol. Cell. Biol.* 13:257–265 (1993)). It is, however, unclear at which stage of vertebral specification RARγ could be involved. RARγ transcripts have been detected posterior to the caudal neuropore in late gastrulating embryos in the mesoderm and overlying neuroectoderm where somites have not yet differentiated. RARγ expression then apparently disappears concomitant with the appearance of somites (Ruberte et al, *Development* 108:213–222 (1990)). These in situ hybridization observations clearly suggest that RARγ plays a role in somite formation and specification at a time where RA administration is known to affect both Hox gene expression and axial specification (Kessel and Gruss, *Cell* 67:89–104 (1991)). RARγ could also be involved in the specification of vertebral identity at a later stage (day 10.5 p.c.), when RARγ transcripts are found in sclerotomies. Such a possibility is supported by the observation that exposure of embryos to RA at this stage can lead to "respecification" of vertebral identities (Kessel, M., *Development* 115:487–501 (1992)). However, this late "respecification" effect could not be correlated with altered Hox gene expression, hence suggesting that RARγ may also be involved in the maintenance of vertebral identities through a mechanism not involving Hox genes. Note that homeotic transformations have not been found in fetuses from VAD dams, perhaps because it may necessitate a vitamin A deprivation too drastic to allow gestation to proceed (see Wilson, J. G., et al., *Am. J. Anat.* 92:189–217 (1953)). That the homeotic transformations described here reflect a true function of RARγ, rather than that of another closely linked gene that may have been affected during gene targeting, is supported by a marked increase in the frequency of their occurrence in mice lacking both RARγ and RARγ1 genes.

The absence of lumbosacral truncations in RARγ null fetuses treated with RA at days 8.5–9.0 p.c., demonstrates that at least some of the functions of the various RARs can be specific. Similar resistance to RA-induced malformations was not observed in RARα1 null homozygotes, even though this receptor is co-expressed with RARγ in the caudal presomitic mesoderm at this developmental stage (Ruberte et al., *Development* 108:213–222 (1990)). Paradoxically, further studies have indicated that RARγ2 is the major RARγ isoform expressed at this stage in the caudal presomitic mesoderm (C. Wolf, Ph. K. and P. C., unpublished results), yet RARγ2 null homozygotes display the same frequency of RA-induced malformations as their WT and heterozygote littermates. Clearly, a lower level of expression of RARγ1 (relative to RARγ2) is sufficient to mediate the lumbosacral truncations which lead to spina bifida. Interestingly, RA administration is still able to induce vertebral homeotic transformations in the lumbosacral and more rostral regions of the axial skeleton of RARγ null homozygotes, thus indicating that these transformations are not mediated by RARγ. The lack of defects in the lumbosacral region of untreated RARγ null homozygotes implies that the RARγ-mediated RA-induced malformations are unlikely to reflect the perturbation of a "normal" function of RARγ, but rather a pharmacological effect with no physiological counterpart. Hence, care should be taken in extrapolating from teratogenic effects to the physiological functions of RA.

It has been recently reported that Hoxa-1 (Hox 1.6) contains a RA response element (Langston and Gudas, *Mech. Dev.* 38:217–228 (1992)) and Hoxa-1 RNA is induced by RA (LaRosa and Gudas, *Proc. Natl. Acad. Sci. USA* 85:329–333 (1988); Simeone et al., *Mech. Dev.* 33:215–228 (1991)). Knock-outs of the Hoxa-1 gene have generated specific alterations (e.g. of the inner ear and of acoustico-facial nerves and ganglia), in the region which corresponds to its rostral domain of expression (Lufkin et al., *Cell* 66:1105–1119 (1991); Chisaka et al., *Nature* 355:516–520

(1992)). No similar alterations were seen in either RARγ or RARα null homozygotes (Lufkin et al., "High postnatal lethality and testis degeneration in retinoic acid receptor α (RARα) null mice," (*Proc. Natl. Acad. Sci. USA*, in press (1993))), indicating that either Hoxa-1 expression is not RA-dependent, or that the different RARs are functionally redundant for Hoxa-1 gene expression. A similar redundancy may account, at least in part, for the lack of significant changes in the levels of the RA-responsive RAR isoforms RARα2 (Leroy et al., *Proc. Natl. Acad. Sci. USA* 88:10138–10142 (1991)) and RARβ2 (Zelent, A., et al., *EMBO J*. 10:71–81 (1991); Mendelsohn et al., *Development* 113:723–734 (1991); and refs therein) in RARγ null homozygotes (FIG. 1*d*) or RARα null homozygotes (for RARβ2) (Lufkin et al., "High postnatal lethality and testis degeneration in retinoic acid receptor α (RARα) null mice," (*Proc. Natl. Acad. Sci. USA*, in press (1993))).

It is widely assumed that RA plays a critical role in limb pattern formation, possibly as a morphogen (reviewed in Tabin, C. J., Cell 66:199–217 (1991)). This assumption has been supported by the demonstration that a topical application of RA can trigger the expression of the Hox genes which are thought to be instrumental in specifying the anteroposterior axis of the limb (reviewed in Duboule, D., *BioEssays* 14:375–384 (1992)). It is remarkable that RARγ null mutants do not display any limb malformations, even though RARγ is uniformly expressed in the limb bud at the time of morphogenesis, and its expression becomes selectively restricted to precartilage condensations at later stages (Dollé et al., *Nature* 342:702–705 (1989); Ruberte et al., *Development* 108:213–222 (1990)). Since RARα (but not RARβ) is ubiquitously expressed in the limbs at these stages, RARγ and RARα may fully finctionally overlap, since limb defects were also not observed in RARα null homozygotes (Lufkin et al., "High postnatal lethality and testis degeneration in retinoic acid receptor α (RARα) null mice," (*Proc. Natl. Acad. Sci. USA*, in press (1993))). Double null mutants for both RARα and RARγ have to be generated to further investigate the actual role of RA in normal limb development.

Functional redundancy in the RA receptor multigene family and variations in mutation penetrance and expressivity.

It has been previously shown that RARγ transcripts, which are first detected at day 8.0 p.c. in all three germ layers in the presumptive posterior region of the embryo, are then found between days 9.5 and 11.5 p.c. uniformly distributed in the mesenchyme of the frontonasal region, pharyngeal arches, limb buds and sclerotomies (Ruberte et al., *Development* 108:213–222 (1990)). At day 12.5 p.c., RARγ transcripts are found in all precartilaginous mesenchymal condensations as well as in the genital tubercle mesenchyme. From day 13.5 p.c., RARγ transcripts become specifically restricted to all cartilages, irrespective of whether they will subsequently ossify or not, and to all differentiating keratinizing squamous epithelia (skin, oral cavity, oesophagus, left wall of the stomach), as well as to developing teeth and whisker follicles. At day 14.5 p.c. and later, RARγ transcripts are found in all three skin layers (Dollé et al., *Development* 110:1133–1151 (1990); Ruberte et al., *Development* 108:213–222 (1990). The present study clearly establishes that the presence of RARγ is not critically required for most of these tissues to be formed or maintained. With the exception of abnormalities of cervical and thoracic vertebrae, no other skeletal malformations were found in RARγ null mutants. Similarly, the tracheal cartilage was the only cartilage to be malformed, and all keratinizing squamous epithelia, including skin, were normal in RARγ null mutants. The absence of malformations in tissues and organs derived from the mesenchyme of the branchial arches and the genital tubercle is also noteworthy.

These apparently discordant observations indicate that RARγ transcripts are expressed in many places in the embryo and in the adult animal where the RARγ protein is either never synthesized or, if synthesized, is not playing any critical role. Alternatively, or additionally, there could be a considerable functional overlap between members of the RA receptor family. Indeed functional redundancy appears to be a recurrent theme among members of multiple gene families (reviewed in Tautz, D., *BioEssays* 14:263–266 (1992); Brookfield, J., *Evolutionary Genet*. 2:553–554 (1992)). Since RARα (essentially RARα1) appears to be ubiquitously expressed, it could possibly substitute for most RARγ functions, the exceptions corresponding to the observed defects. These may correspond to either subsets of genes whose expression is specifically controlled by RARγ, or to cells which express predominantly RARγ. The absence of any detectable abnormalities in RARγ2 null mutant mice represents an extreme case of redundancy, where all RARγ2 functions would be apparently fulfilled by RARγ1 or another RAR. Note, however, that the evolutionary conservation of the RARγ2 isoform from fish to man, both in sequence and expression pattern (Ellinger-Ziegelbauer and Dreyer, *Genes and Dev*. 5:94–104 (1991)) necessarily implies that it performs a specific function. This function may be difficult to uncover, since it may require examination of RARγ2 null animals in the wild and/or a study of a large number of animals: to have a 95% chance of finding significant evidence for a 5% viability disadvantage (which is significant over evolutionary times) would require examination of more than 20,000 individuals (Kimura, M., *Genetics* 47:713–719 (1962); Brookfield, J., *Evolutionary Genet*. 2:553–554 (1992)).

An extensive functional redundancy amongst RARs should in fact not be too surprising, since with the exception of the N-terminal A/B regions, all three RARs and their isoforms are still very similar in their amino acid sequence (Leid et al., *TIBS* 17:427–433 (1992)), and hence may still perform a number of common regulatory functions, albeit possibly with different efficiencies. Variations in these efficiencies, which may be affected by the genetic background, could account for the variable penetrance of most of the abnormalities seen in the RARγ null mutants. The hypothesis that functional redundancy between RARα and RARγ may be at least partially responsible for the observed variations in the penetrance of most of the RARγ null mutant defects is supported by preliminary results obtained with mice lacking both RARγ and RARα1. In contrast to RARγ null homozygotes, all RARγ null/RARα1 null double homozygotes present a complete bilateral agenesis of the Harderian glands. In this respect, it is important to note that RARα1 null homozygotes do not display any abnormal phenotype (Lufkin et al., "High postnatal lethality and testis degeneration in retinoic acid receptor α (RARα) null mice," (*Proc. Natl. Acad. Sci. USA*, in press (1993))).

The variability, within a given animal, in the expressivity of a number of abnormalities of the RARγ null mutant phenotype (eg. Harderian glands) obviously cannot be ascribed to variations in genetic background. However, this variability is also likely to be related, at least in part, to functional redundancy between the various RARs, as exemplified by the complete bilateral agenesis of the Harderian glands in all RARα1 null/RARγ null double homozygotes. Hence, the variations in expressivity of the RARγ null mutation in this bilateral structure most probably reflect the stochastic nature of gene activity in single cells (reviewed in Ko, M. S. H., *BioEssays* 14:341–346 (1992)), which may itself be dependent on variations in RARα1 cellular levels and/or in regulatory factors which synergize with RARα1. Similar stochastic variations may account for the occurrence of unilateral homeotic transformations in the cervical and thoracic regions (FIG. 2 and Table II), and more generally of any asymmetrical malformation of bilateral or symmetrical structures.

Making additional mouse mutants lacking more than one receptor type or isoform should reveal the extent of redundancy between RA receptors, and the actual specific physiological functional role played by each RAR and RXR in retinoid signalling in vivo.

EXAMPLE 2

Function of Retinoic Acid Receptor α (RARα) in the Mouse

High Postnatal Lethality and Testis Degeneration in Retinoic Acid Receptor α (RARα) Mutant Mice To investigate the function of RARα in the mouse, either the whole gene or specifically the RARα1 isoform has been knocked-out. A disruption of the whole gene leads to high postnatal lethality and testis degeneration with no other detectable developmental or postnatal abnormalities, suggesting that besides its requirement for the maintenance of spermatogenesis, the function of RARα is critical only for some homeostatic processes. Interestingly, RARα1 null mutant mice had no detectable phenotype, which suggests a surprising redundancy between RAR isoforms.

Experimental Procedures

RARα Homologous Recombination

Figure 6A:
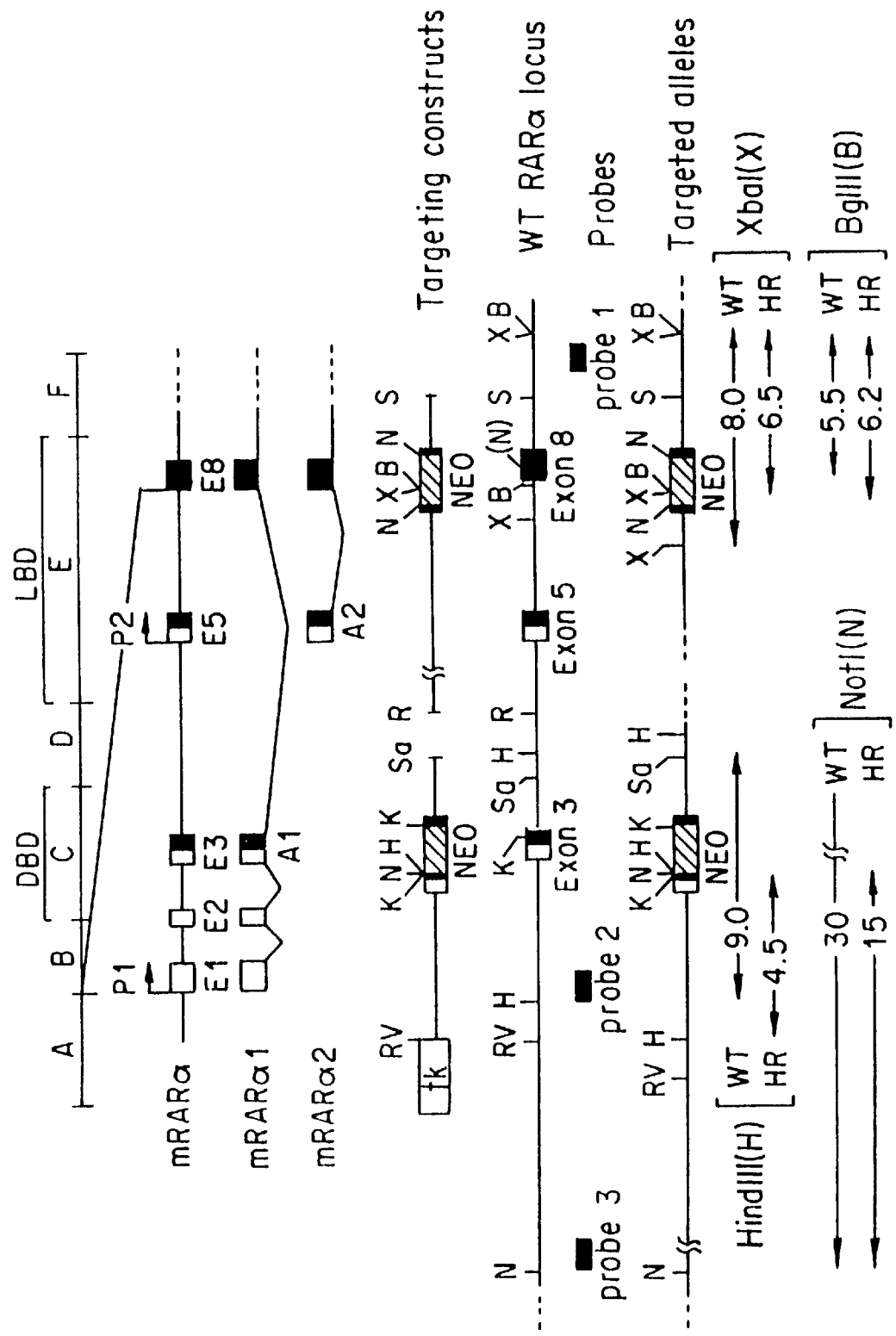
Figure 6B:
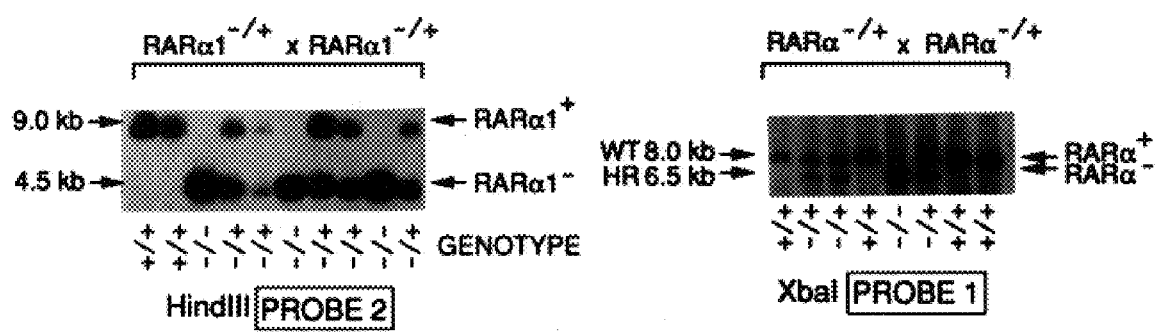

Mutant alleles of the RARα gene were created by homologous recombination using the "replacement" vector strategy (M. R. Capecchi, *Science* 244:1288 (1989)) (FIG. 6a). For the RARα full disruption, the construct was prepared as follows. The 23 kilobase pair (kb) SalI insert from the phage λG2mRARα (Leroy et al., *EMBO J.* 10:59 (1991)) was partially end-filled and subcloned into the partially end-filled BamHI site of pBluescriptSK+ to create plasmid p231. The 11 kb EcoRI-SpeI fragment (containing the A2 and B regions of RARα) from p231 was subcloned into the EcoRI-XbaI sites of pTZ18R to create plasmid p807. Site-directed mutagenesis (using an oligo with 20 nucleotide flanking arms) was performed on single-strand DNA from p807 to insert a seven nucleotide mutation (TGAGCGG) after the CCA encoding the proline at amino acid 19 of the B region (Leroy et al., *EMBO J.* 10:59 (1991)) creating an in-frame stop (TGA) and a unique NotI restriction site to generate plasmid p819, into which the 1.7 kb NotI fragment containing the GTI-II enhancer-driven neomycin gene (purified from p581, Lufkin et al., *Cell* 66:1105 (1991)) was cloned to generate p826B1, which was linearized at the unique SalI site and used for electroporation. p826B 1 has 8 kb of homologous genomic DNA sequence 5', and 3 kb of homologous sequence 3' to the NotI site of the neomycin insertion. For the RARα1 isoform disruption, a 9 kb EcoRV-SalI fragment from λG1mRARα (Leroy et al., *EMBO J.* 10:59 (1991)) was subcloned into pBluescript+ to generate pD182, which was partially digested at the KpnI site (at amino acid 19 of the A1 region) into which was subcloned the 1.4 kb KpnI enhancer-less RSV-TATA box-driven neomycin gene fragment (derived from p581, Lufkin et al., *Cell* 66:1105 (1991)) to generate pD183, which was subsequently digested with EcoRV and ligated with the 2.3 kb GTI-II enhancer-driven HSV-tk gene fragment [purified from p565 (Lufkin et al., *Cell* 66:1105 (1991)) by digesting with EcoRV] to generate plasmid pD209 which was linearized at the unique SpeI site and used for electroporation into D3 embryonic stem cells (Gossler et al., *Proc. Natl. Acad. Sci. USA* 83:9065 (1986); Lufkin et al., *Cell* 66:1105 (1991)). pD209 contains 8.0 kb and 1.0 kb of homologous DNA sequence 5' and 3' respectively, to the site of neomycin insertion. Genomic DNA extraction, Southern blotting, ES cell culture, generation of chimeras, and probe preparation were as described (Lufkin et al., *Cell* 66:1105 (1991)). Probes 1, 2 and 3 correspond to a 1.4 kb XbaI-SpeI fragment from p231, a 0.8 kb BamHI fragment from λG1 mRARα, and a 1.4 kb NotI-SmaI fragment from λG1 mRARα, respectively. Both probes 2 and 3 were used in the case of the RARα1 disruption.

Two types of mutant alleles were generated. The first mutant allele (termed RARα) prevents the synthesis of all isoforms of RARα by disruption of exon 8 which encodes the receptor region B common to all isoforms. The second mutant allele (termed RARα1) selectively prevents the synthesis of the RARα1 isoform by disruption of exon 3 which encodes the RARα1-specific region A1. Following electroporation into D3 embryonic stem (ES) cells (Gossler et al., *Proc. Natl. Acad. Sci. USA* 83:9065 (1986)) and selection in G418 (or G418 and gancyclovir in the case of the RARα1 disruption), resistant ES clones were expanded and analyzed by Southern blotting for a homologous recombination event (data not shown, see FIG. 6a and b). The RARα and RARα1 constructs gave 7 and 3 homologous recombination events per 32 and 22 resistant colonies, respectively. 5 and 3 positive ES clones for RARα and RARα1 mutations were injected into 890 and 498 blastocysts, which resulted in 25 and 23 male chimeric animals, respectively. One of the RARα ES clones (KC25) and 3 of the RARα1 ES clones (KA3, KA5, and KA26) gave germ-line transmission. The heterozygous mice for either mutation appeared healthy, normal, and were fertile. Intercrossing of heterozygous mice for either mutation produced homozygous offspring (FIG. 1b, and below).

RNase Protection Analysis

Figure 6D:
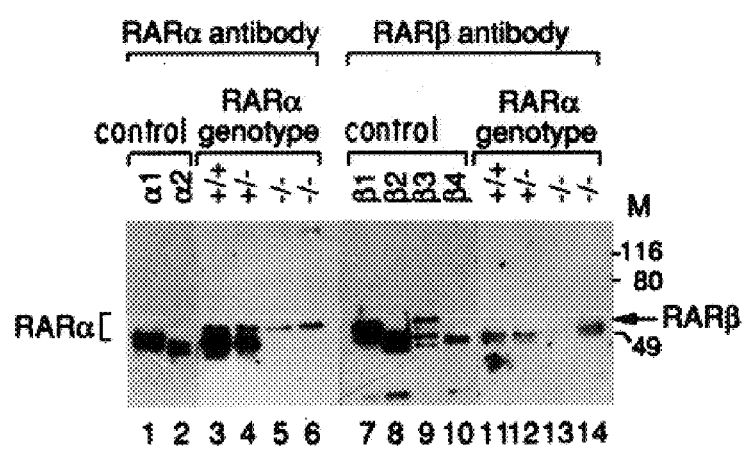
Figure 6C:
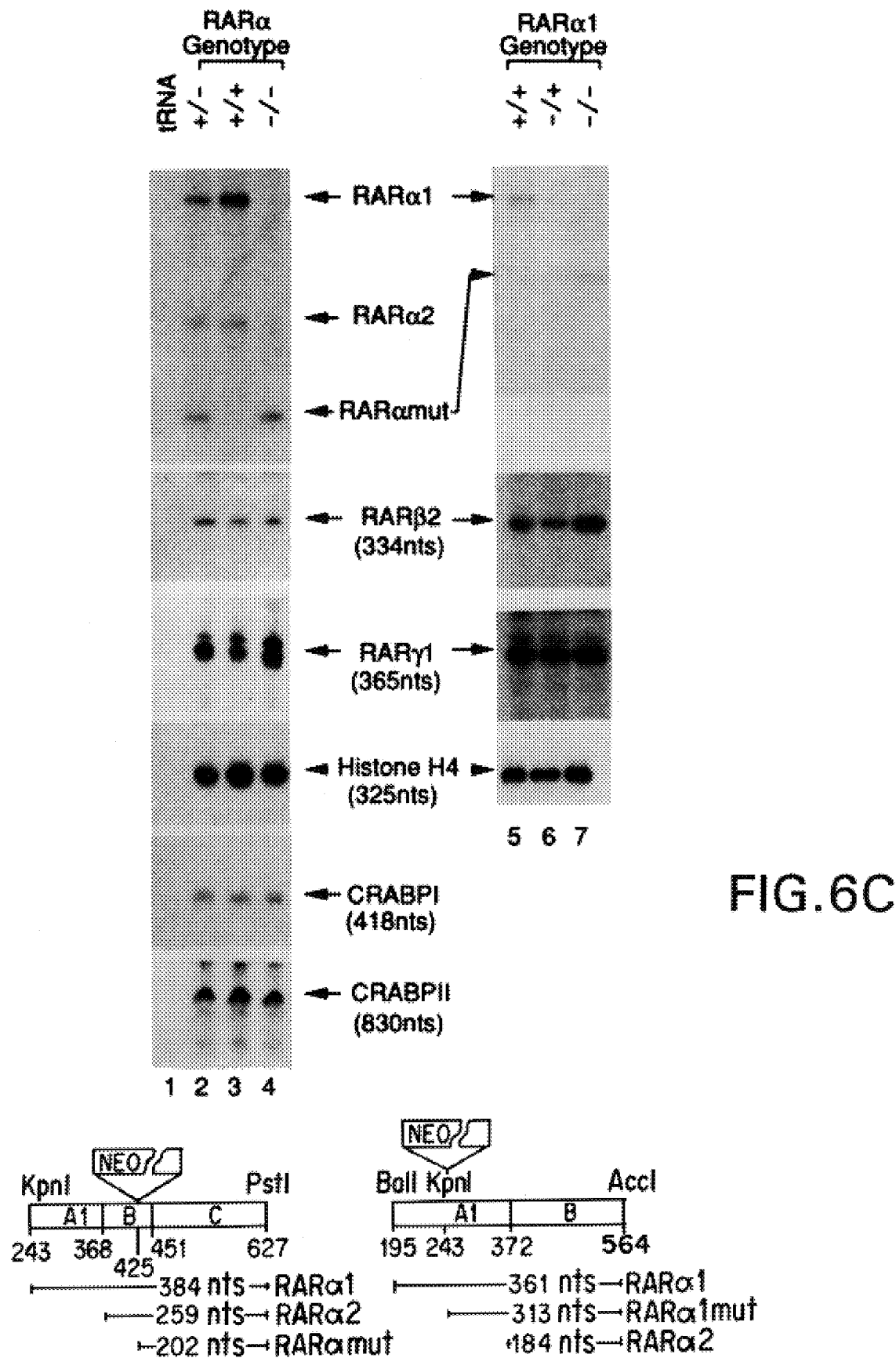
Figure 8A:
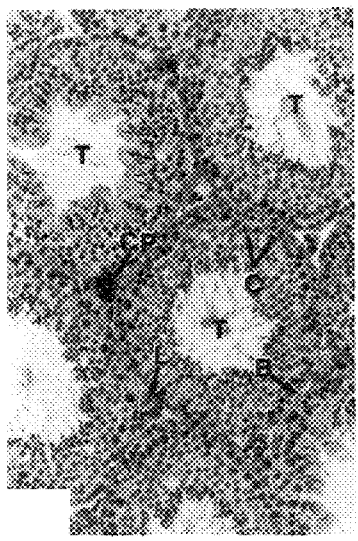
Figure 8B:
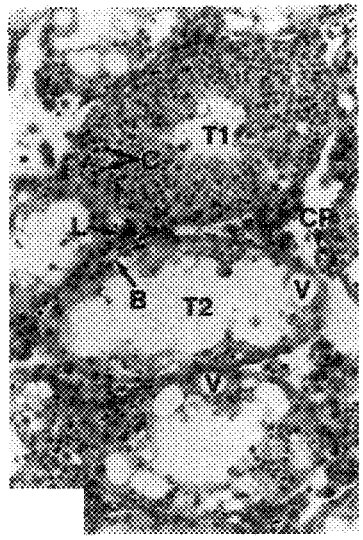
Figure 8C:
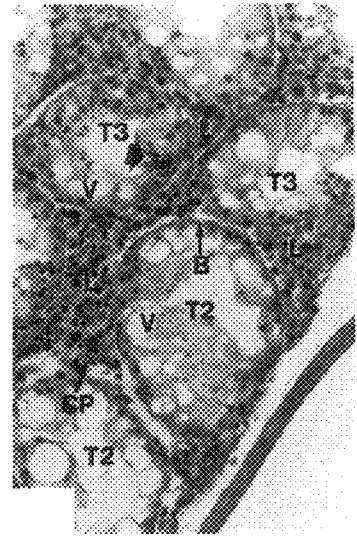
Figure 8D:
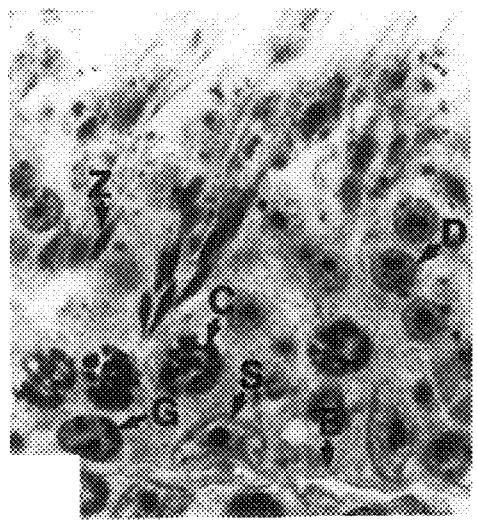
Figure 8E:
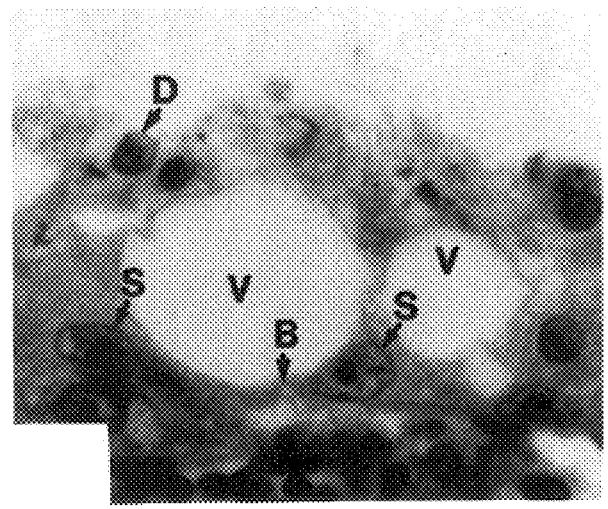
Figure 8F:
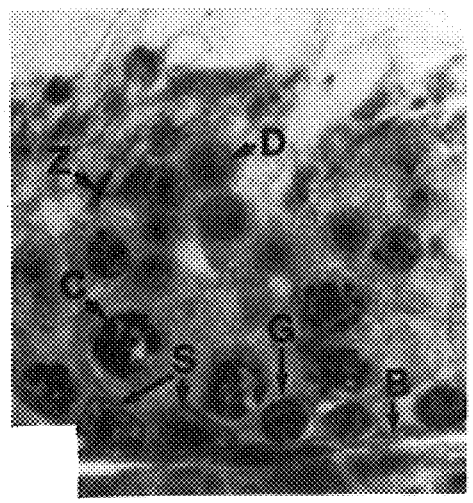
Figure 8G:
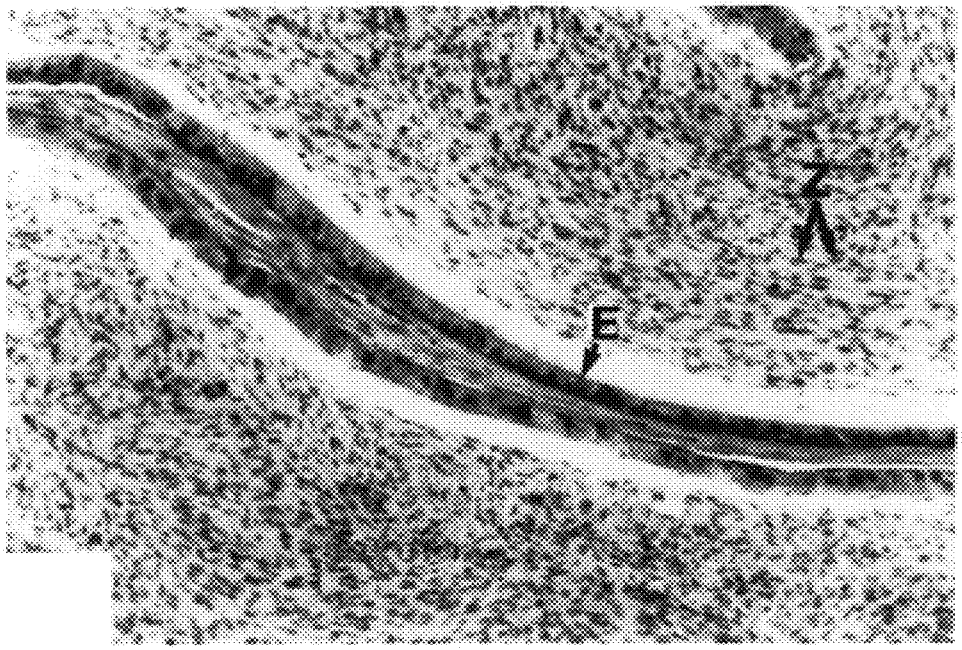
Figure 8H:
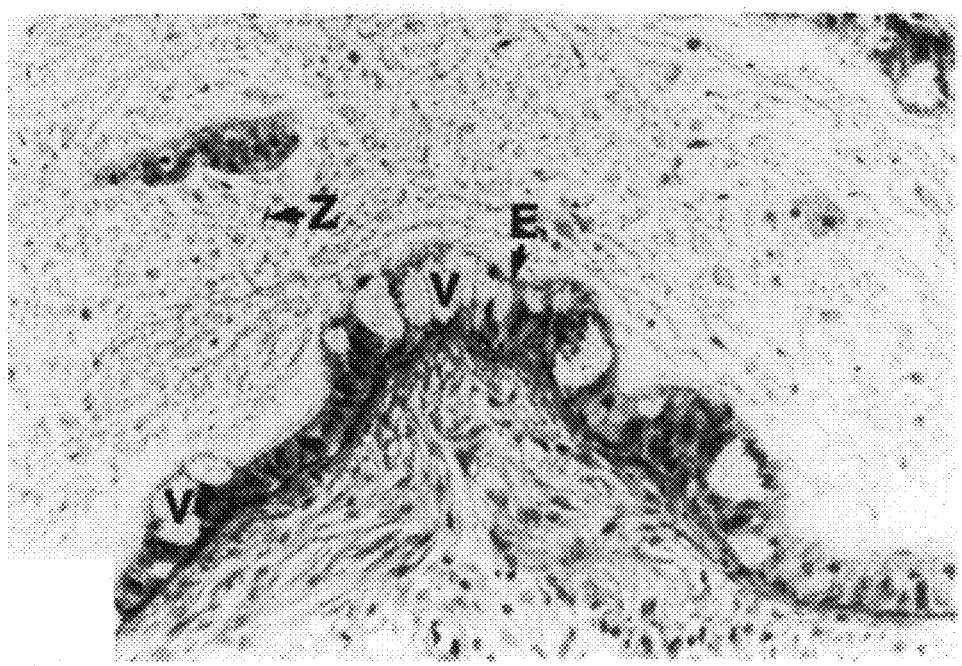

To verify that the RNAs encoding the RARα and RARα1 proteins were disrupted, a RNAse protection assay was performed using RNA from day 13.5 p.c. embryos (a time at which RARα RNA is abundantly expressed, see Ruberte et al., *Development* 111:45 (1991)) (FIG. 6c). RNA was purified by the single-step guanidinium-isothiocyanate-phenol technique as described (P. Chomczynski and N. Sacchi, *Analytical Biochem.* 162:156 (1987)) with the addition of a phenol-chloroform extraction step. 50 μg of embryo RNA was used per hybridization reaction which was at 55° C. for 8–12 hrs. The conditions for probe preparation and RNAse protection were essentially as described (Sambrook et al., eds., *Molecular Cloning: A Laboratory Manual*, Cold Spring Harbor Laboratory Press, Cold Spring Harbor, N.Y. (1987)). Conditions for transcribing with T7 RNA polymerase was as recommended by the supplier (Promega Biotec). Plasmid constructions (used as templates to transcribe antisense [$^{32}$P]-labelled RNA probes) were as follows. For RNAse protection of RARα in the RARα gene disruption, the 384 bp KpnI-PstI RARα cDNA fragment (Leroy et al., *EMBO J.* 10:59 (1991)) spanning the A1-C region was cloned into the KpnI-PstI site of pTZ19U to generate plasmid p971, which was linearized at the unique XmnI site and transcribed with T7 polymerase; for RARα in the RARα1 disruption, the 361 bp BalI-AccI fragment from the RARα1 cDNA (Leroy et al., *EMBO J.* 10:59 (1991)) was subcloned into pBluescriptSK+ which was linearized at the XhoI site and transcribed with T7 polymerase; for CRABPI, the 418 bp EcoRI-AvaI cDNA fragment (C. M. Stoner and L. J. Gudas, *Cancer Research* 49:1497 (1989)) was endfilled with Klenow enzyme at the AvaI site prior to digestion with EcoRI, and then subcloned into the EcoRI-SmaI site of pTZ19U to generate plasmid p948 which was linearized at the unique ScaI site and transcribed with T7 polymerase; the plasmid for the CRABPII RNAse protection contains the 830 bp EcoRI-HindIII CRABPII cDNA (Giguère et al., *Proc. Natl. Acad. Sci. USA* 87:6233 (1990)) fragment cloned into the EcoRI-HindIII sites of pBluescriptSK+ which was linearized at the unique ScaI site and transcribed with T7 polymerase; for mouse Histone H4, the 630 bp EcoRI-HindIII Histone H4 genomic fragment was subcloned into the EcoRI-HindIII site of pTZ19U to generate p323 which was linearized at the unique NaeI site and transcribed with T7 polymerase; for RARγ, nucleotides 235–600 of the RARγ1 cDNA spanning the A1-C regions were amplified by PCR with oligos containing BamHI and EcoRI sites at the end, the PCR fragment was digested with BamHI and EcoRI and subcloned into the BamHI-EcoRI site of pBluescriptSK+, which was linearized with BamHI and transcribed with T7 polymerase; the plasmid for RARβ RNAse protection was created as follows: the 334 bp PstI RARβ2 cDNA fragment spanning the A2-C regions was subcloned into the PstI site of pBluescriptSK+, linearized with BamHI and transcribed with T7 polymerase. The sizes of the protected fragments are as indicated.

Results

Expression of RARα Isoforns

As expected, wild type embryos and embryos heterozygote for the RARα mutation expressed the two major RARα isoforms (RARα1 and RARα2; FIG. 6c, lanes 2 and 3). However, in the RARα null homozygotes, only the mutant form of the RARα RNA was present (RARαmut; FIG. 6c, compare lane 4 with lanes 2 and 3). Similarly, for the RARα1 mutation, wild type and heterozygote embryos expressed wild type RARα1 and α2 RNAs (FIG. 6c, lanes 5 and 6, and data not shown), but only the mutant form of the RARα1 RNA (RARα1 mut) and the RARα2 RNA were detectable in the RARα1 homozygotes (FIG. 6c, compare lane 7 with lanes 5 and 6, and data not shown). Examination of the RNA levels of the two other RARs (RARβ and RARγ) showed no significant variation between wild type, heterozygote or homozygote embryos for either mutation (FIG. 6c), indicating that globally RARα does not play a unique role in controlling RARβ and RARγ whose expression has been shown to be enhanced by retinoic acid (Mendelsohn et al., *Development* 113:723 (1991); Lehmann et al., *Mol. Cell. Biol.* 12:2976 (1992); and refs therein). Verification that no RARα protein was present in the RARα homozygotes was achieved by western blot analysis of nuclear proteins isolated from day 13.5 p.c. RARα wild type, heterozygote, and homozygote embryos (FIG. 1d). For Western blot analysis, the embryo was thawed on ice, transferred to 3 ml of lysis buffer (20 mM KCl, 10 mM Tris-HCl pH 7.0, 1 mM MgCl2, 1.5 mM EDTA, 10% glycerol, 1 mM PMSF) and dounced with 20–30 strokes of an "A" pestle. Complete cellular lysis and liberation of nuclei was verified by microscope analysis of an aliquot. Nuclei were spun out at 2000 g for 5 minutes at 4° C. The cytosolic supernatant was removed and stored at −80° C. Nuclei were subsequently extracted in lysis buffer containing 0.6M KCl and 25% glycerol. Debris was removed by spinning at 105,000 g for 1 hr. Protein concentration was determined by a calorimetric assay (Bio-Rad). Whole cell extracts from Cos-1 transfected cells were prepared as described (Rochette-Egly et al., *J. Cell Biol.* 115:535 (1991)). Sample denaturation, electrophoresis, transfer to nitrocellulose, blocking, and antibody probing were as described (Rochette-Egly et al., *J. Cell Biol.* 115:535 (1991)). Detection of the primary antibody was performed with Protein-A coupled horseradish peroxidase binding followed by chemiluminescence detection as described by the manufacturer (Amersham). Rabbit polyclonal antibodies specific to RARα [RPα(F)] and RARβ [RPβ(F)2] were generated as described (Gaub et al., *Experimental Cell Res.* 201:335 (1992); Rochette-Egly et al., *Mol. Endocrinology* 6:2197 (1992)).

Using antibodies directed against the C-terminal F region of RARα, the RARα protein was readily observed in wild type and heterozygote RARα embryo extracts (FIG. 6d, lanes 3 and 4), whereas no specific RARα protein was detected in RARα homozygotes (FIG. 6d, lanes 5 and 6). In agreement with the results of RNA analysis, immunoblotting with antibodies directed against the F region common to all RARβ isoforms did not reveal any significant variation (within the sensitivity of the assay) between the same protein extracts (compare FIG. 6d, lanes 11–14).

Viability of RARα and RARα1 Null Homozygotes

The viability of RARα and RARα1 null homozygotes was determined by intercrossing heterozygous animals and analyzing the distribution of offspring at various times during gestation and following birth. RARα1 null homozygotes represented ~25% of the offsprings at all gestational and post-natal stages (Table 4, and data not shown). Furthermore, RARα1 homozygotes were fertile and intercrossing of homozygotes generated litters of RARα1 null animals which appear healthy, fertile, and phenotypically normal. Histological analysis and wholemount skeletal staining did not reveal any detectable malformations in the RARα1 null homozygotes. When analyzed during gestation or caesarian-delivered at day 18.5 p.c., RARα null homozygotes also represented ~25% of all embryos and fetuses, demonstrating that full disruption of the RARα gene is not embryonic lethal. No obvious malformations or lesions could be macroscopically or histologically detected. However, genotyping of animals as soon as 12–24 hours post-partum (p.p.) showed a 60% deficiency of RARα null homozygotes. Yet all caesarian-delivered animals survived up to 24 hrs when isolated from their dams, indicating that up to 60% of the homozygotes had been preferentially cannibalized by their mother during this brief period (see Table IV, 1 day p.p.). Analysis at increasingly later times showed a continuing decrease in RARα null homozygotes relative to wild type and heterozygote littermates, with homozygotes representing only 3% of the total population at 1–2 months of age (Table IV). In fact, 75% of the RARα null homozygotes which remain after one day will disappear during the following 1–2 months. Some of these animals showed a slower growth rate after 1–2 weeks, and before death became emaciated and lethargic. No obvious malformations or lesions could be detected, with the exception that 60% of these homozygotes displayed webbed digits on both forelimbs and hindlimbs; however the precise digits fused varied between individuals and between limbs within the same animal (FIG. 7). This interdigital webbing never regressed and persisted until the death of the animal. Alizarin red/alcian blue staining of bone and cartilage showed that the webbed phenotype was restricted to soft tissues (FIG. 7). This phenotype was not seen in wild type or RARα heterozygous animals for which the digits become fully separated by 2 weeks of age.

The small number of remaining RARα homozygotes which survived for more than 2 months surprisingly appeared superficially normal, being of similar size as their wild type or heterozygote littermates, but none of the five males tested (up to the age of 5 months) sired any offspring, even though caged with fertile wild type females. Examination of the testes of four of these males at the age of 4–5 months showed severe degenerative changes of the germinal epithelium (FIG. 8). The parenchyma of the testes of RARα null homozygotes displayed patchy lesions of the seminiferous tubules, with rare tubules which appeared histologically normal (T1, FIG. 8b and f; compare with 2a and d), while adjacent tubules were markedly atrophic (T3, FIG. 8c) and/or mostly devoid of spermatogenic cells (e.g. spermatogonia, spermatocytes, spermatids and spermatozoids; see T2 in FIG. 8b and c, and FIG. 8e). In addition, vacuolation was frequently seen within the cytoplasm of Sertoli cells (v, compare FIG. 8b and c with FIG. 8a, and FIG. 8e with FIG. 8d), and cytoplasmic expansions of these cells often partially filled the lumen of the seminiferous tubules (T2, see FIG. 8b, c and e). The lumen of the epididymal duct of RARα null homozygotes contained very few spermatozoids (Z, compare FIG. 8g and h). Thus, spermatogenesis appeared to be drastically reduced in the testes of RARα null homozygotes, although it was not totally abolished as indicated by the presence of a few spermatozoids in the seminiferous epithelium of rare tubules and in the lumen of the epididymal duct. In contrast no lesions were observed in the seminal vesicles and prostate (not shown).

Involvement of RARα in the Maintenance of Homeostatic Processes

Animals fed a vitamin A-deficient (VAD) diet develop a syndrome, which includes among others the following symptoms: widespread substitution of keratinizing squamous epithelium for normal epithelium, atrophy of several glandular organs, eye lesions, testis degeneration, and emaciation (S. B. Wolbach and P. R. Howe, *J. Exp. Med* 42:753 (1925); B. Underwood, in *The Retinoids* 1, Sporn, et al., eds., Academic Press, Inc., Orlando, Fla., pp. 282–392 (1984); Thompson et al., *Proc. Royal Society* 159:510 (1964)). These animals eventually die. In addition, offspring of VAD females exhibit a broad array of abnormalities which mainly involve the eye, the genito-urinary tract, the kidney, the heart, and the lung (Wilson et al., *Am. J. Anat.* 92:189 (1953)). The present results demonstrate that RARE plays a crucial role in transducing the retinoid signal in the animal, since ~90% of the RARα null homozygotes die before the age of two months. As is the case for the VAD syndrome, some of these animals have a slower rate of growth and become emaciated, even though no specific lethal lesions can be identified macroscopically or histologically. Thus, RARα appears to be involved in the maintenance of some homeostatic processes, as has been previously inferred from its apparently ubiquitous expression in the adult animal (M. Leid et al., *Trends in Biochem. Sci.* 17:427 (1992); Leroy et al., *EMBO J.* 10:59 (1991); Dollé et al., *Development* 110:1133 (1990); Ruberte et al., *Development* 111:45 (1991)). Surprisingly, with the exception of testis degeneration, RARα null homozygotes do not display any of the VAD-associated lesions, and histomorphogenesis is apparently normal. These observations suggest that the other RARs and/or RXRs (M. Leid et al., *Trends in Biochem. Sci.* 17:427 (1992) for refs) may mediate the retinoid signal in the events which are reflected by the occurrence of specific VAD developmental abnormalities and post-natal lesions, or alternatively, that the other RARs and RXRs can substitute for RARA in the retinoid control of these events. Note, however, with respect to this possible redundancy, that the domains of expression of the other RAR and RXR transcripts generally appear to be more restricted than that of RARα (M. Leid et al., *Trends in Biochem. Sci.* 17:427 (1992); Leroy et al., *EMBO J.* 10:59 (1991); Dollé et al., *Development* 110:1133 (1990); Ruberte et al., *Development* 111:45 (1991); Dollé et al., *Nature* 342:702 (1989); Mangelsdorf et al., *Genes & Develop.* 6:329 (1992)). This suggests that either the expression domains of the other RARs are wider than revealed by in situ hybridization, or that in many locations, transcription of the RARα gene does not reflect an actual function of the receptor.

The Role of RA in Spermatogenesis

It has been claimed that vitamin-A (ROL) deficiency leads to testis degeneration which cannot be reversed by RA administration, implying that ROL plays a unique role not only in vision, but also in spermatogenesis (Thompson et al., *Proc. Royal Society* 159:510 (1964); McHowell et al., *J. Reprod. Fertil.* 5:159 (1963)). The present study shows that the presence of RARα, and therefore most probably of RA, is required for maintenance of a functional germ line epithelium in adult males. Interestingly, the degeneration of the germinal epithelium in RARα null homozygotes is similar, if not identical, to that observed in males maintained on a VAD diet (McHowell et al., *J. Reprod. Fertil.* 5:159 (1963); Ismail et al., *Am. J. Anat.* 188:57 (1990); and refs therein). Thus, the results strongly suggest that it is RA, and not ROL, which is required for the maintenance of spermatogenesis. This conclusion is also supported by recent observations which have shown that the repeated administration of high doses of RA can in fact restore spermatogenesis in males fed a VAD diet (H. M. M. Van Pelt, and D. G. De Rooij, *Endocrinol.* 128:697 (1991)). The presence of CRABPI and RARα (Porter et al., *J. Androl.* 6:197 (1985); Eskild et al., *Biol. Reprod.* 44:55 (1991); K. H. Kim and M. D. Griswold, *Mol. Endocrinol.* 4:1679 (1990)) in germ cells further supports the view that RA may be the active retinoid in spermatogenesis. As previously suggested the requirement for ROL may reflect the existence of a blood-testis barrier preventing RA to reach the adluminal compartment of the seminiferous tubules (Porter et al., *J. Androl.* 6:197 (1985); Shingleton et al., *Biochemistry* 28:9641 (1989)). The CRBPI-containing Sertoli cells which form this blood-testis barrier may normally convert ROL to RA to subsequently deliver it to the germ cells (Porter et al., *J. Androl.* 6:197 (1985); Shingleton et al., *Biochemistry* 28:9641 (1989)). Interestingly, it has been proposed (Porter et al., *J. Androl.* 6:197 (1985)) that the blood-testis barrier is less restrictive in birds where the typical mammalian Sertoli-Sertoli cell junctions are absent and spermatogenesis can be restored by RA in ROL-deficient animals (Thompson et al., *Br. J. Nutr.* 23:471 (1969)).

RARα Null Homozygote Phenotype

The selective cannibalism of RARα null homozygote newborns indicate that they exhibit an abnormal phenotype recognized by their mothers. Interestingly, not all null homozygote newborns are eaten, which suggests that the "cannibalizable" phenotype has a variable penetrance, which may be related to the non-homogeneous genetic background of the null homozygote newborns. Also, the variable penetrance of the webbed digit phenotype, which appears to be associated with early death (~2–3 weeks), and the longer survival of a small fraction of RARα null homozygotes (>2 months), may have a similar origin. Moreover, it is noteworthy that the webbing is often different when comparing pairs of limbs of a given animal. This variability, which cannot be accounted for by variation in the genetic background, is most probably related to the stochastic nature of gene activity (reviewed in M. S. H. Ko, *BioEssays* 14:341 (1992)) in the cells which give rise to bilateral and symmetrical structures within an animal.

The transcripts of RARα1, which is the most abundant RARα isoform, are ubiquitously expressed, whereas those of RARα2, which is the second most common RARα isoform, could not be detected by in situ hybridization (Leroy et al., *EMBO J.* 10:59 (1991); Leroy et al., *Proc. Natl. Acad. Sci. USA* 88:10138 (1991)). It is therefore surprising that, in agreement with a recent report (Li et al., *Proc. Natl. Acad. Sci. USA*, 90:1590 (1993)), RARα1 null homozygotes did not exhibit any of the abnormalities seen in RARα null animals. This may mean that RARα1 and RARα2 are essentially functionally redundant, and that RARα2 may have a wider domain of expression than suggested from the in situ hybridization data (note, however, that the global expression of RARα2 was not altered in RARα1 null homozygotes). Alternatively, in most places RARα1 transcription may not reflect an actual function of this isoform, and RARα2 may fulfil most of the function of the RARα gene. In any event, the high degree of conservation of RARα1 across vertebrates indicates that this isoform must perform some specific function conferring a selective advantage (see D. Tautz, *BioEssays* 14:263 (1992); J. Brookfield, *Evolutionary Genet.* 2:553 (1992)) not yet detected. The almost ubiquitous expression of RARα (mainly RARα1) has suggested that it may mediate the RA induction of the RA-responsive RARs, i.e. RARα2, RARβ2, RARγ2 (M. Leid et al., *Trends in Biochem. Sci.* 17:427 (1992); Leroy et al., *Proc. Natl. Acad. Sci. USA* 88:10138 (1991); Mendelsohn et al., *Development* 113:723 (1991); Lehmann et al., *Mol. Cell. Biol.* 12:2976 (1992); and refs therein). No change in the level of their expression was seen in RARα (for RARβ2 and RARγ2) or RARα1 null homozygotes, indicating that if RARα is involved in these inductions, its function must be redundant. Note also that the level of expression of the RA-responsive CRABPII gene (Giguère et al., *Proc. Natl. Acad. Sci. USA* 87:6233 (1990); Durand et al., *Cell* 71:73 (1992)) was unchanged in RARα null homozygotes (FIG. 1c). RARα is also the only RAR whose expression could be detected in the precise rhombencephalic region (see M. Leid et al., *Trends in Biochem. Sci.* 17:427 (1992) for a review) where the product of the RA-inducible homeogene Hoxa-1 (Hox-1.6) (A. W. Langston and L. Gudas, *Mechanisms of Development* 38:217 (1992)) is known to play a critical role during morphogenesis (Lufkin et al., *Cell* 66:1105 (1991); Chisaka et al., *Nature* 355:516 (1992)). Interestingly, no hindbrain or inner ear lesions resembling those resulting from Hoxa-1 knockouts (Lufkin et al., *Cell* 66:1105 (1991); Chisaka et al., *Nature* 355:516 (1992); and M.M., T.L. and P.C., unpublished data) were seen in RARα null homozygotes. Therefore, it appears that either Hoxa-1 expression is not critically dependent on RA-induction in the animal, or that other RARs or RXRs whose expression has not been detected by in situ hybridization in this region of the hindbrain could control the RA-responsiveness of Hoxa-1.

TABLE IV

Viability of RARα$^{-/-}$ and RARα1$^{-/-}$ Offspring

|  | RARα$^{+/-}$x −/− | RARα$^{+/-}$ +/− | offspring +/+ |
|---|---|---|---|
| Gestation day 8.5 to 18.5 | 34 (0.9) | 64 (1.6) | 39 (1.0) |
| 1 day p.p. | 13 (0.4) | 56 (1.6) | 36 (1.0) |
| 2 weeks old | 15 (0.2) | 123 (1.9) | 64 (1.0) |
| 1–2 months | 4 (0.1) | 90 (2.0) | 45 (1.0) |
|  | RARα1$^{+/-}$x −/− | RARα1$^{+/-}$ +/− | offspring +/+ |
| 1–2 months | 52 (0.9) | 108 (1.9) | 58 (1.0) |

The genotypes of offspring from intermatings of either RARα or RARα1 heterozygote animals are given. Different litters were genotyped at the time shown on the left. Hence, one can only compare horizontal rows of numbers. At each time point, the distribution of offspring of the different genotypes is shown in parentheses relative to wild type (+/+). Note that the percentage of RARα null homozygotes decreases with time. This decrease plateaus at 1–2 months with only ~10% of the RARα homozygotes still alive.

EXAMPLE 3

Function of Retinoic Acid Receptor β2 (RARβ2) in the Mouse

Experimental Procedures

Disruption of the RARβ2 Locus

Figure 9A:
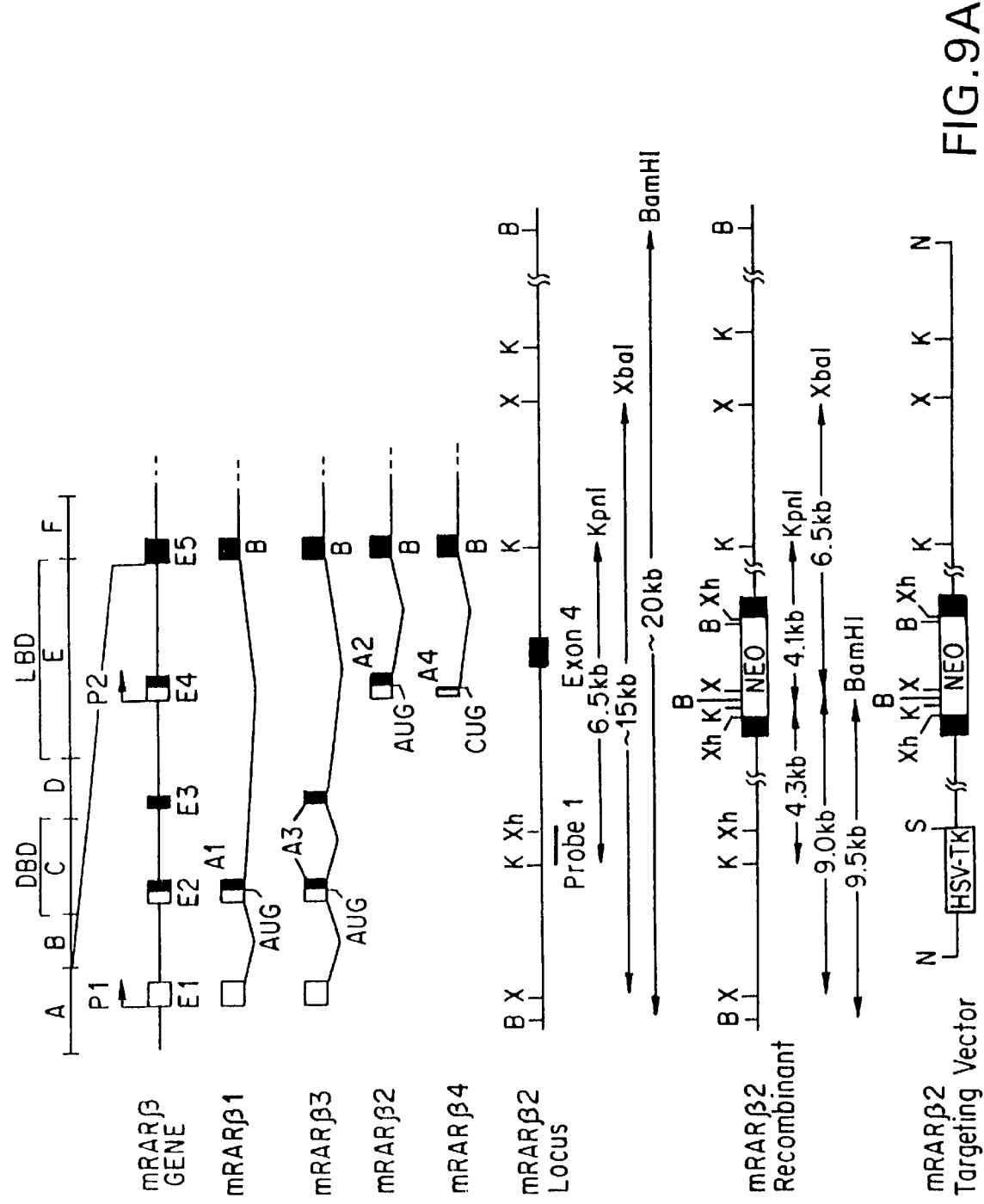

The isolation of genomic clones containing the first exon encoding the mRARβ2 isoform (exon 4, E4, FIG. 9a) was as described (Zelent et al., *EMBO J.* 10:71–81 (1991)). The 6.5 kb and the 3'-adjacent 3.7 kb Kpnl fragments containing the RARβ2 first exon and intronic DNA, respectively, were subcloned into the Kpnl site of the pTZ19r vector (Promega). For construction of the targeting vector the Xhol/Kpnl 5.5 kb fragment containing the mRARβ2 first exon (FIG. 9a) was excised from the pTZ19r vector and subcloned into the pBluescript SK(−) vector (Stratagene). The Xhol site was subsequently destroyed, and a new Xhol site was introduced into the mRARβ2 first exon (exon 4) by site-directed mutagenesis with the oligonucleotide 5'-GATCATGTTTGACTGACTCGAGTGGATGTTCTGTCAG-3' spanning nucleotides 459–491 (Zelent et al., *EMBO J.* 10:71–81 (1991)); in this way both of the potential initiation codons (nucleotide positions 463 and 475, Zelent et al., *EMBO J.* 10:71–81 (1991)) were destroyed. Following introduction of the Xhol site, the 3.7 kb intronic Kpnl fragment (FIG. 9a) was introduced 3' to the 5.5 kb fragment. The GTI-II enhancer-driven neomycin gene (NEO cassette, derived from the p566 vector, Lufkin et al., *Cell* 66:1105–1119 (1991)) was then introduced into the newly created Xhol site of the 5.5 kb (formerly Xhol/Kpnl) fragment (FIG. 9a). Finally the 2.3 kb GTI-II enhancer-driven herpes simplex virus thymidine kinase gene fragment (purified from plasmid p565, Lufkin et al., *Cell* 66:1105–1119 (1991)) was inserted into the pBluescript SK(−) Sall site to yield the mRARβ2-targeting vector (mRARβ2-Δ). For electroporation, mRARβ2-Δ was linearized at its unique Notl site (FIG. 9a). Genomic DNA extraction, Southern blotting, embryonic stem (ES) cell culture, generation of chimeras and probe preparation were as described elsewhere (Lufkin et al., *Cell* 66:1105–1119 (1991)). Probe 1 was the Kpnl/Xhol fragment derived from the 5' end of the 6.5 kb Kpnl fragment containing the mRARβ2 first exon.

RNA Analysis

Total RNA was prepared from 13.5 dpc embryos using the single-step guanidinium-isothiocyanate-phenol technique (Chomczynski et al., *Anal. Biochem.* 162:156–159 (1987)). RT-PCR was performed according to Huet et al., *Development* 118:613–627 (1993). Reactions were carried out in 100 mM Tris-HCl, pH 8.8, 500 mM KCl, 14 mM $MgCl_2$ using 1 μg of RNA per reaction in a final volume of 50 μl. Primer oligonucleotides were as indicated in figure legends. After denaturation at 94° C. for 3 min and annealing for 10 min at 50° C., Taq polymerase and AMV reverse transcriptase were added, and incubation was continued for 15 min at 50° C. PCR amplification was then performed (denaturation 30 sec at 94° C., annealing 30 sec at 55° C., and extension 1 min at 72° C.) for 20 or 30 cycles. The reaction mixtures were electrophoresed on 2% agarose gels, and then transferred to Hybond N filters. Hybridization was carried out with RAR isoform-specific cDNA fragments or oligonucleotide probes. For RNAse protection assays, 30 μg of RNA was used per hybridization reaction. The conditions for preparation of the probes and RNAse protection were as described in *Current Protocols in Molecular Biology*, J. Wiley Interscience, New York, eds. Ausubel et al. (1987).

Protein Analysis

Embryos from RARβ2 heterozygote intercrosses were collected at 14.5 dpc by caesarian section, and genotyped. Nuclear extracts were prepared from wild type, heterozygous and homozygous mutant RARβ2 embryos. Whole cell extracts from transfected COS-1 cells and nuclear extracts from embryos were prepared as described (Gaub et al., *Exp. Cell Research* 201:335–346 (1992); Rochette-Egly et al., *J. Cell Biol.* 115:535–545 (1991)). Western blotting and immunodetection procedures were also as described (Rochette-Egly et al., *J. Cell Biol.* 115:535–545 (1991)), using as antibody preparations rabbit polyclonal antisera specific for RARα ((RPα(F), Gaub et al., *Exp. Cell Research* 201:335–346 (1992)), and RARβ (RPβ(F)2, Rochette-Egly et al., *Molecular Endocrinology* 6:2197–2209 (1992)), and a monoclonal antibody (ascites) directed against the RARβ2 A2-region (Rochette-Egly et al., *Molecular Endocrinology* 6:2197–2209 (1992)). Immunoreactions were visualized using protein A-coupled to horseradish peroxidase, followed by chemiluminescence (Amersham).

Animal Mating and RA Treatment

Timed matings were performed by placing mice in the reversed light-cycle for 3 weeks, followed by placement of males and females together for 3 hours at the midpoint of the dark cycle. Evidence of mating was determined by the presence of a vaginal plug and was considered to be time 0 dpc. For all other matings males and females were left together for the night and the presence of a vaginal plug in the morning was taken as 0.5 dpc. To generate RARβ2−/− mutants expressing the RARβ2/lacZ transgene (Mendelsohn et al., *Development* 113:723–734 (1991)), RARβ2/lacZ+/+ homozygote mice were mated with RARβ2−/− mutants to generate RARβ2+/−/RARβ2/lacZ+/− animals. In a second round of mating RARβ2+/−/RARβ2/lacZ+/− mice were backcrossed with RARβ2/lacZ+/+ transgenic mice to generate males with the genotype RARp2+/−−/RARβ2/LacZ+/+. To analyze the expression of RARβ2/lacZ promoter activity in RARp2−/− mutant embryos, RARβ2+/−/RARβ2/LacZ+/+ males were mated with RARβ2+/− females producing offspring which all contained the transgene, thus allowing comparisons of promoter activity within a given litter containing wild type, heterozygous and homozygous mutant RARβ2 embryos.

For generation of hindbrain malformations timed mating experiments were performed and all-trans RA (Sigma) (25 mg/kg body weight) was administered to the mother by oral gavage at 7.25 dpc. Embryos were collected at 9.0 dpc, yolk sacs were taken for genotyping and embryos were fixed in 4% paraformaldehyde and embedded in paraffin for in situ hybridization on sections. For each embryo, three sets of alternate sections were hybridized to Hoxb-1, Krox-20 and Hoxa-3 probes. These probes have been described previously (Gaunt et al., *Development* 104 *suppl.*:71–82 (1988); Wilkinson et al., *Nature* 337:461–464 (1989); Hunt et al., *Nature* 353:861–864 (1991)). No significant alteration in the Hoxa-3 expression pattern was observed in RA-treated embryos (data not shown). A separate series of embryos was processed for whole-mount in situ hybridization with a digoxigenin-labelled Hoxb-1 riboprobe. Both in situ hybridization procedures were performed as described in Décimo et al. ("In situ Hybridization to Cellular RNA," in *Gene Probes: A Practical Approach*, Vol 2, Hames et al., eds., Oxford University Press, Oxford, England, in press). For induction of limb malformations, all-trans RA was administered at 11.5 dpc (80 mg/kg) and fetuses were collected at 18.5 dpc and analyzed for skeletal malformations. For investigating induction of RARβ2 promoter activity in RARβ2 mutants, 25 mg/kg RA was administered at days 10.5 and 11.5 pc, then embryos were collected and stained for LacZ activity after 4 hours. For whole-mount skeletal analysis, fetuses were collected at 18.5 dpc by ceasarean section and skeletons were prepared as described (Lufkin et al., *Nature* 359:835–841 (1992)). Histological analysis was as in Lohnes et al. (*Cell* 73:643–658 (1993)) and lacZ staining as in Mendelsohn et al. (*Development* 113:723–734 (1991)).

Inactivation of the RARβ2 Isoform

In order to inactivate the RARβ2 isoform, the neomycin-resistance cassette (NEO) was inserted into the RARβ exon 4 (the RARβ2 first exon), which encodes the 5'-untranslated (UT) and A2-region sequences (see FIG. 9a). Prior to insertion of the NEO cassette, the first two potential in-frame initiation codons of the RARβ2 protein were destroyed by site-specific mutagenesis of the region spanning nucleotides 459–491 (see Zelent et al., *EMBO J.* 10:71–81 (1991), and Materials and Methods), while a Xhol site was created to facilitate introduction of the cassette. The targeting construct contained approximately 3 kb of 5' and 6 kb of 3' homologous sequences (FIG. 9a). A cassette containing the herpes simplex virus thymidine kinase gene (HSV-TK) was inserted at the 5' end of the targeting construct in order to allow the use of the positive-negative selection technique (Thomas et al., *Cell* 51:503–512 (1987)) to isolate ES cell clones which have undergone homologous recombination.

Figure 9B:
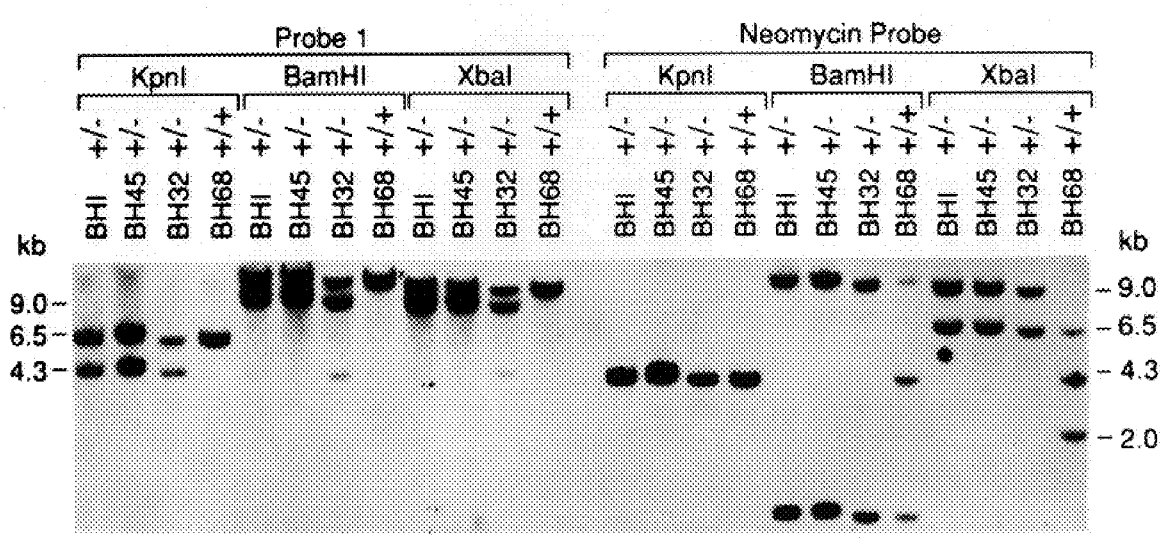

The RARβ2 targeting vector was linearized and electroporated into D3 ES cells (Lufkin et al., *Cell* 66:1105–1119 (1991)). Selection was performed with G418 and gancyclovir. Resistant colonies were expanded and analyzed by Southern hybridization for the presence of the correct targeting event employing a probe derived from DNA sequences located 5' to the border of those contained in the targeting construct (probe 1, FIG. 9a). Three ES cell clones out of 90 analyzed yielded, in addition to the wild type 6.5 kb Kpnl fragment, the 4.3 kb Kpnl fragment expected for the disrupted RARβ2 allele (FIG. 9a and b; clones BH1, BH45 and BH32). To confirm that these ES cell clones had the correct targeting event, additional Southern hybridization experiments were performed (FIG. 9b). DNAs were digested with Kpnl, BamHil and Xbal, and hybridized with either probe 1, a full-length neomycin gene probe or a probe derived from sequences located at the 3' end of the construct (data not shown). The 3 ES clones yielded the appropriate sized restriction fragments in all digests performed (FIG. 9a and b). In addition, Southern blots hybridized with the neomycin gene probe showed the restriction enzyme fragments expected for a single targeting event, indicating that no non-homologous recombination events had occurred in the ES cells which harbored the targeted allele (see FIG. 9b).

Results

RARβ2 Mutant Mice Have a Normal Phenotype

Chimeric mice were generated from the targeted ES cell lines, and all transmitted the disrupted RARβ2 allele to their offspring. RARβ2−/− homozygous offspring were generated at the expected Mendelian frequency from intercrosses of RARβ2+/− heterozygotes (FIG. 10). RARβ2−/− mutants derived from either ES cell line were as fertile as wild type animals, lived as long as their wild type littermates and were apparently normal based on their external appearance. Histological analysis was also performed on two 18.5 day post coitum (dpc) fetuses which were serially sectioned. No malformations were detected. Further analysis of the internal organs from RARβ2−/− adults also did not reveal any abnormalities. RARβ2−/− animals were also examined for possible skeletal and cartilage anomalies using alizarin red and alcian blue double staining, but again, there were no obvious malformations (not shown).

Since RARβ2−/− mutants were apparently normal, it was important to verify that no RARβ2 protein was made. It was also important to rule out the possibility that a downstream initiation event might generate a truncated RARβ2 protein, since there is a methionine codon embedded in a favorable Kozak sequence located between the two zinc fingers of the RARβ2 C-region (Met 113, see Zelent et al., *EMBO J.* 10:71–81 (1991)). Translational initiation from this site would result in a protein of ~39 kilodaltons, lacking the A and B regions as well as the first zinc finger of the DNA binding domain. Nuclear extracts were prepared from 14.5 dpc wild type embryos and from embryos heterozygous and homozygous for the RARβ2 mutant allele. Extracts containing similar amounts of nuclear proteins were first immunoblotted with a rabbit polyclonal antibody specific for the F-region of RARα. The 51 kd RARα1 protein was detected at equivalent levels in wild type, heterozygote and homogygote mutant embryo extracts (FIG. 11). The presence of the RARβ2 protein was determined by immunoprecipitation with a monoclonal antibody specific for the RARβ2 A2-region, followed by Western blot analysis using a polyclonal antibody directed against the F-region of RARβ. RARβ+/+ wild type extracts contained the 51 kd RARβ2 protein (FIG. 11), while extracts derived from RARβ+/− heterozygous embryos retained 30–50% of wild type levels. Extracts prepared from RARβ2−/− homozygotes, however, contained no detectable RARβ2 protein. Since the A2-region-specific antibody used in the immunoprecipitation experiments shown in FIG. 11 would not react with a truncated RARβ2 proteins lacking this amino-terminal sequence, additional immunoblotting experiments were performed using an antibody specific for the RARβ F-region. Neither the putative 39 kd truncated RARβ2 protein (see above) nor any other sign of immunoreactivity could be detected in RARβ2−/− extracts (data not shown), indicating that more C-terminally located methionine codons were not utilized as translational initiation sites in the mutant animals.

Figure 12A:
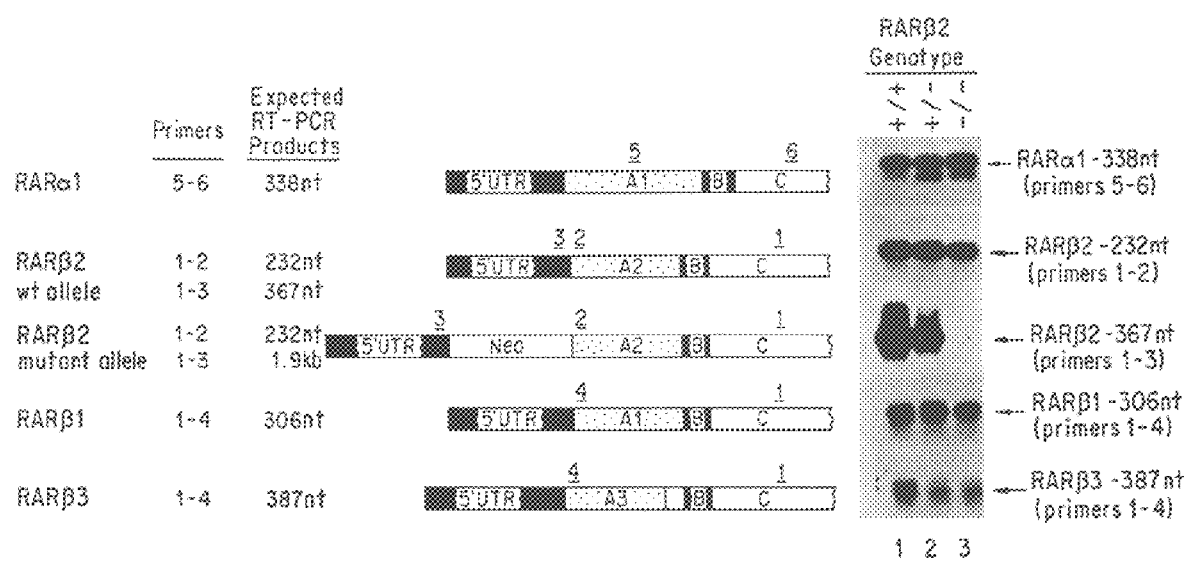

To further demonstrate that no wild type RARβ2 protein could be produced in homozygote mutant embryos, it was determined whether wild type RARβ2 RNA was synthesized in these mutants. Total RNA was prepared from 13.5 dpc wild type, heterozygous and homozygous mutant embryos, and RNAs were identified employing the sensitive polymerase chain reaction coupled to reverse transcription (RT-PCR). Following RT-PCR, cDNA products were subjected to Southern blot analysis employing oligonucleotide probes which distinguish between the different RAR isoforms. To insure that the three RNA preparations were comparable, a cDNA fragment corresponding to the RARα1 isoform was amplified, employing a 5' primer located in the RARα1 A1-region (primer 5, FIG. 12a; see Leroy et al., *EMBO J.* 10:56–69 (1991a)), and a 3' primer located in the RARα C-region (primer 6, FIG. 12a). Equivalent amounts of the expected 338 nt-long RARα1 product were found irrespective of whether RNAs were prepared from RARβ2+/+, RARβ2+/− and RARβ2−/− embryos (FIG. 12a). A second RT-PCR reaction was performed employing a 5' primer located in the RARβ2 first exon (E4, in FIG. 9a) downstream from the site of insertion of the NEO cassette in the RARβ2 gene (primer 2, FIG. 12a), and a 3' primer located in the RARβ2 C-region (primer 1, FIG. 12a). The expected 232nt-long product (FIG. 12a) was obtained at similar levels from all three RNA preparations, indicating that the RARβ2 locus was similarly transcribed in wild type, heterozygote and homozygote mutant embryos. To distinguish between mutant and wild type RARβ2 transcripts, RT-PCR was performed with a 5' primer (primer 3, FIG. 12a) derived from the RARβ2 5'-untranslated region (UTR) located upstream from the site of insertion of the NEO cassette, and the same 3' primer (primer 1, FIG. 12a). This pair of primers should yield a 367ntlong product from wild type RARβ2 RNA, while in embryos harboring the mutant allele, the RT-PCR product would be about 1.9 kb in length due to the insertion of the NEO cassette. For RNA prepared from 13.5 dpc wild-type embryos, the 367nt product corresponding to the wild type RARβ2 cDNA was readily detectable, while it was reduced by about 50% in heterozygous embryos, and not detectable in RARβ2 mutant homozygotes (FIG. 12a). Much longer exposure of the autoradiograph (not shown) indicated that there was no wild type RARβ2 transcript in homozygote embryos. Note that as expected a weak hybridization signal was detected in the RARβ2 null mutant RNA, which corresponded to the 1.9 kb mutant transcript (not shown). Thus, the RARβ2 homozygote mutants appear to be null for both RARβ2 transcript and protein.

The Levels of RARβ1/β3, RARα1/α2 and RARγ1/γ2 Transcripts are Unchanged in RARβ2 Null Mutant Embryos.

The RARβ1/β3 isoforms are generated by alternative splicing of a primary transcript initiating from the 5' distal promoter (P1) and continuing through the RARβ2 first exon (exon 4, which is independently transcribed from the downstream promoter P2; see FIG. 9a; Mendelsohn et al., *Mech. of Development*, in press). Since the RARβ1/β3 and RARβ2 transcripts overlap, it was important to demonstrate that expression of the RARβ1/β3 isoforms was not perturbed in the RARβ2 null mutants. RT-PCR was performed to assess the levels of RARβ1β3 transcripts in wild type, heterozygous and homozygous mutant embryos. A 5'-primer located in the RARβ1/β3 A-region (primer 4, FIG. 12a), and a 3' primer located in the RARβ C-region (primer 1, FIG. 12a) were used to amplify the RARβ1/β3 cDNAs. The expected 306nt-long product corresponding to the RARβ1 isoform was detected at similar levels in RNAs from wild type, heterozygote and homozygote embryos; the 387nt-long RARβ3 product was also detected at approximately the same levels (FIG. 12a, and data not shown). These results show that there was no appreciable change in the steady state levels of the RARβ1/β3 transcripts in the RARβ2 null mutants, and therefore that the presence of the NEO cassette did not affect the splicing of the RARβ1/β3 primary transcript.

Figure 12B:
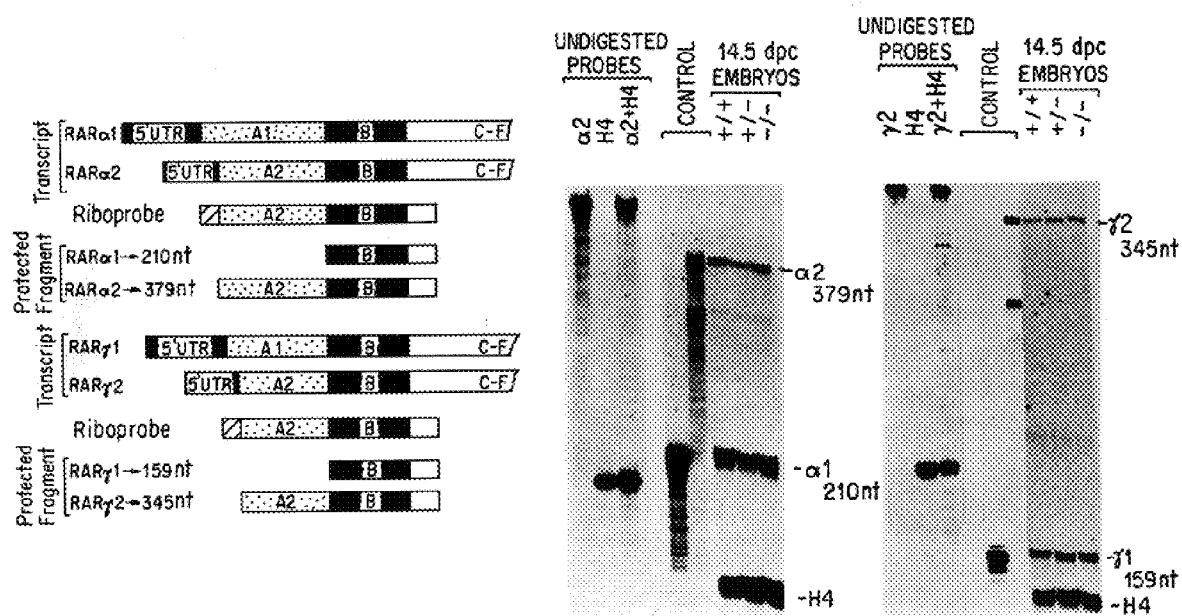

Overexpression of the other RARs could possibly account for the normal phenotype of the RARβ2 null animals. RNase protection experiments were performed using riboprobes (depicted in FIG. 12b) to investigate whether RARβ2 inactivation had an effect on the levels of the RA-inducible RARα2 and RARγ2 transcripts, and on the levels of the non-inducible RARα1 and RARγ1 transcripts. Using an antisense RARα2 RNA probe, similar levels of the 379nt-long protected product corresponding to the RARα2 transcripts were detected in RNAs prepared from wild type, heterozygote or homozygote mutant 13.5 dpc embryos (FIG. 12b). Similar amounts of RARα1 transcripts were also detected in all three preparations (FIG. 12b), consistent with the results of the Western blotting and RT-PCR experiments described above (see FIG. 11 and 12a). Similarly, there was no observable change in the levels of the RNAs encoding the RARγ1 and γ2 isoforms in the RARβ2 null embryos (FIG. 12b). Together these findings demonstrate that RARβ2 was not required for the expression of the other main RAR isoforms, and also that no global compensatory increase of any of these isoforns occurred.

Figure 13A:
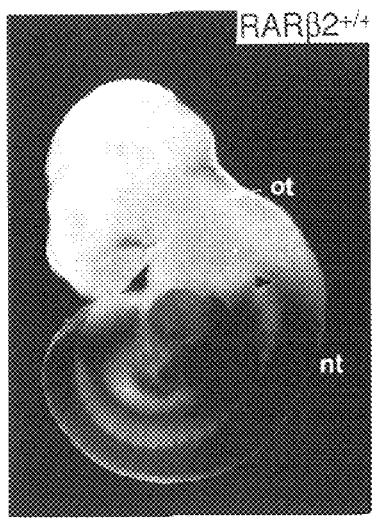

RARβ2 is Not Required for RARβ2 Promoter Activity and RA-inducibility in Transgenic Mice Since the RARβ2 promoter is RA-inducible via a RARE, it was investigated whether the levels of activity of the RARβ2 promoter would be affected in the absence of RARβ2. RARβ2 null animals were crossed with transgenic animals expressing an RARβ2 promoter/lacZ reporter gene (Mendelsohn et al., *Development* 113:723–734 (1991)). Progeny from these crosses were mated, and the resulting offspring were genotyped and stained for β-galactosidase (β-gal) activity at 9.5 dpc, 10.5 dpc, 11.5 dpc and 12.5 dpc. No differences were observed in the intensity nor in the pattern of β-gal activity in the null mutants compared to wild type embryos at the times tested (FIG. 13a, and data not shown). Therefore, if the activity of the RARβ2 promoter is controlled by RA under physiological conditions, RARβ2 is not mandatory for mediating this control.

Figure 13B:
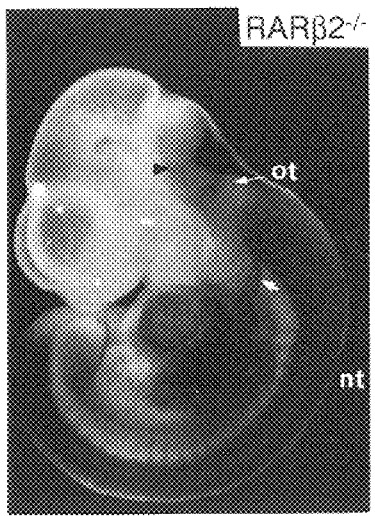
Figure 13C:
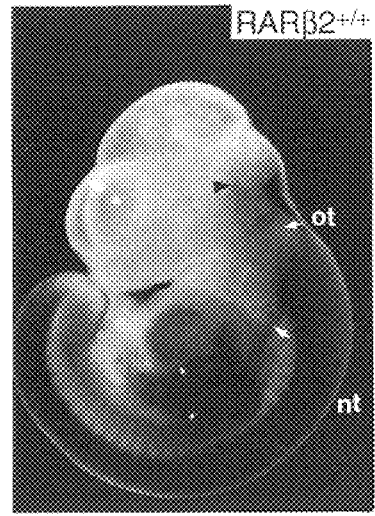

It has been previously reported that the RARβ2 promoter activity is dramatically induced (in transgenic animals) following exposure to RA in utero (Mendelsohn et al., *Development* 113:723–734 (1991) and Mendelsohn et al., *Mech. of Development* (1994) in press; Zimmer et al., *Development* 116:977–983 (1992); Shen et al., *Int. J. Dev. Biol.* 36:465–476 (1992)). This promoter activity was observed in ectopic locations (such as in the rostral hindbrain), and was also increased in regions where the promoter was already active in the absence of RA treatment, such as the spinal cord and the apical ectodermal ridge and core mesenchyme of the limb buds. To determine whether the RARβ2 isoform was required for mediating this up-regulation, RA treatments were performed on days 10.5 and 11.5 pc. Embryos were exposed to 25 mg/kg all-trans RA by maternal gavage, collected after 4 hours, and stained for β-gal activity. 10.5 dpc wild type and homozygous null embryos exhibited comparable induction of RARβ2 promoter activity (FIG. 13a–c). In the hindbrain, the rostral expression boundary of promoter activity shifted cranially, from the level of rhombomere 7 (arrowhead in panel a) to more rostral hindbrain, up to at least rhombomeres 4 (just rostral to the otocyst in panels b and c) and 1 (arrowheads in panels b and c), as well as in discrete regions of the midbrain and forebrain, as previously reported (Zimmer et al., *Development* 116:977–983 (1992), Mendelsohn et al., *Mech. of Development* (1994) in press). Note that promoter activity was lower in rhombomere 5 (otocyst level) than in rhombomere 4. LacZ expression was also induced in the limb buds, by RA treatment on 11.5 dpc, both in the apical ectodermal ridge and in the core mesenchyme of wild type, heterozygous and homozygous embryos (data not shown). Note also the increased activity of the RARβ2 promoter in neural crest cells emigrating in the direction of the heart (FIG. 13b and c, arrows). Thus, the RA-inducibility of the RARβ2 promoter was apparently not impaired in the absence of the RARβ2 isoform.

RARβ2 is Not Mandatory to Mediate the Teratogenic Effects of Retinoic Acid in the Hindbrain and in the Limbs During neurulation, RA-treated embryos develop ill-defined rhombomeric sulci and boundaries, and exhibit a severe truncation of the forebrain (Morris-Kay et al., *EMBO J.* 10:2985–2995 (1991); Conlon et al., *Development* 116:357–368 (1992)). The specific effects of excess RA on hindbrain development has also been studied using various molecular markers available for this segmented region of the brain. Administration of RA to pregnant mice at 7.25 to 8.0 dpc results in subsequent alterations of the pre-otic hindbrain, which were interpreted as transformations of rhombomeres 2 and 3 (R2 and R3), either towards R4 and R5 identities, respectively (Marshall, et al., *Nature* 360:737–741 (1993)) or towards an expanded R4 identity (Morris-Kay et al., *EMBO J.* 10:2985–2995 (1991); Conlon et al., *Development* 116:357–368 (1992)). These conclusions were essentially drawn (i) from the pronounced rostral duplication or expansion of the Hoxb-1 rhombomeric expression domain which is normally restricted to R4 in the segmented hindbrain at 8.5–9.5 dpc, (ii) from alteration in the domains of expression of Krox-20 which is normally expressed in R3 and R5 at 8.5–9.5 dpc and is present only in a narrow band in R5 after RA-treatment, and (iii) from a rostral expansion of the expression domain boundary of Hoxb-2, which normally lies at the R2/R3 boundary. RARβ2 is an obvious candidate for mediating these specific effects of RA, since RA treatment results in an up-regulation of the RARβ2 promoter, shifting its boundary of activity in the hindbrain from rhombomere 7 to more rostral regions (see above).

Figure 14A:
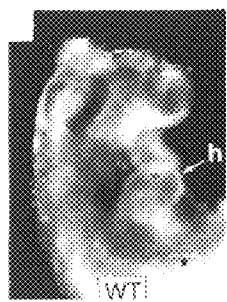
Figure 14B:
Figure 14C:
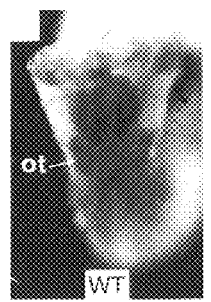
Figure 14D:
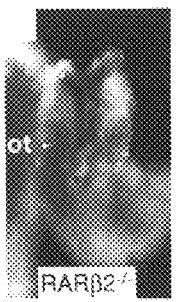
Figure 14E:
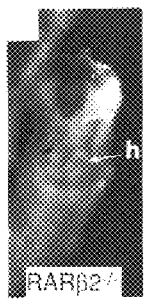
Figure 14F:
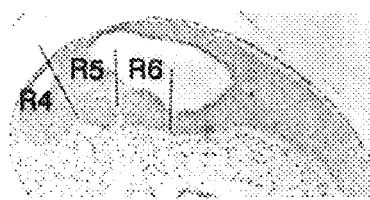
Figure 14F:
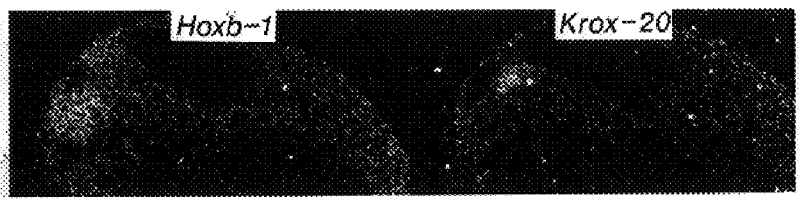
Figure 14G:
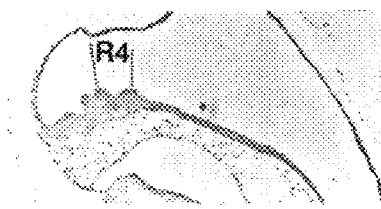
Figure 14G:
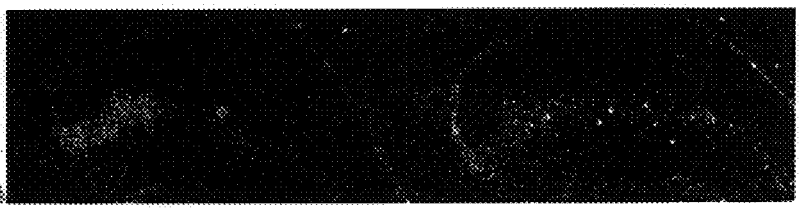
Figure 14H:
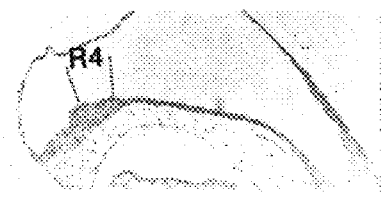
Figure 14H:
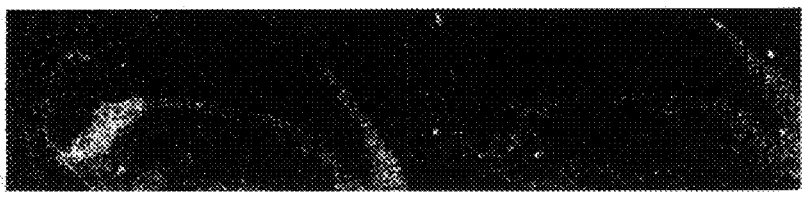

If RARβ2 were required for mediating the effects of excess RA on hindbrain development, the above RA-induced alterations in normal hindbrain segmentation and/or specification should not occur in RARβ2 null mutants. RARβ2+/− intercrosses were set up, and pregnant females were given 25 mg/kg all-trans RA at 7.25 dpc, a dose which is known to produce rhombomeric alterations. Severe truncations of the forebrain were observed at 9.0–9.5 dpc in wild-type, and interestingly also in RARβ2 null RA-treated embryos (FIG. 14a, b, g and h, and data not shown). Hoxb-1 expression was analyzed by whole-mount in situ hybridization. A rostral expansion of the Hoxb-1 transcript domain was observed both in wild type (FIG. 14a and c) and in RARβ2 null mutants (FIG. 14b, d and e). Hoxb-1 transcripts extended more rostrally than the putative R3/R4 boundary, almost to the anterior extremity of the ventral neuroepithelium (see panel e). This rostral expansion of Hoxb-I transcripts in both wild-type and RARβ null embryos was clearly confirmed by in situ hybridization on serial sections (FIG. 14g and h). Krox-20 transcripts were not detected in the putative R3 (FIG. 14g and h), although they were observed caudal to Hoxb-1 transcripts in the putative R5 (FIG. 14f). Hence, the results obtained with RARβ2 null mutant embryos are similar to those previously reported for wild-type embryos treated with RA at similar stages (Morris-Kay et al., *EMBO J.* 10:2985–2995 (1991); Conlon et al., *Development* 116:357–368 (1992)). In light of these results it can be concluded that RARβ2 is not mandatory for the generation of the hindbrain malformations following exposure to excess RA.

RA treatments were also performed at 11.5 dpc to determine whether RARβ2 is required to produce the RA-induced limb malformations which have been previously reported (Kochhar et al., *Tetratology* 7:289–295 (1973); Alles et al., *Teratology* 40:163–171 (1989)). These malformations include truncations of the long bones as well as loss or fusions of digits. RARβ2+/− heterozgygous crosses were performed, and 11.5 dpc embryos were exposed to 80 mg/kg RA in utero. Fetuses were then collected at 18.5 dpc and stained with alizarin red and alcian blue to visualize skeletal and cartilagenous elements. Both wild type and RARβ2 null fetuses exhibited severely malformed limbs compared to untreated animals (FIG. 15, and data not shown). There were no apparent differences between wild type and RARβ2 null fetuses in either the nature or the extent of the malformations produced. In both cases RARβ2+/+ and RARβ2−/− animals had truncated long bones, as well as missing digits as a result of RA excess. Thus, the presence of RARβ2 does not appear to be mandatory to generate RA-induced malformations in the limb.

Discussion

The studies presented here indicate that RARβ2 is apparently dispensable for normal embryonic development and in post-natal life. These studies also show that RA-induced abnormalities are produced in the hindbrain and limbs of RARβ2 null mutants to the same extent as in wild type animals, demonstrating that RARβ2 is not mandatory to transduce the teratological RA signal in these structures.

Lack of Developmental and Adult Abnormalities in RARβ2 Null Mutants

Animals lacking the RARβ2 isoform exhibit an apparently normal phenotype at all stages of their life. This finding is reminiscent of recent studies showing that mice deficient for the RARα1 (Li et al., *Proc. Natl. Acad. Sci. USA* 90:1590–1594 (1993); Lufkin et al., *Proc. Natl. Acad. Sci. USA* 90:7225–7229 (1993)) or RARγ2 (Lohnes et al., *Cell* 73:643–658 (1993)) isoforms are apparently indistinguishable from their wild type littermates. In contrast, animals lacking all of the RARα or RARγ isoforms were affected, exhibiting post-natal lethality and vitamin A deficiency (VAD)-like defects (Lohnes et al., *Cell* 73:643–658 (1993); Lufkin et al., *Proc. Natl. Acad. Sci. USA* 90:7225–7229 (1993)). In each of the RAR gene knockouts reported to date, it is probable that other RARs, which are temporally and spatially coexpressed with the disrupted RAR, fulfill some of the functions of the inactivated receptor(s); in other words there is some functional redundancy in the RAR family. However, since the various RAR isoforms are well conserved across vertebrate evolution, they must perform at least one specific function, not yet discovered, either because the proper conditions have not been employed to reveal it, or because this function gives a slight vital advantage that cannot be detected over a few generations. Recent in situ hybridization studies indicate that at least two RAR isoforms are in general expressed in a given tissue. The RARα1 isoform appears to be expressed essentially everywhere in the developing embryo, while the RARβ1/β3 and RARβ2 expression domains are partially overlapping (see also Mendelsohn et al., *Mech. of Development* in press). In contrast, the extent of overlap between the RARβ and RARγ transcripts seems to be very limited, and their expression patterns are often complementary (Dollé et al., *Nature* 342:702–705 (1989) and Dollé et al., *Development* 110:1133–1151 (1990); Ruberte et al., *Development* 108:213–222 (1990); Ruberte et al., *Development* 111:45–60 (1991) and Ruberte et al., *Development* 118:267–282 (1993)). Thus, there are at least 2 RAR candidates, which could functionally compensate for the lack of the RARβ2 isoform, RARα1 and to a lesser degree RARβ1/β3. Supporting this possibility, double mutants which lack RARα1 in addition to RARβ2 die at birth and are severely malformed.

The possibility that some RARs can operate interchangeably for a number of functions does not necessarily imply that they perform in an identical manner, exhibiting equal DNA binding affinities and transactivation properties for the same RA target genes. More likely, some subsets of target genes are activated preferentially by certain isoforms, but can also be activated by other isoforms, albeit less efficiently. However, for all that can be detected under the present conditions, this redundancy would be sufficient to preserve the realization of the normal cascade of RA-dependent events in RARβ2 null mutant. Moreover, as shown by the present results, this functional "interchangeability" occurs in the absence of any global compensatory increase of the other RAR isoforms.

RARβ2 is Not Mandatory for RA-inducibility of RARα2, RARβ2 and RARγ2 Transcripts.

The findings that the RARβ2, α2 and γ2 promoters are up-regulated upon RA administration to cells in culture, and that RARβ32 transcripts (Osumi-Yamashita et al., *Develop. Growth and Differ.* 34(2):199–209 (1992); Harnish et al., *Differentiation* 45:103–108 (1990) and Harnish et al., *Developmental Dynamics* 149:239–246 (1992); Rowe et al., *Development* 11:1007–1016 (1991 b)) and promoter activity (Mendelsohn et al., *Development* 113:723–734 (1991) and Mendelsohn et al., *Mech. of Development* in press; Shen et al., *Int. J. Dev. Biol.* 36:465–476 (1992); Zimmer et al., *Development* 116:977–983 (1992)) are up-regulated in RA excess and down-regulated upon RA deprivation in mouse embryos (U1-Haq et al., *Proc. Natl. Acad Sci. USA* 88:8272–8276 (1991); S. Ward and G. Morriss-Kay, personal communication), led us to investigate whether RARβ2 plays an autoregulatory role in maintaining or inducing its own RA-dependent promoter activity, as well as the activity of the RARα2 and RARγ2 promoters. There was no significant change in steady state transcript levels of RARα2, β2 and γ2 isoforms in RARβ2 null mutants compared to wild type animals. In addition, it was found that the activity of the RARβ2 promoter fused to the lacZ reporter gene remained unchanged in transgenic animals lacking the RARβ2 isoform. Furthermore, this reporter gene was induced to the same extent by RA excess in wild type and mutant animals. Taken together, these results indicate that RARβ2 is not required to maintain or induce its own promoter activity nor is it required for the normal synthesis of RARα2, β2 and γ2 mRNAs. It also does not appear that the levels of RARγ1/β3 transcripts are affected by the lack of RARβ2, indicating that RARβ2 is also not mandatory to mediate the RA-dependent relief of the elongation block which appears to preclude the expression of RARβ1 /β3 isoforms in the absence of RA (Mendelsohn et al., *Mech. of Development* in press). All of these results may indicate that RARβ2 is never mediating the effect of RA on the expression of these various RA-responsive RAR isoforms, and that in its absence another RAR (e.g. RARα1) could substitute for it. Alternatively, under normal circumstances, RARβ2 could preferentially mediate these RA responses. In this respect however, note that there was no observable global modification in the levels of RARα2, RARβ2 and RARγ2 transcripts in RARα null mutants (Li et al., *Proc. Natl. Acad. Sci. USA* 90:1590–1594 (1993); Lufkin et al., *Proc. Natl. Acad. Sci. USA* 90:7225–7229 (1993)).

RARβ2 is Not Mandatory to Mediate the Teratogenic Effects of RA in the Hindbrain and in the Limbs RA excess results in overexpression and/or ectopic expression of RARβ2 transcripts at sites which later develop abnormally, such as the craniofacial region, the limbs, and the hindbrain (see above for refs), probably reflecting the presence of abnormally high levels of RA at these sites due to the condition of RA excess (Rossant et al., *Genes Dev.* 5:133–1344 (1991); Balkan et al., *Proc. Natl Acad. Sci. USA* 89:3347–3351 (1992). These altered expressions of the RARβ2 isoform raise the question as to whether this could be the cause of the teratological abnormalities resulting from RA excess. Wild-type and RARβ2 null mutant embryos were challenged in utero with teratogenic doses of RA, and we compared the malformations produced in both cases. In the hindbrain, the normal rostral boundary of RARβ2 promoter activity is at the level of rhombomere 7, and following RA-treatment, this boundary is shifted to include more rostral rhombomeres, where alterations in rhombomeric segmentation and gene expression are also observed (see above for refs.). It is clearly demonstrated here that the presence of RARβ2 isoform is not required to generate this shift in RARβ2 promoter activity and the RA-induced morphological and molecular hindbrain alterations. Similar results were obtained when the limb malformations generated by RA treatment at 11.5 dpc in wild type and RARβ2 mutant fetuses were examined. The same abnormalities were observed in both cases, includings losses of digits and truncations of the radius and ulna. Thus, the results demonstrate that RARβ2 is not mandatory for mediating the RA-induced teratogenic effects in hindbrain and limbs. This is in contrast with the specific requirement of RARγ for the generation of truncations of the lumbo-sacral region by RA excess (Lohnes et al., *Cell* 73:643–658 (1993)). Additional studies with other RAR single and double mutants will be necessary to discriminate between several possibilities, namely (i) that these teratological effects are never mediated by RARβ2, (ii) that they are normally mediated by RARβ2 which can be substituted by e.g. RARα1 in the absence of RARβ2, and (iii) that several RARs can similarly mediate these effects.

EXAMPLE 4

Function of Retinoic Acid Receptor RXRα in the Mouse

Experimental Procedures

Targeting Vectors and Homologous Recombination

Genomic clones for the mRXRα locus were obtained by screening a genomic library established in λEMBL3 from D3 ES cell DNA, with a mRXRα cDNA probe. Exon mapping of these clones showed that the RXRα gene extends over 30 kb and that its exonic organization is similar to that of the RXRγ gene (Liu and Linney, *Mol. Endocrinol.* 9:651–658 (1993)). In particular, most of the DNA binding domain is encoded in a single exon (exon 4; this exon contains the sequences corresponding to nucleotides 541 to 871 of the RXRα cDNA (numbering according to the genbank sequence No. M848 17)). To construct the targeting vector, a 8 kb HindIII genomic fragment, containing exons 3 and 4, was first inserted into a plasmid harboring the GTI.11-tk cassette (Lufkin et al., *Cell* 66.1105–1119 (1991)), yielding pHR(RXRα).1. Subsequently, a 1 kb EcoRI-XbaI fragment which contains exon 4 was removed and replaced with a PGK-NEO(A+) cassette derived from pKJ-1. This plasmid, pHR(RXRα).2, was linearized with NotI and electroporated into D3 or H1 ES cells as previously described (Lufkin et al., *Cell* 66:1105–1119 (1991)). After selection with G418 and gancyclovir (Lufkin et al., *Cell* 66:1105–1119 (1991)) resistant clones were expanded and analyzed by Southern Blotting.

Histological Procedures

Mouse embryos and fetuses were fixed in Bouin's fluid, processed for paraplast embedding, sectioned at 7 μm and stained with hematoxylin and eosin or with Groat's hematoxylin and Mallory's trichrome (Mark et al., *Development* 119:319–338 (1993)).

In Situ Hybridization Analysis

For in situ hybridization, embryos at 9.5 and 10.5 dpc were fixed in 4% paraformaldehyde and embedded in paraffin. All sections were collected on 4 or 5 sets of slides which were hybridized to α-cardiac actin, myosin heavy chain α(MHCα), myosin light chain 1 atrial (MLC1A) probes. At each developmental stage, heterozygous (+/−) and wild-type (WT; +/+) littermate embryos were processed in the same way for comparison. Probe labelling, in situ hybridization and emulsion autoradiography were performed as described in (Decimo et al, In: *Gene Probes*, B. D. Hames, S. Higgins, eds. Vol. II (1994)).

Three-Dimensional Computer Reconstruction

The same image processing configuration as described by Mark et al. (Mark et al., *Development* 119:319–338 (1993)) was employed.

Electron Microscopy

Two RXRα−/− and two WT fetuses (14.5 dpc) were fixed by intraventricular perfusion with 2% parafolmaldehyde and 2.5% glutaraldehyde in 0.05M cacodylate buffer (pH 7.2, 4° C.). The eyes and the hearts were removed and immersed during 6 hours in the same fixative at 4° C. They were then washed overnight in cacodylate buffer. After post-fixation in 1% osmium tetroxide in cacodylate buffer for 1 hour at 4° C., they were dehydrated in graded series of ethanol and propylene oxide and embedded in Epon. Semithin sections (2 μm) were stained with toluidine blue for light microscopy. Ultrathin sections were contrasted as usual with uranyl acetate and lead citrate, and examined in a Phillips 301 electron microscope operating at 80 Kv.

Results

Generation of Mice and ES Cells Carrying Mutated RXRα Genes

Figure 16A:
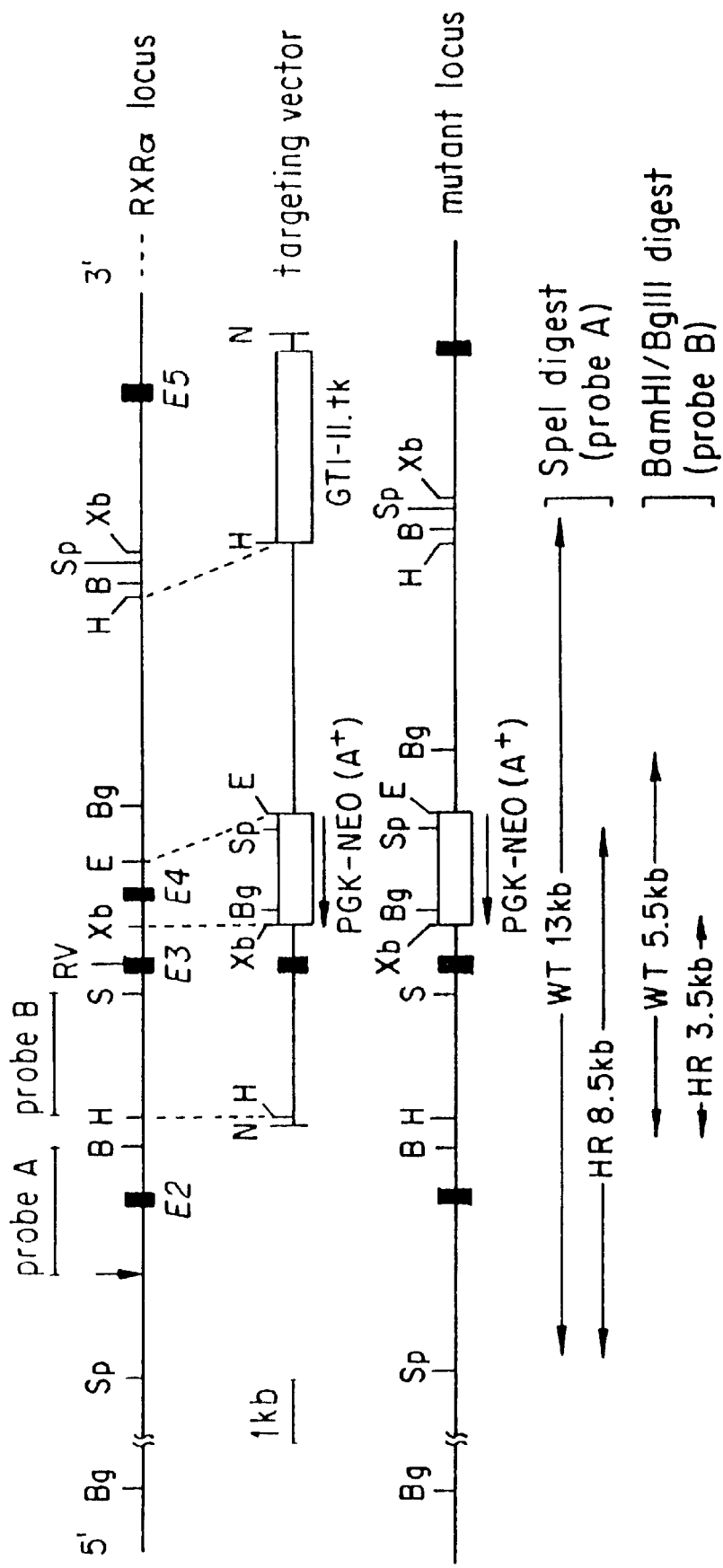

A replacement-type vector and positive-negative selection (Cappechi, *Science* 244:1288–1292 (1989)) was used to target the RXRα gene. In this vector, a 1 kb EcoRI/XbaI fragment containing exon 4 (which encodes most of the RXRαDBD) was removed and replaced with a cassette containing the neomycine phosphotransferase (NEO) gene and the PGK polyadenylation sequences under the control of the PGK promoter (PGK-NEO(A+), FIG. 16a). After electroporation into 129sv derived D3 or H1 ES cells and selection with G418 and gancyclovir, 3 resistant clones were positive for homologous recombination as judged from Southern Blot analysis of SpeI digested DNA with probe A (FIG. 16a, and data not shown). These positive clones were further analyzed with an internal probe (probe B) and a NEO probe to confirm that the expected targeting event had occurred, and also to exclude random integrations of the vector or other rearrangements at the RXRα locus (data not shown). Two clones, FP104 (derived from D3 ES cells) and FM23 (derived from H1 ES cells), were injected into C57/Bl6 blastocysts and the resulting chimeric males were crossed with wild-type (WT) C57/Bl6 females. Chimeras derived from either of these two clones transmitted the mutation through their germline. Both lines of animals exhibited a similar phenotype, both at the heterozygote and homozygote stages (see below).

Figure 16B:
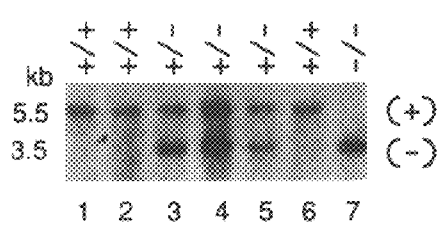
Figure 16C:
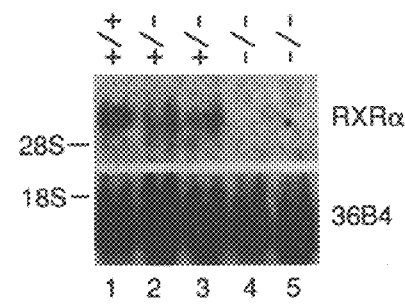
Figure 16D:
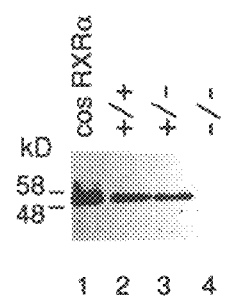

Heterozygous animals were fertile, and WT (+/+), heterozygous (+/−), and homozygous (−/−) embryos were obtained from crosses between heterozygous mice (see FIG. 16b). Northern Blot analysis of total RNA extracted from 12.5 dpc embryos failed to detect RXRα transcripts in (−/−) embryos (FIG. 16c). Therefore, even though the mutation could have conceptually generated RXRα transcripts that would just be lacking the sequences from exon 4, it appears that insertion of the PGK-NEO cassette in antisense orientation resulted in impaired transcription and/or processing of the RXRα RNA. Western blot analysis of nuclear extracts of 12.5 dpc embryos with an anti-RXRα antibody confirmed that no RXRα protein was synthesized in homozygous (−/−) embryos (FIG. 16d). Thus the mutation that was generated is a null mutation for the RXRα gene.

In order to detect possible functional interactions between RXRα and RARs, RXRα+/− mice were crossed with mice heterozygous for a null allele of the RARγ or RARα genes (Lohnes et al., Cell 73:643–658 (1993); Lufkin et al., Cell 66:1105–1119 (1991)). These breedings generated fertile double heterozygous RXRα+/−RARα+/− and RXRα+/−RARγ+/− animals which were crossed to produce embryos carrying mutations in both RXRα and ether RARα or γ genes (see below).

Postnatal Growth Deficiency in RXRα+/− Animals

It was noticed that RXRα heterozygote mice were often smaller than their WT littermates, even though analysis of the weights of 42 animals at birth did not reveal any significant differences between RXRα heterozygote and WT pups (not shown). Animals were thus weighed at 2–3 weeks of age, and the weight of each mouse was expressed relative to the mean weight of WT offsprings in the same litter, which was taken as 1 (FIG. 17). It is readily apparent that the weight distributions of heterozygous and wild type animals are different, heterozygous animals being on average 10% smaller than their WT littermates. In addition, a significant proportion of RXRα+/− mice were severely growth-deficient, with weights of less than 80% that of average WT siblings (see FIG. 17, 0.5 to 0.8 classes; note that such a pronounced growth deficiency was seen at a much lower frequency in WT animals). Several of these runt animals died after a few weeks. The weight deficit observed at 2–3 weeks of age was maintained in surviving adult RXRα+/− animals, which on average also exhibited a 10% weight deficit with respect to WT mice (not shown). Therefore, heterozygosity for the RXRα mutation resulted in postnatal growth deficiency, which was moderate in most animals, but more severe in about 10% of the RXRα+/− mice which were runt and usually die early. A similar growth deficiency phenotype was noticed irrespective of whether the mice were on a pure 129sv or a mixed 129sv-C57/Bl6 genetic background.

The RXRα Null Mutation is Embryonic Lethal

No living RXRα−/− null mutants could be recovered from litters obtained from RXRα+/− intercrosses (Table V). Furthermore, no living homozygous mutant fetuses were found when delivered by cesarean at 18.5 dpc, suggesting that the RXRα null mutation is embryonic lethal. However, living RXRα−/− null embryos were obtained at 16.5 dpc and at earlier stages. These embryos were often edemic, slightly smaller than their WT or heterozygous littermates, and had a whiter appearance due to a poor vascular irrigation (compare FIG. 18a with 18b; data not shown). In addition, a significant number of RXRα−/− animals recovered between 12.5 dpc and 16.5 dpc were dead (in all cases, the death of these embryos was estimated to be posterior to 11 dpc). Embryos (including the dead ones) that could be genotyped at 12.5 dpc and at later stages (which presumably include all the embryos that reached the age of 11 days) showed a significant deficit in the number of RXRα−/− null embryos (17% instead of the expected 25% frequency). Thus, in addition to the death observed at mid to late gestation, a significant fraction of RXRα−/− null embryos disappears at earlier stages. However, no deficit of RXRα−/− embryos could be observed within embryos genotyped at 9.5 and 10.5 dpc, but the fraction of dead or severely retarded embryos at these stages was higher in the RXRα−/− null mutant population (30%) than in the WT and RXRα+/− populations (11% and 9%, respectively). These dead RXRα−/− embryos were often much smaller than their living counterparts and appeared arrested at previous stages of development (not shown). However, given the overall high rate of embryo death at these early stages, it is difficult to distinguish the fraction of dead RXRα−/− null embryos which died because of their genotype from those that died as part of the 10% population of embryos being "normally" resorbed at these stages. In any case, these data suggest that RXRα performs important functions during early stages of development. The characterization of this "early lethal phenotype" will require careful analysis of a large number of RXRα null embryos at these stages.

Several RXRα null embryos were examined histologically at all stages between 10.5 and 16.5 dpc. Besides cardiac and ocular malformations (see below), the development of several organs appeared delayed with respect to WT or heterozygote embryos. These included the liver and the lungs (after 13.5 dpc) and the skin (at 16.5 dpc), which were all delayed by about 24 hours (data not shown). This developmental delay was also observed for the fusion of the palatal shelves and development of the teeth (not shown).

TABLE V

Viability of RXRα Mutants

| stage | RXRα genotype | | | | | |
|---|---|---|---|---|---|---|
| (dpc) | +/+ | +/− | −/− | +/+ | +/− | −/− |
| 9.5 | 4 | 10 (2) | 5 (3) | 37 (4) | 56 (5) | 37 (12) |
| 10.5 | 34 (4) | 46 (3) | 32 (9) | [28%] | [43%] | [28%] |
| 11.5 | 21 (3) | 47 (2) | 12 (5) | | | |
| 12.5 | 29 | 31 (2) | 13 (2) | | | |
| 13.5 | 11 (2) | 36 (3) | 15 (6) | 132 (3) | 247 (11) | 79 (35) |
| 14.5 | 41 (1) | 86 (2) | 25 (10) | [29%] | [53%] | [17%] |
| 15.5 | 23 | 36 (2) | 13 (6) | | | |
| 16.5 | 28 | 58 (2) | 13 (11) | | | |
| 18.5 | 4 (1) | 8 | 1 (1) | | | |
| Newborn | 8 | 29 | 0 | | | |

The number of dead or resorbed embryo and fetuses is given in parentheses; the distribution of RXRα+/+, RXRα+/− and RXRα−/− animals is given in brackets.

Heart Malformations in RXRα Null Embryos

Histological analysis of 13.5–16.5 dpc embryos revealed several defects in the heart of RXRα null mutants. It is likely that the mid to late gestation lethality of RXRα−/− embryos is due to these malformations which result in functionally impaired hearts.

In WT embryos the formation of a trabecular layer of myocutes in the ventricular myocardium begins around day 9.5 of gestation (Challice et al., Tissue & Cell 6.447–462 (1973)). A relatively thin compact or subepicardial layer is formed by 10.5 dpc, to further enlarge during the next days. In almost all RXRα–/– embryos examined between 13.5 and 16.5 dpc, the thickness of the compact layer (CL) of the myocardium was markedly reduced compared with WT embryos, while in comparison the trabecular layer (TL) appeared more normal (compare CL and TL in FIGS. 19*a* and 19*e* with FIGS. 19*b* and 19*f*). This reduction in thickness of the compact layer was variable from embryo to embryo and in the more extreme conditions the wall of the ventricular myocardium was reduced to a single cell layer. The walls of the atrium were also thinner in mutant animals, but the difference was not as pronounced as in the ventricular wall (not shown). No differences were observed between the myocardium of RXRα–/– embryos and their WT littermates at 10.5 dpc (compare CL and TL in FIG. 19*c* with 19*d*) and 12.5 dpc (see Table VI; not shown). However one out of 4 of the 11.5 dpc mutants examined displayed an extremely thin ventricular wall (not shown), thus suggesting a variability in the timing of appearance of this abnormality. Whether this variable expressivity of the thin myocardium phenotype reflects the mixed genetic background of these mutants is unknown. In any event, these variations probably account for the relatively large time window at mid-late gestation stages (11.5–14.5 dpc) during which RXRα–/– mutants die (Table V).

In WT embryos, septation of the ventriculoarterial region is completed by 14.5 dpc. In 2 out of 9 RXRα–/– embryos examined between 14.5–16.5 dpc, the membranous portion of the ventricular septum was incomplete (see IVC in FIG. 3*h*) and the upper part of the muscular ventricular septum was also absent (Table VI; data not shown). This malformation may be related to a delay in development, since it was not observed in the 16.5 dpc mutant examined.

The deficit in the ventricular cardiac myocytes population could result from an impaired capacity of RXRα–/– cells to differentiate into cardiac myocytes or from a reduction in the rate of proliferation of normally differentiated cardiac myocytes. To examine a possible role of RXRα in cardiac myocyte differentiation, in situ hybridization analyses were performed on 9.5 and 10.5 dpc RXRα null mutant embryos using cardiac α actin, α myosin heavy chain (αMHC) and atrial myosin light chain (MCLlA) anti mRNA probes. At these stages, these genes are strongly expressed in the heart and constitute therefore markers for cardiac myocyte differentiation. Comparable signals were observed in the hearts of both mutant and WT embryos (data not shown). Therefore the absence of RXRα does not prevent the synthesis of muscle mRNA characteristic of cardiac myocytes.

On the basis of ultrastructural and cytochemical properties, the myocytes located in the compact layer appear less differentiated than those of the trabecular layer (Rumyantsev, Int. Rev. Cytology 91:187–273 (1977)). Electron microscopy (EM) examination of trabecular cells of WT 14.5 dpc fetuses showed highly organized myofibrils (data not shown), whereas organized myofibrils were extremely scarce in cells at the outer margin of the compact layer. The first mutant myocardium analyzed by EM was severely affected (comparable to the one shown in FIG. 19*b*). In this specimen, the cells located in the outer region of the myocardium were already highly differentiated, with well organized myofibrils (with visible Z line, Z in FIG. 20*d*) and prominent sarcomeric reticulum (SR, FIG. 20*d*). The ultrastructural aspect of these cells was very similar to that of trabecular cells of WT hearts (compare FIGS. 20*b* and 20*d* compact layer in mutant with 20*e* trabecular layer of WT). The myocardium of the second 14.5 dpc mutant examined was more mildly affected and a compact layer could clearly be detected histologically (data not shown). EM examina-

TABLE VI

Abnormalities in RXRα null mutants examined at various developmental stages (10.5–16.5 dcp)

|  | 10.5 (6) | 11.5 (4) | 12.5 (4) | 13.5 (5) | 14.5 (6) | 15.5 (2) | 16.5 (1) |
|---|---|---|---|---|---|---|---|
| Heart Abnormalities | | | | | | | |
| Thinner myocardium | 0/6 | 1/4 | 0/4 | 4/5 | 6/6 | 2/2 | 1/1 |
| Interventricular communication | NA (a) | NA (a) | NA (a) | NA (a) | 1/6 | 1/2 | 0/1 |
| Eye Abnormalities | | | | | | | |
| Shorter ventral retina | NA (b) | NA (b) | 8/8 | 10/10 | 12/12 | 4/4 | 2/2 |
| Ventral rotation of the lens | NA (c) | 0/8 | 8/8 | 10/10 | 12/12 | 4/4 | 2/2 |
| Thicker cornea | NA (d) | NA (d) | 6/8 | 10/10 | 12/12 | 4/4 | 2/2 |
| Absence of anterior chamber | NA (e) | NA (e) | NA (e) | NA (e) | NA (e) | 4/4 | 2/2 |
| Close roots of eyelids | NA (f) | NA (f) | 6/8 | 10/10 | 12/12 | 4/4 | 2/2 |
| Abnormal sclera | NA (g) | NA (g) | NA (g) | NA (g) | NA (g) | NA (g) | 2/2 |
| Coloboma of the optic nerve | NA (h) | NA (h) | NA (h) | NA (h) | 12/12 | 4/4 | 2/2 |
| Persistent retrolenticular membrane | NA (i) | NA (i) | NA (i) | NA (i) | 12/12 | 4/4 | 2/2 |

The number of embryos/fetuses examined at each time is given in parenthesis.
NA: not applicable.
(a): interventricular communication is normally present until 13.5 dpc.
(b): the dorsal and ventral retina are not distinguishable until 12.5 dpc.
(c): the lens is not detached from the surface ectoderm at 10.5 dpc.
(d): the cornea develops after 11.5 dpc.
(e): an anterior chamber is not always present until 15.5 dpc.
(f): the roots of the eyelids are not distinguishable until 12.5 dpc.
(g): a well differentiated sclera is not present until 16.5 dpc.
(h): the closure of the choroid fissure is not completed until 14.5 dpc.
(i): mesenchymal cells are normally present in the vitreous body until 13.5 dpc.

Differentiation and Proliferation of Cardiac Myocytes in RXRα Null Mutants tion of the cells at the external margin of this "compact layer" showed that these cells were most often similar to cells located at a similar position in the WT myocardium (not shown). However, organized myofibrils (with a visible Z line) could occasionally be seen in these cells (not shown), which indicates that they may be in a more advanced differentiation state than in the WT myocardium. Together, these observations show that RXRα null mutants are impaired in their capacity to maintain the cells of the presumptive compact layer in a relative undifferentiated state.

The reduction in the size of the compact layer could be due to a decrease in the rate of proliferation of the cells located at the periphery of the myocardium. The percentage of cells in the process of mitosis in that region in both WT and mutants was determined. Surprisingly, the percentage of mitotic cells was only slightly reduced, if at all, in 14.5 dpc mutants compared with WT (2.38% and 1.82% in the severely and mildly affected mutants respectively, and 2.49% in the WT embryo). The rate of DNA synthesis by monitoring bromodeoxyuridine (BrdU) incorporation in WT and RXRα null mutant embryos at 12.5–13.5 dpc was also investigated. No drastic difference in the proportion of BrdU positive nuclei was observed in the myocardium between the WT and mutant embryos (data not shown).

Heart, outflow tract and aortic arch malformations in double RXRα/RARγ and RXRα/RARα mutants A reduced thickness of the ventricular myocardium was also observed at 14.5 and 15.5 dpc in RXRα-/- embryos carrying additional heterozygous or homozygous mutations in either the RARα or RARγ genes, but this reduction was not more severe than that observed in RXRα-/- embryos (data not shown). Interestingly, one 14.5 dpc RXRα+/- RARγ-/- mutant fetus (out of 6 14.5 and 15.5 dpc fetuses) displayed a thin ventricular myocardium (Table VII), thus suggesting some functional synergy between RXRα and RARγ during development of the ventricular myocardium (no myocardium defect was seen in RARγ-/- fetuses, see Lohnes et al., Cell 73: 643–658 (1993)).

In the one RXRα-/-RARγ-/- null mutant embryo examined at 14.5 dpc, the proximal portion of the aorticopulmonary septum was missing, but both the aorta and pulmonary trunk could be distinguished in the more distal portion of the heart outflow tract, resulting in a partial persistent truncus arteriosus ("partial" PTA; data not shown). A similar partial PTA was found in 1 out of 6 14.5 dpc RXRα-/-RARα+/-. However, the 15.5 dpc RXRα-/-RARγ-/- mutant embryo exhibited a complete agenesis of the aorticopulmonary septum ("complete" PTA). A similar "complete" PTA was also found in the single 14.5 dpc RXRα-/-RARα-/- mutant that was analyzed, indicating a functional synergism between RXRα and RARα or γ for the formation of the aorticopulmonary septum.

Some of the RXR/RAR double mutants also exhibited various abnormalities of aortic arch derivatives (Table VII, and data not shown). In the 14.5 dpc RXRα-/-RARγ-/- fetus, the right pulmonary artery arose from the innominate artery (not shown). In the RXRα-/-RARα-/- mutant, the ductus arteriosus was missing. In one out of 6 RXRα-/- RARα+/- embryos, the right subclavian artery arose from the descending aorta and passed dorsally to the esophagus, resulting in a retroesophageal right subclavian artery (not shown; note that this embryo was different from the RXRα-/-RARα+/- embryo that displayed the "partial" PTA phenotype). Both the PTA defect and aortic arch abnormalities were never found in single RXRα or RARα or RARγ null mutants and are therefore specific for double mutants.

TABLE VII

Heart, Aortic arch and eye abnormalities in RXRα/RARγ and RXRα/RARα double mutants

|  | RXRα+/- RARγ-/- |  | RXRα-/- RARγ+/- | RXRα-/- RARγ-/- |  |  | RXRα+/- RARα-/- | RXRα-/- RARα+/- | RXRα-/- RARα-/- | RXRα-/- |  |
|---|---|---|---|---|---|---|---|---|---|---|---|
| Stages (dpc) | 14.5 | 15.5 | 14.5 | 12.5 | 14.5 | 15.5 | 14.5 | 14.5 | 14.5 | 14.5 | 15.5 |
| Number of fetuses examined | 3 | 3 | 2 | 1 | 1 | 1 | 2 | 6 | 1 | 6 | 2 |
| Heart Abnormalities |  |  |  |  |  |  |  |  |  |  |  |
| Thinner myocardium | 1/3 | 0/3 | 1/2 | 0/1 | 1/1 | 1/1 | 0/2 | 4/6 | 1/1 | 6/6 | 2/2 |
| Interventricular communication | 0/3 | 0/3 | 0/2 | NA (f) | 1/1 | 1/1 | 0/2 | 4/6 | 1/1 | 1/6 | 1/2 |
| Persistent truncus arteriosus | 0/3 | 0/3 | 0/2 | 0/1 | 1/1 (a) | 1/1 | 0/2 | 1/6 (a) | 1/1 | 0/6 | 0/2 |
| Aortic Arch Abnormalities | 0/3 | 0/3 | 0/2 | 0/1 | 1/1 | 0/1 | 0/2 | 1/6 | 1/1 | 0/6 | 0/2 |
| Eye Abnormalities |  |  |  |  |  |  |  |  |  |  |  |
| Shorter ventral retina | 6/6 (b) | 6/6 (b) | 4/4 | 2/2 | 2/2 | 2/2 | 0/4 | 12/12 | 2/2 | 12/12 | 4/4 |
| Ventral rotation of the lens | 6/6 | 6/6 | 4/4 | 2/2 | 2/2 | 2/2 | 0/4 | 12/12 | 2/2 | 12/12 | 4/4 |
| Thicker cornea | 2/6 | 2/6 | 4/4 | 2/2 | 2/2 | 2/2 | 0/4 | 12/12 | 2/2 | 12/12 | 4/4 |
| Absence of anterior chamber | NA (c) | 4/6 | NA (c) | NA (c) | NA (c) | 2/2 | NA (c) | NA (c) | NA (c) | NA (c) | 4/4 |
| Closer roots of eyelids | 6/6 | 6/6 | 4/4 | NA (d) | NA (d) | NA (d) | 0/4 | 12/12 | 2/2 | 12/12 | 4/4 |
| Eversion of the neural retina | 0/6 | 0/6 | 0/4 | 0/2 | 2/2 | 2/2 | 0/4 | 2/12 (e) | 2/2 | 0/12 | 0/4 |
| Coloboma of the optic nerve | 1/6 | 0/6 | 4/4 | NA (g) | 2/2 | 2/2 | 0/4 | 11/12 | 2/2 | 12/12 | 4/4 |
| Coloboma of the iris | 0/6 | 0/6 | 0/4 | NA (h) | 2/2 | 2/2 | 0/4 | 2/12(e) | 1/2 | 0/12 | 0/12 |
| Retrolenticular membrane | 5/6 | 6/6 | 4/4 | NA (i) | 2/2 | 2/2 | 0/4 | 12/12 | 2/2 | 12/12 | 4/4 |
| Corneal-lenticular stalk | 0/3 | 0/6 | 0/4 | 2/2 | 2/2 | 2/2 | 0/4 | 0/12 | 0/2 | 0/12 | 0/4 |

NA: not applicable.
(a): "partial" persistent truncus arteriosus (see text).
(b): mild reduction.
(c): an anterior chamber is not always present until 15.5 dpc.
(d): eyelids are not present in the mutants.
(e): unilateral in both fetuses.
(f): interventricular communication is normally present until 13.5 dpc.
(g): the choroid fissure is not closed at 12.5 dpc.
(h): the closure of the choroid fissure is not completed until 14.5 dpc.
(i): mesenchymal cells are normally present in the vitreous body until 13.5 dpc.

Eye Defects in RXRα Mutant Embryos

Figure 18A:
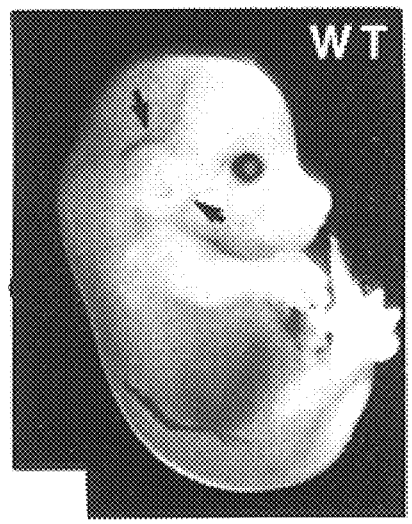
Figure 18B:
Figure 18C:
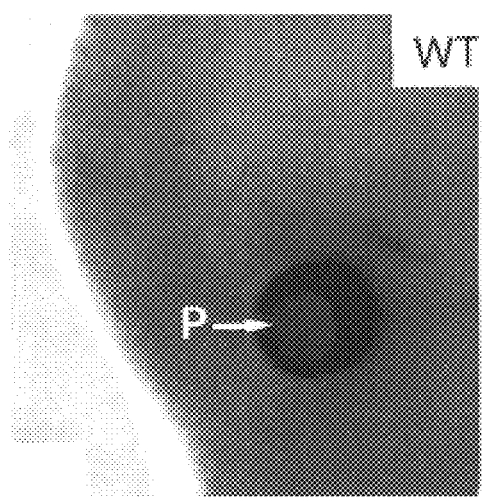

Abnormal eyes were observed bilaterally by external inspection in all RXRα null homozygotes collected at stages posterior to 13.5 dpc (compare FIG. 18c with 18d, 21e with 21f, 22a with 22b, and 23d with 23e; data not shown). The size of the palpebral fissure was reduced and pigmented tissue was less visible in the ventral portion of the eye. Two rotations of the eye globe were also apparent in the mutant eyes: one around a dorsoventral axis towards the snout; and one along a rostro-caudal axis towards the ventral side. These rotations were reflected by the lack of coincidence between the margins of the eyelids and the rim of the pupilla in mutant eyes (compare FIG. 22a with 22b; see also the tridimensional reconstruction, FIG. 23d).

Figure 21A:
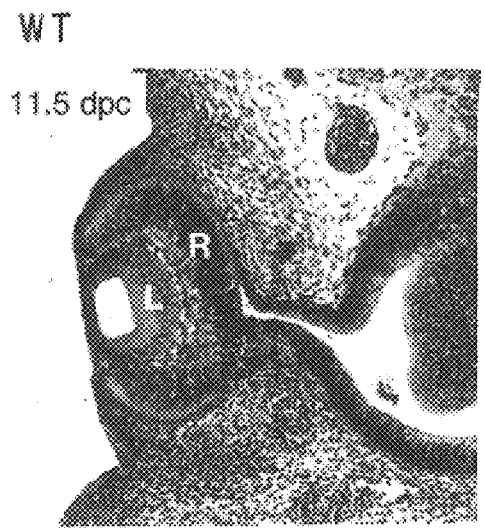
Figure 21B:
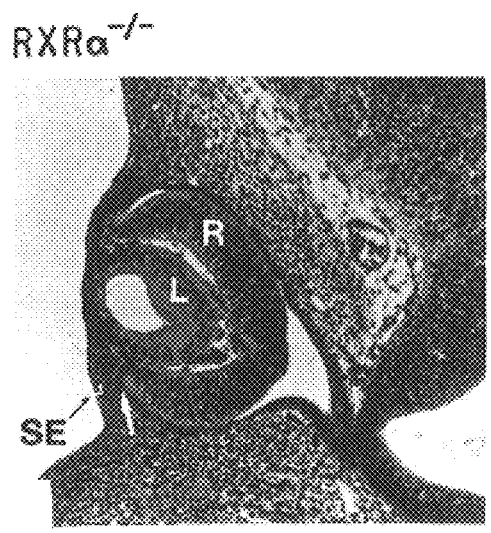
Figure 21C:
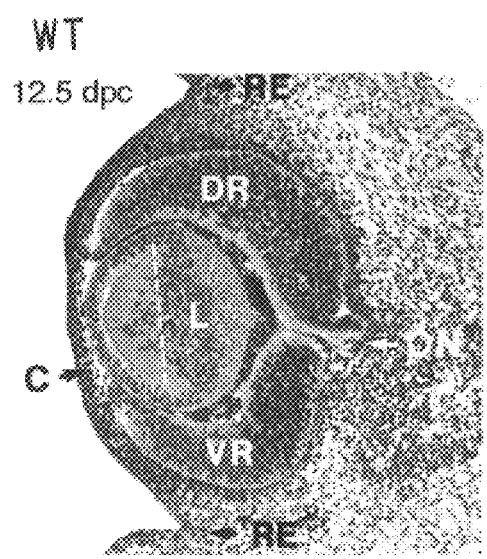
Figure 21D:
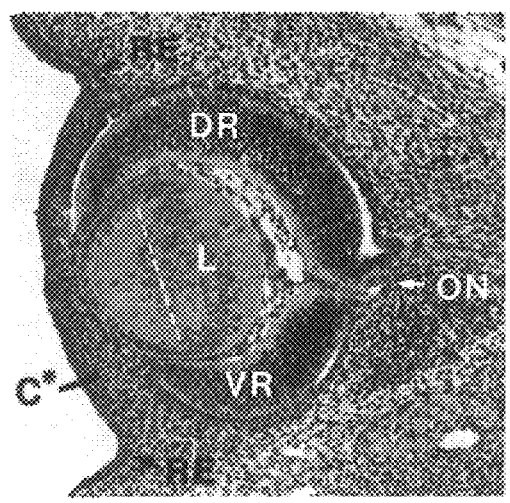
Figure 21E:
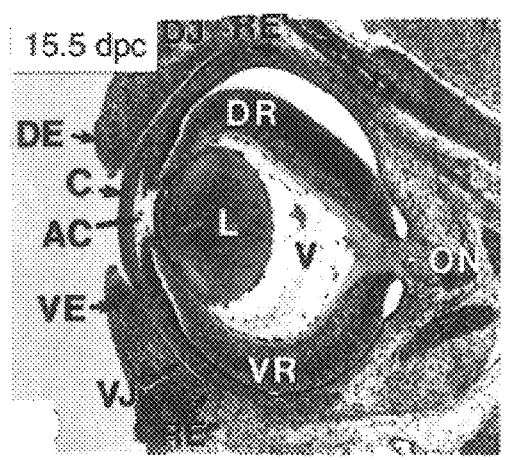
Figure 21F:
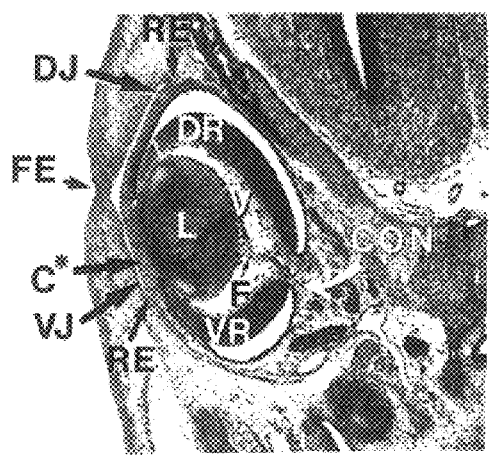
Figure 22A:
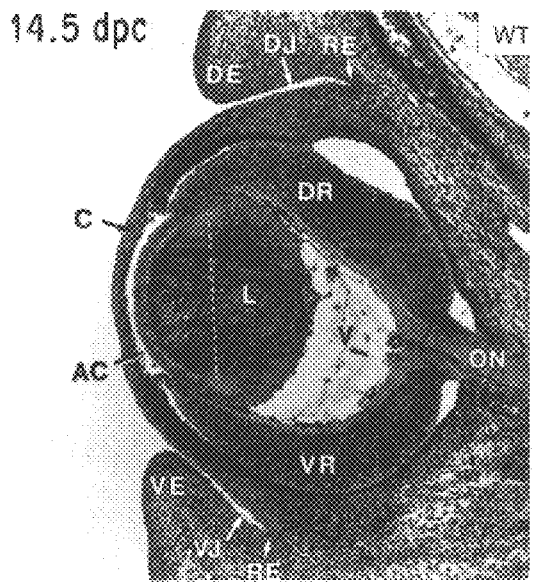
Figure 22B:
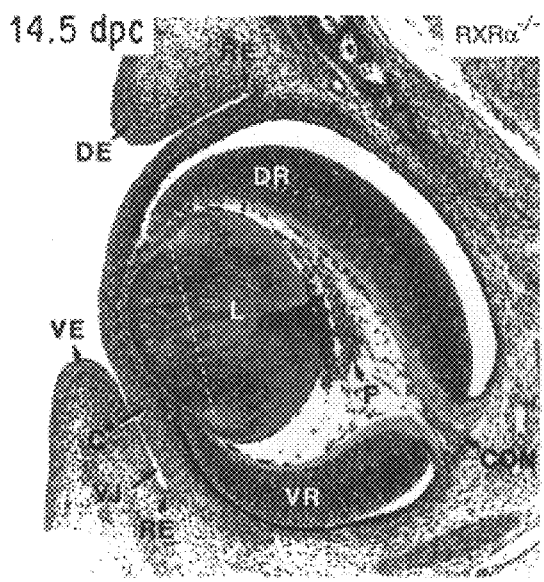
Figure 22C:
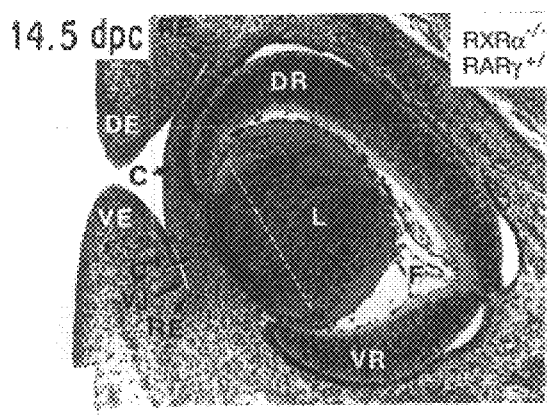

In all RXRα-/- mutant embryos analyzed histologically between 12.5 and 16.5 dpc (14 embryos), the ventral portion of the retina (VR) was bilaterally reduced in size with respect to its dorsal counterpart (DR, compare FIG. 21c and 21e [WT] with 21d and 21f RXRα-/-, and FIG. 22a with 22b). Note that the ventral and dorsal retina, which are defined with respect to the horizontal plane passing through the papilia (i.e., the optic nerve exit point) have similar sizes in wild type fetuses. The extent of this reduction was however variable from embryo to embryo. In the 4 11.5 dpc embryos analyzed, the ventral edge of the optic cup was located further away from the surface ectoderm than the dorsal edge (compare FIG. 21a with 21b), which suggests that the ventral portion of the optic cup was already shortened at this stage (note that it becomes possible to distinguish the dorsal and ventral retina only at day 12.5 dpc when the axons emanating from the neural retina start to leave the optic cup). The optic cup was apparently normal at 10.5 dpc (6 embryos; not shown). All RXRα mutant eyes analyzed between 12.5 and 16.5 dpc were also characterized by a ventral rotation of the lens (of about 10°; compared dotted line in the lens of FIG. 21c and 22a [WT] with 21d and 22b RXRα-/-). This rotation is likely to be a consequence of the reduction of the size of the ventral retina.

Figure 22D:
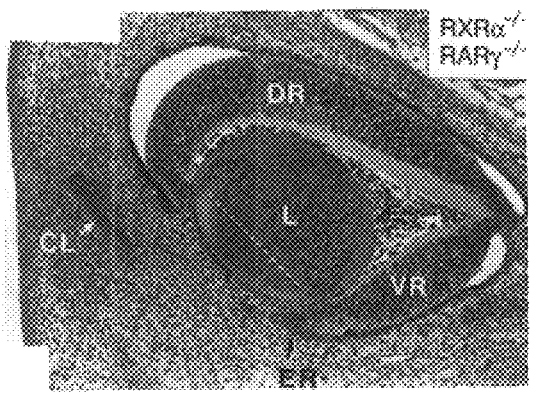
Figure 22E:
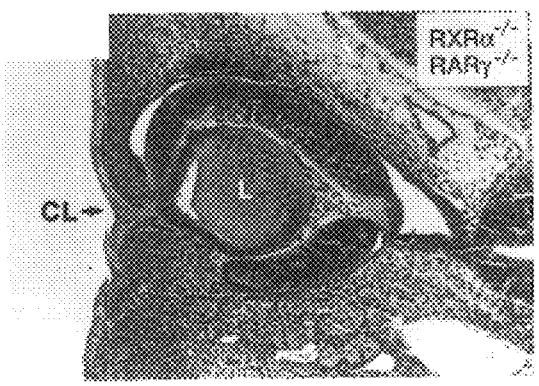
Figure 22F:
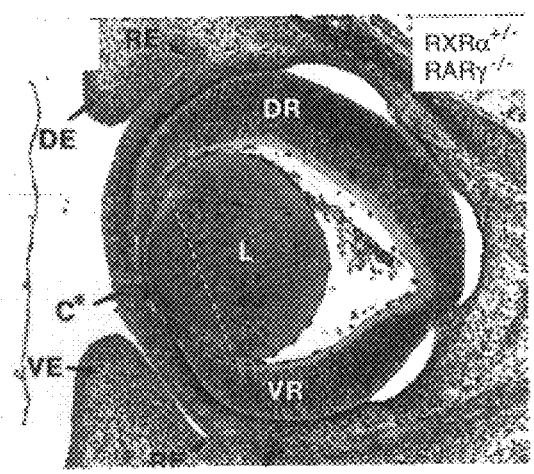

In the mouse, the development of the cornea begins at 11.5–12.5 dpc with the migration of mesenchymal cells between the surface ectoderm and the lens vesicle (Pei and Rhodin, Anat. Rec. 168:108–126 (1970)). All RXRα-/- eyes examined at 13.5–16.5 dpc had an abnormal cornea which was characterized by a thickening of the corneal stroma (compare C in FIG. 22a and 22i [WT] with C* in FIG. 22b and 22j RXRα-/-). This feature was visible both in the dorsal and ventral portions of the cornea, but was always more pronounced ventrally. The cells close to the lens were more compacted than the cells beneath the surface ectoderm, which appeared less differentiated, more loosely organized and often in the progress of migration (CS; FIG. 22j, and electron microscopy data not shown). The thickening of the cornea was also clearly seen in 6 out of 8 eyes examined at 12.5 dpc (compare C in FIG. 21c with C* in FIG. 21d).

The space formed between the cornea and the lens by 15 dpc in WT fetuses is called the anterior chamber. In all RXRα null mutants examined at 15.5–16.5 dpc (3 fetuses), the corneal stromal cells were very close to, or in direct contact with the lens, resulting in a marked reduction in the size or an absence of the anterior chamber (compare FIG. 21 e with 21 f, and data not shown).

At 13.5 dpc, the eyelids develop ventrally and dorsally to the eye as mesenchymal outgrowths covered by ectoderm. They grow towards each other and fuse by 15.5–16.5 dpc (Juriloff and Harris, Teratology 40:59–66 (1989)). Histological examination of RXRα-/- 13.5–15.5 dpc fetuses, showed that the ventral and dorsal eyelids were always located closer to each other, as compared to their WT counterpart at identical developmental stages, resulting in a smaller palpebral fissure (compare FIG. 22a with 22b; see also the tridimensional reconstructions in FIG. 23d and 23e, and the external aspect of the eye in FIG. 18c and 18d). This "closer eyelid" phenotype may not correspond to a defect of the eyelids themselves, which appeared normal in size, but to a closer position of the sites of origin of the eyelids ("roots of the eyelids"; these sites define also the limit of the future conjunctival space). At 12.5 dpc the origins of the eyelids are already identifiable as indentations of the surface ectoderm (RE; FIG. 21c). These indentations were located in a more anterior position in mutants when compared to WT, which resulted in a shortening of the distance separating these sites (compare RE in FIG. 21c and 21d). Another aspect of this abnormal position of the roots of the eyelids was a hypoplasia of the conjunctival sac in 15.5 and 16.5 dpc mutants, which was always more pronounced on the ventral side (compare VJ in FIG. 21e and 21f; data not shown).

Figure 22G:
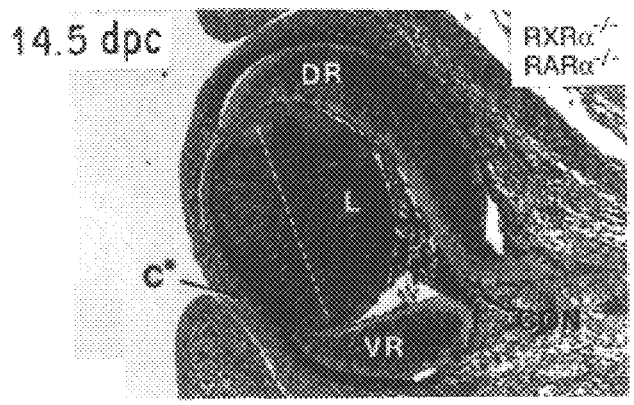
Figure 22H:
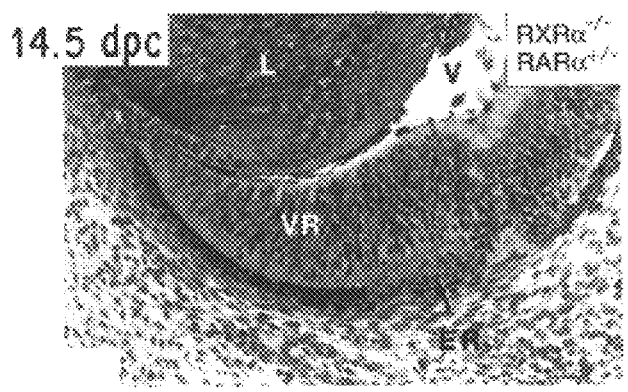
Figure 22I:
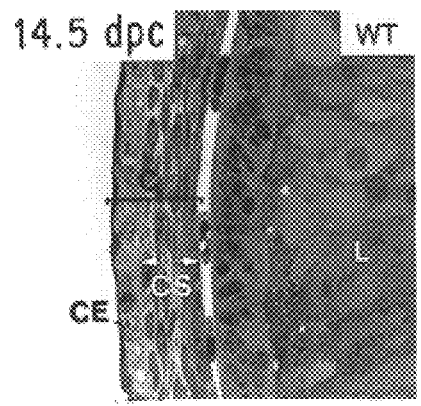
Figure 22J:
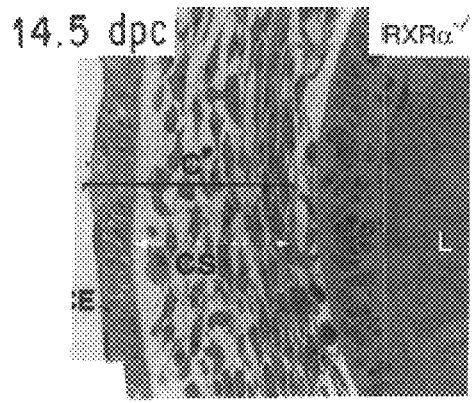
Figure 22K:
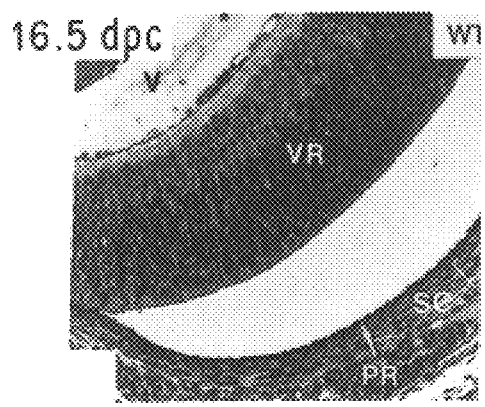
Figure 22L:
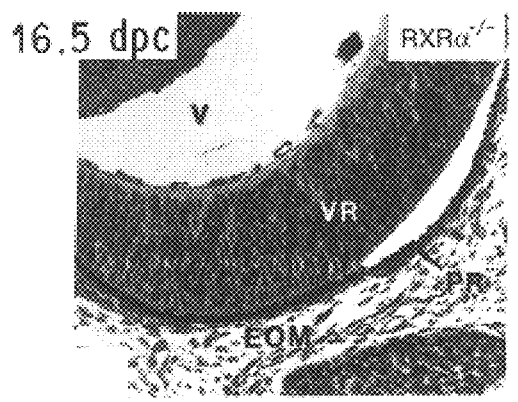

An additional eye abnormality detected in RXRα-/- mutant embryos corresponded to a poor development of the sclera (compare FIG. 22k with 22l). This defect, as well as the defects affecting the cornea, anterior chamber and possibly eyelids, is likely to result in an abnormal behavior of extraocular neural crest derived mesenchymal cells, which contribute to the formation of these structures (see also discussion).

In 11.5 to 13.5 dpc WT embryos, the vitreous body communicates with the periocular mesenchyme through the optic fissure. At this stage mesenchymal and vascular cells which enter through the optic fissure, are present in the vitreous body. At 14.0 dpc, the closure of the optic fissure is completed (Pei and Rhodin, Anat. Rec. 168:108–126 (1970)). In all RXRα-/- mutant eyes examined between 14.5–16.5 dpc (9 fetuses), the closure of the optic fissure was incomplete, leaving a small communication between the vitrous body and periocular mesenchyme, resulting in a coloboma of the optic nerve (CON; compare FIG. 21e and 22a [WT] with 21f and 22b RXRα-/-). This cleft allowed mesenchymal cells to enter the vitreous body, resulting in the presence of a large number of mesenchymal cells in this cavity (persistent retrolenticular membrane, F in FIG. 21f and 22b). In WT embryos such cells are normally abundant until 13.5 dpc, to become scarce at 14.5 dpc (FIG. 22a) and completely disappear at 15.5 dpc (FIG. 21e). It could be proposed that both coloboma of the optic nerve and the persistent retrolenticular membrane could result from a general developmental delay in RXRα-/- embryos at the 14.5 dpc stage. However, this is unlikely since these abnormalities were also detected in fetuses at 15.5 dpc (FIG. 21f) and 16.5 dpc (Table VI; data not shown).

Similar Eye Malformations Occur in RXRα-/- and RXRα+/-RARγ-/- Embryos

Histological analysis of RXRα+/-RARγ-/- fetuses at 14.5 dpc and 15.5 dpc revealed similar eye malformations than those detected in RXRα-/- embryos. All RXRα+/-RARγ-/- fetuses were characterized by a closer position of the root of the eyelids (FIG. 22f), which resulted in a reduction of the size of the palpebral fissure. This feature was readily recognizable by external inspection in two fetuses out of 6 (FIG. 18e). The size of the ventral retina was also moderately reduced in all these mutants (compare FIG. 22a [WT] with 22f [mutant]), and the lens displayed a ventral rotation of comparable magnitude as the one seen in RXRα-/- eyes (compare FIG. 22f with 22b). Only one eye out of 12 (Table VII) showed a coloboma of the optic nerve.

However, most RXRα+/−RARγ−/− eyes exhibited a fibrous retrolenticular membrane (Table VII). A thickening of the corneal stroma was observed in 4 eyes out of 12 (compare FIG. 22a and 22b with 22f) and the development of the anterior chamber was impaired in 4 out of 6 eyes (Table VII). Therefore RXRα+/−RARγ−/− embryos can exhibit all of the eye malformations seen in RXRα homozygote null mutants, albeit often in a milder form. Note in this respect that RARγ−/− (Lohnes et al., Cell 73:643–658 (1993)) and RXRα+/− embryos (not shown) never displayed any eye malformation. These observations suggest the existence of a functional synergy between RXRα and RARγ at some stages of eye development.

Figure 18D:
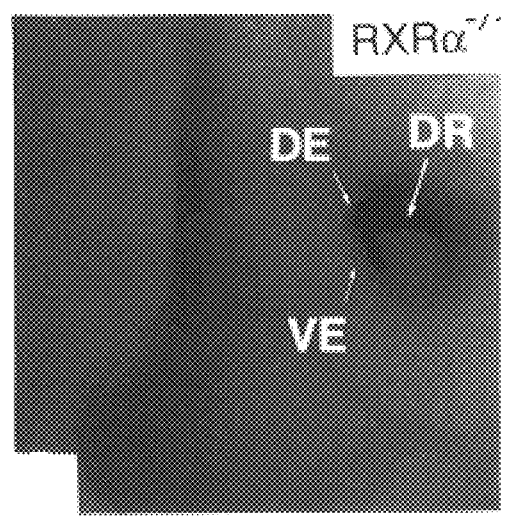
Figure 18E:
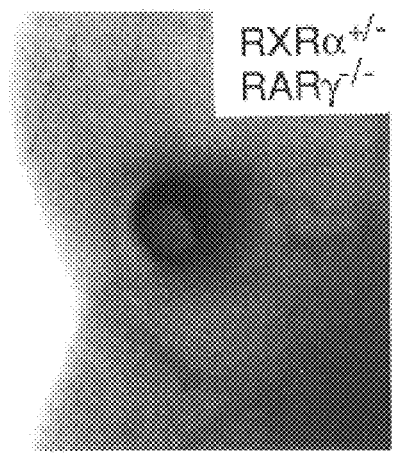
Figure 18F:
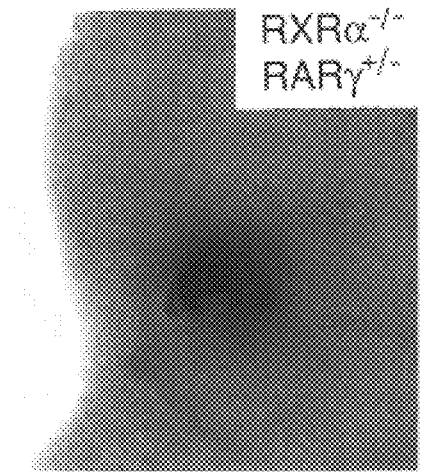

Increased Severity of Eye Malformations in RXRα−/−RARγ+/− and RXRα−/− RARγ−/− Double Mutants In 14.5 dpc RXRα−/−RARγ+/− (2 fetuses) the reduction in size of the palpebral fissure was enhanced with respect to RXRα−/− eyes and the ventral portion of the eye was completely masked by the ventral eyelid (compare FIG. 18d with 18f). Histological examination confirmed that the eyelids were located very close to each other in these embryos compared with the RXRα null mutants (compare VE and DE in FIG. 22c and 22b). The ventral portion of the cornea was absent and replaced with a thick portion of mesenchymal tissue, whereas the dorsal aspect of the cornea was still identifiable, but markedly reduced in size with respect to RXRα−/− eyes (compare C* in FIG. 22c and 22b). The ventral rotation of the lens was also accentuated in these mutants (compare dotted line in FIG. 22c and 22b).

Figure 18G:
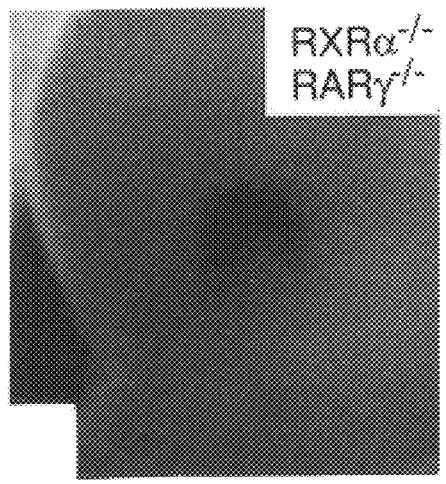

In the 14.5 and 15.5 dpc RXRα−/−RARγ−/− fetuses, the eyes were entirely buried beneath mesenchymal tissue and thus had a blurry external appearance (FIG. 18g). The cornea and anterior chamber were absent and replaced by a thick layer of mesenchymal tissue which was in direct contact with the lens (FIG. 22d). This internal location of the eye behind a thick layer of mesenchymal tissue was already seen in the eyes of the 12.5 dpc double mutant (FIG. 22e). The eyelids were also not formed in the double mutant fetuses. The invagination of surface ectoderm at the lower and upper part of the eye (which corresponds to the anlage of the conjunctival sac and defines the region of formation of the future eyelids) was absent in both eyes of the RXRα/RARγ double null 12.5 dpc embryo examined (compare FIG. 22e with 21c [WT] and 21d RXRα−/−). The ventral rotation of the lens was also markedly enhanced in these mutants and this was correlated with a increased reduction in the size of the ventral retina (see dotted line in FIG. 22d).

Figure 23A:
Figure 23B:
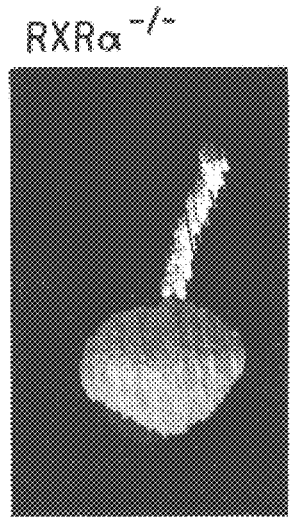
Figure 23C:
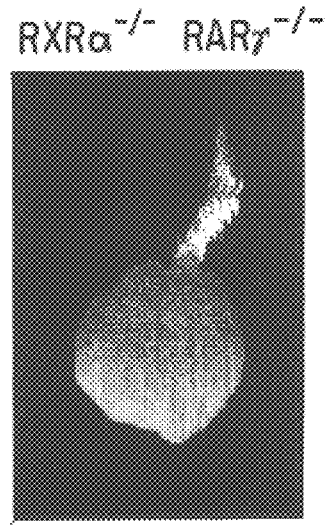
Figure 23D:
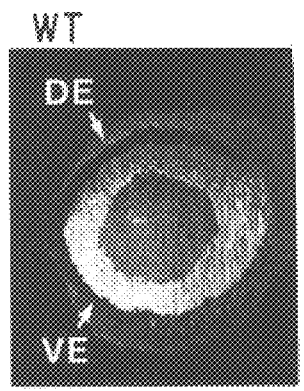
Figure 23E:
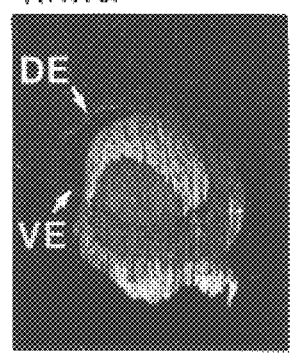
Figure 23F:
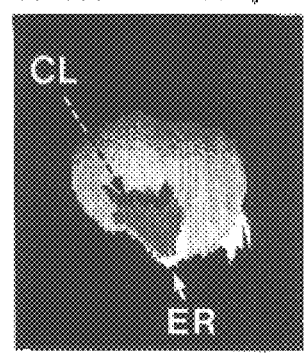
Figure 23G:
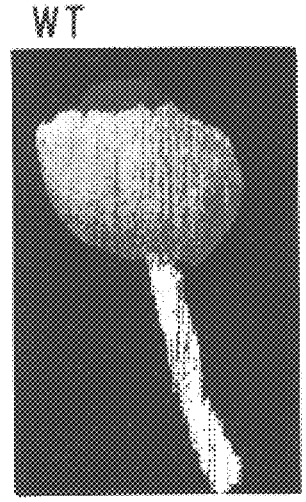
Figure 23H:
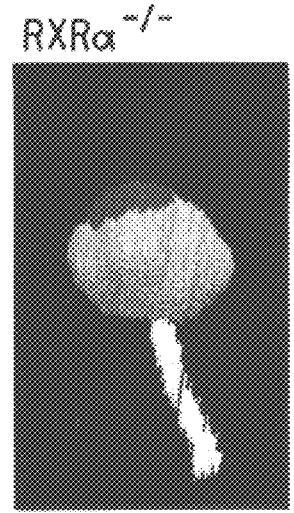
Figure 23I:
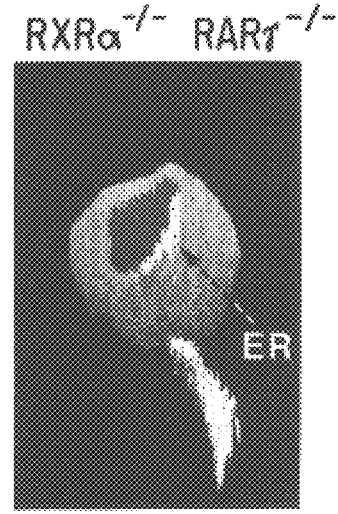

Besides these defects which correspond to more severe forms of defects already found in RXRα null mutants, additional malformations were detected in RXRα−/−RARγ−/− double mutant eyes that were never seen in RXRα−/− eyes. Both the 14.5 and 15.5 dpc double mutants displayed a bilateral eversion of the retina (ER; FIG. 22d) at the level of the ventral iris, resulting in an absence of the ventral iris and a coloboma of the iris (FIG. 23f and 23i). All RXRα−/−RARγ−/− eyes also displayed a persistent corneal-lenticular stalk (CL; FIGS. 22d, 22e and 23f). This malformation corresponds to a failure of the lens and the surface ectoderm to separate, an event which is normally taking place by 11.5 dpc.

Eye Defects in RXRα/RARα Double Mutants

Figure 18H:
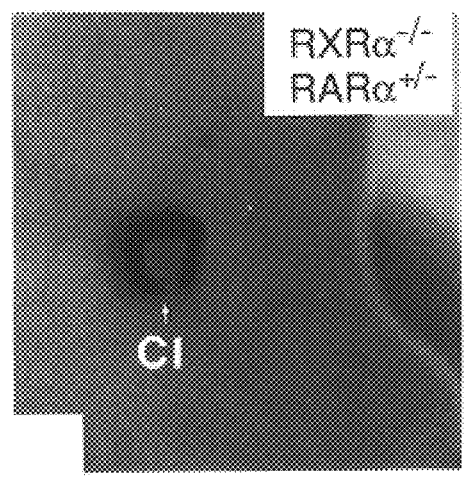
Figure 19A:
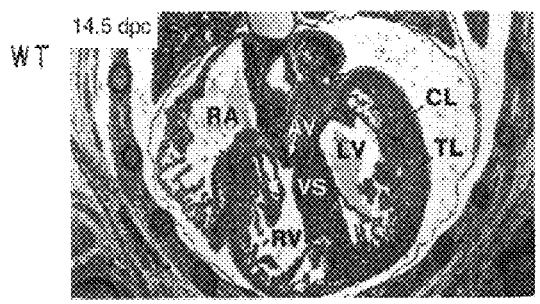
Figure 19B:
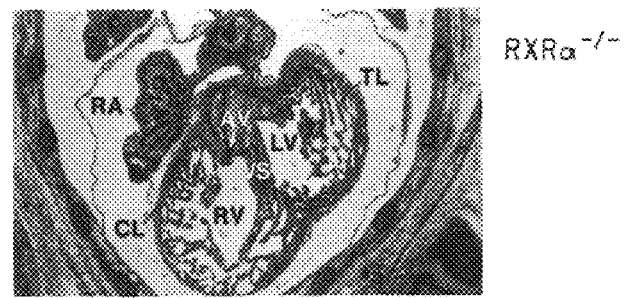
Figure 19C:
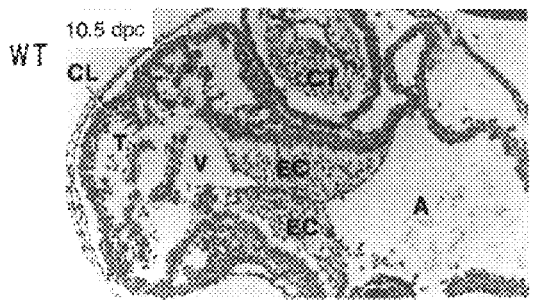
Figure 19D:
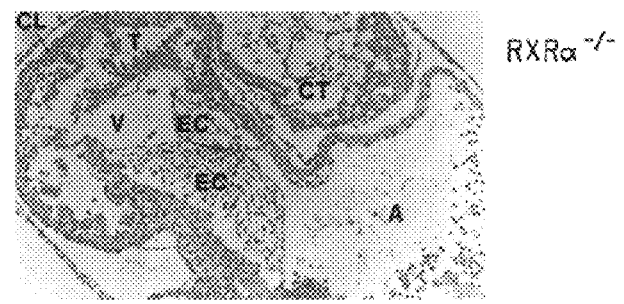
Figure 19E:
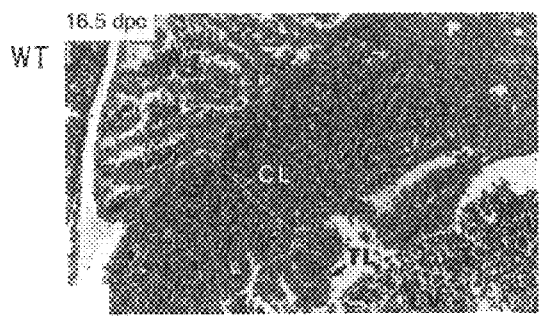
Figure 19F:
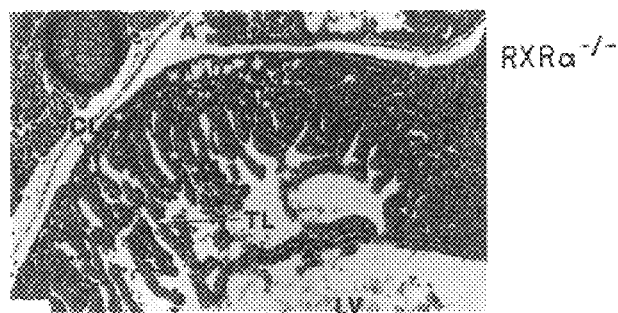
Figure 19G:
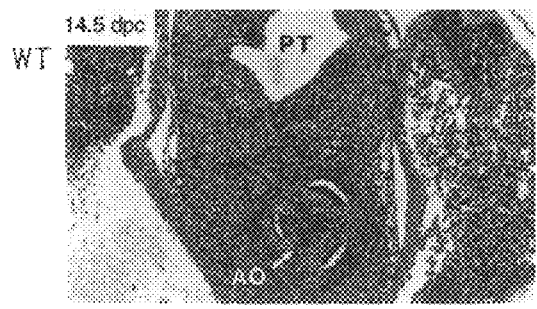
Figure 19H:
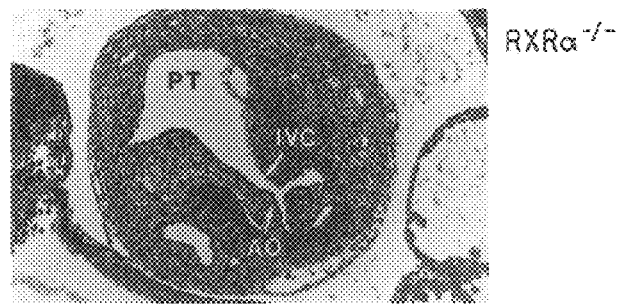
Figure 20A:
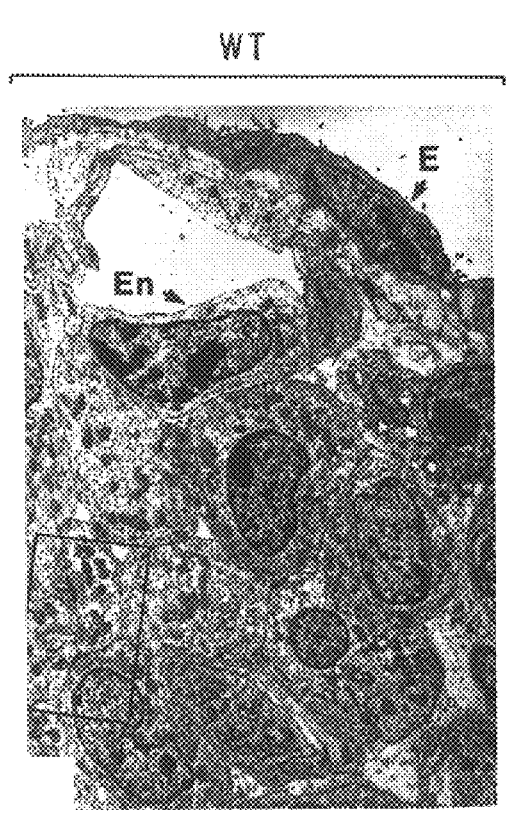
Figure 20B:
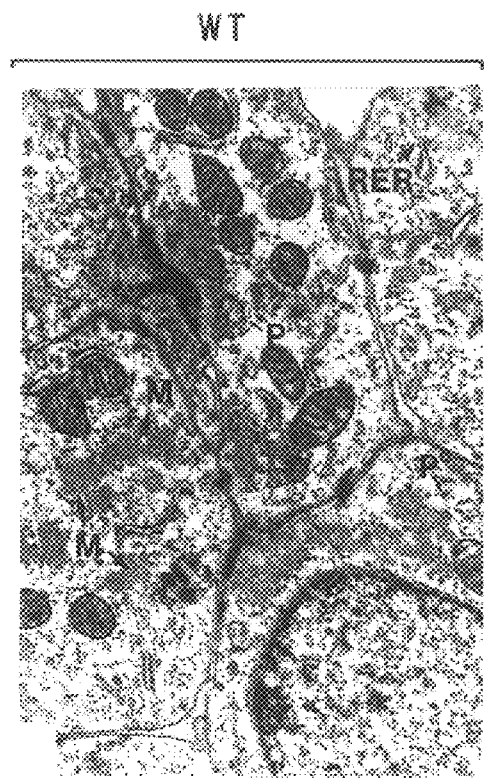
Figure 20C:
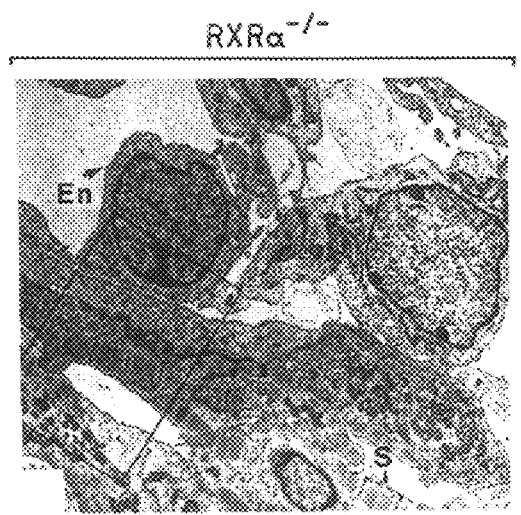
Figure 20D:
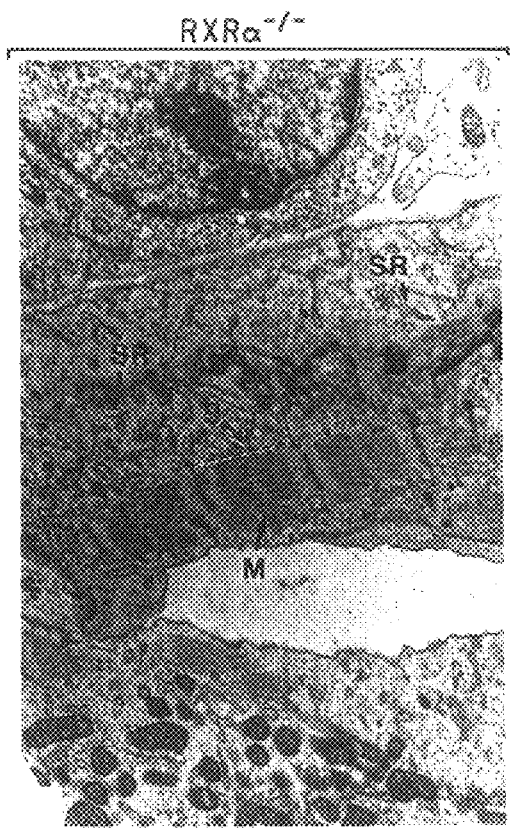

RXRα−/−RARα+/− and RXRα−/−RARα−/− double mutants displayed additional defects in the ventral portion of the retina. Two out of six 14.5 dpc RXRα−/−RARα+/− fetuses exhibited an unilateral eversion of the retina (ER; FIG. 22h) extending along the line of closure of the choroid fissure from the optic nerve exit point to the iris, thus corresponding to a unilateral coloboma of the pigmented retina. In both cases the ventral iris was absent, resulting in a ipsilateral coloboma of the iris (not shown) which was readily visible externally (CI; FIG. 18h). The 14.5 dpc RXRα−/−RARα−/− fetus displayed unilaterally an eversion of the pigment retina (from the optic nerve exit point to the iris); the other eye showed a similar eversion in which the iris was not affected, which resulted in a bilateral coloboma of the pigmented retina, and an unilateral coloboma of the iris. These observations, together with the fact that eversion of the retina was never observed in RXRα−/− mutants, suggest that RXRα and RARα can synergize to control the normal process of closure of the choroid fissure.

In the single 14.5 dpc RXRα−/−RARα−/− double null mutant studied, both the dorsal and ventral retinas of both eyes were reduced in size with respect to WT and RXRα−/− eyes (compare FIG. 22g with 22a and 22b). It is interesting to note that, in contrast to what was observed in the RXRα/RARγ double mutants, the corneal malformations were not enhanced in the RXRα/RARα double mutant eyes (compare C* in FIG. 22g with C* in FIG. 22b and 22c).

Two RXRα+/—RARα−/− 14.5 dpc fetuses were also analyzed; they did not exhibit any eye abnormality (Table VII; data not shown).

Discussion

The results reported here demonstrate that RXRα is an essential gene in the mouse, since all RXRα null mutants die during embryonic development. Most of the RXRα−/− embryos die at mid to late gestation stages, most probably from cardiac failure. A significant proportion (about 30%) of RXRα null mutants disappear however earlier before 10.5 dpc. The reason for this early lethality is currently unknown, but it may reflect an important function of RXRα during early mouse development, which can however be rescued in most instances. These results also demonstrate that RXRα exerts a crucial role in the development of the ventricular myocardium and in eye morphogenesis. Several features of the RXRα mutant phenotype, as well as observations made on compound RXRα/RAR mutants point to a convergence in the signalling pathways that depend on RXRα and RARs.

Role of RXRα in the Development of the Eye

The development of the eye is a highly complex process which involves multiples interactions between neuroectodermal cells (forming the retina, optic nerve and part of the iris), neural crest derived mesenchymal cells (forming the cornea, choroid, sclera, eyelids, stromal part of the iris and surface ectodermal cells (forming the lens and epithelia of the cornea and eyelids). RXRα null mutants display several eye abnormalities. These include malformations of the anterior segment (thickening of the corneal stroma, absence of anterior chamber, closer roots of eyelids and hypoplasia of the conjunctival sac), abnormal sclera, shortening of the ventral retina, ventral rotation of the lens, coloboma of the optic nerve and persistent retrolenticular membrane. It is likely that the rotation of the lens is a direct consequence of the reduction of the size of the ventral retina, since it is known that the position of the equator of the lens depends on interaction with the neural retina.

The malformation of the structures of the anterior segment, as well as the malformation of the sclera, affect structures formed from neural crest-derived extraocular mesenchymal cells. In the case of the defects of the cornea and eyelids, a phenotypic synergy was observed between mutations in the RXRα and RARγ genes, since the malformations of these structures seen in RXRα null animals were markedly enhanced in their severity in mutants lacking in addition either one or both alleles of RARγ; furthermore, RXRα+/–RARγ–/– fetuses reproduced the cornea and eyelid defects of RXRα null mutants. The specific expression of RARγ in periocular mesenchymal cells at 9.5–11.5 dpc suggests that abnormal behavior of these neural crest-derived cells is involved in the genesis of these defects. In this respect, the mesectodermal cells in the RXRα/RARγ double null mutant seem to have been completely deprogrammed since they are unable to form, even in a rudimentary manner, structures such as the cornea and eyelids, and just seem to fill the available space (see FIG. 22d and e). The precise developmental processes which are altered in RXRα null or compound RXRα/RARγ mutants may involve abnormal cell proliferation, abnormal cell migration and/or abnormal cellular interactions.

It is worth stressing that RARγ is not essentially required for the developmental patterning of the anterior portion of the eye since the eyes were correctly developed in RARγ null mutants (Lohnes et al., Cell 73:643–658 (1993)). The occurrence of an abnormal corneal stroma, a hypoplastic conjunctival sac and the lack of an anterior chamber in double RARα2γ or RARβ2γ mutants points to a functional redundancy between RARγ and other RARs in the regulation of the corresponding developmental processes. However, the fact that no malformation of neural crest derived structure occured in RARαβ2 double null eyes, as well as the fact that RXRα/RARα double null eyes did not exhibit more severe malformations of the these structures than single RXRα null eyes, argues in favor of RARγ as being the "major" RAR involved in the development of the anterior segment of the eye. Whether RARγ is also involved in the development of the sclera could not be determined from these mutants, but is likely since this structure was not formed in double RARα2γ and β2γ mutants.

The shortening of the ventral retina is another defect present in RXRα null mutants for which mutations in RXRα and in RARγ display a clear phenotypic synergy, since this defect occured in all RXRα+/–RARγ–/– eyes and was increased in severity RXRα–/–RARγ+/– and RXRα–/–RARγ–/– double mutants. The involvement of RARγ (which is not expressed in the retina itself but in the surrounding extraocular mesenchyme) in the genesis of this defect suggests that this abnormality may result (at least in part) from a defect affecting extraocular mesenchymal cells. In all RXRα null mutants examined at 11.5 and 12.5 dpc, an aberrant presence of mesenchymal cells was observed in front of the ventral part of the optic cup (see FIG. 21b and d). This ventral invasion of mesectodermal tissue was also dramatically accentuated in the 12.5 dpc RXRα/RARγ double mutant eyes (FIG. 22e). From these observations and from the genetic data implicating extraocular tissue in the genesis of the shortening of the ventral retina, it can be proposed that aberrant outgrowth of mesenchymal cells in front of the ventral part of the optic cup around 11 dpc results in the "reshaping" of the optic cup with a concomittant "backward push" of its ventral margin. Two additional observations support that mechanism: (i) the optic cup appeared normal in mutant embryos at 10.5 dpc, excluding therefore a defect in the primary formation of the ventral part of the optic cup; (ii) no difference in the rate of proliferation was seen between ventral and dorsal neural retinas of WT and RXRα null mutants at 14.5 dpc. This latter observation suggests that the observed shortening of the ventral retina is unlikely to result from a differential growth between ventral and dorsal retinas. Such a differential growth mechanism would also decrease the relative size of the ventral retina with respect to the dorsal retina over time, which was clearly not observed since the relative shortening of the ventral retina (and the resulting rotation of the lens) was similar in 12.5 and 16.5 dpc mutants.

The Drosophila RXR homolog, ultraspiracle (usp), has also been implicated in the proper development of the ventral retina in Drosophila. This similarity with the RXRα phenotype may reflect a function of RXR conserved between Drosophila and mouse in the dorso-ventral patterning of the eye. In this respect, it is interesting to note that the function of usp is required in non retinal cells (Oro et al., Development 115:449–462 (1992)), which is a situation reminiscent of the mechanism proposed above for the reduction of the ventral retina in RXRα mutants.

The coloboma of the optic nerve seen in all RXRα null mutants (after 14.5 dpc) is likely to result from a developmental arrest, since the closure of the optic fissure at this level is completed at 14.0 dpc. Additional defects of the closure of the optic fissure, such as coloboma of the iris and coloboma of the pigment retina, were detected in double RXRα/RAR mutants (Table VII). Together, these observations suggest that RXRα and RARs control processes involved in the closure of the optic fissure. In this respect, a more severe complete coloboma of the retina (which is a failure of the optic fissure to close) was often seen in VAD fetuses and in double RARαγ null mutants (Warkany and Schraffenberger, Arcl. Ophth. 35:150–169 (1946)). The difference between these severe abnormalities and the milder defects seen in RXRα null or compound RXRα/RAR mutants could reflect either an incomplete expressivity of the phenotype in these mutants, or the involvment of RXRα in only a subset of the serie of morphogenetic processes involved in the closure of the optic fissure (Geeraets, Am. J. Anat. 145:411–432 (1976)). The eversions of the neural retina seen in the RXRα/RAR compound mutants is likely to reflect an abberant differentiation of the outer layer of the optic cup into neural retina. Interestingly, such an aberrant differentiation has also been observed in RARαγ double mutants as well as in zebrafish embryos treated with RA. These observations suggest a role for RA, RARs and RXRα in the determination of the differentiation state of the neural and pigment retina.

The persistent retrolenticular membrane defect seen in RXRα null mutants could result from the penetration of mesenchymal cells through the cleft resulting from the coloboma of the optic nerve or from a failure of the primary vitrous to degenerate. The occurence of such a persistent retrolenticular membrane in RXRα+/–RARγ–/– mutants in the absence of coloboma of the optic nerve supports that latter possibility.

Function of RXRα in the Development of the Heart

From 13.5 dpc onwards, a reduction in the thickness of the compact layer of the myocardium was seen in most RXRα null mutants and the myocardium of mutants appeared essentially "trabecular". The trabeculae, as well as the muscular interventricular septum, also appeared thinner. Therefore a reduction in the number of cardiac myocytes occurs in all the myocardial compartments in RXRα null mutants. Electron microscopy examination of RXRα–/– mutant and WT myocardial cells at 14.5 dpc revealed two interesting features: (i) a more advanced degree of differentiation of the cells of the "compact" (subepicardial) zone in mutants; (ii) looser compaction between the myocyte cells in the mutant compared to WT, with frequent wide gaps between the cellular membranes of neighboring cells. It is possible that this weaker "cementing" of the cells which would normally contribute to the compact layer could lead them to adopt "trabecular-like" morphological structures and thus account for the trabecular aspect of the myocardium of mutants.

It was observed that cardiac myocytes proliferate at a comparable rate in WT and RXRα null mutants at 12.5–14.5 dpc. This is in apparent contradiction with the markedly reduced cell number in the mutant myocardium after 13.5 dpc. Two possible mechanisms could be considered to explain this paradox. (i) The proliferation of cardiac myocytes may actually be slightly reduced in mutants (for instance by 10–20% which cannot be excluded by the preliminary data). Such a difference could result in a substantial decrease in the cell number in the mutant relative to WT after several generations. This model is supported by the more advanced differentiation state of the cardiac myocytes in mutants since it is known that the rate of proliferation of cardiac myocytes decreases with differentiation. Careful measurements of the growth rates of the ventricular myocytes in several WT and mutants should in the future clarify that possibility. (ii) In the absence of any significant difference in the growth rate between WT and mutant cardiac myocytes, one has to assume that the reduced number of cells in the myocardium of mutants results from loss of cells. In this respect, no evidence was found for cell death in the myocardium of RXRα null mutants (from histological and EM examination). It is possible also that the looser cellular contacts observed in mutants could lead to the detachment of some myocardial cells, which may than be carried away in the circulation.

Retinoic acid is a signal implicated in myocardial development since a "spongy myocardium" is among the congenital defects found in the offsprings of VAD dams. Therefore, the myocardial defect observed in RXRα null mutants could reflect the impairment of a retinoid dependent process involved in the correct development of the myocardium. In this respect, a drastic reduction of the compact layer of the myocardium has also been seen in some double RARαγ mutants. In addition, the occurence of a thin myocardium in a single 14.5 dpc RXRα+/−/RARγ−/− double mutant fetus suggests that both RXRα and RARs could be involved in the regulation of this RA-dependent process (see below).

Mutations of N-Myc and the Wilms' tumor gene WT-1 have also been shown to produce a hypoplasia of the ventricular myocardium. Whether the pathways affected by these genes and those depending on RXRα are related is currently unknown.

Several RXRα/RAR double mutants were also characterized by aortic arch defects and/or a persistent truncus arteriosus (Table VII). Very similar malformations can be produced in chick embryos by ablation of neural crest cells at the level of rhombomeres 6, 7 and caudal unsegmented portion of the rhombencephalon. Such defects are also found in several types of RAR double mutants and belong to the fetal VAD syndrome (Wilson et al., *Am. J. Anat.* 92:189–217 (1953)). These observations suggest a coordinate role for RXRα and RARs in the RA-dependent processes controlling the normal participation of neural crest derivatives in the formation of the aortico-pulmonary septum and in the determination of the normal pattern of aortic arch derivatives.

Role of RXRα in Retinoid Signaling

The developmenal defects seen in RXRα mutants have been described previously in the fetal VAD syndrome. As previously stated, a "spongy myocardium" was one of the congenital defects resulting from maternal vitamin A deprivation. Shortening of the ventral retina (and ventral rotation of the lens), thickening of the corneal stroma, persistent retrolenticular membrane, closer eyelids and coloboma of the optic nerve are among the most common eye malformations found in offsprings of VAD dams (Warkany and Schraffenberger, *Arcl. Ophth.* 35:150–169 (1946)). These similarities between the defects occuring in RXRα null mutants and those occuring in the VAD state suggest that RXRα is essential for several aspects of vitamin A action. It is also possible that the growth deficiency observed in heterozygote animals corresponds to an impairement of the growth promoting function of vitamin A. RXRα could be implicated in the mediation of the retinoid signal in two ways: either as a receptor for 9cis RA or as a heterodimeric partner required by RARs for efficient binding to retinoic acid response elements. The results presented here do not allow any conclusion to be drawn concerning the possible role of a 9cis RA dependent regulatory function of RXRα in the events perturbed by the RXRα mutation. Two sets of observations (detailed below) support however the idea that RXRα/RAR heterodimers could be implicated in several aspects of RXRα function.

Several defects seen in RXRα mutants fetuses have also been found in double RAR mutants: a trabecular ventricular myocardium in RARαγ double null fetuses; absence of anterior chamber, hypoplasia of the conjunctival sac, abnormal corneal stroma, absence of sclera and coloboma of the optic nerve in RARβ2γ and αγ double mutants; retrolenticular membrane in most RAR double mutants.

The analysis of compound RXRα/RAR mutants also demonstrates that a genetic interaction between RXRα and RARs is involved in several developmental processes: (i) the same eye and myocardium malformations arise in RXRα−/− and RXRα+/−RARγ−/− fetuses; (ii) several ocular malformations arising in RXRα mutants are markedly enhanced in their severity when the RXRα null mutation is associated with heterozygous or homozygous null alleles of the RARγ gene; (iii) malformations not present in single RXRα mutants, such as persistent truncus arteriosus, aortic arch malformations, eversion of the neural retina, coloboma of the iris or pigment retina or persistent corneal-lenticular stalk, arise in double mutants. The phenotypic similarity between the RXRα mutants and the double RAR mutants, together with the functional synergy between the RXRα and RAR mutations clearly shows a convergence of the functions of RXRα and RARs which supports the concept of RXR/RAR heterodimers as being the entities regulating the corresponding regulatory processes. However, it cannot be excluded that RXRα and RARs regulate distinct processes which could be coordinately involved in the development of the affected structures.

It is worth stressing that several of the above mentioned functional interactions between RXRα and RARs require only heterozygocity for one of the 2 genes. If one supposes that this synergy does not reflect the formation of heterodimers between the two types of molecules, but rather that RXRα and RARs regulate separate events which coordinately control the relevant processes (for instance if RXRα and RARs control respectively the production of a ligand and its receptor), then one would also have to assume that these regulatory functions of RXRα or RARs would be very sensitive to gene dosage. Eventhough such a model cannot be excluded, the data disclosed here fit better with the heterodimer model, in which heterozygocity for one gene reduces the quantity of corresponding heterodimers by half, and thus could bring this quantity below a critical threshhold.

The shortening of the ventral retina, ventral rotation of the lens and increased thickening of the ventral portion of the cornea are features consistently present in RXRα null mutants, and which are also part of the VAD syndrome. However, these malformations have never been seen in any of the RAR double mutants described here, including the double RARαγ mutants which recapitulate all the other ocular defects of the VAD syndrome. The result from the double RXRα/RARγ mutants however clearly indicate that RARs have a function in the control of the normal processes affected in this defect (see above). It is therefore possible that there is a extreme functional redundancy among RARs in this system. Alternatively, the crucial role of RXRα in the patterning of the ventral part of the eye could reflect a function of RXRα not solely involving RXR/RAR heterodimers. This possibility is also in agreement with the complete penetrance of this defect in RXRα+/-RARγ-/- fetuses, which is difficult to reconcile with the idea of the requirement of only a low level of RXR/RAR heterodimers. In this respect, it has been shown that the embryonic mouse retina synthesizes RA and that the RA-synthesizing enzymes are different in the dorsal and ventral parts of the retina (McCaffrey et al., *Develop. Biol.* 158:390–399 (1993)). It is tempting to speculate that the ventral enzyme could be involved in the synthesis of 9cis RA which could act specifically as a ligand for RXRα.

Specificity, Redundancy and Variation in Expressivity

RXRα has clearly a specific role for the correct development of the ventricular myocardium and several structures of the eyes. In situ hybridisation analysis of the distribution of RXR transcripts during the stages studied here have revealed a uniform low level of expression of both RXRα and RXRβ. However, given that the signals detected in this study were close to background hybridization, it was not possible determine whether RXRα and β transcripts are indeed coexpressed in all tissues. In addition, no information concerning the distribution of RXR proteins is available to date. It is therefore not possible at present to conclude whether the defects seen in RXRα null mutants represent the absence of a specific function of RXRα, that other RXRs cannot fulfill, or represent the reduction below a critical level of RXR (any type) in the affected cells.

The requirement by multiple members of the nuclear receptor family for heterodimerization with RXR for efficient DNA binding has led to the suggestion that RXRs may possess pleiotropic functions involved in the biological action of several ligands (see introduction). The relatively limited phenotype of RXRα null mutants is thus rather surprising. In addition, the defects observed are all related to the developmental function of vitamin A (see above) and do not hint to interference with other signalling pathways. This could suggest the existence of a large degree of functional redundancy among RXRs for their putative function as heterodimeric DNA binding partners. In this respect, it is noteworthy that almost none of the vast array of defects associated with RAR deficiency are found in RXRα mutants. A functional redundancy among RXRs is also suggested by the fact that some RXRβ null mutants are viable and display no apparent abnormality. The occurence of specific malformations only in the double RXRα/RAR mutants also shows that in the presence of a full set of RARs, other RXRs are able to substitute for the loss of RXRα.

Some variation in the expressivity of the myocardium phenotype (see result section) was observed. Moreover, two RXRα-/-RARα+/- or one RXRα-/-RARγ+/- animals had a myocardium of normal aspect at 14.5 dpc (Table 3). These variations could reflect the mixed 129sv/C57BI6 genetic background of most of the mutants analyzed. In this respect, it should be noted the compound RXRα/RAR mutants had a larger C57BI6 contribution than the single RXRα null mutants which in all cases had a 129sv contribution greater than 75%. It will be interesting in the future to see whether changing the genetic background of RXRα mutants will alter the expressivity and penetrance of the myocardial defect.

EXAMPLE 5

Abnormal Spermatogenesis in RXRβ Mutant Mice

Introduction

The three Retinoid X Receptors, RXRα, β, and γ, are members of the vertebrate nuclear receptor superfamily (Leid et al., *Cell* 68;377–395 (1992a); Leid et al., *Trends Biochem. Sci.* 17:427–433 (1992b); Mangelsdorf et al., *Gene Develop.* 6:329–344 (1992); Mangelsdorf et al., "The retinoid receptors," In *The Retinoids*, Second Edition, M. B. Spom, A. B. Roberts, and D. S. Goodman, eds. (New York: Raven press), pp. 319–338 (1994); Kastner et al., "Role of nuclear retinoic acid receptors in the regulation of gene expression," In: *Vitamin A in Health and Disease* (ed. R. Blomhoff), pp.189–238, Marcel Dekker, New York (1994b); Chambon, *Semin Cell Biol.* 5:115–125 (1994); Giguère, *Endocrine Rev.* 15:61–79 (1994); Glass, *Endocrine Rev.* 15:391–407 (1994). In the mouse, RXRα and RXRβ transcripts appear to be widely expressed in the embryo and in adult tissues, whereas the distribution of RXRγ transcripts is more restricted (Mangelsdorf et al., *Gene Develop.* 6:329–344 (1992); Dolléet al., *Mechanisms of Development* 45:91–104 (1994; Liu and Linney, *Mol. Endocrinol.* 7: 651–658 (1993); Nagata et al., *Gene* 142:183–189 (1994)). In vitro DNA binding studies and studies in transfected cells cultured in vitro have provided evidence indicating that RXRs could be involved in several signaling pathways. Firstly, as 9-cis RA (9C-RA)-dependent transcriptional regulators, RXR homodimers may transduce some of the effects of the active retinoid derivatives of vitamin A. Secondly, RXRs may also play a role in the retinoid signaling pathway, as heterodimeric partners for the retinoic acid receptors (RARα, β and γ) which act as all-trans RA (T-RA)- or 9C-RA-dependent transcriptional regulators. Thirdly, RXRs may be involved as heterodimeric partners in additional signaling pathways mediated by other nuclear receptors, which include the thyroid hormone receptors (TRs), the vitamin D3 receptor (VDR) and the peroxisome proliferator activated receptors (PPARs) (for reviews, see the above refs and Desvergnes and Wahli, In: *Inducible gene expression*. (P. A. Baeuerle Ed.), Birkhauser, Boston Vol. 1, Chap. 5, pp 142–176 (1994)). Finally, RXRs may also be the heterodimeric partners of a number of orphan nuclear receptors, including members of the FXR/RLD-1/LXR/UR family (Forman et al., *Cell* 81:687–693 (1995a); Apfel et al., *Mol. Cell. Biol.* 14:7025–7035 (1994); Willy et al., *Gene Develop.* 9:1033–1045 (1995); Song et al., *Proc. Natl. Acad Sci. USA* 91:10809–10813 (1994); Teboul et al., *Proc. Natl. Acad. Sci. USA* 92:2096–2100 (1995); Seol et al., *Mol. Endocrinol.* 9:72–85 (1995); note that UR has also been named OR-1 or RIP15), members of the NGFI-B/NURR-1 family (Perlmann and Jansson, *Gene Develop.* 9:769–782 (1995); Forman et al., *Cell* 81:541–550 (1995b)) and the orphan receptor MB67 (Baes et al., *Mol. Cell. Biol.* 14:1544–1552 (1994)).

Whether RXRs engaged in heterodimeric associations act as 9C-RA-dependent transcriptional regulators to synergistically control initiation of transcription, or are transcriptionally silent, simply allowing their partners to bind efficiently to the response elements of their cognate target genes, is largely unknown. Several studies performed in vitro and in transfected cultured cells have suggested that the 9C-RA-dependent transcriptional activity of the RXR partner is dependent on both the nature and the ligand occupancy of the heterodimeric partner, as well as on the nature of the bound response element (Kurokawa et al., *Nature* 371:528–531 (1994); Durand et al., *EMBO J* 13:5370–5382 (1994); Forman et al., *Cell* 81:541–550 (1995b); Perlmann and Jansson, *Gene Develop.* 9:769–782 (1995); Willy et al., *Gene Develop.* 9:1033–1045 (1995)).

In contrast to the wealth of information related to the functions of RXRs in vitro, very little is known to date concerning the actual physiological role of RXRs in vivo. Notably, it is unknown whether, as a receptor for 9C-RA, RXR transduces some of the multiple effects of retinoids. In this respect, it is noteworthy that most of the abnormalities found in vitamin A deficient fetuses or adult mice are reproduced in mice bearing mutations in one or several RARs, which demonstrate that RARs are involved in the physiological transduction of the RA signal (Lohnes et al., *Cell* 73:643–658 (1993); Lohnes et al., *Development* 120:2723–2748 (1994); Lufkin et al., *Proc. Natl. Acad. Sci. USA* 90:7225–7229 (1993); Mendelsohn et al., *Development* 120:2749–2771 (1994)). The possible function of RXRα has been investigated by examining homozygous null mice generated by targeted disruption of the RXRα gene in ES cells (Kastner et al., *Cell* 78:987–1003 (1994a); Sucov et al., *Gene Develop.* 8:1007–1018 (1994)). These mutants exhibit fetal heart and eye defects similar to those occurring in the fetal vitamin A deficiency (VAD) syndrome, thus suggesting that RXRα mediates some of the effects of vitamin A. Moreover, these studies have revealed a strong synergy between mutations in RAR and RXR genes for the generation of abnormalities which were either less severe in single RXR or RAR mutants, or not present at all. It was also shown that some specific RXR/RAR pairs are much more efficient than others at generating some of the abnormalities seen in the fetal VAD syndrome (Kastner et al., *Cell* 78:987–1003 (1994)). Taken together, these data strongly suggest that RAR/RXR heterodimers are the major functional units responsible for transducing the retinoid signal during development.

We now report the generation of RXRβ null mutant mice. Approximately 50% of these mutants die in utero or very shortly after birth for unknown reasons. Surprisingly, the remaining null mutants are externally indistinguishable from their wild type or heterozygous littermates. However, RXRβ$^{-/-}$ males are sterile, due to abnormal germ cell maturation, leading to oligo-astheno-teratozoospermia. These sperm abnormalities most probably reflect an indispensable function of RXRβ in the Sertoli cells, which in prepubertal mutant males start to accumulate lipid droplets. The possible involvement of PPARs in the generation of the testis abnormalities seen in RXRβ null mutants is discussed.

Materials and Methods
Targeting Vectors and Homologous Recombination

Genomic clones for the mouse RXRβ (mRXRβ) locus were obtained by screening a genomic library established in λEMBL3 from 129/Sv mouse DNA with a mRXRβ CDNA probe. The structure of the mRXRβ locus was identical to that reported by Nagata et al., *Gene* 142:183–189 (1994). To construct the targeting vector, a 10 kb NotI-XhoI fragment containing the entire RXRβ locus was inserted into Bluescript SK$^-$. A HindIII site was then created by site-directed mutagenesis in exon 3 at the boundary between the B and C regions. Subsequently, the 1.5 kb HindIII-EcoRI fragment containing sequences encoding the entire RXRβ DNA binding domain was removed and replaced with a PGK-NEO (A+) cassette (derived from pKJ-1,Adra et al., *Gene* 60:65–74 (1987)), which was cloned in antisense orientation. This plasmid, pHR(RXRβ) was linearized with XhoI and electroporated into D3 ES cells as previously described (Lufkin et al., *Cell* 66:1105–1119 (1991)). After selection with G418, resistant clones were expanded, genomic DNA prepared, restricted with SpeI and analysed by Southern blotting with probe A (FIG. 24a). 3 positive clones were obtained which were confirmed with HindIII or KpnI digests using probe A, as well as a NEO probe. All 3 clones were injected into C57BL/6 blastocysts, and chimeras derived from two clones (HA9 and HA67) transmitted the mutant allele through their germline. Routine genotyping of the mice was subsequently performed on BamHl-restricted DNA using probe B (FIG. 24a, b).

Histological Procedures

Sections (7 μm thick) from Bouin-fixed, paraffin-embedded testes were dewaxed and stained either with Groat's hematoxylin and Mallory's trichrome (Mark et al., *Development* 119:319–338 (1993)) or by the periodic Acid Schiff reaction (the Shiff's reagent was made from pararosaniline (C.I.N°42500; Sigma) according to Longley's method (Gabe, *Techniques Histologiques*, Masson et Cie, Paris (1968))) followed by a 3 min counterstain with Harris hematoxylin solution (Merck).

Histochemistry, Immunohistochemistry and in Situ Hybridization on Frozen Tissues Sections (10 μm-thick) from unfixed frozen tissues were collected on poly-L-lysine-coated slides. The sections were either (i) hydrated for 3 min in PBS (prior to staining with oil red O or with osmium tetroxyde) or (ii) fixed for 10 min in 4% paraformaldehyde in PBS at 24° C. (prior to the demonstration of acid phosphatase activity), (iii) fixed for 3 min in 100% acetone at −20° C., then air-dried (prior to anti-phospholipid immunostaining) or (iv) fixed in Zamboni's fixature for 15 min. then treated with 1% $H_2O_2$ to block endogenous peroxidase, prior to staining with the anti-RXRβ antibody. Staining with the lipid soluble dye oil red 0 (C.I.N° 26125; Sigma) in isopropanol/water for 3 min was performed as indicated by Lillie, *Histopathologic Technic and Practical Histochemistry*, 3rd Edition, McGraw Hill Book Company, New York (1965); the sections were counterstained with Harris hematoxylin (5 sec), rinsed in tap water (3 min), then mounted in glycerol-PBS (9:1). Oxidation of unsaturated lipids by osmium tetroxide was achieved by covering the sections with a drop of this fixative (1% in PBS) for 5 min; after rinsing in distilled water, the sections were counterstained with 1% methyl green (C.I. N° 42590; Sigma, purified by chloroform extraction) and mounted in glycerol-PBS. The detection of cholesterol was performed according to Hershberger's modification of the Schultz method (Lillie, *Histopathologic Technic and Practical Histochemistry*, 3rd Edition, McGraw Hill Book Company, New York (1965)). The demonstration of acid phosphatase activity in situ was performed according to Burstone, as reported by Lillie, *Histopathologic Technic and Practical Histochemistry*, 3rd Edition, McGraw Hill Book Company, New York (1965): paraformaldehyde-fixed tissue sections were incubated for 2 hr at 24° C. in 0.1M sodium acetate buffer pH 5.2 containing the substrate naphthol AS-BI phosphate (Sigma) and the diazonium salt fast red violet LB (Sigma). A monoclonal antibody against phosphatidylcholine (MC22-33F; Mark et al., *J. Histochem. Cytochem.* 40:827–838 (1992)) was used to immunolocalize phospholipid-containing cytoplasmic inclusions on acetone-fixed tissue sections, as previously described. Sections from an adult mouse ovary and the replacement of MC22-33F by nonimmune rat IgM served as positive and negative controls of the immunostaining procedure. Immunostaining with an anti-RXRβ antibody (Sugawara et al., *Endocrinology* 4:1766–1774 (1995); 1/4000 diluted in TBST) was performed using the ABC Elite system (Vector, Burlingame, Calif.) according to the manufacturers instructions. Sections of RXR$^{-/-}$ testis reacted with the anti-RXRβ antibody served as negative controls.

The RXR probes used for in situ hybridization were synthesized from cDNA fragments covering the entire open reading frame (Dollé et al., *Mechanisms of Development* 45:91–104 (1994)). In situ hybridization was performed on 10 μm frozen sections and the sections were stained with hematoxylin.

Electron Microscopy

Mice were perfused intracardially with a 2.5% solution of glutaraldehyde in 0.1M cacodylate buffer (pH 7.4). Testes and epididymides were removed and immersed in the same fixative overnight at 4° C. They were then rinsed with this buffer, postfixed for 1 hour at 4° C. in cacodylate buffered osmium tetroxide, dehydrated with graded alcohols, and embedded in epon. For light microscopy, semi-thin sections (1 μm thick) were stained with toluidine blue. Ultra-thin sections were contrasted with uranyl acetate and lead citrate and examined with a Philips 208 electron microscope at 80 kV.

Results

RXRβ Mutant Mice

The RXRβ gene was disrupted by homologous recombination in embryonic stem (ES) cells with a replacement-type vector in which the genomic sequences encoding the DNA binding domain (3' region of exon 3 and exon 4) were replaced with a PGK-NEO(A+) cassette (FIGS. 24a and b). Chimeric males derived from two mutant ES clones (HA67 and HA9) transmitted the mutation, thus generating two lines of mutant mice. For both lines, crosses between heterozygotes (RXR$^{+/-}$) yielded viable homozygote mutants (RXRβ$^{-/-}$), which were externally indistinguishable from their WT and heterozygote littermates. Homozygote females were fertile, but males were sterile (see below).

Figure 24C:
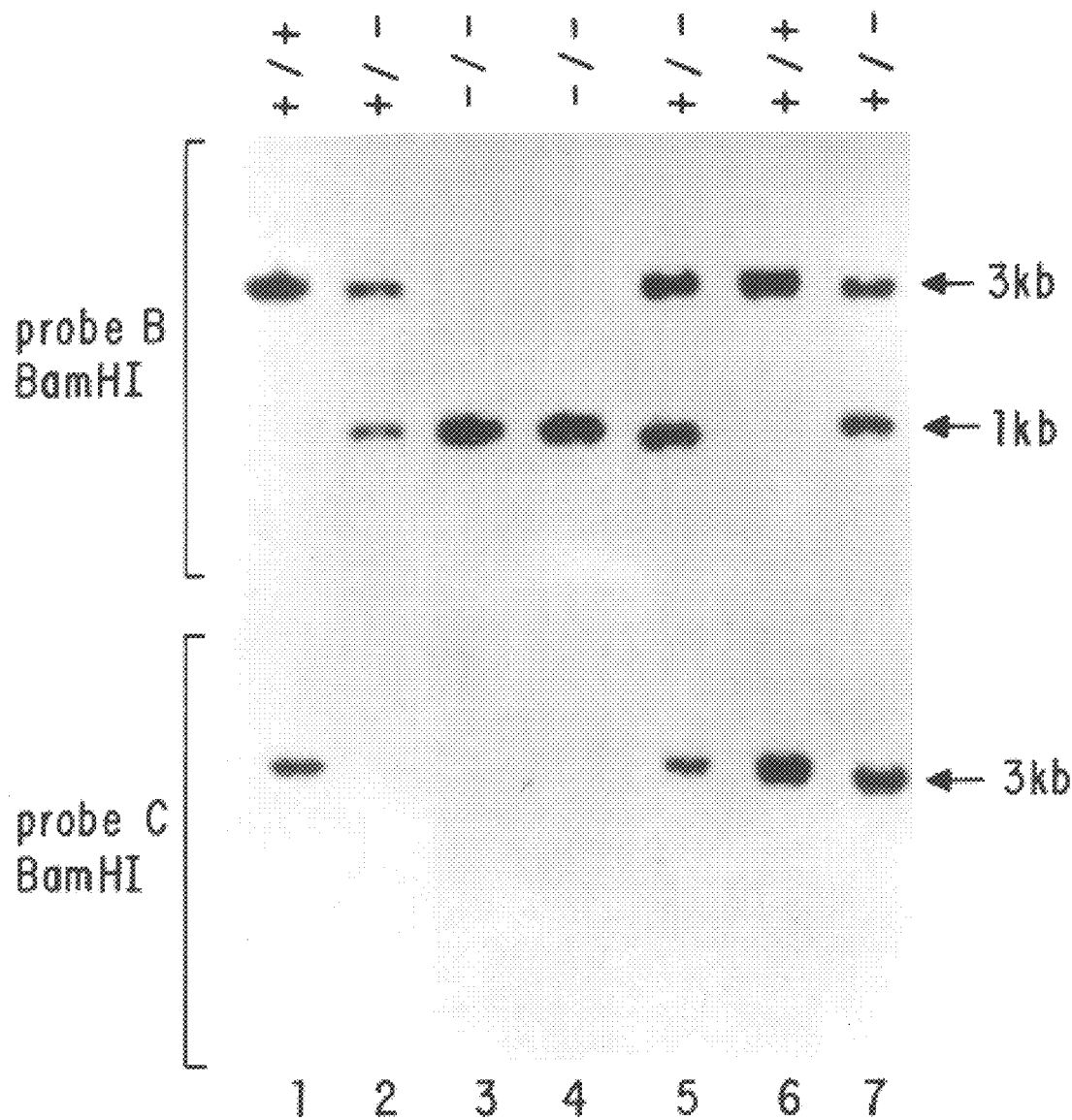
Figure 25A:
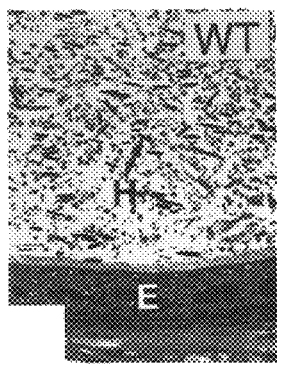
Figure 25B:
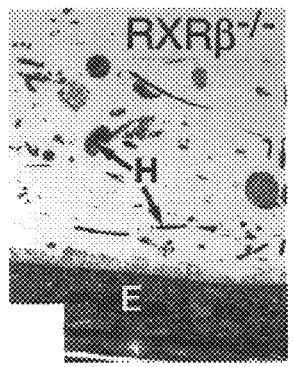
Figure 25C:
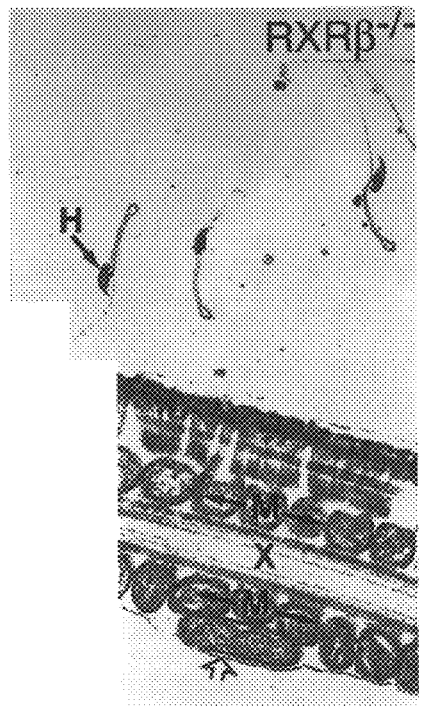
Figure 25D:
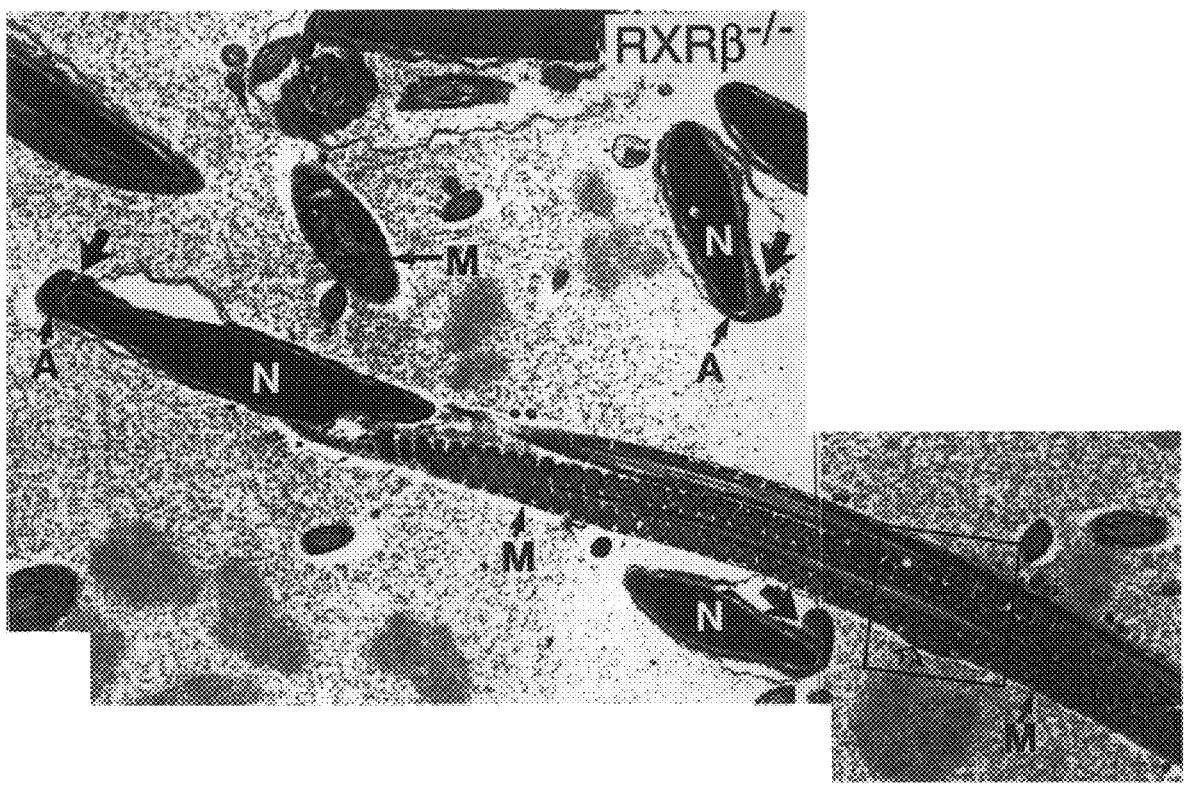
Figure 25E:
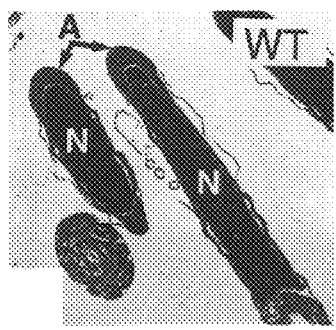
Figure 25F:
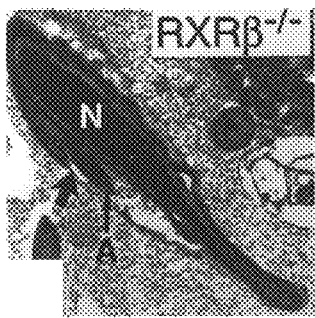
Figure 25G:
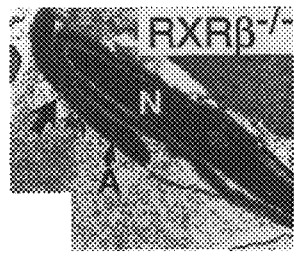

As expected, a probe spanning the genomic region encoding the RXRβ DNA binding domain did not detect any hybridizing fragment in homozygotes (probe C in FIG. 24c). Therefore, even though RXRP exons 1, 2 and 5–9 are still present in the genome of homozygotes, a functional DNA-binding RXRP protein cannot be produced in the mutants. RT-PCR analysis of total RNA isolated from several tissues showed that transcripts corresponding to exon 2, as well as transcripts containing exons 5 to 9, were present at a low level in RXRβ$^{-/-}$ mice when compared to wild type (less than 10%, data not shown). We cannot therefore exclude that some RXRβ peptides could be present at low levels in mutants. In any event, it is unlikely that the abnormalities observed might result from a dominant effect of such putative peptides, since heterozygous animals never displayed any defect. Thus, the present disruption of the RXRβ gene most probably corresponds to a null mutation.

Embryonic and Perinatal Death of a Fraction of RXRβ$^{-/-}$ Mutants

When genotyped at 2–3 weeks of age, the numbers of RXRβ$^{-/-}$ mutants derived from intercrosses between RXRβ$^{+/-}$ males and either RXRβ$^{+/-}$ or RXRβ$^{-/-}$ females were significantly lower (P<0.005) than expected from a Mendelian ratio (Table VIII). A significant deficit was also observed among one day-old newborns and 18.5 dpc (days post-coitum) caesarean-delivered fetuses (Table VIII), suggesting that some of the missing RXRβ$^{-/-}$ mutants died in utero or shortly after birth.

It appears therefore that RXRβ is important for embryonic development in a fraction of embryos. It is presently unclear when this embryonic death occurs, and whether the incomplete penetrance of that phenotype results from heterogeneity in the genetic background of the mutants. That the deficit in RXRβ$^{-/-}$ animals is more pronounced in newborns than in caesarean-delivered 18.5 dpc fetuses (Table VIII), suggests that death at, or shortly after birth also accounts for some of the missing RXRβ$^{-/-}$ mutants. It is noteworthy, however, that the caesarean-delivered mutants had a normal appearance, breathed normally and could survive for at least 12 hours when left in isolation. Thus, some of the homozygote mutants may be eliminated through selective maternal cannibalism, similarly to what had been previously reported in the case of RARγ mutants (Lohnes et al., *Cell* 73:643–658 (1993)). Even though a few RXRβ$^{-/-}$ mice died during the first weeks after birth, the majority of RXRβ$^{-/-}$ mutants that survived through the gestational and perinatal periods had a viability comparable to that of WT or heterozygous littermates.

Oligo-astheno-teratozoospermia and Abnormal Spermiogenesis in RXRβ$^{-/-}$ Males Seven RXRβ$^{-/-}$ males were tested for fertility over a 6 month period. None sired any offspring, even though each of them produced many vaginal plugs. The testes of all RXRβ$^{-/-}$ males were normally descended in the scrotum; the genital ducts (i.e. epididymis, vas deferens) and the accessory glands (i.e. seminal vesicle, prostate and bulbourethral glands) were macroscopically and histologically normal (E in FIG. 25b, and results not shown).

In contrast to the epididymides of adult WT mice, which on histological sections were packed with sperm (H, FIG. 25a), those of adult RXRβ$^{-/-}$ mutants (2 to 10 months of age) contained only sparse, elongated or sickle-shaped nuclear profiles characteristic of differentiated spermatozoa (H, FIG. 25b) along with unidentified cellular debris. Moreover, whereas almost all spermatozoa removed from WT caudal epididymis became highly mobile when suspended in phosphate buffered saline (see Bishop, D. W. In: *Sex and Internal Secretions*, volume 2 (ed. Young, W. C.), Williams & Wilkins, Baltimore, pp. 707–797 (1961)), about 95% of the RXRβ$^{-/-}$ caudal epididymal spermatozoa remained immobile under the same conditions. A majority of the RXRβ$^{-/-}$ spermatozoa also exhibited a coiling of the tail (FIG. 25c, arrowheads), an abnormality that was rarely seen in wild type counterparts. It is noteworthy that this coiling was not seen in testicular spermatids, and therefore presumably occurred in the epididymis.

Additional abnormalities were revealed by electron-microscopic examination of RXRβ$^{-/-}$ epididymal spermatozoa. Many acrosomes (about 30%) appeared indented (large arrow in FIGS. 25d, f and g) and/or partially detached from the nuclear envelop (compare A, FIG. 25e with f and g) Some spermatozoa lacked an acrosome (not shown). Indented acrosomes were also seen in few WT spermatozoa (about 7%), but this indentation was never as marked as in mutants. Thus, the high frequency of such defects in mutant spermatozoa strongly suggests that the attachment of the acrosomal membrane to the nucleus (N) is impaired in RXRβ$^{-/-}$ mutants. In addition to these acrosomal defects, local failure of the mitochondria to arrange helicoidally around the axoneme in the middle piece of the mutant spermatozoa tail was often observed (in about 1–2% of the spermatozoa; open arrow and insert in FIG. 25d). This defect was never seen in WT epididymal spermatozoa. Interestingly, these abnormal acrosomes and mitochondrial sheaths were also found in step 16 spermatids within the testis (not shown), and therefore correspond to defects in the process of spermiogenesis (i.e., the maturation of spermatids to spermatozoa within the germinal epithelium).

Taken together, these data indicate that oligo-astheno-teratozoospermia (i.e. severe reduction in the number, reduced mobility and high percentage of abnormalities of the spermatozoa in the semen) is responsible for the sterility of RXRβ$^{-/-}$ males.

Defective Spermiation in the Mutant Seminiferous Tubules

The criteria originally described by Oakberg, *Amer. J Anat.* 99:507–516 (1956) and revised by Russell et al., *Histological-and histopathological evaluation of the testis*, Cache River Press, U.S.A. (1990) were used to identify the germ cell types and define the stage of the seminiferous epithelium cycle. In brief, germ cell types were identified primarily by the size and shape of their nuclei, the distribution of chromatin in the nucleus and the position of the nucleus within the cell. Spermatids were also classified according to the size and shape of the acrosomic system. The latter is strongly periodic acid Schiff (PAS)-positive on sections from Bouin-fixed, paraffin-embedded tissue (A in FIGS. 26*e, f* and I), and is deeply stained by toluidine blue on semithin sections from epon-embedded material (e.g. A in FIGS. 26*c* and *d*). Round spermatid maturation is divided into 8 steps (1 to 8) reflecting the degree of acrosome development. Elongate spermatid maturation is also divided into 8 steps (9 to 16) based on the shape of the nucleus and acrosome and the extent of head elongation. The stage of a given seminiferous tubule is defined by a specific association of germ cell types. In normal mice, there are 12 stages designated I to XII, each corresponding to one of the first 12 steps of spermiogenesis. At late stage VII, all the nuclei of the elongated spermatids align at the luminal side of the seminiferous epithelium (FIG. 26*c*), and the spermatozoa are released into the lumen of the seminiferous tubules at early stage VIII. Late stages of the cycle (i.e. IX to XII, see FIG. 26*e*) only contain one generation of contain one generation of spermatids (instead of two generations at stages I to early stage VIII).

Figure 26C:
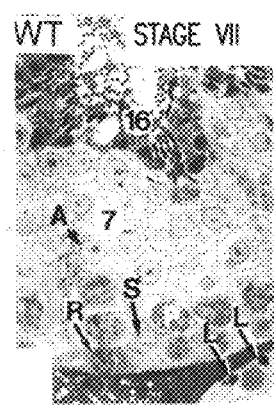
Figure 26D:
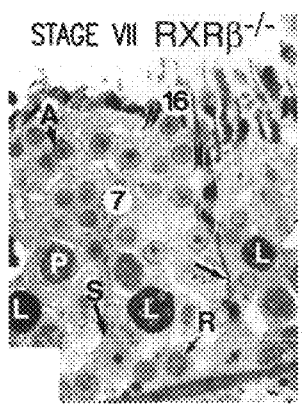
Figure 26E:
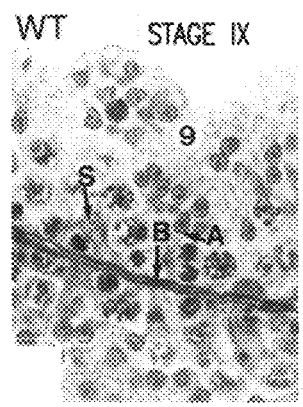
Figure 26F:
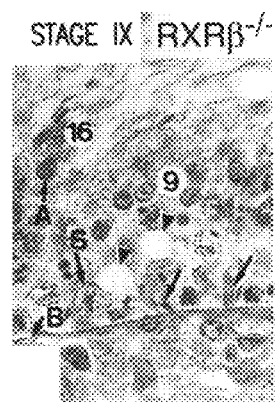

The diameter of the semiferous tubules of the six 2 month-old and the six 5–6 month-old RXRβ$^{-/-}$ males which were analyzed, was normal (compare T in FIGS. 26*a* and *b*). The 12 stages of the cycle of the seminiferous epithelium were readily identifiable (FIGS. 26*c–f*, and data not shown) and the proportion of the various germ cell types was apparently normal. However, some of the late spermatids failed to align at the luminal side of tubules at late stage VII (unlabelled arrow in FIG. 26*d*). In addition, almost all stage IX tubules as well as some stage X tubules contained two generations of elongated spermatids, namely a normal (step 9 or step 10) and a retained generation (step 16, arrows in FIG. 26*f*). In stage IX tubules, the heads of the retained spermatids were scattered throughout the seminiferous tubule epithelium, being most abundant at the periphery of the tubules, and were often lying close to the basement membrane (unlabelled arrows in FIG. 26*f*). At the electron microscopic level, these remnants of elongated spermatids were located within the cytoplasm of Sertoli cells (arrow in FIG. 27). In addition, these phagocytosed spermatids reacted strongly for the detection of fragmented DNA by the TUNEL method (Gavrieli et al., *J. Cell. Biol.* 119:493–501 (1992); data not shown). Therefore, defective spermiation (i.e. spermatid release), accompanied by phagocytosis of the retained late spermatids by the Sertoli cells, occurs in RXRβ$^{-/-}$ testes. This defect is likely to account for the near absence of spermatozoa in the epididymides of the RXRβ$^{-/-}$ mice.

Lipid Accumulation in Mutant Sertoli Cells

Paraffin sections of all adult (i.e. 2-month-old and older) RXRβ$^{-/-}$ testes revealed also the presence of large, rounded, clear "vacuoles" located at the periphery of every seminiferous tubule (arrowheads in FIGS. 26*b* and *f*, compare with 26*a* and *e*). These "vacuoles" were strongly osmiophilic on semi-thin sections from resin-embedded material (L in FIG. 26*d* and FIGS. 29*d, f* and *g*), suggesting that they contained lipids. In unfixed frozen sections, they reacted with osmium tetroxide (compare T in FIGS. 28*c* and *d*), thus demonstrating the unsaturated character of the lipids (see Gabe, *Techniques Histologiques*, Masson et Cie, Paris (1968)). The lipid dye oil red O, which stains mainly triglycerides and sterols, also stained strongly the tubules of RXRPβ$^{-/-}$ mutants (compare T in FIGS. 28*a* and *b*), while the Schultz's test for sterols gave a negative response (not shown), suggesting therefore that the droplets contain triglycerides. These droplets were also devoid of phospholipids, since they failed to react with MC22-33F, a monoclonal antibody directed against phosphatidylcholine [FIG. 28*e*; note that the lipids present in granuloma cells, the female equivalent of the Sertoli cells, react strongly with this antibody (G, FIG. 28*f*)]. Together, these histochemical and immunohistochemical properties of the "vacuoles" indicate that they essentially correspond to droplets of unsaturated triglycerides. Acid phosphatase positive granules (probably lysosomal in nature) were consistently associated with the lipid droplets (arrows in FIG. 28*i*; also compare T in FIGS. 28*g* and *h*). It is noteworthy that in WT testis both the triglycerides and the acid phosphatase activity were almost exclusively confined to the Leydig cells (Y in FIG. 28*g*, and data not shown). At the electron microscopic level, these RXRβ$^{-/-}$ tubular triglyceride droplets were strictly confined to the cytoplasm of the Sertoli cells and were not limited by a membrane (L, FIG. 27).

To investigate the evolution of the lipid droplets with age, we examined semi-thin sections of osmium-fixed testis from 29 day-old, as well as from 2, 6, 8 and 12 month-old animals (FIGS. 29*a–h*). Lipid droplets were scarce and small in wild type testes at all ages (see e.g. L in FIG. 26*c*). In RXRβ$^{-/-}$ testes, abundant small lipid droplets were already detected in all 29 day-old mutant males analysed (4 animals; compare T in FIGS. 29*a* and *b*). Note that these animals had not yet completed their first round of spermatogenesis (Russell et al., *Histological-and histopathological evaluation of the testis*, Cache River Press, U.S.A. (1990)). The size of these lipid droplets increased gradually with the age of the mutant (L, FIGS. 29*d, f* and *g*), and in 6 month-old males, some of these droplets were already larger than the Sertoli cell nuclei (L, FIGS. 26*d*, 27 and 29*f*). In old animals, many tubules were devoid of Sertoli cells, but filled with lipids (L, FIG. 29*h*). It appears therefore that the ultimate death of the Sertoli cells is preceded by a progressive increase in lipid content with age.

It has been suggested that the enzyme "hormone sensitive lipase" (HSL) may be important for controlling lipid metabolism in Sertoli cells, since it is inactivated in cryptorchid testes, in which lipids accumulate within the Sertoli cells (Stenson-Holst et al., *FEBS Lett.* 355:125–130 (1994)). However, northern blot analysis of HSL transcript levels in 2 month-old males did not reveal any difference between WT and RXRβ$^{-/-}$ adult testes (data not shown).

Degeneration of the Seminiferous Epithelium in Old RXRβ Mutant Mice

Figure 26G:
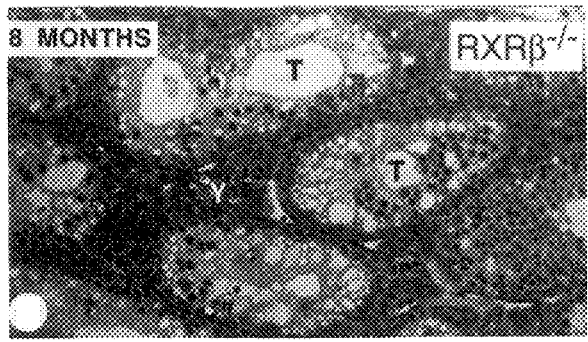

Histological sections through both testes of all 8–10 month old RXRβ$^{-/-}$ mice (5 males) showed seminiferous tubules with abnormalities similar to those seen in 5–6 month-old males and, in addition, tubules with reduced diameters which exhibited different degree of germ cell loss (T in FIG. 26g). These ranged from tubules with normal populations of mitotic (i.e. spermatogonia) and meiotic (e.g. zygotene or pachytene spermatocytes) germ cells, but lacking spermatids, to tubules containing Sertoli cells only. Germ cell loss appeared to result mainly from sloughing off of apparently healthy immature germ cells (i.e. pachytene spermatocytes and/or round spermatids) into the lumen of the tubules (e.g. step 7 spermatids in FIG. 26i), and was apparently preceded by the appearance of large irregular pockets of empty space in the seminiferous epithelium (V, in FIG. 26i). This second type of vacuole, which does not contain lipids (V in FIG. 29g) constitutes in rodent testes an unspecific, early degenerative event (reviewed in Yuan and McEntee, "Testicular degeneration, rat," In: *Monographs on Pathology of Laboratory Animals.* Genital System. T. C. Jones, U. Mohr and R. D. Hunt (eds), Springer-Verlag, Heidelberg, pp. 212–225 (1987)).

Figure 26H:
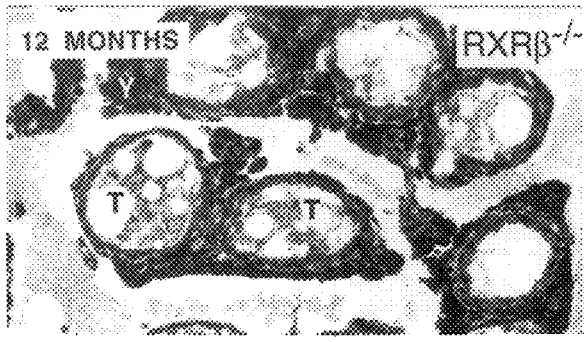
Figure 26I:
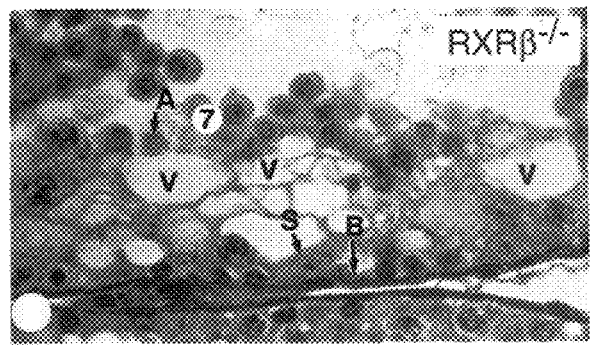
Figure 26J:
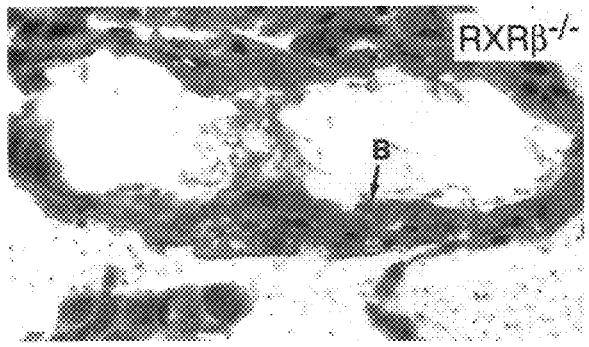

In all testes of 11–12 month old RXRβ$^{-/-}$ males, up to half of the seminiferous tubules were replaced by tubular ghosts consisting of a thickened and convoluted basement membrane, which were filled with lipids (FIGS. 26h and j, and 29h).

RXRα and RXRβ Transcripts Localization and Immunolocalization of RXRβ in the Seminiferous Epithelium The localization of RXRβ transcripts in the seminiferous epithelium of wild type males was analysed by in situ hybridization. RXRβ transcripts were present in every seminiferous tubule (T, FIG. 30b); the strongest signals were detected in the basal portion of the epithelium (where most of the Sertoli cell cytoplasm is located), while weaker signals were observed in the more luminal portions (FIG. 30d). Interestingly, the silver grains were often radially aligned in this latter part of the epithelium, which is consistent with a localization in the cytoplasmic processes of Sertoli cells (FIG. 30d, and data not shown). Immunoperoxidase staining of wild type seminiferous tubules with an antibody directed against RXRβ showed a positive signal only in the cell nuclei which on the basis of their localization at the periphery of the seminiferous tubules and their triangular shapes were identified as those of the Sertoli cells. Germ cells, e.g. pachytene spermatocytes (P), round spermatids (RS) and elongated spermatids (ES), were not stained (FIG. 30f). As expected, no staining was detected in the RXRβ$^{-/-}$ seminiferous epithelium (FIG. 30g). These data indicate that RXRβ testicular expression is restricted to Sertoli cells and does not depend on the stage of the seminiferous tubule.

Figure 30A:
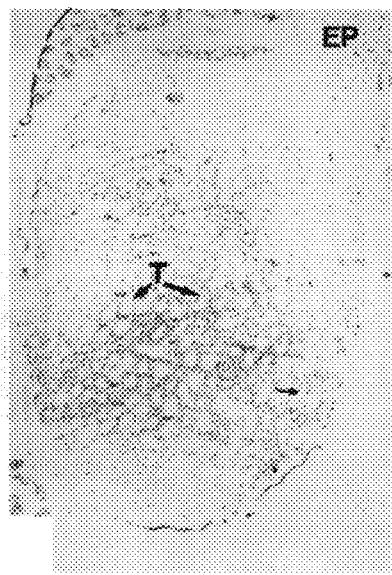
Figure 30B:
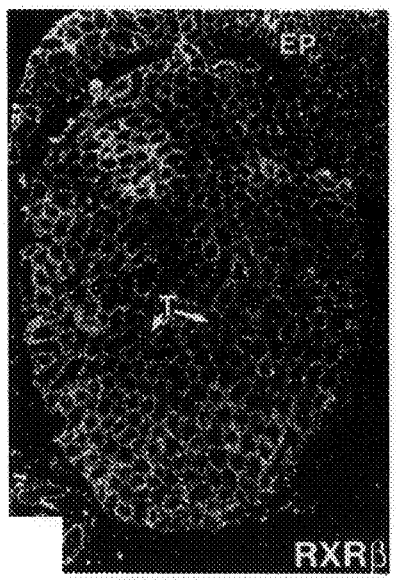
Figure 30C:
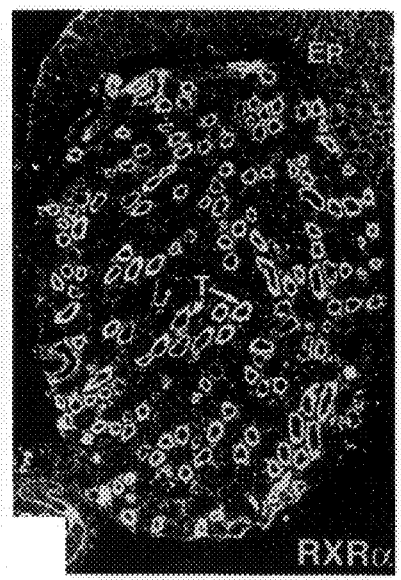
Figure 30D:
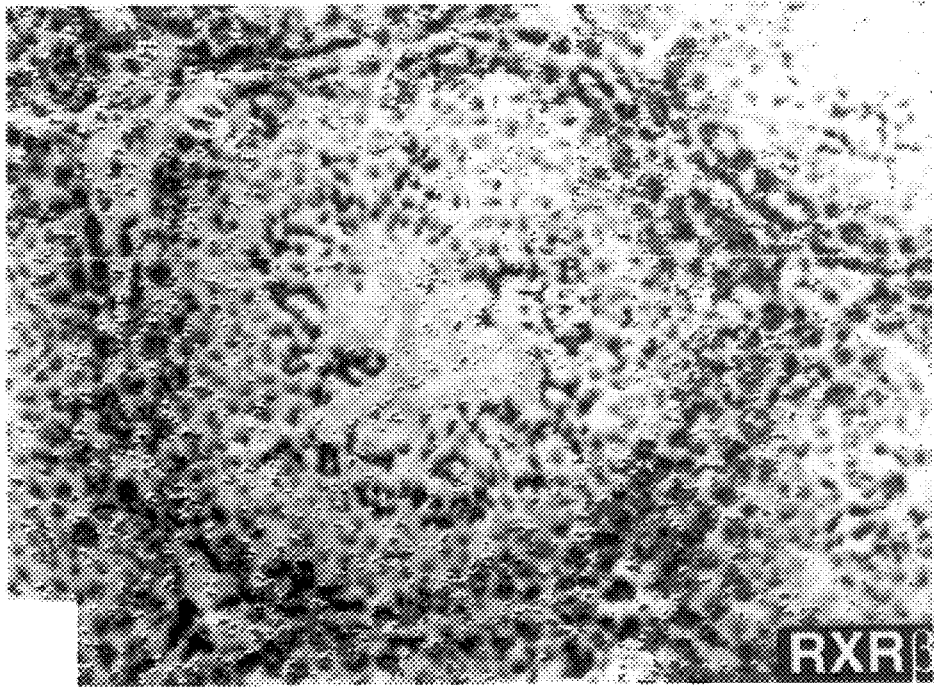
Figure 30E:
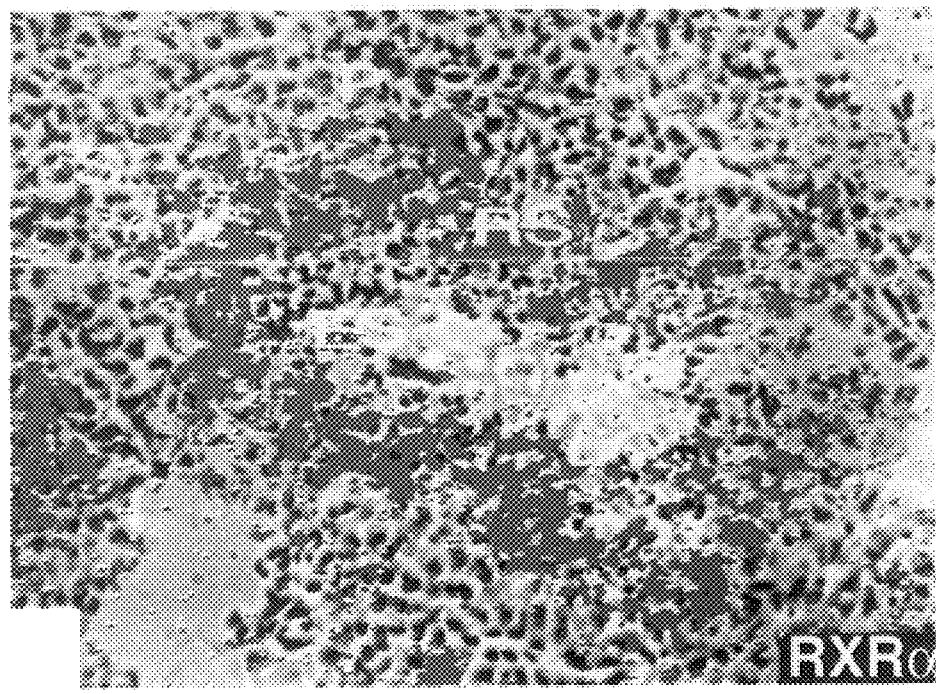
Figure 30F:
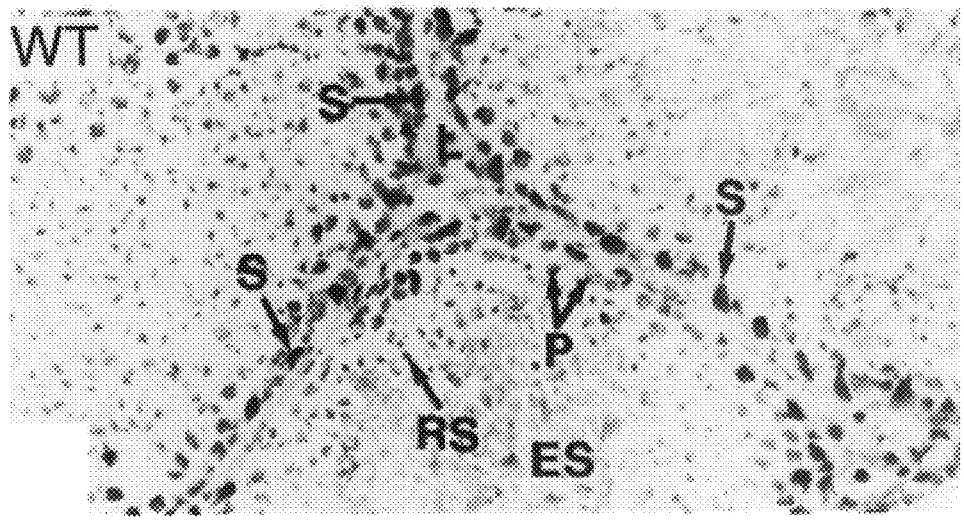
Figure 30G:
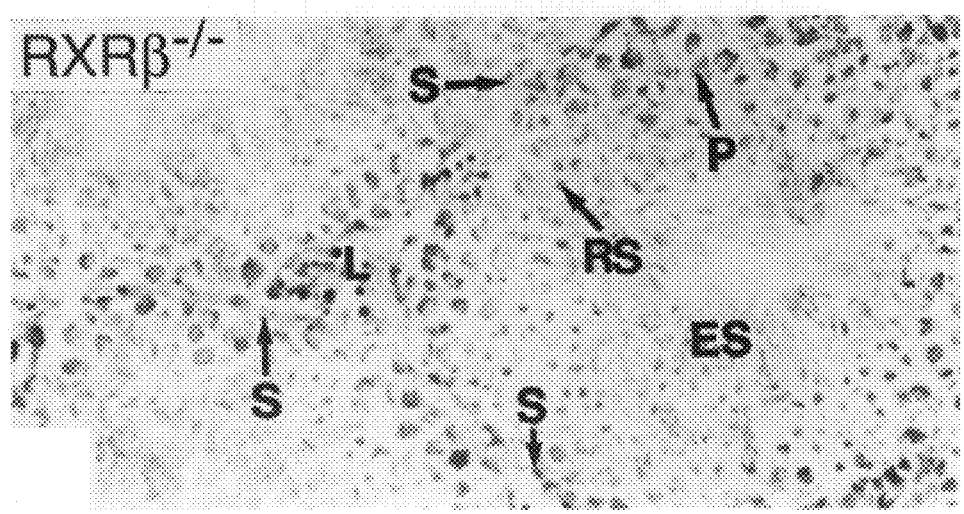

RXRα transcripts were also present in the testis; however, their localization was apparently restricted to some round spermatids in a subset of tubules (FIG. 30c and e). Therefore, within the seminiferous epithelium, the distributions of RXRα and RXRβ transcripts do not appear to overlap. In contrast, RXRγ transcripts could not be detected in the testis (data not shown).

TABLE VIII

Viability of RXRβ Mutants

| | RXRβ mutant intercrosses | | | | |
|---|---|---|---|---|---|
| | ♀+/- x ♂+/- | | | ♀-/- x ♂+/- | |
| | +/+ | +/- | -/- | +/- | -/- |
| ~3 week-old | 132 | 288 | 73 | 128 | 38 |
| | (1) | (2.2) | (0.55) | (1) | (0.3) |
| 1 day-old | 15 | 33 | 5 | 70 | 29 |
| | (1) | (2.2) | (0.3) | (1) | (0.4) |
| 18.5 dpc fetuses | 76 | 129 | 56 | 66 | 39 |
| | (1) | (1.7) | (0.7) | (1) | (0.6) |
| Expected mendelian ratio | 1 | 2 | 1 | 1 | 1 |

Table VIII: Viability of RXRβ mutants. The numbers and genotypes of living mice (3 weeks old or 1 day-old) or fetuses (delivered by Caesarean section at gestational day 18.5) are given. The values given in parentheses indicate the ratio with respect to the number of WT (heterozygote intercrosses) or heterozygotes (homozygote/heterozygote crosses).

Discussion

Abnormal Spermatogenesis and Degeneration of the Seminiferous Epithelium

We demonstrate here that RXRβ is essential for spermatogenesis in the mouse: RXRβ null mutant males exhibit abnormalities in spermiogenesis (i.e. spermatid maturation) and spermiation (i.e. spermatid release). Interestingly, mutant Sertoli cells exhibit concomitantly an early and a progressive cytoplasmic accumulation of unsaturated triglycerides. These observations raise the question whether Sertoli cells and germ cells are independently affected by the lack of RXRβ, or whether one cell type is primarily affected. Abnormal Sertoli cells could be impaired in their ability to correctly assist the maturation and release of spermatids (Redenbach and Vogel, *Eur. J. Cell Biol.* 54:277–290 (1991);Jegou, *Int. Rev. Cyt.* 147:25–95 (1993);Griswold, *Biol. Reprod* 52: 211–216 (1995)); alternatively, the lipid accumulation in Sertoli cells could result from widespread phagocytosis of abnormal spermatids Russell et al., *Histological-and histopathological evaluation of the testis*, Cache River Press, U.S.A. (1990)).

Three lines of evidence strongly suggest that Sertoli cells may be primarily affected in RXRβ null mutants. Firstly, in wild type testes, RXRβ appears to be solely expressed in Sertoli cells. Secondly, at puberty, Sertoli cell abnormalities precede by at least a week the appearance of abnormal spermatids in RXRβ$^{-/-}$ mutants. Indeed, lipid droplets were detected in Sertoli cells of 29 day-old mutants, before the completion of the first spermatogenic cycle (Russell et al., *Histological-and histopathological evaluation of the testis*, Cache River Press, U.S.A. (1990), and refs therein). Therefore, at least the earliest lipid accumulation observed in Sertoli cells cannot be ascribed to the phagocytosis of retained late spermatids. Thirdly, lipid droplets in Sertoli cells were not observed at any stages in testes of RARA mutant mice (Lufkin et al., *Proc. Natl. Acad. Sci. USA* 90:7225–7229 (1993); FIG. 31a, and data not shown) nor in vitamin A-deficient rats (Huang and Marshall, *Biol. Reprod.* 28:1163–1172 (1983)) or mice (FIG. 31b, and data not shown), even though there is also in these cases a failure of spermatid release accompanied by a phagocytosis of retained spermatids. Thus, lipid accumulation is not a necessary consequence of impaired spermiation. Taken together, these observations suggest that the accumulation of lipids observed in Sertoli cells of RXRβ null mutants reflects a primary metabolic defect.

It is well established that Sertoli cell/germ cell interactions are critical for sperm maturation and spermiation (for reviews, see Griswold, *Biol. Reprod* 52: 211–216 (1995); Jegou, *Int. Rev. Cyt.* 147:25–95 (1993)). Each maturing spermatid is encased by Sertoli cell cytoplasm which is thought to assist its maturation and its release by as yet poorly understood mechanisms. Thus, the defects of spermiogenesis and spermiation in RXRβ$^{-/-}$ mutant testes could reflect an altered function of Sertoli cells. The occurrence of large lipid droplets within Sertoli cells has been described in several pathological conditions associated with defective spermatogenesis, such as cryptorchidism (Fleeger et al., *J. Reprod. Fert.* 15:1–7 (1968); reviewed in Johnson, A. D., "Testicular lipids," In: *The Testis*, volume 2, Johnson et al, eds; Academic Press, New York. pp 194–258 (1970)) or androgen insensitivity (the tfm mice, Chung and Hamilton, *Cell Tiss. Res.* 160:69–80 (1975)). Furthermore, high levels of lipids are frequently observed in the testes in cases of human sterility (Johnson, "Testicular lipids," In: *The Testis, volume* 2, Johnson et al., eds; Academic Press, New York. pp.194–258 (1970); and refs therein). These observations, together with those made here for RXRβ null mutants, suggest that a faulty lipid metabolism in Sertoli cells could lead to defective spermatogenesis.

The physiological role of lipids during spermatogenesis is unknown. Lipid catabolism might be required solely to generate the energy needed during the transformation of spermatids into spermatozoa and/or their release into the lumen of the seminiferous tubule. Alternatively, some lipids may perform more specific functions as signaling molecules and/or cofactors. In this respect, it is noteworthy that PERF15, the major component of the perinuclear theca (the structure involved in anchoring the acrosomal membrane to the nuclear envelope), has been recently characterized as a homolog of fatty acid binding protein (FABP) and adipocyte lipid binding protein (Oko and Morales, *Dev. Biol.* 166:235–245 (1994)). If a lipid ligand is indeed required for the function of this protein, the unavailability of such a ligand in RXRβ null mutants could contribute to the detachment of the acrosomal membrane from the nuclear envelope seen in the spermatozoa of these mutants.

Which Signaling Pathway Is Affected in RXRβ$^{-/-}$ Mutant Testes?

The defects observed in RXRβ$^{-/-}$ testes could reflect a requirement of 9-cis RA for spermatogenesis and/or the participation of RXRβ as a partner for another nuclear receptor that requires heterodimerization with RXRs in order to bind to the response elements of its cognate target genes. The roles of retinoids in the testis have been documented from studies of vitamin A deprived (VAD) animals (reviewed in Eskild and Hansson, "Vitamin A functions in the reproductive organs," In: *Vitamin A in Health and Disease* (R. Blomhoff, Ed.), Marcel Dekker, New York, pp. 531–559 (1994)). VAD testes are characterized by a rapid degeneration of the seminiferous epithelium, since almost all the germ cells are lost within the first 8 days following the initial weight loss (Eskild and Hansson, "Vitamin A functions in the reproductive organs," In: *Vitamin A in Health and Disease* (R. Blomhoff, Ed.), Marcel Dekker, New York, pp. 531–559 (1994); see also FIG. 31*b*). It is therefore noteworthy that the RXRβ$^{-/-}$ seminiferous tubules keep their normal cellular architecture at least until 6 months of age. Thus, the function of retinoids in the maintenance of the structure of the seminiferous epithelium does not appear to be precociously impaired in RXRβ$^{-/-}$ mutants. Furthermore, extensive lipid accumulation has not been reported in the Sertoli cells of VAD animals (see also FIG. 31*b*; and our unpublished data), suggesting that the defect in lipid metabolism seen in RXRβ$^{-/-}$ mice does not reflect the existence of a 9-cis RA-dependent step in this metabolism. The testicular phenotype of RARα null mutants matches closely the lesions resulting from VAD (Lufkin et al., *Proc. Natl. Acad Sci USA* 90:7225–7229 (1993) and FIG. 31), and is clearly different from the RXRβ$^{-/-}$ mutant phenotype, since testicular degeneration can occur at much earlier stages in RARα mutants (i.e. before the completion of puberty) in the absence of lipid droplet accumulation (P. Gorry, M. M. and P. C., unpublished results). Thus, the retinoid signal which is necessary for spermatogenesis appears to be transduced by RARα which is expressed in Sertoli cells and spermatids (Eskild et al., *Biol. Reprod.* 44:53–61 (1991)), and, if one assumes that RARα requires a RXR partner for its function in seminiferous epitheliurn, this partner is most probably RXRα. Whether the function of RXRβ in the testis involves in any way the transduction of a retinoid signal will ultimately require the generation of mouse lines bearing mutations which selectively affect the 9-cis RA-dependent function(s) of RXRβ.

Members of the peroxisome proliferator-activated nuclear receptor (PPAR) superfamily have been recently implicated as transcriptional regulators of several genes involved in lipid metabolism and have been shown to be activated by various fatty acids (for review see Desvergne and Wahli, "PPAR: a key nuclear factor in nutrient/gene interactions?" In. *Inducible gene expression* (P. A. Baeuerle Ed.), Birkhauser, Boston Vol. 1, Chap. 5, pp.142–176 (1995)). The accumulation of lipids in RXRβ$^{-/-}$ mutant Sertoli cells could therefore reflect an impaired PPAR function. RXRβ may act as an heterodimeric partner for PPARβ which appears to be highly expressed in Sertoli cells. Whether RXRβ could act as a 9C-RA independent heterodimeric PPAR partner in the testis will require a genetic analysis of PPAR function in the testis, and the generation of compound RXRβ/PPARs mutants. In this respect, we note that PPARα mutant mice have been produced recently, which do not exhibit testicular defects (Lee et al., *Mol. Cell. Biol.* 15:3012–3022 (1995)).

Since RXRβ is the most abundant (if not the only) RXR expressed in Sertoli cells, all nuclear receptors which require RXR as a dimerization partner might be functionally impaired in these cells. The present alteration of the lipid metabolism may reflect the impairment of just one of these pathways (possibly the PPAR pathway), and other biochemical defects not detectable at the cytological level may exist in RXRβ null mutant Sertoli cells. Thus, the lipid metabolism defect may not necessarily be the primary cause (or the only cause) responsible for the impaired spermatogenesis. In this respect, we note that in the frog *Rana nigromaculata*, a steroid hormone, 17α,20α-dihydroxy-4-pregnen-3-one, induces spermiation (Kobayashi et al., *Endocrinology* 133:321–327 (1993)). If a similar molecule is required for mammalian spermiation, and if its effect is transduced by a RXR partner, then the lack of RXRβ could lead to the defect in spermiation observed in RXRβ$^{-/-}$ mutants.

Functional Redundancy Among RXRs

The defect observed in RXRβ null mice is surprisingly mild in view of the pleiotropic role that has been postulated for RXRs, either as heterodimeric partner for several nuclear receptors and/or as receptors for 9-cis RA. Since RXRα and RXRβ appear to be widely expressed during embryogenesis and in adult tissues, it is possible that RXRα may functionally compensate for the loss of RXRβ in most instances. In this respect, the complete penetrance, as well as the absence of variation in its expressivity, of the lipid metabolism defect observed in Sertoli cells of RXRβ null mutants, may correspond to a case in which such a redundancy cannot operate, given the apparent absence of RXRα expression in Sertoli cells. On the other hand, the partial penetrance of the embryonic lethal phenotype of RXRβ mutants could result from a partial functional redundancy amongst RXRs. Interestingly, the developmental phenotype of RXRα null mutants affects also a limited set of structures (the heart and the eye, see Kastner et al., *Cell* 78:987–1003 (1994); Sucov et al., *Gene Develop.* 8:1007–1018 (1994)). Moreover, the heart malformations seen in RXRα$^{-/-}$ embryos vary greatly in their severity from mutant to mutant, and RXRα/RXRβ double null mutants display much more severe developmental abnormalities than RXRα$^{-/-}$ single mutants (our unpublished results). In particular, their early cardiac defects are much more severe than those presented by RXRα single mutants. Thus, as previously observed for the RARs (Lohnes et al., Development 120:2723–2748 (1994) ;Mendelsohn et al., *Development* 120:2749–2771 (1994)), the RXRs can be functionally redundant, since RXRβ appears to be able to substitute for the lack of RXRα in many developmental instances.

Conclusion

The RXRβ mutant mice described here offer a new model for further understanding spermatogenesis. In particular, they should provide valuable tools to study the role of Sertoli cells in germ cell maturation and spermiation. Since lipid accumulation has also been observed in the Sertoli cells of human patients with fertility problems, our results raise the possibility that RXRβ mutations may be involved in some cases of human male sterility. Finally, these mice, together with mice mutated in other RXRs or putative RXR heterodimeric partners will be useful to study genetically the physiological role of RXRs and of their interaction with other members of the nuclear receptor superfamily.

The disclosure of all references, patent applications and patents, if any, recited herein are hereby incorporated by reference in their entirety.

What is claimed is:

1. A transgenic male mouse whose germ cells and somatic cells contain a homozygous disruption in the endogenous gene encoding RARα (Retinoic acid receptor alpha) wherein said disruption comprises the insertion of a selectable marker sequence, and wherein said disruption results in the lack of expression of said receptor and confers a sterile phenotype in said male mouse.

2. A transgenic mouse whose germ cells and somatic cells contain a homozygous disruption in the endogenous gene encoding RARγ (Retinoic acid receptor gamma), wherein said disruption comprises the insertion of a selectable marker sequence, and wherein said disruption results in the lack of expression of said receptor and confers a phenotype of malformation of the tracheal cartilaginous rings in said mouse.

3. A transgenic male mouse whose germ cells and somatic cells contain a homozygous disruption in the endogenous gene encoding RXRβ (Retinoid X receptor beta), wherein said disruption comprises the insertion of a selectable marker sequence, and wherein said disruption results in the lack of expression of said receptor and confers a sterile phenotype in said male mouse.

4. A transgenic mouse embryo whose germ cells and somatic cells contain a homozygous disruption in the endogenous gene encoding RXRα (Retinoid X receptor alpha), wherein said disruption comprises the insertion of a selectable marker sequence, and wherein said disruption confers a phenotype of ocular malformation in said mouse.

5. The embryo of claim 4, which is further homozygous or heterozygous for a disruption in the endogenous gene encoding RARα.

6. The embryo of claim 4, which is further homozygous or heterozygous for a disruption in the endogeneous gene encoding RARγ.

7. The embryo of claim 4, which is further homozygous for a disruption in the endogenous gene encoding RXRβ.

8. A method of identifying the subtype or isoform of a retinoic acid or retinoid X receptor bound by an agent, said method comprising:

(a) administering said agent to the transgenic mouse of claim 1, 2, 3 or 4;

(b) determining the amount of agent bound by said transgenic mouse lacking expression of said receptor subtype or isoform; and (c) comparing said amount to the amount of said agent bound by a mouse without said disruption and exhibiting normal expression of said receptor.

9. A method of identifying an agent which is an antagonist or agonist of a subtype or specific isotype of a retinoic acid or retinoid X receptor comprising:

(a) administering said agent to the transgenic mouse of claim 1, 2, 3 or 4;

(b) determining the effect said agent has on the development of said transgenic mouse lacking expression of said receptor subtype or specific isotype; and (c) comparing said effect to the effect of said agent on a mouse without said disruption and exhibiting normal expression of said receptor subtype or specific isotype.

10. A method of identifying an agent which is an antagonist or agonist of a subtype or specific isotype of a retinoic acid or retinoid X receptor, comprising:

(a) administering said agent to the transgenic mouse of claim 1, 2, 3 or 4;

(b) determining the effect said agent has on the expression of a retinoic acid inducible gene sequence in said transgenic mouse lacking expression of said receptor subtype or specific isotype; and (c) comparing said effect to the effect of said agent on the expression of a retinoic acid inducible gene sequence in a mouse without said disruption and exhibiting normal expression of said receptor subtype or specific isotype.

11. The method of claim 8 wherein said mouse has further been altered to contain a DNA sequence comprising a RARE (Retinoic acid receptor response element) or RXRE (Retinoid X receptor response element) operably linked to a marker sequence.

* * * * *

UNITED STATES PATENT AND TRADEMARK OFFICE
CERTIFICATE OF CORRECTION

PATENT NO. : 6,031,149
DATED : February 29, 2000
INVENTOR(S) : Chambon et al.

It is certified that error appears in the above-identified patent and that said Letters Patent is hereby corrected as shown below:

Title page,
Item [54], the Title of the Invention, please delete "GENETICALLY ENGINEERED MICE CONTAINING ALTERATIONS IN THE GENES ENCODING RETINOIC ACID RECEPTOR PROTEINS" and insert therein -- GENETICALLY ENEGINEERED MICE CONTAINING ALTERATIONS IN THE GENES ENCODING RETINOIC ACID RECEPTOR AND RETINOID X RECEPTOR PROTEINS --.

Item [62], Related U.S. Application Data, in its entirety, and insert the following:
-- Continuation-in-part of U.S. Appl. No. 08/373,224, which is a 371 application claiming benefit of PCT/USA94/05746, filed May 18, 1994, which is a continuation-in-part of U.S. Appl. No. 08/062,850, filed May 18, 1993. --.

Column 22,
Lines 12-19, please delete "A HSV TK expression cassette, derived from p511 (Lufkin et al., *Cell* 66:1105-1119 (1991)), was then cloned into the unique SalI site present in the polycloning site of pTZ 19U, to yield the final targeting vector designated γ6.1. This construct had 2.8 kb and 3.2 kb of homologous sequence 5' and 3' of the NEO insert respectively, and was linearized at the unique HindIII site in the polylinker prior to electroporation of D3 Es cells."

Column 35,
Line 58, after "neomycin insertion.", please insert -- Plasmid p TZ18Rp826B1 was deposited on December 16, 1997 with American Type Culture Collection at the address of 12301 Parklawn Drive, Rockville, MD 20852, USA, now located at 10801 University Blvd., Manassas, VA 20110-2209, USA, and given an accession number 209557. --

Column 52,
Line 10, after "Southern Blotting.", please insert -- Plasmid pPolyIIIpHR(RXRα).2 was deposited on December 16, 1998 with American Type Culture Collection at the address of 12301 Parklawn Drive, Rockville, MD 20852, USA, now located at 10801 University Blvd., Manassas, VA 20110-2209, USA, and given an accession number 209556. --

Column 70,
Line 15, after "(FIG. 24*ai*, b)", please insert -- Plasmid pBSK-pHR(RXRβ) was deposited on December 16, 1997 with American Type Culture Collection at the address of 12301 Parklawn Drive, Rockville, MD 20852, USA, now located at 10801 University Blvd., Manassas, VA 20110-2209, USA, and given an accession number 209555. --

UNITED STATES PATENT AND TRADEMARK OFFICE
CERTIFICATE OF CORRECTION

PATENT NO. : 6,031,149
DATED : February 29, 2000
INVENTOR(S) : Chambon et al.

It is certified that error appears in the above-identified patent and that said Letters Patent is hereby corrected as shown below:

Column 80, claim 8,
Line 21, please delete "claim 1, 2, 3 or 4." and insert therein -- claim 1, 2, 3, 4 or 12. --.
Line 27, please delete "of said receptor" and insert therein -- of said receptor subtype or isoform --.

Column 80, claim 9,
Line 32, please delete "claim 1, 2, 3 or 4." and insert therein -- claim 1,2, 3, 4 or 12. --.

Column 80, claim 10,
Line 44, please delete "claim 1, 2, 3 or 4." and insert therein -- claim 1, 2, 3, 4 or 12. --.
Please add the following claims:
-- 12. A transgenic mouse whose germ cells and somatic cells contain a heterozygous disruption in the endogenous gene encoding RXRα (Retinoid X receptor alpha), wherein said disruption comprises the insertion of a selectable marker sequence into one allele of said gene, and wherein said disruption confers a phenotype of postnatal growth deficiency in said mouse.

13. The mouse of claim 12, which is further heterozygous for a disruption in the endogenous gene encoding for RARα.

14. The mouse of claim 12, which is further homozygous or heterozygous for a disruption in the endogenous gene encoding RARγ. --

Signed and Sealed this

Twenty-sixth Day of February, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,031,149
DATED         : February 29, 2000
INVENTOR(S)   : Chambon et al.

It is certified that error appears in the above-identified patent and that said Letters Patent is hereby corrected as shown below:

Title page,
Item [54], the Title of the Invention, please delete "GENETICALLY ENGINEERED MICE CONTAINING ALTERATIONS IN THE GENES ENCODING RETINOIC ACID RECEPTOR PROTEINS" and insert therein -- GENETICALLY ENGINEERED MICE CONTAINING ALTERATIONS IN THE GENES ENCODING RETINOIC ACID RECEPTOR AND RETINOID X RECEPTOR PROTEINS --.

Item [62], Related U.S. Application Data, in its entirety, and insert the following:
-- Continuation-in-part of U.S. Appl. No. 08/373,224, which is a 371 application claiming benefit of PCT/US94/05746, filed May 18, 1994, which is a continuation-in-part of U.S. Appl. No. 08/062,850, filed May 18, 1993. --.

Column 22,
Lines 12-19, please delete "A HSV TK expression cassette, derived from p511 (Lufkin et al., *Cell* 66:1105-1119 (1991)), was then cloned into the unique SalI site present in the polycloning site of pTZ 19U, to yield the final targeting vector designated γ6.1. This construct had 2.8 kb and 3.2 kb of homologous sequence 5' and 3' of the NEO insert respectively, and was linearized at the unique HindIII site in the polylinker prior to electroporation of D3 Es cells."

Column 35,
Line 58, after "neomycin insertion.", please insert -- Plasmid pTZ18Rp826B1 was deposited on December 16, 1997 with American Type Culture Collection at the address of 12301 Parklawn Drive, Rockville, MD 20852, USA, now located at 10801 University Blvd., Manassas, VA 20110-2209, USA, and given an accession number 209557. --

Column 52,
Line 10, after "Southern Blotting.", please insert -- Plasmid pPolyIIIpHR(RXRα).2 was deposited on December 16, 1998 with American Type Culture Collection at the address of 12301 Parklawn Drive, Rockville, MD 20852, USA, now located at 10801 University Blvd., Manassas, VA 20110-2209, USA, and given an accession number 209556. --

Column 70,
Line 15, after "(FIG. 24*a, b*)", please insert -- Plasmid pBSK-pHR(RXRβ) was deposited on December 16, 1997 with American Type Culture Collection at the address of 12301 Parklawn Drive, Rockville, MD 20852, USA, now located at 10801 University Blvd., Manassas, VA 20110-2209, USA, and given an accession number 209555

UNITED STATES PATENT AND TRADEMARK OFFICE
CERTIFICATE OF CORRECTION

PATENT NO. : 6,031,149
DATED : February 29, 2000
INVENTOR(S) : Chambon et al.

It is certified that error appears in the above-identified patent and that said Letters Patent is hereby corrected as shown below:

<u>Column 80, claim 8,</u>
Line 21, please delete "claim 1, 2, 3 or 4." and insert therein -- claim 1, 2, 3, 4 or 12. --.
Line 27, please delete "of said receptor" and insert therein -- of said receptor subtype or isoform --.

<u>Column 80, claim 9,</u>
Line 32, please delete "claim 1, 2, 3 or 4." and insert therein -- claim 1, 2, 3, 4 or 12. --.

<u>Column 80, claim 10,</u>
Line 44, please delete "claim 1, 2, 3 or 4." and insert therein -- claim 1, 2, 3, 4 or 12. --.

This certificate supersedes Certificate of Correction issued February 26, 2002.

Signed and Sealed this

Fourth Day of June, 2002

*Attest:*

*Attesting Officer*

JAMES E. ROGAN
*Director of the United States Patent and Trademark Office*